United States Patent
Kataoka et al.

(10) Patent No.: US 7,557,110 B2
(45) Date of Patent: Jul. 7, 2009

(54) PYRAZOLO[1,5-A] PYRIMIDINE DERIVATIVES

(75) Inventors: Kenichiro Kataoka, Hino (JP); Naotaka Suzuki, Tokyo (JP); Tomomi Kosugi, Hino (JP); Minoru Imai, Hino (JP); Hiroaki Makino, Hino (JP); Mika Takakuwa, Hino (JP); Gen Unoki, Hino (JP); Aiko Fujino, Hino (JP); Yasuhiro Oue, Hino (JP); Yuko Yamakoshi, Hino (JP); Satoshi Sugiura, Hino (JP); Robert Dale Mitchell, Walden Essex (GB); James Donald Simpson, Walden Essex (GB); John Clifford Harris, Walden Essex (GB); Joelle Le, Walden Essex (GB)

(73) Assignee: Teijin Pharma Limited, Tokyo (JP)

( * ) Notice: Subject to any disclaimer, the term of this patent is extended or adjusted under 35 U.S.C. 154(b) by 164 days.

(21) Appl. No.: 10/547,080

(22) PCT Filed: Mar. 1, 2004

(86) PCT No.: PCT/JP2004/002522

§ 371 (c)(1),
(2), (4) Date: May 5, 2006

(87) PCT Pub. No.: WO2004/076458

PCT Pub. Date: Sep. 10, 2004

(65) Prior Publication Data

US 2006/0189632 A1    Aug. 24, 2006

Related U.S. Application Data

(60) Provisional application No. 60/500,695, filed on Sep. 8, 2003.

(30) Foreign Application Priority Data

Feb. 28, 2003 (GB) .................................. 0304665.3
Dec. 19, 2003 (GB) .................................. 0329446.9

(51) Int. Cl.
C07D 487/04 (2006.01)
A61K 31/519 (2006.01)

(52) U.S. Cl. .................................... 514/259.3; 544/281
(58) Field of Classification Search ................ 544/281; 514/259.3

See application file for complete search history.

(56) References Cited

U.S. PATENT DOCUMENTS 6,235,741 B1    5/2001    Bilodeau et al.

FOREIGN PATENT DOCUMENTS

| EP | 0 591 528 A1 | 4/1994 |
|---|---|---|
| EP | 628559 A1 | 12/1994 |
| EP | 0941994 A1 | 9/1999 |
| EP | 1505068 A1 | 9/2005 |
| WO | 98/54093 A1 | 12/1998 |
| WO | 00/53605 A1 | 9/2000 |
| WO | WO 04/000844 A1 | 12/2003 |
| WO | WO 2004/022559 A1 | 3/2004 |
| WO | WO 2004/022560 A1 | 3/2004 |
| WO | WO 2004/022561 A1 | 3/2004 |
| WO | WO 2004/022562 A1 | 3/2004 |
| WO | WO 2004/026229 A1 | 4/2004 |
| WO | 2005/077954 A2 | 8/2005 |

OTHER PUBLICATIONS

T. Shiota, et al. "Synthesis and Structure-Activity Relationship of a New Series of Potent Angiotensin II Receptor Antagonists: Pyrazolo[1, 5-α] pyrimidine Derivatives," *Chemical & Pharmaceutical Bulletin*, 1999, 47(7), pp. 928-938.

T. Novinson, et al., "Synthesis and Antifungal Properties of Certain 7-Alkylaminopyrazolo [1, 5-α] pyrimidines," *Journal of Medicinal Chemistry*, 1977, 20(2), pp. 296-299.

SoftFocus Library Data Sheet, Kinase Directed, SFK03 SFK/DS, Aug. 7, 2002.

International Search Report dated Sep. 1, 2008.

*Primary Examiner*—Bruck Kifle
(74) *Attorney, Agent, or Firm*—Sughrue Mion, PLLC

(57) ABSTRACT

The Pyrazolo[1,5-a]pyrimidine derivatives represented by formula I and their pharmaceutically acceptable salts exhibit excellent kinase inhibiting activity. Drugs comprising the compounds as effective ingredients are therefore expected to be useful as therapeutic or prophylactic agents for a protein kinase mediated disorder in which kinase is implicated, such as inflammatory disease, autoimmune disease, destructive bone disorder, cancer and/or tumour growth.

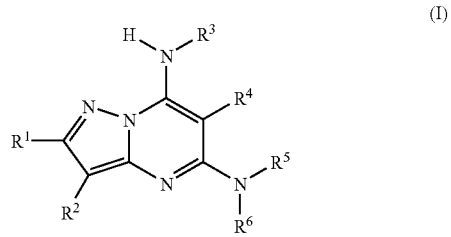

53 Claims, 8 Drawing Sheets

FIGURE1: The p38 MAPK cascade

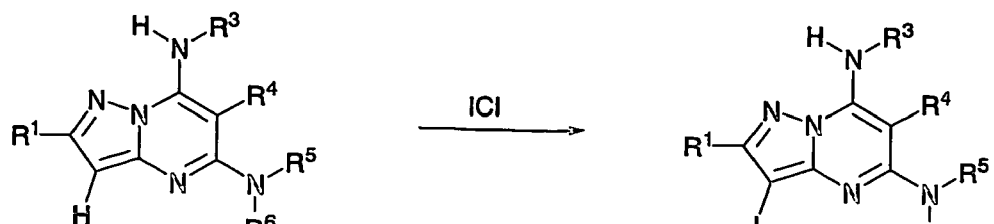
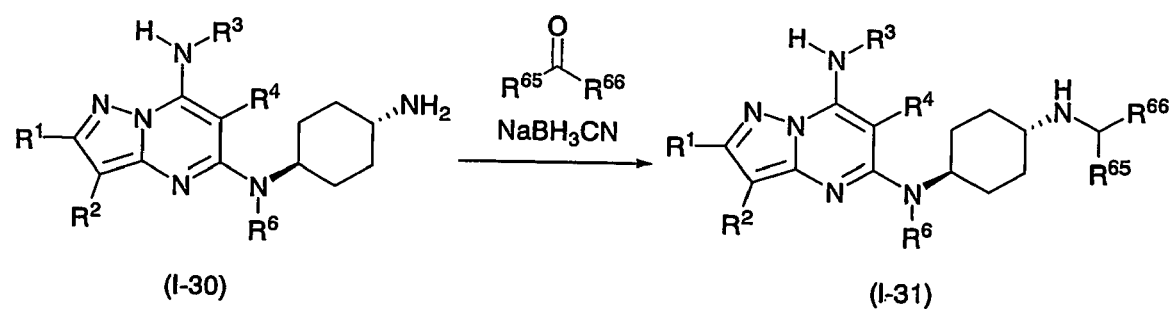
FIGURE 8

PYRAZOLO[1,5-A] PYRIMIDINE DERIVATIVES

This is a national stage of Application No. PCT/JP2004/002522 filed Mar. 1, 2004, which claims benefit of priority to U.S. Provisional App. No. 60/500,695, filed Sep. 8, 2003.

FIELD OF THE INVENTION

The present invention relates to novel compounds, their use in the inhibition of protein kinases, their use in medicine and particularly in the prevention and/or treatment of a wide variety of diseases including inflammatory disorders, cancer, angiogenesis, diabetes and neurological disorders. The invention also provides processes for the manufacture of said compounds, compositions containing them and processes for manufacturing such compositions.

BACKGROUND ART

Protein kinases are a family of enzymes that catalyse the phosphorylation of hydroxyl groups in proteins. Approximately 2% of the genes encoded by the human genome are predicted to encode protein kinases. The phosphorylation of specific tyrosine, serine, or threonine residues on a target protein can dramatically alter its function in several ways including activating or inhibiting enzymatic activity, creating or blocking binding sites for other proteins, altering subcellular localisation or controlling protein stability. Consequently, protein kinases are pivotal in the regulation of a wide variety of cellular processes, including metabolism, proliferation, differentiation and survival (Hunter, T. Cell, 1995, 80, 224-236). Of the many different cellular functions known to require the actions of protein kinases, some represent targets for therapeutic intervention for certain disease (Cohen, P. Nature Rev. Drug Disc., 2002, 1,309-315).

It is known that several diseases arise from, or involve, aberrant protein kinase activity. In humans, protein tyrosine kinases are known to have a significant role in the development of many diseases including diabetes, cancer and have also been linked to a wide variety of congenital syndromes (Robertson, S. C. Trends Genet. 2000, 16, 265-271). Serine/threonine kinases also represent a class of enzymes, inhibitors of which are likely to have relevance to the treatment of cancer, diabetes and a variety of inflammatory disorders (Adams, J. L. et al. Prog. Med. Chem. 2001, 38, 1-60).

One of the principal mechanisms by which cellular regulation is affected is through the transduction of extracellular signals across the membrane that in turn modulate biochemical pathways within the cell. Protein phosphorylation represents one course by which intracellular signals are propagated from molecule to molecule resulting finally in cellular responses. These signal transduction cascades are regulated and often overlapping as evidenced by the existence of many protein kinases as well as phosphatases. It is currently believed that a number of disease and/or disorders are a result of either aberrant activation or inhibition in the molecular components of kinase cascades.

Three potential mechanisms for inhibition of protein kinases have been identified thus far. These include a pseudosubstrate mechanism, an adenine mimetic mechanism and the locking of the enzyme into an inactive conformation by using surfaces other than the active site (Taylor, S. S. Curr. Opin. Chem. Biol. 1997, 1, 219-226). The majority of inhibitors identified/designed to date act at the ATP-binding site. Such ATP-competitive inhibitors have demonstrated selectivity by virtue of their ability to target the more poorly conserved areas of the ATP-binding site (Wang, Z. et al. Structure 1998, 6, 1117-1128).

There exists a need for the provision of further compounds that are inhibitors of protein kinases.

MAPKAP-K2 (mitogen-activated protein kinase-activated protein kinase 2) is a serine/threonine kinase that operates immediately downstream of the p38 kinase in the stress-induced MAPK pathway (FIG. 1).

The p38 kinase pathway is involved in transducing the effects of a variety of stress-related extracellular stimuli such as heat shock, UV light, bacterial lipopolysaccharide, and pro-inflammatory cytokines. Activation of this pathway results in the phosphorylation of transcription and initiation factors, and affects cell division, apoptosis, invasiveness of cultured cells and the inflammatory response (Martin-Blanco, Bioessays 22, 637-645 (2000)).

p38 kinase itself activates a number of protein kinases other than the MAPKAP kinases such as Mnk1/2, PRAK and MSK1 (FIG. 1). The specific and/or overlapping functions of the majority of these targets have yet to be resolved. This pathway has been of particular interest for the discovery of new anti-inflammatory agents. Previous strategies to intervene this pathway have involved the development of selective inhibitors of p38 kinase. Such inhibitors are effective both for inhibiting pro-inflammatory cytokine production in cell-based models and animal models of chronic inflammations (Lee et al., Immunopharmacology 47, 185-201 (2000)). p38 kinase knockout mouse is embryonic lethal. And cells derived from such embryos have demonstrated a number of abnormalities in fundamental cell responses. These observations indicate that caution should be paid to the long-term therapy with p38 kinase inhibitors.

An alternative strategy for the development of anti-inflammatory agents could be the inhibition of this pathway at the level of MAPKAP-K2. Human MAPKAP-K2 has two proline-rich domains at its N-terminus followed by the kinase domain and the C-terminal regulatory domain. This kinase has low homology with other serine/threonine kinases except MAPKAP-K3 and -K4. The C-terminal regulatory domain contains a bipartite nuclear localisation signal and a nuclear export signal. The crystal structure of inactive MAPKAP-K2 has been resolved (Meng, W. et al. J. Biol. Chem. 277, 37401-37405 (2002)). Activation of MAPKAP-K2 by p38 kinase occurs via selective phosphorylation of threonine residues 222 and 334 (Stokoe et al., EMBO J. 11, 3985-3994 (1992)). MAPKAP-K2 has an amphiphilic A-helix motif located within its C-terminal region that is likely to block the binding of substrates. The dual phosphorylation by p38 kinase has been proposed to reposition this motif resulting in enhanced catalytic activity (You-Li et al., J. Biol. Chem. 270, 202-206 (1995)). MAPKAP-K2 is present in the nucleus of unstimulated cells, and translocates to the cytoplasm upon cell stimulation. This kinase is known to phosphorylate a number of nuclear transcription factors as well as cytosolic proteins such as heat shock proteins and 5-lipoxygenase (Stokoe et al., FEBS Lett. 313, 307-313 (1992), Werz, et al., Proc. Natl. Acad. Sci. USA 97, 5261-5266 (2000), Heidenreich, et al., J. Biol. Chem. 274, 14434-14443 (1999), Tan, et al., EMBO J. 15, 4629-4642 (1996), Neufeld, J. Biol. Chem. 275, 20239-20242 (2000)). All such substrates contain a unique amino acid motif (XX-Hyd-XRXXSXX, where Hyd is a bulky hydrophobic residue) that is required for efficient phosphorylation by MAPKAP-K2 (Stokoe et al., Biochem. J. 296, 843-849 (1993)).

Currently MAPKAP-K2 is the only p38 kinase substrate for which a specific function has been identified. A specific role for MAPKAP-K2 in mediating the inflammatory response has been strongly indicated by the phenotype of the MAPKAP-K2-deficient mouse (MAPKAP-K2$^{-/-}$) (Kotlyarov, et al., Nature Cell Biol. 1, 94-97 (1999)). This mouse is viable and normal except for a significantly reduced inflammatory response. Recently it has also been shown that MAPKAP-K2 deficiency results in a marked neuroprotection from ischaemic brain injury (Wang et al., J. Biol Chem. 277, 43968-43972 (2002)). MAPKAP-K2 is believed to regulate the translation and/or stability of important pro-inflammatory cytokine mRNAs. It is thought to function via phosphorylation of proteins that bind to the AU-rich elements found within untranslated regions of these cytokines. The identity of these proteins is currently under investigation.

MAPKAP-K2 therefore represents an intervention point in the stress-induced kinase cascade for perturbation of the inflammatory response.

DISCLOSURE OF THE INVENTION

As a result of much diligent research directed toward achieving the object stated above, the present inventors have completed the present invention upon discovering that the novel Pyrazolo[1,5-a]pyrimidine derivatives represented by formula I below and their pharmaceutically acceptable salts exhibit excellent kinase inhibiting activity.

In other words, the present invention provides as follows:

(1) A Compound of Formula I:

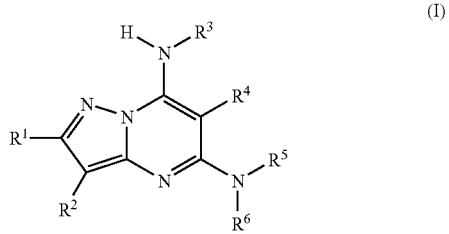

wherein $R^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^2$ is hydrogen, halogen, —CN, —NO$_2$, —CHO, -G-R$^7$ [G is a bond, —C(=O)— or —O—C(=O)—; and $R^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^8$ (R$^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —NR$^9$R$^{10}$ (R$^9$ is as defined for R$^8$; R$^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl; provided that when R$^7$ is C6-C14 optionally substituted aryl or optionally substituted heteroaryl, then G is not a bond], —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^{13}$, which may be the same or different, are as defined for R$^8$), —SR$^9$ (R$^9$ is as defined for R$^8$) or —S(O)$_m$R$^9$ (R$^9$ is as defined for R$^8$; m is 1 or 2);

$R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl [As substituents of C6-C14 aryl may be mentioned one or more selected from the group consisting of halogen, —CN, —NO$_2$, —CHO, -G-R$^{15}$ {G is a bond, —C(=O)— or —O—C(=O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X is O, S, N—CN or NH), —NR$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) and —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)], unsubstituted heterocyclyl, substituted heterocyclyl [As substituents of heterocyclyl may be mentioned one or more selected from the group consisting of halogen, —CN, —NO$_2$, —CHO, -G-R$^{23}$ {G is a bond, —C(=O)— or —O—C(=O)—; R$^{23}$ is as defined for R$^{15}$}, —NR$^{24}$C(=O)R$^{25}$ (R$^{24}$ is as defined for R$^8$; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), —NR$^{24}$C(=X)NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$R$^{24}$ (R$^{24}$ is as defined for R$^8$; m is 0, 1 or 2) and —SO$_2$NR$^{28}$R$^{29}$ (R$^{28}$ and R$^{29}$, which may be the same or different, are as defined for R$^8$; R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ is as defined for R$^8$), —SR$^{30}$ (R$^{30}$ is as defined for R$^8$), —NR$^{30}$R$^{31}$ (R$^{30}$ and R$^{31}$, which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$ (R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$SO$_2$R$^{31}$ (R$^{30}$ and R$^{31}$, which may be the same or different, are as defined for R$^8$);

R$^5$ is C1-C8 substituted alkyl, C2-C8 optionally substituted alkenyl, C2-C8 optionally substituted alkynyl, C3-C8 substituted cycloalkyl [As substituents of C3-C8 cycloalkyl may be mentioned one or more selected from the group consisting of halogen, —CN, —NO$_2$, —CHO, -G-R$^{34}$ {G is a bond, —C(=O)— or —O—C(=O)—; R$^{34}$ is as defined for R$^{15}$}, —NR$^{35}$C(=O)R$^{36}$ (R$^{35}$ is as defined for R$^8$; R$^{36}$ is as defined for R$^{12}$), —NR$^{35}$C(=X)OR$^{37}$ (R$^{35}$ and R$^{37}$, which may be the same or different, are as defined for R$^8$; X is O, S, N—CN or NH ), —NR$^{35}$C(=X)NR$^{37}$R$^{38}$ (R$^{35}$, R$^{37}$ and R$^{38}$, which may be the same or different, are as defined for R$^8$; X is O, S, N—CN or NH) and —NR$^{35}$SO$_2$R$^{37}$ (R$^{35}$ and R$^{37}$, which may be the same or different, are as defined for R$^8$)], unsubstituted heterocyclyl, substituted heterocyclyl [As substituents of heterocyclyl may be mentioned one or more selected from the group consisting of halogen, —CN, —NO$_2$, —CHO, -G-R$^{39}$ {G is a bond, —C(=O)— or, —O—C(=O)—; R$^{39}$ is as defined for R$^{15}$}, —NR$^{40}$C(=O)R$^{41}$ (R$^{40}$ is as defined for R$^8$; R$^{41}$ is as defined for R$^{12}$), —NR$^{40}$C(=X)OR$^{42}$ (R$^{40}$ and R$^{42}$, which may be the same or different, are as defined for R$^8$; X is O, S, N—CN or NH), —NR$^{40}$C(=X)NR$^{42}$R$^{43}$ (R$^{40}$, R$^{42}$ and R$^{43}$, which may be the same or different, are as defined for R$^8$; X is O, S, N—CN or NH) and —NR$^{40}$SO$_2$R$^{42}$ (R$^{40}$ and R$^{42}$, which may be the same or different, are as defined for R$^8$)], optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl or —NR$^{44}$R$^{45}$ (R$^{44}$ and R$^{45}$, which may be the same or different, are C1-C8 optionally substituted alkyl; R$^{44}$ and R$^{45}$ together may be taken together with the nitrogen to which they are attached to form a mono heterocycle with 5-7 members and optionally containing, in addition to the nitrogen, one or two additional heteroatoms selected from N, O and S, the said mono heterocycle may optionally be substituted with one or more substituents);

R$^6$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl;

with the provisos:
that R$^1$, R$^2$ and R$^4$ are not all H;
that R$^4$ is not pentafluorophenyl;
that R$^5$ is not a group represented as the following (a):
(a) C1-C6 alkyl or C3-C6 cycloalkyl, in which an alkyl group or a cycloalkyl group optionally may be substituted by phenyl or by one or more fluoro substituents;

and pharmaceutically acceptable salts, and other pharmaceutically acceptable biohydrolyzable derivatives thereof, including esters, amides, carbamates, carbonates, ureides, solvates, hydrates, affinity reagents or prodrugs.

(2) A compound of formula I-b:

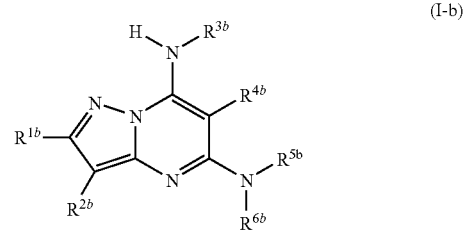

(I-b)

wherein R$^{1b}$ is hydrogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl;

R$^{2b}$ is hydrogen, halogen, —CN, —NO$_2$, —CHO or -G-R$^{52}$ {G is a bond, —C(=O)— or —O—C(=O)—; and R$^{52}$ is C1-C6 optionally substituted alkyl, C2-C6 optionally substituted alkenyl, C2-C6 optionally substituted alkynyl, C3-C8 optionally substituted cycloalkyl, optionally substituted arylalkyl, optionally substituted heteroarylalkyl, optionally substituted arylalkenyl, optionally substituted heteroarylalkenyl, optionally substituted arylalkynyl, optionally substituted heteroarylalkynyl, —OR$^{53}$ (R$^{53}$ is hydrogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl), —NR$^{54}$R$^{55}$, —NR$^{54}$C(=O)R$^{55}$, —SR$^{54}$, optionally substituted aryl or optionally substituted heteroaryl; provided that when R$^{52}$ is optionally substituted aryl or optionally substituted heteroaryl then G is not a bond; wherein R$^{54}$ and R$^{55}$, which may be the same or different, are as defined for R$^{53}$; or wherein R$^{54}$ and R$^{55}$ together form an optionally substituted ring that optionally contains one or more heteroatoms selected from N, O and S};

R$^{3b}$ is C1-C8 optionally substituted alkyl, C2-C8 optionally substituted alkenyl, C2-C8 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl;

$R^{4b}$ is hydrogen, halogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl, optionally substituted heteroarylalkynyl, $-OR^{56}$, $-SR^{56}$, $-NR^{56}R^{57}$ or $-NR^{56}C(=O)R^{57}$;

wherein $R^{56}$ and $R^{57}$, which may be the same or different, are as defined for $R^{53}$; or wherein $R^{56}$ and $R^{57}$ together form an optionally substituted ring which optionally contains one or more heteroatoms;

$R^{5b}$ is C1-C6 substituted alkyl, C2-C6 optionally substituted alkenyl, C2-C6 optionally substituted alkynyl, C3-C8 substituted cycloalkyl, optionally substituted heterocyclyl or optionally substituted heterocyclylalkyl;

$R^{6b}$ is hydrogen, C1-C6 optionally substituted alkyl, C2-C6 optionally substituted alkenyl, C2-C6 optionally substituted alkynyl or C3-C8 optionally substituted cycloalkyl;

with the provisos:

that $R^{1b}$, $R^{2b}$ and $R^{4b}$ are not all H;

that $R^{4b}$ is not pentafluorophenyl;

that $R^{5b}$ is not a group represented as the following (a):

(a) C1-C6 alkyl or C3-C6 cycloalkyl, in which an alkyl group optionally may be substituted by phenyl or by one or more fluoro substituents;

and pharmaceutically acceptable salts, and other pharmaceutically acceptable biohydrolyzable derivatives thereof, including esters, amides, carbamates, carbonates, ureides, solvates, hydrates, affinity reagents or prodrugs.

(3) The compound as (1) wherein $R^1$ is hydrogen or C1-C8 optionally substituted alkyl.

(4) The compound as (1) wherein $R^1$ is hydrogen.

(5) The compound as any one of (1), (3) or (4) wherein $R^2$ is $-NO_2$, $-OC(=O)R^7$, $-CO_2R^8$ or $-CONR^9R^{10}$; wherein $R^7$, $R^8$, $R^9$ and $R^{10}$ are as defined in claim 1.

(6) The compound as any one of (1), (3) or (4) wherein $R^2$ is $-NR^9C(=O)R^{12}$, $-NR^9C(=X)OR^{13}$, $-NR^9C(=X)NR^{13}R^{14}$, $-NR^9SO_2R^{13}$, $-SR^9$ or $-S(O)_mR^9$; wherein $R^9$, $R^{12}$, $R^{13}$, $R^{14}$ and X are as defined in claim 1; m is 1 or 2.

(7) The compound as any one of (1), (3) or (4) wherein $R^2$ is C1-C8 optionally substituted alkyl, C3-C8 optionally substituted cycloalkyl or optionally substituted arylalkyl.

(8) The compound as any one of (1), (3) or (4) wherein $R^2$ is hydrogen, halogen, $-CN$ or $-SCH_3$.

(9) The compound as any one of (1), (3) or (4) wherein $R^2$ is halogen.

(10) The compound as any one of (1), (3) or (4) wherein $R^2$ is F.

(11) The compound as any one of (1), (3) or (4) wherein $R^2$ is hydrogen.

(12) The compound as any one of (1), (3) to (11) wherein $R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl, unsubstituted heteroaryl, substituted heteroaryl, optionally substituted arylalkyl or optionally substituted heteroarylalkyl.

(13) The compound as any one of (1), (3) to (11) wherein $R^3$ is C6-C14 substituted aryl.

(14) The compound as any one of (1), (3) to (11) wherein $R^3$ is C6-C14 substituted aryl {As substituents of C6-C14 aryl may be mentioned one or more selected from the group consisting of halogen, $-CN$, $-NO_2$, -G-$R^{15}$, $-NR^{17}C(=O)R^{19}$ and $-S(O)_mR^{17}$; wherein $R^{15}$, $R^{17}$, $R^{19}$ or G are as defined in claim 1; m is 0, 1 or 2.}.

(15) The compound as any one of (1), (3) to (11) wherein $R^3$ is C6-C14 substituted aryl [As substituents of C6-C14 aryl may be mentioned one or more selected from the group consisting of halogen, $-CN$, $-NO_2$, -G-$R^{15}$ {G is a bond or $-C(=O)-$; $R^{15}$ is C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl, $-OR^{16}$ or $-NR^{17}R^{18}$}, $-NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2.].

(16) The compound as any one of (1), (3) to (11) wherein $R^3$ is C6-C14 substituted aryl [As substituents of C6-C14 aryl may be mentioned one or more selected from the group consisting of halogen, $-CN$, $-NO_2$, -G-$R^{15}$ {G is a bond; $R^{15}$ is C6-C14 optionally substituted aryl, optionally substituted heterocyclyl, optionally substituted heterocyclylalkyl, $-OR^{16}$ or $-NR^{17}R^{18}$}, $-NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2.].

(17) The compound as any one of (1), (3) to (11) wherein $R^3$ is C6-C14 substituted aryl [As substituents of C6-C14 aryl may be mentioned one or more selected from the group consisting of halogen, $-CN$, $-NO_2$, -G-$R^{15}$ {G is a bond or $-C(=O)-$; $R^{15}$ is C1-C8 optionally substituted alkyl, C3-C8 optionally substituted cycloalkyl, $-OR^{16}$ or $-NR^{17}R^{18}$}, $-NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2.].

(18) The compound as any one of (1), (3) to (11) wherein $R^3$ is C6-C14 substituted aryl [As substituents of C6-C14 aryl may be mentioned one or more selected from the group consisting of halogen, $-CN$, $-NO_2$, -G-$R^{15}$ {G is a bond or $-C(=O)-$; $R^{15}$ is C1-C8 optionally substituted alkyl, C3-C8 optionally substituted cycloalkyl, $-OR^{16}$ or $-NR^{17}R^{18}$}, $-NR^{17}C(=O)R^{19}$ and $S(O)_mR^{17}$; wherein $R^{16}$, $R^{17}$, $R^{18}$ or $R^{19}$, which may be the same or different, are hydrogen, C1-C8 optionally substituted alkyl, C3-C8 optionally substituted cycloalkyl; m is 0, 1 or 2.].

(19) The compound as any one of (1), (3) to (11) wherein $R^3$ is C6-C14 substituted aryl [As substituents of C6-C14 aryl may be mentioned one or more selected from the group consisting of halogen, $-CN$, $-NO_2$ and -G-$R^{15}$ {G is $-C(=O)-$; $R^{15}$ is C1-C8 optionally substituted alkyl, C3-C8 optionally substituted cycloalkyl, C6-C14 optionally substituted aryl, optionally substituted heterocyclyl, $-OR^{16}$ or $-NR^{17}R^{18}$}; wherein $R^{16}$, $R^{17}$ or $R^{18}$ are as defined in claim 1.].

(20) The compound as any one of (1), (3) to (11) wherein $R^3$ is unsubstituted heterocyclyl.

(21) The compound as any one of (1), (3) to (11) wherein $R^3$ is substituted heterocyclyl.

(22) The compound as any one of (1), (3) to (11) wherein $R^3$ is substituted heterocyclyl [As substituents of heterocyclyl may be mentioned one or more selected from the group consisting of halogen, $-CN$, $-NO_2$, -G-$R^{23}$, $-NR^{24}C(=O)R^{25}$ and $-S(O)_mR^{24}$; wherein $R^{23}$, $R^{24}$, $R^{25}$ or G are as defined in claim 1; m is 0, 1 or 2.].

(23) The compound as any one of (1), (3) to (11) wherein $R^3$ is unsubstituted bicyclic heteroaryl.

(24) The compound as any one of (1), (3) to (11) wherein $R^3$ is substituted bicyclic heteroaryl [As substituents of bicyclic heteroaryl may be mentioned one or more selected from the group consisting of halogen, $-CN$, $-NO_2$, -G-$R^{23}$, —NR$^{24}$C(=O)R$^{25}$ and —S(O)$_m$R$^{24}$; wherein R$^{23}$, R$^{24}$, R$^{25}$ or G are as defined in claim 1; m is 0, 1 or 2.].

(25) The compound as any one of (1), (3) to (24) wherein R$^4$ is halogen, C1-C8 optionally substituted alkyl, C3-C8 optionally substituted cycloalkyl, optionally substituted arylalkyl, optionally substituted heterocyclylalkyl, —OR$^{30}$; wherein R$^{30}$ is as defined in claim 1.

(26) The compound as any one of (1), (3) to (24) wherein R$^4$ is C1-C8 optionally substituted alkyl.

(27) The compound as any one of (1), (3) to (24) wherein R$^4$ is methyl.

(28) The compound as any one of (1), (3) to (24) wherein R$^4$ is hydrogen.

(29) The compound as any one of (1), (3) to (28) wherein R$^5$ is C3-C8 substituted cycloalkyl, unsubstituted heterocyclyl or substituted heterocyclyl.

(30) The compound as any one of (1), (3) to (28) wherein R$^5$ is C3-C8 substituted cycloalkyl [As substituents of cycloalkyl may be mentioned one or more selected from the group consisting of halogen, —CN, C1-C8 optionally substituted alkyl, C2-C8 optionally substituted alkenyl, C3-C8 optionally substituted cycloalkyl and —NR$^{17}$R$^{18}$; wherein R$^{17}$ or R$^{18}$ is as defined in claim 1].

(31) The compound as any one of (1), (3) to (28) wherein R$^5$ is substituted cyclohexyl [As substituents of cyclohexyl may be mentioned one or more selected from the group consisting of halogen, —CN, C1-C8 optionally substituted alkyl, C2-C8 optionally substituted alkenyl, C3-C8 optionally substituted cycloalkyl and —NR$^{17}$R$^{18}$; wherein R$^{17}$ or R$^{18}$ is as defined in claim 1].

(32) The compound as any one of (1), (3) to (28) wherein R$^5$ is 4-amino-cyclohexyl.

(33) The compound as any one of (1), (3) to (28) wherein R$^5$ is unsubstituted heterocyclyl or substituted heterocyclyl [As substituents of heterocyclyl may be mentioned one or more selected from the group consisting of halogen, —CN, C1-C8 optionally substituted alkyl, C2-C8 optionally substituted alkenyl, C3-C8 optionally substituted cycloalkyl and —NR$^{17}$R$^{18}$; wherein R$^{17}$ or R$^{18}$ is as defined in claim 1]

(34) The compound as any one of (1), (3) to (28) wherein R$^5$ is unsubstituted piperidin-3-yl, unsubstituted piperidin-4-yl or unsubstituted pyrrolidin-3-yl.

(35) The compound as any one of (1), (3) to (28) wherein R$^5$ is substituted piperidin-3-yl, substituted piperidin-4-yl or substituted pyrrolidin-3-yl.

(36) The compound as any one of (1), (3) to (28) wherein R$^5$ is substituted piperidin-3-yl, substituted piperidin-4-yl or substituted pyrrolidin-3-yl [As their substituents may be mentioned one or more selected from the group consisting of halogen, —CN, C1-C8 optionally substituted alkyl, C2-C8 optionally substituted alkenyl and C3-C8 optionally substituted cycloalkyl]

(37) The compound as any one of (1), (3) to (36) wherein R$^6$ is hydrogen.

(38) The compound as any one of (1), (3) to (36) wherein R$^6$ is C1-C8 optionally substituted alkyl or optionally substituted arylalkyl.

(39) A compound of the formula II-26:

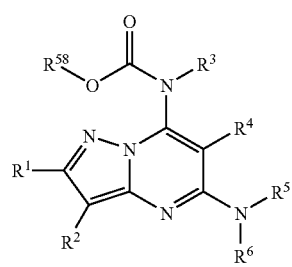

(II-26)

wherein R$^1$-R$^6$ are as defined in claim 1; R$^{58}$ is C1-C8 optionally substituted alkyl or optionally substituted arylalkyl;

with the provisos:

that R$^1$, R$^2$ and R$^4$ are not all H.

(40) A compound of the formula III-01:

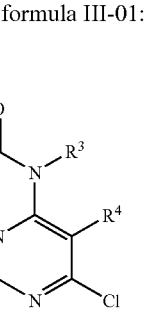

(III-01)

wherein R$^1$-R$^4$ are as defined in claim 1; R$^{58}$ is C1-C8 optionally substituted alkyl or optionally substituted arylalkyl;

with the provisos:

that R$^1$, R$^2$ and R$^4$ are not all H.

(41) A compound of the formula IV:

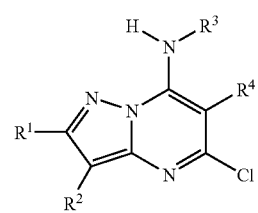

(IV)

wherein R$^1$-R$^4$ are as defined in claim 1;

with the provisos:

that R$^1$, R$^2$ and R$^4$ are not all H;

that R$^4$ is not optionally substituted aryl or optionally substituted heteroaryl.

(42) The compound as any one of (39), (40) or (41) wherein R$^1$ is hydrogen;

(43) The compound as any one of (39), (40) or (41) wherein R$^2$ is hydrogen, halogen, —CN, C1-C8 optionally substituted alkyl, C3-C8 optionally substituted cycloalkyl, —OR$^8$ (R$^8$ is hydrogen or C1-C8 optionally substituted alkyl), —NR$^9$R$^{10}$ (R$^9$ and R$^{10}$, which may be the same or different, hydrogen or C1-C8 optionally substituted alkyl), —C(=O)NR$^9$R$^{10}$ (R$^9$ and R$^{10}$, which may be the same or different, are hydrogen, C1-C8 optionally substituted alkyl, C3-C8 optionally substituted cycloalkyl, C6-C14 optionally substituted aryl or optionally substituted heterocyclyl), —NR$^9$C(=O)R$^{12}$ (R$^9$ is hydrogen or C1-C8 optionally substituted alkyl; R$^{12}$ is C1-C8 optionally substituted alkyl, C3-C8 optionally substituted cycloalkyl, C6-C14 optionally substituted aryl or optionally substituted heterocyclyl), —NR$^9$C(=O)OR$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —NR$^9$C(=O)NR$^{13}$R$^{14}$ (R$^9$ and R$^{13}$, which may be the same or different, are hydrogen or C1-C8 optionally substituted alkyl; R$^{14}$ is C1-C8 optionally substituted alkyl, C3-C8 optionally substituted cycloalkyl, C6-C14 optionally substituted aryl or optionally substituted heterocyclyl), —NR$^9$SO$_2$R$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —SR$^9$ (R$^9$ is hydrogen, C1-C8 optionally substituted alkyl, C3-C8 optionally substituted cycloalkyl, C6-C14 optionally substituted aryl or optionally substituted heterocyclyl) or —SO$_2$R$^9$ (R$^9$ is C1-C8 optionally substituted alkyl, C3-C8 optionally substituted cycloalkyl, C6-C14 optionally substituted aryl or optionally substituted heterocyclyl).

(44) The compound as any one of (39), (40) or (41) wherein R$^3$ is substituted phenyl [As substituents of phenyl may be mentioned one or more selected from the group consisting of halogen, —CN, —NO$_2$, C1-C8 optionally substituted alkyl, C2-C8 optionally substituted alkynyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl), —NR$^{17}$R$^{18}$ (R$^{17}$ and R$^{18}$, which may be the same or different, are hydrogen or C1-C8 optionally substituted alkyl) and —C(=O)NR$^{17}$R$^{18}$ (R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl)], unsubstituted bicyclic heteroaryl, substituted bicyclic heteroaryl [As substituents of bicyclic heteroaryl may be mentioned one or more selected from the group consisting of halogen, —CN, —NO$_2$, C1-C8 optionally substituted alkyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl), —NR$^{17}$R$^{18}$ (R$^{17}$ and R$^{18}$, which may be the same or different, are hydrogen or C1-C8 optionally substituted alkyl), —NHC(=O)R$^{19}$ (R$^{19}$ is C1-C8 optionally substituted alkyl, C3-C8 optionally substituted cycloalkyl, C6-C14 optionally substituted aryl or optionally substituted heterocyclyl) and —SR$^{17}$ (R$^{17}$ is C1-C8 optionally substituted alkyl)].

(45) The compound as any one of (39), (40) or (41) wherein R$^4$ is hydrogen, methyl or ethyl.

(46) The compound as (39) wherein R$^5$ is preferably selected from cyclohexyl [As substituents of cyclohexyl may be mentioned one or more selected from the group consisting of halogen, C1-C8 optionally substituted alkyl, —OH and —NH$_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —NH$_2$].

(47) The compound as (39) wherein R$^6$ is hydrogen.

(48) The compound as any one of (39), (40) or (41) wherein R$^{58}$ is tert-butyl or benzyl.

(49) The compound as (39) wherein R$^1$ is hydrogen; R$^2$ is hydrogen, —CN, —SCH$_3$, —NH$_2$, —COOH or COCF$_3$; R$^3$ is substituted phenyl (As substituents of phenyl may be mentioned one or more selected from the group consisting of halogen, —CN, —OH, —OCH$_3$, —OEt, —COOH); R$^4$ is hydrogen or —CH$_3$; R$^5$ is 4-amino-cyclohexyl or piperidin-3-yl; R$^6$ is hydrogen; R$^{58}$ is tert-butyl;

with the provisos that R$^1$, R$^2$ and R$^4$ are not all H.

(50) The compound as (40) wherein R$^1$ is hydrogen; R$^2$ is hydrogen, —CN, —SCH$_3$, —NH$_2$, —COOH or COCF$_3$; R$^3$ is substituted phenyl (As substituents of phenyl may be mentioned one or more selected from the group consisting of halogen, —CN, —OH, —OCH$_3$, —OEt, —COOH); R$^4$ is hydrogen or —CH$_3$; R$^{58}$ is tert-butyl; with the provisos that R$^1$, R$^2$ and R$^4$ are not all H

(51) The compound as (41) wherein R$^1$ is hydrogen; R$^2$ is hydrogen, —CN, —SCH$_3$, —NH$_2$, —COOH or COCF$_3$; R$^3$ is substituted phenyl (As substituents of phenyl may be mentioned one or more selected from the group consisting of halogen, —CN, —OH, —OCH$_3$, —OEt, —COOH); R$^4$ is hydrogen or —CH$_3$; with the provisos that R$^1$, R$^2$ and R$^4$ are not all H.

(52) A process for the manufacture of a compound as defined in any one of (1), (3) to (38) wherein removal of Boc protecting group from compound II.

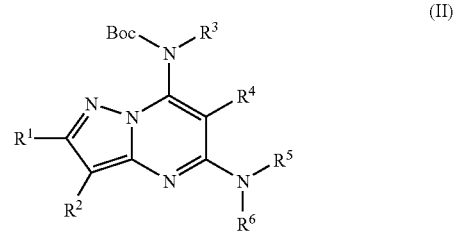

(53) A process for the manufacture of a compound as defined in any one of (1), (3) to (38) wherein compound III

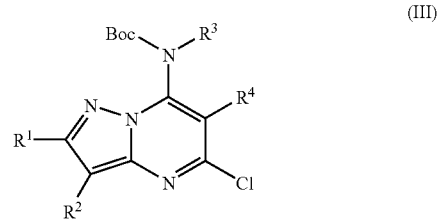

is reacted with a compound of the formula R$^5$R$^6$NH.

(54) A process for the manufacture of a compound as defined in any one of (1), (3) to (38) wherein compound IV

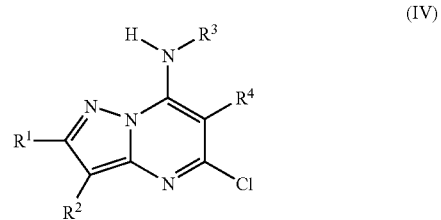

is reacted with a compound of the formula $R^5R^6NH$.

(55) A process for the manufacture of a compound as defined in any one of (1), (3) to (38) wherein compound IV

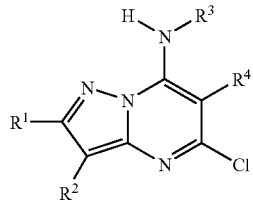
(IV)

is reacted with di-tert-butyl dicarbonate.

(56) A process for the manufacture of a compound as defined in any one of (1), (3) to (38) wherein compound V

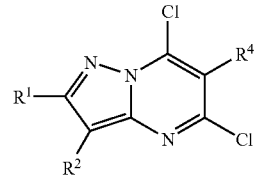
(V)

is reacted with a compound of the formula $R^3NH_2$ or $R^3NH(COCH_3)$.

(57) A process for the manufacture of a compound as defined in any one of (1), (3) to (38) wherein compound VI

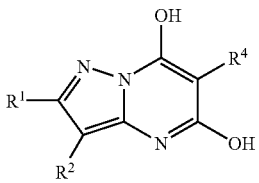
(VI)

is reacted with phosphorus oxychloride or phenyl phosphonic dichloride.

(58) A process for the manufacture of a compound as defined in any one of (1), (3) to (38) wherein compound VII

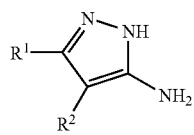
(VII)

is reacted with a compound of the formula $R^4CH(CO_2Me)_2$ or $R^4CH(CO_2Et)_2$.

(59) A process for the manufacture of a compound as defined in any one of (1), (3) to (38) wherein compound V-01

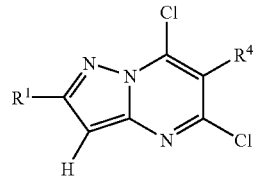
(V-01)

is reacted with a halogenating, thiocyanating or acylating agent.

(60) A process for the manufacture of a compound as defined in any one of (1), (3) to (38) wherein compound IV-01

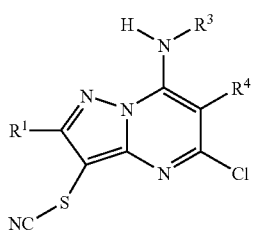
(IV-01)

is reacted with a Grignard reagent.

(61) A process for the manufacture of a compound as defined in any one of (1), (3) to (38) wherein compound II-01

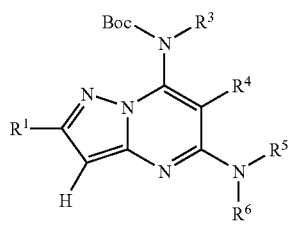
(II-01)

is reacted with a halogenating agent.

(62) A process for the manufacture of a compound as defined in any one of (1), (3) to (38) wherein compound II-01

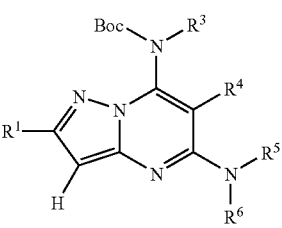
(II-01)

is reacted with a compound of the formula $(CF_3CO)_2O$.

(63) A process for the manufacture of a compound as defined in any one of (1), (3) to (38) wherein compound II-03

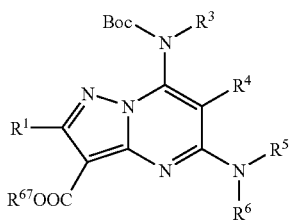

(II-03)

is reacted with hydroxide for a hydrolysis of ester group; $R^{67}$ is methyl or ethyl.

(64) A process for the manufacture of a compound as defined in any one of (1), (3) to (38) wherein compound II-04

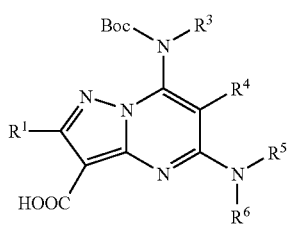

(II-04)

is reacted with a compound of the formula $R^9R^{10}$ in the presence of a peptide coupling agent.

(65) A process for the manufacture of a compound -as defined in any one of (1), (3) to (38) wherein compound II-06

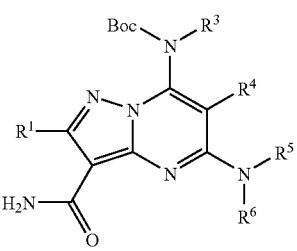

(II-06)

is rearranged via isocyanate intermediate under Hofmann rearrangement conditions, followed by removal of carbonate.

(66) A process for the manufacture of a compound as defined in any one of (1), (3) to (38) wherein compound II-08

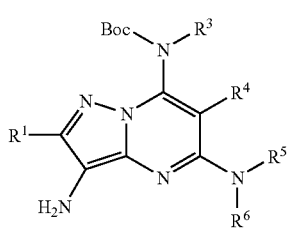

(II-08)

is reacted with a compound of the formula $R^{12}COCl$, $R^{12}COOH$, $R^{10}SO_2Cl$, $R^{10}NCO$ or $R^{10}NCS$.

(67) A process for the manufacture of a compound as defined in any one of (1), (3) to (38) wherein compound II-13

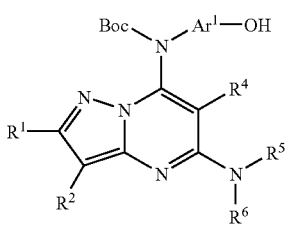

(II-13)

is condensed with an alcohol derivative under Mitsunobu conditions; $Ar^1$ represents C6-C14 optionally substituted aryl or optionally substituted heteroaryl.

(68) A process for the manufacture of a compound as defined in any one of (1), (3) to (38) wherein compound II-15

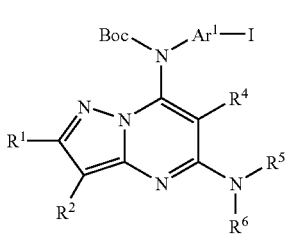

(II-15)

is reacted with a boronic acid derivative in the presence of metal catalysis under Suzuki-Miyaura coupling conditions; $Ar^1$ represents C6-C14 optionally substituted aryl or optionally substituted heteroaryl.

(69) A process for the manufacture of a compound as defined in any one of (1), (3) to (38) wherein compound II-15

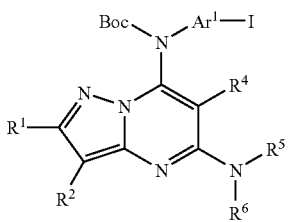

(II-15)

is reacted with a 1-alkyne in the presence of metal catalyst under Sonogashira coupling conditions; $Ar^1$ represents C6-C14 optionally substituted aryl or optionally substituted heteroaryl.

(70) A process for the manufacture of a compound as defined in any one of (1), (3) to (38) wherein compound II-18

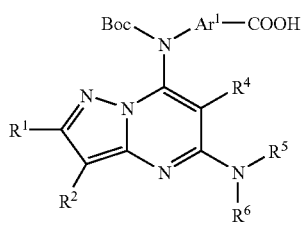
(II-18)

is reacted with a compound of the formula $R^{16}R^{17}NH$ in the presence of a peptide coupling agent; $Ar^1$ represents C6-C14 optionally substituted aryl or optionally substituted heteroaryl.

(71) A process for the manufacture of a compound as defined in any one of (1), (3) to (38) wherein compound II-20

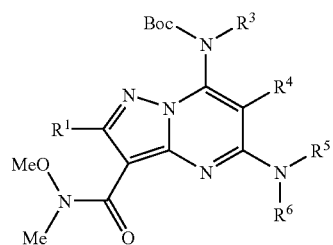
(II-20)

is reacted with an alkyl lithium reagent.

(72) A process for the manufacture of a compound as defined in any one of (1), (3) to (38) wherein compound II-22

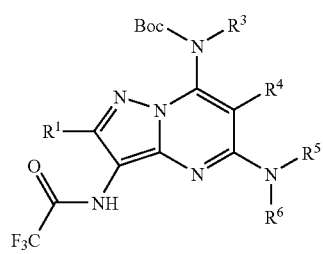
(II-22)

is reacted with alkyl halide, followed by removal of trifluoroacetyl group.

(73) A process for the manufacture of a compound as defined in any one of (1), (3) to (38) wherein compound II-08

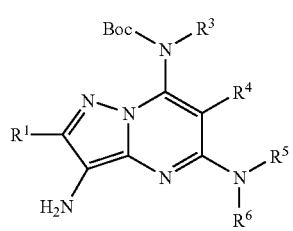
(II-08)

is reacted with an aldehyde in the presence of reducing agent.

(74) A process for the manufacture of a compound as defined in any one of (1), (3) to (38) wherein compound II-24

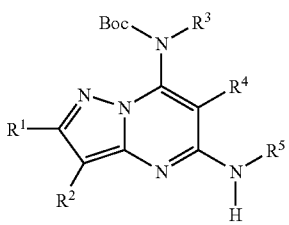
(II-24)

is reacted with alkyl halide in the presence of sodium hydride

(75) A process for the manufacture of a compound as defined in any one of (1), (3) to (38) wherein compound I-26

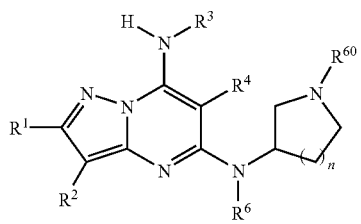
(I-26)

is reacted with hydrogen in the presence of Palladium on activated carbon or with chloroformate followed by methanol; R60 is benzyl or p-MeO-benzyl; n is 1, 2 or 3.

(76) A process for the manufacture of a compound as defined in any one of (1), (3) to (38) wherein compound V-04

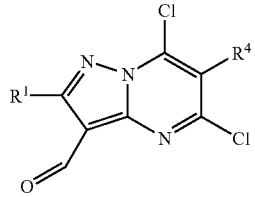
(V-04)

is reacted with reducing agent or diol derivative for formation of acetal.

(77) A composition comprising a compound as defined in any one of (1), (3) to (38) in combination with a pharmaceutically acceptable carrier, diluent or excipient.

(78) The composition as (77) further comprising one or more active agents.

(79) A process for the manufacture of a composition as defined in (77) or (78) comprising combining a compound as defined in any one of (1), (3) to (38) with the pharmaceutically acceptable carrier or diluent, optionally with an additional active agent.

(80) A compound as defined in any one of (1), (3) to (38), or a composition as defined in any one of (77) or (78), for use in medicine.

(81) A compound as defined in any one of (1), (3) to (38), or a composition as defined in any one of (77) or (78), for inhibiting protein kinase.

(82) A compound as defined in any one of (1), (3) to (38), or a composition as defined in any one of (77) or (78), for selectively inhibiting MAPKAP-K2.

(83) A compound as defined in any one of (1), (3) to (38), or a composition as defined in any one of (77) or (78), for selectively inhibiting CDK.

(84) A compound as defined in any one of (1), (3) to (38), or a composition as defined in any one of (77) or (78), for use in the prevention or treatment of a protein kinase-mediated disorder.

(85) The compound or composition as (84), wherein the disorder is a neurodegenerative/neurological disorder (including dementia), inflammatory disease, a disorder linked to apoptosis, particularly neuronal apoptosis, stroke, sepsis, autoimmune disease, destructive bone disorder, proliferative disorder, diabetes, cancer, tumour growth, infectious disease, allergy, ischemia reperfusion injury, heart attack, angiogenic disorder, organ hypoxia, vascular hyperplasia, cardiac hypertrophy and/or thrombin induced platelet aggregation.

(86) The compound or composition as (84), wherein the disorder is inflammatory disease and/or autoimmune disease.

(87) The compound or composition as (84), wherein the disorder is autoimmune disease.

(88) The compound or composition as (87), wherein the autoimmune disease is rheumatoid arthritis, systemic lupus erythematosus, glomerulonephritis, scleroderma, Sjogren's syndrome, juvenile rheumatoid arthritis, psoriatic arthritis, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

(89) The compound or composition as (87), wherein the autoimmune disease is rheumatoid arthritis, psoriasis, ankylosing spondylitis, juvenile rheumatoid arthritis, psoriatic arthritis or Crohn's disease.

(90) A method of treating or preventing a protein kinase-mediated disorder in an individual, which method comprises administering to said individual a compound as claimed in any one of (1), (3) to (38) or a composition as defined in (77) or (78).

(91) The method as (90) wherein the individual is in need of the treatment or prevention of the disorder.

(92) The method as (90) or (91) wherein the disorder is a neurodegenerative/neurological disorder (including dementia), inflammatory disease, a disorder linked to apoptosis, particularly neuronal apoptosis, stroke, sepsis, autoimmune disease, destructive bone disorder, proliferative disorder, diabetes, cancer, tumour growth, infectious disease, allergy, ischemia reperfusion injury, heart attack, angiogenic disorder, organ hypoxia, vascular hyperplasia, cardiac hypertrophy and/or thrombin induced platelet aggregation.

(93) The method as (90) or (91) wherein the disorder is autoimmune disease.

(94) The method as (93) wherein the autoimmune disease is rheumatoid arthritis, psoriasis, ankylosing spondylitis, juvenile rheumatoid arthritis, psoriatic arthritis or Crohn's disease.

(95) The method as (90) to (94) wherein one or more active agent is administered to the individual simultaneously, subsequently or sequentially to administering the compound.

(96) Use of a compound as defined in any one of (1), (3) to (38) in the manufacture of a medicament for the prevention or treatment of a protein kinase-mediated disorder.

(97) Use as (96) wherein the disorder is a neurodegenerative/neurological disorder (including dementia), inflammatory disease, a disorder linked to apoptosis, particularly neuronal apoptosis, stroke, sepsis, autoimmune disease, destructive bone disorder, proliferative disorder, diabetes, cancer, tumour growth, infectious disease, allergy, ischemia reperfusion injury, heart attack, angiogenic disorder, organ hypoxia, vascular hyperplasia, cardiac hypertrophy and/or thrombin induced platelet aggregation.

(98) Use as (96) wherein the disorder is autoimmune disease.

(99) Use as (98) wherein the autoimmune disease is rheumatoid arthritis, psoriasis, ankylosing spondylitis, juvenile rheumatoid arthritis, psoriatic arthritis or Crohn's disease.

(100) Use as (96) or (97) wherein one or more active agent is administered to the individual simultaneously, subsequently or sequentially to administering the compound.

(101) An assay for determining the activity of the compounds as defined in any one of (1), (3) to (38), comprising providing a system for assaying the activity and assaying the activity of a compound as defined in any one of (1), (3) to (38).

(102) The assay as (101) wherein the assay is for the protein kinase inhibiting activity of the compound.

(103) A method of inhibiting the activity or function of a protein kinase, which method comprises exposing a protein kinase to a compound as defined in any one of (1), (3) to (38) or a composition as defined in (77) or (78).

(104) The method as (103) which is performed in a research model, in vitro, in silico or in vivo such as in an animal model.

BRIEF DESCRIPTION OF THE DRAWINGS

FIGS. 2-8 show general reaction schemes for the preparation of compounds of Formula I.

BEST MODE FOR CARRYING OUT THE INVENTION

Figure 1:
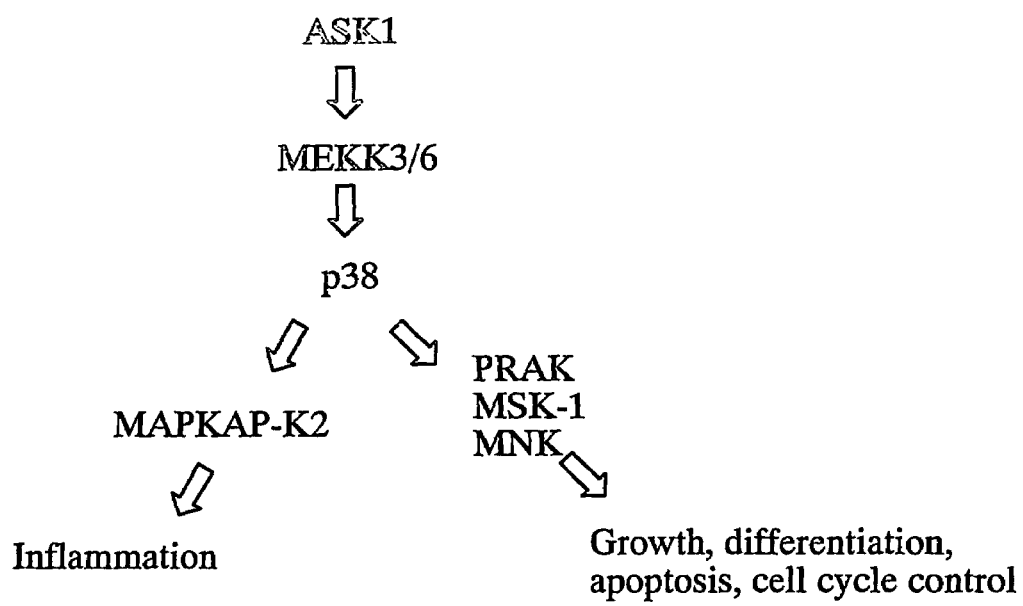
FIG. 1 shows the p38 MAPK cascade.

In a first aspect the invention provides a compound of formula I:

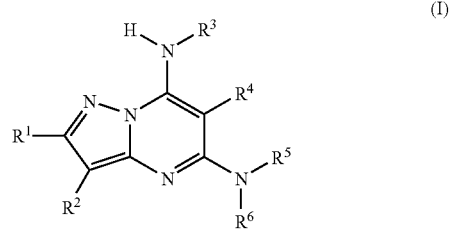

wherein $R^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^2$ is hydrogen, halogen, —CN, —NO$_2$, —CHO, -G-R$^7$ [G is a bond, —C(=O)— or —O—C(=O)—; and R$^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —$OR^8$ ($R^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —$NR^9R^{10}$ ($R^9$ is as defined for $R^8$; $R^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —$OCH_3$), —$R^{11}$ ($R^{11}$ is an optionally substituted saturated heterocyclyl with 5 to 7 members containing one to four heteroatoms selected from N, O and S), C6-C14 optionally substituted aryl or optionally substituted heteroaryl; provided that when $R^7$ is C6-C14 optionally substituted aryl or optionally substituted heteroaryl, then G is not a bond], —$NR^9C(=O)R^{12}$ ($R^9$ is as defined for $R^8$; $R^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —$NR^9C(=X)OR^{13}$ (R and $R^{13}$, which may be the same or different, are as defined for $R^8$; X is O, S, N—CN or NH), —$NR^9C(=X)NR^{13}R^{14}$ ($R^9$, $R^{13}$ and $R^{14}$, which may be the same or different, are as defined for $R^8$; X is O, S, N—CN or NH), —$NR^9SO_2R^{13}$ ($R^9$ and $R^{13}$, which may be the same or different, are as defined for $R^8$), —$SR^9$ ($R^9$ is as defined for $R^8$) or —$S(O)_mR^9$ ($R^9$ is as defined for $R^8$; m is 1 or 2);

$R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl [As substituents of C6-C14 aryl may be mentioned one or more selected from the group consisting of halogen, —CN, —$NO_2$, —CHO, -G-$R^{15}$ {G is a bond, —C(=O)— or —O—C(=O)—; $R^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —$OR^{16}$ ($R^{16}$ is as defined for $R^8$) or —$NR^{17}R^{18}$ ($R^{17}$ and $R^{18}$, which may be the same or different, are as defined for $R^8$)}, —$NR^{17}C(=O)R^{19}$ ($R^{17}$ is as defined for $R^8$; $R^{19}$ is as defined for $R^{12}$), —$NR^{17}C(=X)OR^{18}$ ($R^{17}$ and $R^{18}$, which may be the same or different, are as defined for $R^8$; X is O, S, N—CN or NH), —$NR^{17}C(=X)NR^{18}R^{20}$ ($R^{17}$, $R^{18}$ and $R^{20}$, which may be the same or different, are as defined for $R^8$; X is O, S, N—CN or NH), —$NR^{17}SO_2R^{18}$ ($R^{17}$ and $R^{18}$, which may be the same or different, are as defined for $R^8$), —$S(O)_mR^{17}$ ($R^{17}$ is as defined for $R^8$; m is 0, 1 or 2) and —$SO_2NR^{21}R^{22}$ ($R^{21}$ and $R^{22}$, which may be the same or different, are as defined for $R^8$; $R^{21}$ and $R^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)], unsubstituted heterocyclyl, substituted heterocyclyl [As substituents of heterocyclyl may be mentioned one or more selected from the group consisting of halogen, —CN, —$NO_2$, —CHO, -G-$R^{23}$ {G is a bond, —C(=O)— or —O—C(=O)—;

$R^{23}$ is as defined for $R^{15}$}, —$NR^{24}C(=O)R^{25}$ ($R^{24}$ is as defined for $R^8$; $R^{25}$ is as defined for $R^{12}$), —$NR^{24}C(=X)OR^{26}$ ($R^{24}$ and $R^{26}$, which may be the same or different, are as defined for $R^8$; X is O, S, N—CN or NH), —$NR^{24}C(=X)NR^{26}R^{27}$ ($R^{24}$, $R^{26}$ and $R^{27}$, which may be the same or different, are as defined for $R^8$; X is O, S, N—CN or NH), —$NR^{24}SO_2R^{26}$ (wherein $R^{24}$ and $R^{26}$, which may be the same or different, are as defined for $R^8$), —$S(O)_mR^{24}$ ($R^{24}$ is as defined for $R^8$; m is 0, 1 or 2) and —$SO_2NR^{28}R^{29}$ ($R^{28}$ and $R^{29}$, which may be the same or different, are as defined for $R^8$ ; $R^{28}$ and $R^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)], optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —$OR^{30}$ ($R^{30}$ is as defined for $R^8$), —$SR^{30}$ ($R^{30}$ is as defined for $R^8$), —$NR^{30}R^{31}$ ($R^{30}$ and $R^{31}$, which may be the same or different, are as defined for $R^8$), —$NR^{30}C(=O)R^{32}$ ($R^{30}$ is as defined for $R^8$;

and $R^{32}$ is as defined for $R^{12}$), —$NR^{30}C(=X)OR^{31}$ ($R^{30}$ and $R^{31}$, which may be the same or different, are as defined $R^8$; X is O, S, N—CN or NH), —$NR^{30}C(=X)NR^{31}R^{33}$ ($R^{30}$, $R^{31}$ and $R^{33}$, which may be the same or different, are as defined for $R^8$; X is O, S, N—CN or NH) or —$NR^{30}SO_2R^{31}$ ($R^{30}$ and $R^{31}$, which may be the same or different, are as defined for $R^8$);

$R^5$ is C1-C8 substituted alkyl, C2-C8 optionally substituted alkenyl, C2-C8 optionally substituted alkynyl, C3-C8 substituted cycloalkyl [As substituents of C3-C8 cycloalkyl may be mentioned one or more selected from the group consisting of halogen, —CN, —$NO_2$, —CHO, -G-$R^{34}$ {G is a bond, —C(=O)— or —O—C(=O)—; $R^{34}$ is as defined for $R^{15}$}, —$NR^{35}C(=O)R^{36}$ ($R^{35}$ is as defined for $R^8$; $R^{36}$ is as defined for $R^{12}$), —$NR^{35}C(=X)OR^{37}$ $R^{35}$ and $R^{37}$, which may be the same or different, are as defined for $R^8$; X is O, S, N—CN or NH), —$NR^{35}C(=X)NR^{37}R^{38}$ ($R^{35}$, $R^{37}$ and $R^{38}$, which may be the same or different, are as defined for $R^8$; X is O, S, N—CN or HH) and —$NR^{35}SO_2R^{37}$ ($R^{35}$ and $R^{37}$, which may be the same or different, are as defined for $R^8$)], unsubstituted heterocyclyl, substituted heterocyclyl [As substituents of heterocyclyl may be mentioned one or more selected from the group consisting of halogen, —CN, —$NO_2$, —CHO, -G-$R^{39}$ {G is a bond, —C(=O)— or —O—C(=O)—; $R^{39}$ is as defined for $R^{15}$}, —$NR^{40}C(=O)R^{41}$ ($R^{40}$ is as defined for $R^8$; $R^{41}$ is as defined for $R^{12}$), —$NR^{40}C(=X)OR^{42}$ ($R^{40}$ and $R^{42}$, which may be the same or different, are as defined for $R^8$; X is O, S, N—CN or NH), —$NR^{40}C(=X)NR^{42}R^{43}$ ($R^{40}$, $R^{42}$ and $R^{43}$, which may be the same or different, are as defined for $R^8$; X is O, S, N—CN or NH) and —$NR^{40}SO_2R^{42}$ ($R^{40}$ and $R^{42}$, which may be the same or different, are as defined for $R^8$)], optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl or —$NR^{44}R^{45}$ ($R^{44}$ and $R^{45}$, which may be the same or different, are C1-C8 optionally substituted alkyl; $R^{44}$ and $R^{45}$ together may be taken together with the nitrogen to which they are attached to form a mono heterocycle with 5-7 members and optionally containing, in addition to the nitrogen, one or two additional heteroatoms selected from N, O and S, the said mono heterocycle may optionally be substituted with one or more substituents);

$R^6$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl;

with the provisos:
that $R^1$, $R^2$ and $R^4$ are not all H;
that $R^4$ is not pentafluorophenyl;
that $R^5$ is not a group represented as the following (a):
(a) C1-C6 alkyl or C3-C6 cycloalkyl, in which an alkyl group or a cycloalkyl group optionally may be substituted by phenyl or by one or more fluoro substituents;

and pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

For the purposes of this invention, alkyl relates to both straight chain or branched alkyl radicals of 1 to 8 carbon atoms including, but not limited to, methyl, ethyl, n-propyl, isopropyl, n-butyl, sec-butyl, isobutyl, tert-butyl, n-pentyl, isopentyl, neopentyl, tert-pentyl, 2-methylpentyl, 4-methylpentyl, 1-ethylbutyl, n-hexyl, n-heptyl, 2-methylhexyl, 5-methylhexyl, 1,1-dimethylpentyl, 6-methylheptyl and n-octyl.

The term "cycloalkyl" means a cycloalkyl radical of 3 to 8 carbon atoms including but is not limited to, cyclopropyl, cyclobutyl, cyclopentyl, cyclohexyl, cycloheptyl and cyclooctyl.

The term "alkenyl" means a straight chain, branched or ring structured alkenyl radical of 2 to 8 carbon atoms and containing one or more carbon-carbon double bonds and includes, but is not limited to, vinyl, allyl, isopropenyl, 1-propenyl, 2-butenyl, 1-butenyl, 2-methyl-1-propenyl, 2-methyl-3-pentenyl, 1-pentenyl, 2-pentenyl, 4-methyl-1-pentenyl, 1-hexenyl, 2-hexenyl, 2-cyclopentenyl, 2-cyclohexenyl, 2-heptenyl, 2-octenyl, 3-cyclopentenyl, 1,3-butadienyl and 1,5-hexadienyl. When they have cis and trans geometrical isomers, both isomers are included.

The term "alkynyl" means a straight chain or branched alkynyl radical of 2 to 8 carbon atoms and containing one or more carbon-carbon triple bonds and includes, but is not limited to, ethynyl, 2-propynyl, 1-propynyl, 1-butynyl, 2-butynyl, 3-hexynyl, 3-methyl-1-butynyl, 3,3-dimethyl-1-butynyl, 3-pentynyl, 2-pentynyl, 2-hexynyl, 3-hexynyl, 4-hexynyl, 1-methyl-3-pentynyl, 1-methyl-3-hexynyl, 2-heptynyl and 2-octynyl.

"Aryl" means an aromatic 6-10 membered hydrocarbon containing one ring or being fused to one or more saturated or unsaturated rings including, but not limited to, phenyl, naphthyl, anthracenyl, 5-indanyl and 5,6,7,8-tetrahydro-2-naphthyl.

"Heteroaryl" means an aromatic 5-10 membered heterocyclic ring containing 1 to 4 heteroatoms selected from N, O or S and containing one ring or being fused to one or more saturated or unsaturated rings. Examples of heteroaryl include, but are not limited to, monovalent group including furan, thiophene, pyrrole, oxazole, isoxazole, thiazole, isothiazole, imidazole, pyrazole, triazole, thiadiazole, oxadiazole, tetrazole, pyridine, pyrazine, pyrimidine, pyridazine, benzofuran, dibenzofuran, benzothiophene, indole, benzimidazole, benzothiazole, benzoxazole, quinoline, isoquinoline, quinazoline, quinoxaline, purine, pteridine, phenoxazine and phenozine.

"Saturated heterocyclyl" means a 3-10 membered saturated ring containing 1 to 4 heteroatoms selected from N, O or S and containing one ring or being fused to one or more saturated rings; the saturated heterocyclyl is fully saturated. Examples of saturated heterocyclyl include, but are not limited to, monovalent group including piperidine, piperazine, morpholine, pyrrolidine, imidazolidine, pyrazolidine and quinuclidine.

"Heterocyclyl" means a 3-10 membered ring system containing 1 to 4 heteroatoms selected from N, O or S. The heterocyclyl system can contain one ring or may be fused to one or more saturated or unsaturated rings; the heterocyclyl can be fully saturated, partially saturated or unsaturated and includes, but is not limited to, heteroaryl and saturated heterocyclyl; the heterocyclyl can contain one or two —(C=O)— or —(C=S)— groups. Examples of heterocyclyl include, but are not limited to, monovalent group including furan, thiophene, pyrrole, pyrroline, pyrrolidine, oxazole, oxazolidine, isoxazolidine, thiazole, thiazolidine, isothiazole, isothiazolidine, imidazole, imidazoline, imidazolidine, pyrazole, pyrazoline, pyrazolidine, triazole, thiadiazole, oxadiazole, tetrazole, pyran, tetrahydropyran, thiopyran, tetrahydrothiopyran, pyridine, pyrazine, pyrimidine, pyridazine, benzofuran, dibenzofuran, benzothiophene, indole, benzimidazole, benzothiazole, benzoxazole, chromane, isochromane, quinoline, decahydroquinoline, isoquinoline, quinazoline, quinoxaline, purine, pteridine, azetidine, morpholine, thiomorpholine, piperidine, homopiperidine, piperazine, homopiperazine, indoline, isoindoline, phenoxazine, phenazine, phenothiazine, quinuclidine, acridine, carbazole, cinnoline, dioxane, dioxolane, dithiane, dithiazine, dithiazole, dithiolane, indolizine, indazole, isoindole, isoxazole, napthyridine, oxathiazole, oxathiazolidine, oxazine, oxadiazine, phthalazine, quinolizine, tetrahydrofuran, tetrazine, thiadiazine, thiatriazole, thiazine, thianaphthalene, triazine, 1,3-dioxane, 2,5-dihydrofuran, oxazoline, trithiane, piperidin-2-one, 3H-isobenzofuran-1-one, epsilon-caprolactam, 2-furanone, 2-pyrrolidone, tetrahydro-3H-pyrazol-3-one, piperazin-2-one, coumarin, tetrahydro-2-pyrimidinone, glutarimide and morpholine-3,5-dione.

"Arylalkyl" used herein is a group comprising a combination of the aryl and the alkyl. Examples thereof include, but are not limited to, benzyl, phenethyl, (2-naphthyl)-methyl, 3-phenylpropyl, 4-phenylbutyl and 5-(1-naphthyl) pentyl.

"Heterocyclylalkyl" is a group comprising a combination of the heterocyclyl and the alkyl. Examples thereof include, but are not limited to, 2-pyridylmethyl, 3-pyridylmethyl, 4-pyridylmethyl, 3-furilmethyl, 2-(3-indolyl)ethyl, 2-morpholinoethyl, 2-piperidinoethyl, 2-(4-pyridyl)-ethyl, 3-(1-piperadinyl)-propyl, 3-(2-thienyl)-propyl, and 2-(1-imidazole)ethyl.

"Arylalkenyl" is a group comprising a combination of the aryl and the alkenyl. Examples thereof include, but are not limited to, styryl, cinnamyl and 4-phenyl-2-butenyl. When they have cis and trans geometrical isomers, both isomers are included.

"Heterocyclylalkenyl" used herein is a group comprising a combination of the heterocyclyl and the alkenyl. Examples thereof include, but are not limited to, (3-pyridyl)vinyl, 3-(3-thienyl)propene-2-yl, 3-(4-morpholinyl)-1-propenyl and 4-(1-piperidyl)-2-butenyl. When they have cis and trans geometrical isomers, both isomers are included.

"Arylalkynyl" used herein is a group comprising a combination of the aryl and the alkynyl. Examples thereof include, but are not limited to, phenylethynyl and 4-phenyl-2-butynyl.

"Heterocyclylalkynyl" used herein is a group comprising a combination of the heterocyclyl and the alkynyl. Examples thereof include, but are not limited to, 4-(4pyridyl)-2-butynyl and 5-(1-piperazinyl)-2-pentynyl.

Halogen means F, Cl, Br or I.

Suitable substituents include F, Cl, Br, I, —CN, —NO$_2$, —CHO, -G-R$^{46}$ {G is a bond, —C(═O)—, or —O—C(═O)—; R$^{46}$ is optionally substituted C1-C8 alkyl, optionally substituted C2-C8 alkenyl, optionally substituted C2-C8 alkynyl, optionally substituted C3-C8 cycloalkyl, optionally substituted C6-C14 aryl, optionally substituted heterocyclyl, —OR$^{47}$ or —NR$^{47}$R$^{48}$}, —NR$^{47}$C(═O)R$^{48}$, —NR$^{47}$C(═O)OR$^{48}$, —NR$^{47}$C(═O)NR$^{48}$R$^{49}$, —NR$^{47}$SO$_2$R$^{48}$, —S(O)$_m$R$^{47}$, —NR$^{47}$SO$_2$R$^{48}$ or —SO$_2$NR$^{47}$R$^{48}$; wherein optionally substituted C1-C8 alkyl means C1-C8 alkyl which may be optionally substituted with one or more F, Cl, Br, I, —CN, —NO$_2$, —CHO, heterocyclyl, —OR$^{47}$, —NR$^{47}$R$^{48}$, —NR$^{47}$C(═O)R$^{48}$, —COOR$^{47}$, —CONR$^{47}$R$^{48}$ and —S(O)$_m$ R$^{47}$;

wherein optionally substituted C2-C8 alkenyl means C2-C8 alkenyl which may be optionally substituted with one or more F, Cl, Br, I, —CN, —NO$_2$, —CHO, heterocyclyl, —OR$^{50}$, —NR$^{50}$R$^{51}$, —NR$^{50}$C(═O)R$^{51}$, —COOR$^{50}$, —CONR$^{50}$R$^{51}$ and —S(O)$_m$R$^{50}$;

wherein optionally substituted C2-C8 alkynyl means C2-C8 alkynyl which may be optionally substituted with one or more F, Cl, Br, I, —CN, —NO$_2$, —CHO, heterocyclyl, —OR$^{50}$, —NR$^{50}$R$^{51}$, —NR$^{50}$C(═O)R$^{51}$, —COOR$^{50}$, —CONR$^{50}$R$^{51}$ and —S(O)$_m$R$^{50}$;

wherein optionally substituted C3-C8 cycloalkyl means C3-C8 cycloalkyl which may be optionally substituted with one or more F, Cl, Br, I, —CN, —NO$_2$, —CHO, heterocyclyl, —OR$^{50}$, —NR$^{50}$R$^{51}$, —NR$^{50}$C(═O)R$^{51}$, —COOR$^{50}$, —CONR$^{50}$R$^{51}$ and —S(O)$_m$R$^{50}$;

wherein optionally substituted C6-C14 aryl means C6-C14 aryl which may be optionally substituted with one or more F, Cl, Br, I, —CN, —NO$_2$, —CHO, heterocyclyl, —OR$^{50}$, —NR$^{50}$R$^{51}$, —NR$^{50}$C(═O)R$^{51}$, —COOR$^{50}$, —CONR$^{50}$R$^{51}$ and —S(O)$_m$R$^{50}$;

wherein optionally substituted heterocyclyl means heterocyclyl which may be optionally substituted with one or more F, Cl, Br, I, —CN, —NO$_2$, —CHO, heterocyclyl, —OR$^{50}$, —NR$^{50}$R$^{51}$, —NR$^{50}$C(═O)R$^{51}$, —COOR$^{50}$, —CONR$^{50}$R$^{51}$ and —S(O)$_m$R$^{50}$;

R$^{47}$, R$^{48}$, R$^{49}$, R$^{50}$ and R$^{51}$, which may be the same or different, are hydrogen, C1-C8 alkyl, C3-C8 cycloalkyl, C6-C14 aryl, heterocyclyl, arylalkyl or heterocyclylalkyl; m=0, 1 or 2.

R$^1$ is preferably hydrogen or C1-C6 optionally substituted alkyl. More preferably R$^1$ is hydrogen.

R$^2$ is preferably selected from hydrogen, halogen, —CN, C1-C8 optionally substituted alkyl, C3-C8 optionally substituted cycloalkyl, —OR$^8$ (R$^8$ is hydrogen or C1-C8 optionally substituted alkyl), —NR$^9$R$^{10}$ (R$^9$ and R$^{10}$, which may be the same or different, hydrogen or C1-C8 optionally substituted alkyl), —C(═O)NR$^9$R$^{10}$ (R$^9$ and R$^{10}$, which may be the same or different, are hydrogen, C1-C8 optionally substituted alkyl, C3-C8 optionally substituted cycloalkyl, C6-C14 optionally substituted aryl or optionally substituted heterocyclyl), —NR$^9$C(═O)R$^{12}$ (R$^9$ is hydrogen or C1-C8 optionally substituted alkyl; R$^{12}$ is C1-C8 optionally substituted alkyl, C3-C8 optionally substituted cycloalkyl, C6-C14 optionally substituted aryl or optionally substituted heterocyclyl), —NR$^9$C(═O)OR$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —NR$^9$C(═O)NR$^{13}$R$^{14}$ (R$^9$ and R$^{13}$, which may be the same or different, are hydrogen or C1-C8 optionally substituted alkyl; R$^{14}$ is C1-C8 optionally substituted alkyl, C3-C8 optionally substituted cycloalkyl, C6-C14 optionally substituted aryl or optionally substituted heterocyclyl), —NR$^9$SO$_2$R$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —SR$^9$ (R$^9$ is hydrogen, C1-C8 optionally substituted alkyl, C3-C8 optionally substituted cycloalkyl, C6-C14 optionally substituted aryl or optionally substituted heterocyclyl) or —SO$_2$R$^9$ (R$^9$ is C1-C8 optionally substituted alkyl, C3-C8 optionally substituted cycloalkyl, C6-C14 optionally substituted aryl or optionally substituted heterocyclyl).

More preferably R$^2$ is hydrogen, halogen, —CN or —SCH$_3$. Still more preferably R$^2$ is hydrogen;

R$^3$ is preferably selected from C6-C14 substituted aryl [As substituents of C6-C14 aryl may be mentioned one or more selected from the group consisting of halogen, —CN, —NO$_2$, -G-R$^{15}$ {G is a bond or —C(═O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl) or —NR$^{17}$R$^{18}$ (R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl)}, —NR$^{17}$C(═O)R$^{19}$ (R$^{17}$ is hydrogen or C1-C8 optionally substituted alkyl; R$^{19}$ is C1-C8 optionally substituted alkyl, C3-C8 optionally substituted cycloalkyl, C6-C14 optionally substituted aryl or optionally substituted heterocyclyl) and —S(O)$_m$ R$^{17}$ (R$^{17}$ is C1-C8 optionally substituted alkyl, C3-C8 optionally substituted cycloalkyl; m is 0 or 2)], unsubstituted heterocyclyl, substituted heterocyclyl [As substituents of heterocyclyl may be mentioned one or more selected from the group consisting of halogen, —CN, —NO$_2$, -G-R$^{23}$ {G is a bond or —C(═O)—; R$^{23}$ is C1-C8 optionally substituted alkyl, C3-C8 optionally substituted cycloalkyl, C6-C14 optionally substituted aryl, optionally substituted heterocyclyl, —OR$^{16}$ (R$^{16}$ is hydrogen, C1-C8 optionally substituted alkyl, C3-C8 optionally substituted cycloalkyl, C6-C14 optionally substituted aryl or optionally substituted heterocyclyl) or —NR$^{17}$R$^{18}$ (R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl)}, —NR$^{24}$C(═O)R$^{25}$ (R$^{24}$ is hydrogen or C1-C8 optionally substituted alkyl; R$^{25}$ is C1-C8 optionally substituted alkyl, C3-C8 optionally substituted cycloalkyl, C6-C14 optionally substituted aryl or optionally substituted heterocyclyl) and —S(O)$_m$R$^{24}$ (R$^{24}$ is C1-C8 optionally substituted alkyl or C3-C8 optionally substituted cycloalkyl; m is 0 or 2)].

More preferably R$^3$ is substituted phenyl [As substituents of phenyl may be mentioned one or more selected from the group consisting of halogen, —CN, —NO$_2$, C1-C8 optionally substituted alkyl, C2-C8 optionally substituted alkynyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl), —NR$^{17}$R$^{18}$ (R$^{17}$ and R$^{18}$, which may be the same or different, are hydrogen or C1-C8 optionally substituted alkyl) and —C(=O)NR$^{17}$R$^{18}$ (R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl)], unsubstituted bicyclic heteroaryl, substituted bicyclic heteroaryl [As substituents of bicyclic heteroaryl may be mentioned one or more selected from the group consisting of halogen, —CN, —NO$_2$, C1-C8 optionally substituted alkyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl), —NR$^{17}$R$^{18}$ (R$^{17}$ and R$^{18}$, which may be the same or different, are hydrogen or C1-C8 optionally substituted alkyl), —NHC(=O)R$^{19}$ (R$^{19}$ is C1-C8 optionally substituted alkyl, C3-C8 optionally substituted cycloalkyl, C6-C14 optionally substituted aryl or optionally substituted heterocyclyl) and —SR$^{17}$ (R$^{17}$ is C1-C8 optionally substituted alkyl)].

R$^4$ is preferably selected from hydrogen, C1-C8 optionally substituted alkyl, C3-C8 optionally substituted cycloalkyl, optionally substituted aryl. More preferably R$^4$ is hydrogen, methyl or ethyl.

R$^5$ is preferably selected from C3-C8 substituted cycloalkyl [As substituents of C3-C8 cycloalkyl may be mentioned one or more selected from the group consisting of halogen, —CN, C1-C8 optionally substituted alkyl, —OR$^{30}$ (R$^{30}$ is hydrogen or C1-C8 optionally substituted alkyl), —NR$^{30}$R$^{31}$ (R$^{30}$ and R$^{31}$, which may be the same or different, are hydrogen or C1-C8 optionally substituted alkyl) and —NHC(=O)R$^{32}$ (R$^{32}$ is C1-C8 optionally substituted alkyl, C3-C8 substituted cycloalkyl, C6-C14 optionally substituted aryl or optionally substituted heterocyclyl)], unsubstituted heterocyclyl, substituted heterocyclyl [As substituents of heterocyclyl may be mentioned one or more selected from the group consisting of halogen, —CN, C1-C8 optionally substituted alkyl, —OR$^{16}$ (R$^{16}$ is hydrogen or C1-C8 optionally substituted alkyl), —NR$^{17}$R$^{18}$ (R$^{17}$ and R$^{18}$, which may be the same or different, are hydrogen or C1-C8 optionally substituted alkyl) and —NHC(=O)R$^{41}$ (R$^{41}$ is C1-C8 optionally substituted alkyl, C3-C8 substituted cycloalkyl, C6-C14 optionally substituted aryl or optionally substituted heterocyclyl)].

More preferably R$^5$ is preferably selected from cyclohexyl [As substituents of cyclohexyl may be mentioned one or more selected from the group consisting of halogen, C1-C8 optionally substituted alkyl —OH and —NH$_2$], unsubstituted saturated heterocyclyl or substituted saturated heterocyclyl [As substituents of heterocyclyl may be mentioned one or more selected from the group consisting of halogen, C1-C8 optionally substituted alkyl —OH and —NH$_2$].

Still more preferably R$^5$ is 4-amino-cyclohexyl, piperidin-3-yl, piperidin-4-yl or pyrrolidin-3-yl.

R$^6$ is preferably selected from hydrogen and C1-C8 optionally substituted alkyl. More preferably R$^6$ is hydrogen.

As preferred combinations of the groups mentioned as preferred examples of R$^1$-R$^6$ in formula I according to the invention, there may be mentioned the following combinations 1) to 10).

1) In formula I, wherein R$^1$ is hydrogen, R$^2$ is hydrogen, R$^3$ is C6-C14 aryl group substituted by C6-C14 optionally substituted aryl or optionally substituted heterocyclyl [wherein C6-C14 aryl group as R$^3$ may be substituted by one or more substituents selected from the group consisting of halogen, —CN, —NO$_2$, C1-C8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned one or more selected from the group consisting of halogen, C1-C8 optionally substituted alkyl, —OH and —NH$_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —NH$_2$] and R6 is hydrogen.

2) In formula I, wherein R$^1$ is hydrogen, R$^2$ is hydrogen, R$^3$ is C6-C14 aryl group substituted by —OR$^{16}$ (R$^{16}$ is C1-C8 optionally substituted alkyl, optionally substituted arylalkyl or optionally substituted heterocyclylalkyl) [wherein C6-C14 aryl group as R$^3$ may be substituted by one or more substituents selected from the group consisting of halogen, —CN, —NO$_2$, C1-C8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned one or more selected from the group consisting of halogen, C1-C8 optionally substituted alkyl, —OH and —NH$_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —NH$_2$] and R6 is hydrogen.

3) In formula I, wherein R$^1$ is hydrogen, R$^2$ is hydrogen, R$^3$ is C6-C14 aryl group substituted by -G-R$^{15}$ {G is —(CO)—; R$^{15}$ is C1-C8 optionally substituted alkyl, C3-C8 optionally substituted cycloalkyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl) or —NR$^{17}$R$^{18}$ (R$^{17}$ and R$^{18}$, which may be the same or different, are hydrogen, C1-C8 optionally substituted alkyl, C3-C8 optionally substituted cycloalkyl, C6-C14 optionally substituted aryl or optionally substituted heterocyclyl)} [wherein C6-C14 aryl group as R$^3$ may be substituted by one or more substituents selected from the group consisting of halogen, —CN, —NO$_2$, C1-C8 optionally substituted alkyl, —OR$^{16}$ (R$^{16}$ is hydrogen, C1-C8 optionally substituted alkyl), —NR$^{17}$R$^{18}$ (R$^{17}$ and R$^{18}$, which may be the same or different, are hydrogen or C1-C8 optionally substituted alkyl)], R$^4$ is C1-C8 optionally substituted alkyl, R$^5$ is cyclohexyl [As substituents of cyclohexyl may be mentioned one or more selected from the group consisting of halogen, C1-C8 optionally substituted alkyl, —OH and —NH$_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —NH$_2$] and R6 is hydrogen.

4) In formula I, wherein R$^1$ is hydrogen, R$^2$ is hydrogen, R$^3$ is unsubstituted bicyclic heteroaryl or substituted bicyclic heteroaryl [As substituents of bicyclic heteroaryl may be mentioned one or more selected from the group consisting of halogen, —CN, —NO$_2$, C1-C8 optionally substituted allyl, C6-C14 optionally substituted aryl, optionally substituted heterocyclyl, —OR$^{16}$ (R$^{16}$ is hydrogen, C1-C8 optionally substituted alkyl, optionally substituted arylalkyl or optionally substituted heterocyclylalkyl), —NR$^{17}$R$^{18}$ (R$^{17}$ and R$^{18}$, which may be the same or different, are hydrogen or C1-C8 optionally substituted alkyl), —NH(CO)R$^{19}$ (R$^{19}$ is C1-C8 optionally substituted alkyl, C3-C8 optionally substituted cycloalkyl, C6-C14 optionally substituted aryl or optionally substituted heterocyclyl) and —$SR^{17}$ ($R^{17}$ is C1-C8 optionally substituted alkyl)], $R^4$ is C1-C8 optionally substituted alkyl, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

5) In formula I, wherein $R^1$ is hydrogen, $R^2$ is F, $R^3$ is C6-C14 aryl group substituted by C6-C14 optionally substituted aryl or optionally substituted heterocyclyl [wherein C6-C14 aryl group as $R^3$ may be substituted by one or more substituents selected from the group consisting of halogen, —CN, —$NO_2$, C1-C8 optionally substituted alkyl, —$OR^{16}$ ($R^{16}$ is hydrogen, C1-C8 optionally substituted alkyl), —$NR^{17}R^{18}$ ($R^{17}$ and $R^{18}$, which may be the same or different, are hydrogen or C1-C8 optionally substituted alkyl)], $R^4$ is hydrogen, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

6) In formula I, wherein $R^1$ is hydrogen, $R^2$ is F, $R^3$ is C6-C14 aryl group substituted by —$OR^{16}$ ($R^{16}$ is C1-C8 optionally substituted alkyl, optionally substituted arylalkyl or optionally substituted heterocyclylalkyl) [wherein C6-C14 aryl group as $R^3$ may be substituted by one or more substituents selected from the group consisting of halogen, —CN, —$NO_2$, C1-C8 optionally substituted alkyl, —$OR^{16}$ ($R^{16}$ is hydrogen, C1-C8 optionally substituted alkyl), —$NR^{17}R^{18}$ ($R^{17}$ and $R^{18}$, which may be the same or different, are hydrogen or C1-C8 optionally substituted alkyl)], $R^4$ is hydrogen, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

7) In formula I, wherein $R^1$ is hydrogen, $R^2$ is F, $R^3$ is C6-C14 aryl group substituted by -G-$R^{15}$ {G is —(CO)—; $R^{15}$ is C1-C8 optionally substituted alkyl, C3-C8 optionally substituted cycloalkyl, C6-C14 optionally substituted aryl, optionally substituted heterocyclyl, —$OR^{16}$ ($R^{16}$ is hydrogen, C1-C8 optionally substituted alkyl, optionally substituted arylalkyl or optionally substituted heterocyclylalkyl) or —$NR^{17}R^{18}$ ($R^{17}$ and $R^{18}$, which may be the same or different, are hydrogen, C1-C8 optionally substituted alkyl, C3-C8 optionally substituted cycloalkyl, C6-C14 optionally substituted aryl or optionally substituted heterocyclyl)} [wherein C6-C14 aryl group as $R^3$ may be substituted by one or more substituents selected from the group consisting of halogen, —CN, —$NO_2$, C1-C8 optionally substituted alkyl, —$OR^{16}$ ($R^{16}$ is hydrogen, C1-C8 optionally substituted alkyl), —$NR^{17}R^{18}$ ($R^{17}$ and $R^{18}$, which may be the same or different, are hydrogen or C1-C8 optionally substituted alkyl)], $R^4$ is hydrogen, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

8) In formula I wherein $R^1$ is hydrogen, $R^2$ is F, $R^3$ is unsubstituted bicyclic heteroaryl or substituted bicyclic heteroaryl [As substituents of bicyclic heteroaryl may be mentioned one or more selected from the group consisting of halogen, —CN, —$NO_2$, C1-C8 optionally substituted alkyl, C6-C14 optionally substituted aryl, optionally substituted heterocyclyl, —$OR^{16}$ ($R^{16}$ is hydrogen, C1-C8 optionally substituted alkyl, optionally substituted arylalkyl or optionally substituted heterocyclylalkyl), —$NR^{17}R^{18}$ ($R^{17}$ and $R^{18}$, which may be the same or different, are hydrogen or C1-C8 optionally substituted alkyl), —NH(CO)$R^{19}$ ($R^{19}$ is C1-C8 optionally substituted alkyl, C3-C8 optionally substituted cycloalkyl, C6-C14 optionally substituted aryl or optionally substituted heterocyclyl) and —$SR^{17}$ ($R^{17}$ is C1-C8 optionally substituted alkyl)], $R^4$ is hydrogen, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

9) In formula I, wherein $R^1$ is hydrogen, $R^2$ is halogen, —CN or —$SCH_3$, $R^3$ is C6-C14 optionally substituted aryl, optionally substituted bicyclic heteroaryl, $R^4$ is hydrogen, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

10) In formula I, wherein $R^1$ is hydrogen, $R^2$ is halogen or —CN, $R^3$ is C6-C14 optionally substituted aryl, optionally substituted bicyclic heteroaryl, $R^4$ is C1-C8 optionally substituted alkyl, $R^5$ is cyclohexyl [As substituents of cyclohexyl may be mentioned one or more selected from the group consisting of halogen, C1-C8 optionally substituted alkyl, —OH and —$NH_2$], unsubstituted saturated heterocyclyl or substituted saturated heterocyclyl [As substituents of heterocyclyl may be mentioned one or more selected from the group consisting of halogen, C1-C8 optionally substituted alkyl, —OH and —$NH_2$] and R6 is hydrogen.

The compounds of the first aspect may be provided as a salt, preferably as a pharmaceutically acceptable salt of the compounds of formula I. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid, trifluoroacetic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are non-toxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms. The compounds of the invention may exist in trans or cis form. The first aspect of the invention covers all of these compounds.

As specific examples of compounds of the formula I above there may be mentioned compounds listed in Table A below.

Wherein "Me", "Et", "n-Pr", "i-Pr", "n-Bu", "t-Bu" and "Ph" mean "methyl group", "ethyl group", "n-propyl group", "isopropyl group"; "n-butyl group", "tert-butyl group" and "phenyl group" respectively.

TABLE A
| Compound No. | R¹ | R² | R⁴ | R³ | NR⁵R⁶ |
|---|---|---|---|---|---|
| 1 | H | CN | H | 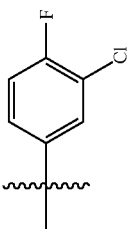 | 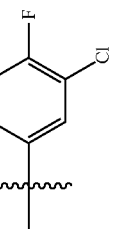 |
| 2 | H | Br | H | 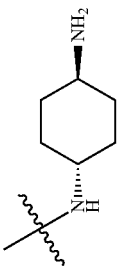 | 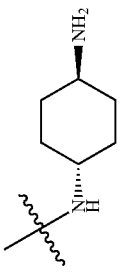 |
| 3 | Me | H | H | 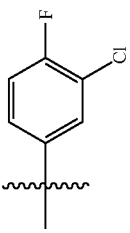 | 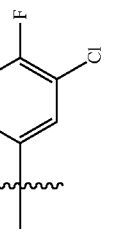 |
| 4 | t-Bu | H | H | 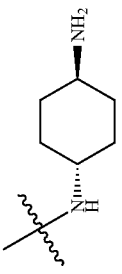 | 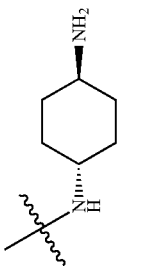 |
| 5 | Ph | H | H | 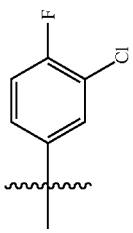 | 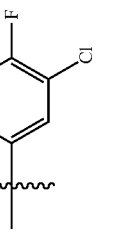 |
| 6 | Me | Br | H | 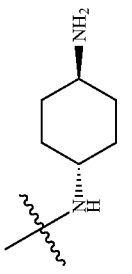 | 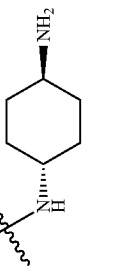 |

TABLE A-continued

| Compound No. | R¹ | R² | R⁴ | R³ | NR⁵R⁶ |
|---|---|---|---|---|---|
| 7 | H | Cl | H | 4-fluoro-3-chlorophenyl | trans-4-aminocyclohexylamino |
| 8 | t-Bu | Br | H | 4-fluoro-3-chlorophenyl | trans-4-aminocyclohexylamino |
| 9 | H | COOEt | H | 4-fluoro-3-chlorophenyl | trans-4-aminocyclohexylamino |
| 10 | H | H | Me | 4-fluoro-3-chlorophenyl | trans-4-aminocyclohexylamino |
| 11 | H | H | n-Pr | 4-fluoro-3-chlorophenyl | trans-4-aminocyclohexylamino |
| 12 | H | H | Ph | 4-fluoro-3-chlorophenyl | trans-4-aminocyclohexylamino |
| 13 | H | Br | H | (4-fluoro-3-chlorobenzyl) | trans-4-aminocyclohexylamino |

TABLE A-continued

| Compound No. | R¹ | R² | R⁴ | R³ | NR⁵R⁶ |
|---|---|---|---|---|---|
| 14 | H | Br | n-Pr | 3-Cl-4-F-phenyl | trans-4-aminocyclohexylamino |
| 15 | H | H | Me | 2-Cl-phenyl | trans-4-aminocyclohexylamino |
| 16 | H | H | Et | 2-Cl-phenyl | trans-4-aminocyclohexylamino |
| 17 | H | H | but-3-en-1-yl (with Me) | 2-Cl-phenyl | trans-4-aminocyclohexylamino |
| 18 | H | Br | Me | 3-Cl-4-F-phenyl | trans-4-aminocyclohexylamino |
| 19 | H | H | but-3-en-1-yl (with Me) | 3-Cl-4-F-phenyl | trans-4-aminocyclohexylamino |

TABLE A-continued

| Compound No. | R¹ | R² | R⁴ | R³ | NR⁵R⁶ |
|---|---|---|---|---|---|
| 20 | H | Br | Me | 2-Cl-phenyl | trans-4-aminocyclohexyl-NH- |
| 21 | H | H | Ph | Me | trans-4-aminocyclohexyl-NH- |
| 22 | H | H | benzyl | 2-Cl-phenyl | trans-4-aminocyclohexyl-NH- |
| 23 | H | H | Et | 3-Cl-4-F-phenyl | trans-4-aminocyclohexyl-NH- |
| 24 | H | H | benzyl | 3-Cl-4-F-phenyl | trans-4-aminocyclohexyl-NH- |
| 25 | H | H | Et | 2-F-phenyl | trans-4-aminocyclohexyl-NH- |
| 26 | H | H | Et | 4-Cl-phenyl | trans-4-aminocyclohexyl-NH- |

TABLE A-continued

| Compound No. | R¹ | R² | R⁴ | R³ | NR⁵R⁶ |
|---|---|---|---|---|---|
| 27 | H | H | Et | 3-MeO-phenyl | trans-4-aminocyclohexylamino |
| 28 | H | H | Et | 4-MeO-phenyl | trans-4-aminocyclohexylamino |
| 29 | H | H | Et | 2-Me-phenyl | trans-4-aminocyclohexylamino |
| 30 | H | H | Et | 3,4-diMe-phenyl | trans-4-aminocyclohexylamino |
| 31 | H | H | Et | 4-EtO-phenyl | trans-4-aminocyclohexylamino |
| 32 | H | H | Me | 4-EtO-phenyl | trans-4-aminocyclohexylamino |
| 33 | H | H | Et | 4-phenoxy-phenyl | trans-4-aminocyclohexylamino |

TABLE A-continued

| Compound No. | R¹ | R² | R³ | R⁴ | NR⁵R⁶ |
|---|---|---|---|---|---|
| 34 | H | H | 3-(NMe₂)-phenyl | Et | trans-4-aminocyclohexylamino |
| 35 | H | H | 4-(benzyloxy)phenyl | Et | trans-4-aminocyclohexylamino |
| 36 | H | H | 4-(SMe)phenyl | Et | trans-4-aminocyclohexylamino |
| 37 | H | H | 3-chlorophenyl | Et | trans-4-aminocyclohexylamino |
| 38 | H | H | 2-chlorobenzyl | Et | trans-4-aminocyclohexylamino |
| 39 | H | H | 2-phenylethyl | Et | trans-4-aminocyclohexylamino |

TABLE A-continued

| Compound No. | R¹ | R² | R⁴ | R³ | NR⁵R⁶ |
|---|---|---|---|---|---|
| 40 | H | H | Et | 4-F, 3-Cl benzyl (quaternary C with methyl) | trans-4-aminocyclohexyl-NH- |
| 41 | H | H | Et | 2-methylbut-3-en-2-yl (allyl dimethyl) | trans-4-aminocyclohexyl-NH- |
| 42 | H | H | Et | 2-MeO-phenyl (α-methyl) | trans-4-aminocyclohexyl-NH- |
| 43 | H | H | Et | 4-F, 3-Cl benzyl (α-methyl) | piperidin-3-yl-NH- |
| 44 | H | H | Et | 4-F, 3-Cl benzyl (α-methyl) | piperidin-4-yl-NH- |
| 45 | H | H | Et | 2-Cl-phenyl (α-methyl) | piperidin-4-yl-NH- |
| 46 | H | H | Et | 2-methylbut-3-en-2-yl | trans-4-aminocyclohexyl-NH- |

TABLE A-continued

| Compound No. | R¹ | R² | R⁴ | R³ | NR⁵R⁶ |
|---|---|---|---|---|---|
| 47 | H | I | H | 2-Cl-phenyl | trans-4-aminocyclohexyl-NH- |
| 48 | H | I | H | 4-OEt-phenyl | trans-4-aminocyclohexyl-NH- |
| 49 | H | I | H | 3-Cl-4-F-phenyl | trans-4-aminocyclohexyl-NH- |
| 50 | H | Br | H | 3-Cl-4-F-phenyl | 3-aminopiperidinyl |
| 51 | H | H | 4-hydroxybutyl | 4-OMe-phenyl | trans-4-aminocyclohexyl-NH- |
| 52 | H | H | 4-hydroxybutyl | 3,4-di-OMe-phenyl | trans-4-aminocyclohexyl-NH- |
| 53 | H | H | 4-hydroxybutyl | 4-(pentyloxy)phenyl | trans-4-aminocyclohexyl-NH- |

TABLE A-continued

| Compound No. | R¹ | R² | R³ | R⁴ | NR⁵R⁶ |
|---|---|---|---|---|---|
| 54 | H | H | 3,4,5-tri(OMe)phenyl | Et | trans-4-aminocyclohexylamino |
| 55 | H | H | 3-Cl-4-OMe-phenyl | Et | trans-4-aminocyclohexylamino |
| 56 | H | H | 4-(4-methylbutoxy)phenyl | Et | trans-4-aminocyclohexylamino |
| 57 | H | H | 4-(4-methylphenoxy)phenyl | Et | trans-4-aminocyclohexylamino |
| 58 | H | H | 3,4-di(OMe)phenyl | Et | trans-4-aminocyclohexylamino |
| 59 | H | H | 3-Br-phenyl | Et | trans-4-aminocyclohexylamino |

TABLE A-continued

| Compound No. | R¹ | R² | R⁴ | R³ | NR⁵R⁶ |
|---|---|---|---|---|---|
| 60 | H | H | Et | 3-iodophenyl | trans-4-aminocyclohexyl |
| 61 | H | H | Et | 3-ethoxyphenyl | trans-4-aminocyclohexyl |
| 62 | H | H | Et | 3,4-dimethoxyphenyl | piperidin-3-yl |
| 63 | H | H | Et | 4-(4-methylphenoxy)phenyl | piperidin-3-yl |
| 64 | H | CN | H | 4-ethoxyphenyl | trans-4-aminocyclohexyl |
| 65 | H | H | Me | 4-(methylthio)phenyl | trans-4-aminocyclohexyl |
| 66 | H | H | Me | 3-(N,N-dimethylaminocarbonylmethoxy)phenyl | trans-4-aminocyclohexyl |

TABLE A-continued
| Compound No. | R¹ | R² | R³ | R⁴ | NR⁵R⁶ |
|---|---|---|---|---|---|
| 67 | H | H | 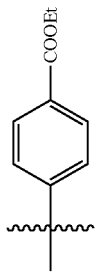 | Me | 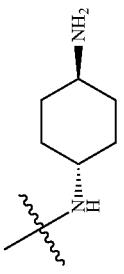 |
| 68 | H | H | 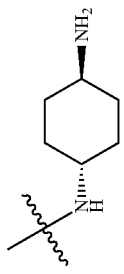 | Me | 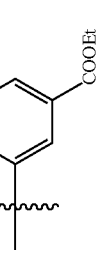 |
| 69 | H | H | 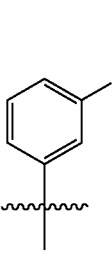 | Et | 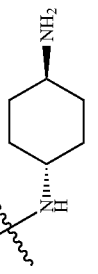 |
| 70 | H | H | 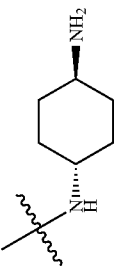 | Et | 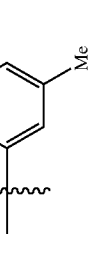 |
| 71 | H | H | 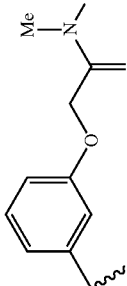 | Et | 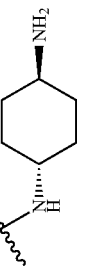 |
| 72 | H | H | 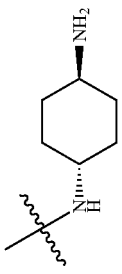 | Et | 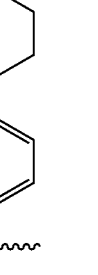 |
| 73 | H | H | 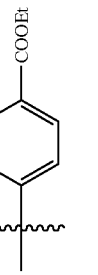 | Et | 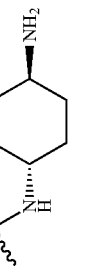 |

TABLE A-continued
| Compound No. | R¹ | R² | R³ | R⁴ | NR⁵R⁶ |
|---|---|---|---|---|---|
| 74 | H | H | 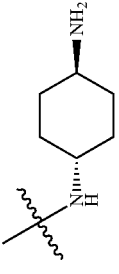 | Et | 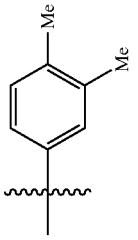 |
| 75 | H | H | 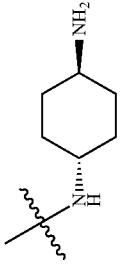 | Et | 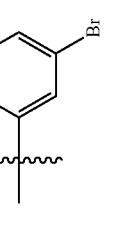 |
| 76 | H | H | 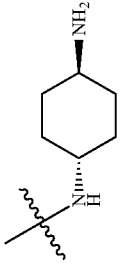 | Me | 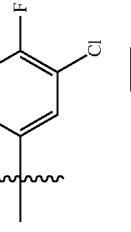 |
| 77 | H | H | 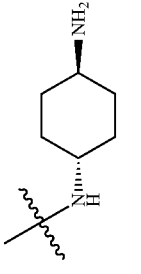 | Me | 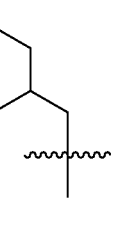 |
| 78 | H | SMe | 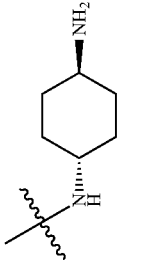 | H |  |
| 79 | H | H | 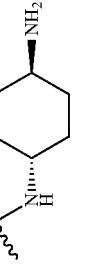 | Me |  |

TABLE A-continued

| Compound No. | R¹ | R² | R⁴ | R³ | NR⁵R⁶ |
|---|---|---|---|---|---|
| 80 | H | H | Me | 2-F-phenyl | trans-4-aminocyclohexyl-NH- |
| 81 | H | H | Me | 3-OEt-phenyl | trans-4-aminocyclohexyl-NH- |
| 82 | H | H | Me | 4-NH₂-benzyl | trans-4-aminocyclohexyl-NH- |
| 83 | H | H | Me | 3-I-phenyl | trans-4-aminocyclohexyl-NH- |
| 84 | H | H | Me | 4-CF₃-phenyl | trans-4-aminocyclohexyl-NH- |
| 85 | H | H | Me | 3-Cl-phenyl | trans-4-aminocyclohexyl-NH- |
| 86 | H | H | Me | neopentyl (CMe₃-CH₂-) | trans-4-aminocyclohexyl-NH- |

TABLE A-continued
| Compound No. | R¹ | R² | R⁴ | R³ | NR⁵R⁶ |
|---|---|---|---|---|---|
| 87 | H | H | Me |  |  |
| 88 | H | H | Me |  |  |
| 89 | H | H | Me |  |  |
| 90 | H | H | Me | 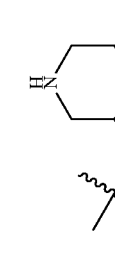 | 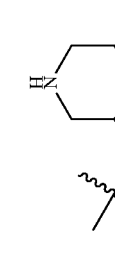 |
| 91 | H | H | Me |  |  |
| 92 | H |  | Me |  |  |
| 93 | H | H | Et |  |  |

TABLE A-continued

| Compound No. | R¹ | R² | R⁴ | R³ | NR⁵R⁶ |
|---|---|---|---|---|---|
| 94 | H | 2-(1,3-dioxan-2-yl) | Me | 4-ethoxyphenyl | trans-4-aminocyclohexylamino |
| 95 | H | H | Me | 4-(hydroxymethyl)phenyl | trans-4-aminocyclohexylamino |
| 96 | H | H | Me | 4-(aminomethyl)phenyl | trans-4-aminocyclohexylamino |
| 97 | H | H | Me | 3-(hydroxymethyl)phenyl | trans-4-aminocyclohexylamino |
| 98 | H | H | Me | 1H-indazol-5-yl | trans-4-aminocyclohexylamino |
| 99 | H | H | Me | 4-(4-methylpiperazin-1-yl)butyl | trans-4-aminocyclohexylamino |
| 100 | H | H | Me | t-Bu | trans-4-aminocyclohexylamino |

TABLE A-continued
| Compound No. | R¹ | R² | R⁴ | R³ | NR⁵R⁶ |
|---|---|---|---|---|---|
| 101 | H | H | Me | 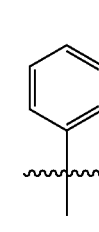 | 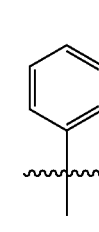 |
| 102 | H | H | Me | Ph | 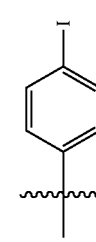 |
| 103 | H | H | Me | 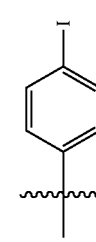 | 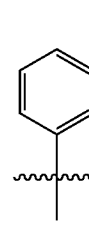 |
| 104 | H | H | Me | 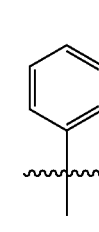 | 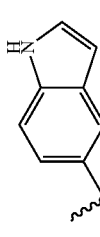 |
| 105 | H | H | Me | 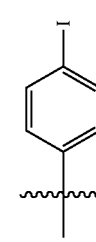 |  |
| 106 | H | H | Me | 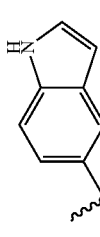 | 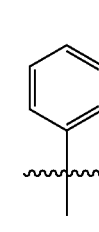 |
| 107 | H | H | Me |  | 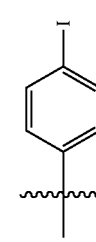 |

TABLE A-continued

| Compound No. | R¹ | R² | R⁴ | R³ | NR⁵R⁶ |
|---|---|---|---|---|---|
| 108 | H | H | Me | CH₂CH₂-morpholine (4-N-morpholinyl ethyl via gem-dimethyl carbon) | trans-4-aminocyclohexyl-NH- |
| 109 | H | H | Me | CH₂CH₂CH₂-morpholine (4-N-morpholinyl propyl via gem-dimethyl carbon) | trans-4-aminocyclohexyl-NH- |
| 110 | H | H | Me | CH₂CH₂-OMe | trans-4-aminocyclohexyl-NH- |
| 111 | H | H | Me | 2-methylbenzothiazol-5-yl | trans-4-aminocyclohexyl-NH- |
| 112 | H | H | Me | benzothiazol-6-yl | trans-4-aminocyclohexyl-NH- |
| 113 | H | H | Et | 4-OMe-3-CF₃-phenyl | trans-4-aminocyclohexyl-NH- |
| 114 | H | H | i-Pr | 4-OEt-phenyl | trans-4-aminocyclohexyl-NH- |

TABLE A-continued

| Compound No. | R¹ | R² | R⁴ | R³ | NR⁵R⁶ |
|---|---|---|---|---|---|
| 115 | H | H | i-Pr | 3-Cl,4-F-phenyl | trans-4-aminocyclohexyl-NH- |
| 116 | H | H | Et | 4-(piperidin-1-yl)phenyl | trans-4-aminocyclohexyl-NH- |
| 117 | H | H | Et | 4-(morpholin-4-yl)phenyl | trans-4-aminocyclohexyl-NH- |
| 118 | H | H | Me | 4-(imidazol-1-yl)phenyl | trans-4-aminocyclohexyl-NH- |
| 119 | H | H | Me | pyridin-2-yl | trans-4-aminocyclohexyl-NH- |

TABLE A-continued
| Compound No. | R¹ | R² | R⁴ | R³ | NR⁵R⁶ |
|---|---|---|---|---|---|
| 120 | H | H | Me | Ph | 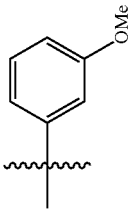 |
| 121 | H | H | Me | 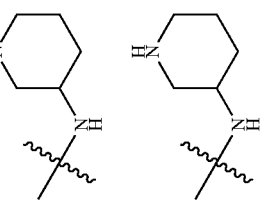 3-OMe-C₆H₄ | 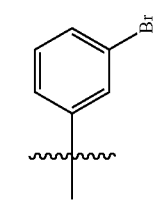 |
| 122 | H | H | Me | 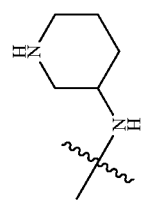 3-Br-C₆H₄ | 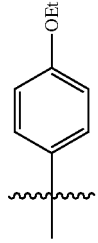 |
| 123 | H | H | Me |  4-OEt-C₆H₄ | 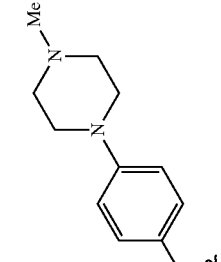 |
| 124 | H | H | Et | 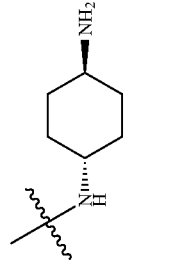 4-(4-Me-piperazin-1-yl)-C₆H₄ | 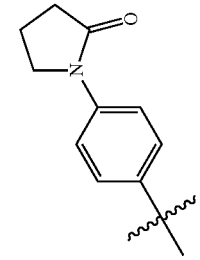 trans-4-aminocyclohexyl |
| 125 | H | H | Et | 4-(2-oxopyrrolidin-1-yl)-C₆H₄ | trans-4-aminocyclohexyl |

TABLE A-continued
| Compound No. | R¹ | R² | R⁴ | R³ | NR⁵R⁶ |
|---|---|---|---|---|---|
| 126 | H | H | Me | 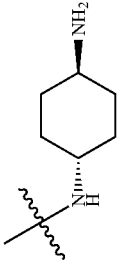 | 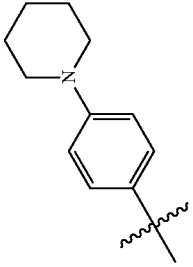 |
| 127 | H | H | Me | 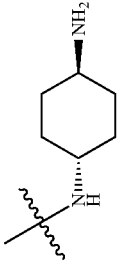 | 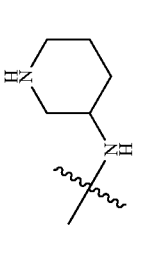 |
| 128 | H | H | Et | 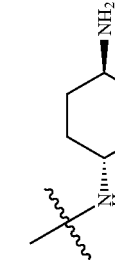 | 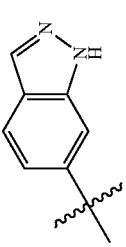 |
| 129 | H | H | Me | 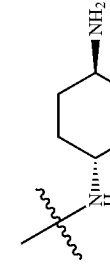 | 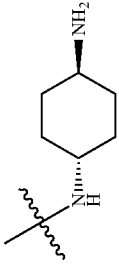 |
| 130 | H | H | Me | 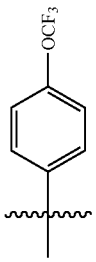 | 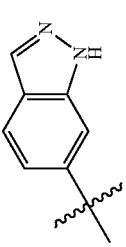 |
| 131 | H | H | Me | 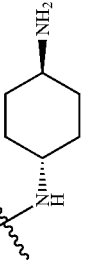 | 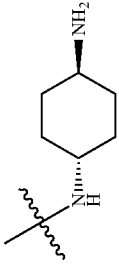 |

TABLE A-continued

| Compound No. | R¹ | R² | R⁴ | R³ | NR⁵R⁶ |
|---|---|---|---|---|---|
| 132 | H | 2,5,5-trimethyl-1,3-dioxan-2-yl | Me | 4-ethoxyphenyl | trans-4-aminocyclohexylamino |
| 133 | H | H | Me | 4-ethoxyphenyl | pyridin-3-ylamino |
| 134 | H | H | Me | 4-ethoxyphenyl | (1-methylpiperidin-3-yl)amino |
| 135 | H | H | Me | 4-ethoxyphenyl | pyridin-4-ylamino |
| 136 | H | H | Et | 4-benzyloxyphenyl | (4-(cinnamylamino)cyclohexyl)amino |
| 137 | H | H | Et | 4-ethoxycarbonyl-3-chlorophenyl | trans-4-aminocyclohexylamino |

TABLE A-continued
| Compound No. | R¹ | R² | R⁴ | R³ | NR⁵R⁶ |
|---|---|---|---|---|---|
| 145 | H | H | Me | 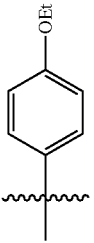 |  |
| 146 | H | H | Me | 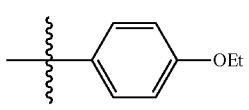 | 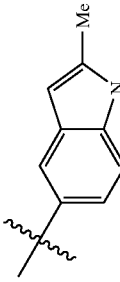 |
| 147 | H | H | Me | 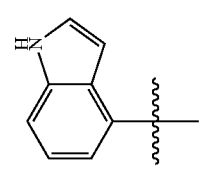 | 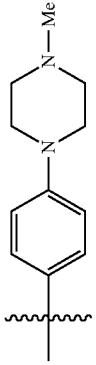 |
| 148 | H | H | Me | | |
| 149 | H | H | Me | | |
| 150 | H | H | Me | | |

TABLE A-continued
| Compound No. | R¹ | R² | R⁴ | R³ | NR⁵R⁶ |
|---|---|---|---|---|---|
| 151 | H | H | Et | 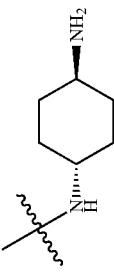 | 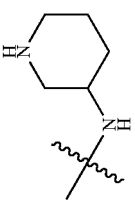 |
| 152 | H | H | Me | 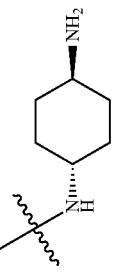 | 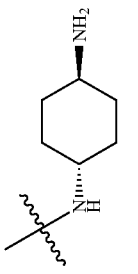 |
| 153 | H | H | Me | 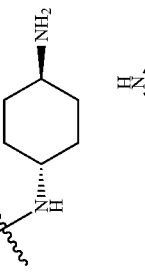 | 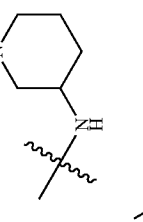 |
| 154 | H | Et | Me | 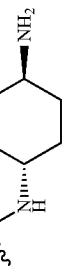 | |
| 155 | H | H | Me | | |
| 156 | H | H | Me | | |
| 157 | H | H | Ph | | |

TABLE A-continued

| Compound No. | R¹ | R² | R⁴ | R³ | NR⁵R⁶ |
|---|---|---|---|---|---|
| 158 | H | Et | Me | 4-OEt-phenyl | piperidin-3-ylamino |
| 159 | H | H | Et | 4-Br-phenyl | trans-4-aminocyclohexylamino |
| 160 | H | H | Et | 4-Br-phenyl | piperidin-3-ylamino |
| 161 | H | H | Me | 4-OEt-phenyl | n-propylamino |
| 162 | H | H | Me | 4-OEt-phenyl | allylamino |
| 163 | H | cyclopropyl | Me | 4-OEt-phenyl | trans-4-aminocyclohexylamino |
| 164 | H | cyclopropyl | Me | 4-OEt-phenyl | piperidin-3-ylamino |

TABLE A-continued

| Compound No. | R¹ | R² | R⁴ | R³ | NR⁵R⁶ |
|---|---|---|---|---|---|
| 165 | H | i-Pr | Me | 4-OEt-C₆H₄ | trans-4-aminocyclohexyl |
| 166 | H | i-Pr | Me | 4-OEt-C₆H₄ | 3-aminopiperidinyl |
| 167 | H | H | Et | Ph | trans-4-aminocyclohexyl |
| 168 | H | H | Et | 4-I-C₆H₄ | trans-4-aminocyclohexyl |
| 169 | H | Cl | Et | 4-I-C₆H₄ | 3-aminopiperidinyl |
| 170 | H | CN | H | 2-Cl-C₆H₄ | trans-4-aminocyclohexyl |
| 171 | H | H | OMe | 3-Cl-4-F-C₆H₃ | 3-aminopiperidinyl |

TABLE A-continued

| Compound No. | R¹ | R² | R³ | R⁴ | NR⁵R⁶ |
|---|---|---|---|---|---|
| 172 | H | H | 4-F, 3-Cl phenyl | OMe | trans-4-aminocyclohexylamino |
| 173 | H | H | 4-OEt phenyl | OMe | 3-aminopiperidinyl |
| 174 | H | H | isobenzofuran-1(3H)-one-5-yl | Me | 3-aminopiperidinyl |
| 175 | H | H | 4-CONH₂ phenyl | Et | trans-4-aminocyclohexylamino |
| 176 | H | H | 4-OBn phenyl | Me | trans-4-aminocyclohexylamino |
| 177 | H | H | 4-C(Me)₃ phenyl | Me | trans-4-aminocyclohexylamino |
| 178 | H | H | 4-NMe₂ phenyl | Me | trans-4-aminocyclohexylamino |

TABLE A-continued

| Compound No. | $R^1$ | $R^2$ | $R^4$ | $R^3$ | $NR^5R^6$ |
|---|---|---|---|---|---|
| 179 | H | H | Me | 4-(OCF₃)-phenyl-CH₂- | trans-4-aminocyclohexylamino |
| 180 | H | H | Me | 4-Cl-phenyl-CH₂- | trans-4-aminocyclohexylamino |
| 181 | H | H | Me | cyclopropyl-CH₂- | trans-4-aminocyclohexylamino |
| 182 | H | H | Me | MeO-CH₂CH₂- | trans-4-aminocyclohexylamino |
| 183 | H | H | Me | isobutyl-CH₂- (Me₂CHCH₂CH₂-) | trans-4-aminocyclohexylamino |
| 184 | H | H | Me | benzyl | trans-4-aminocyclohexylamino |
| 185 | H | H | Me | piperidin-1-yl-CH₂CH₂- | trans-4-aminocyclohexylamino |

TABLE A-continued
| Compound No. | R¹ | R² | R⁴ | R³ | NR⁵R⁶ |
|---|---|---|---|---|---|
| 186 | H | H | Me | 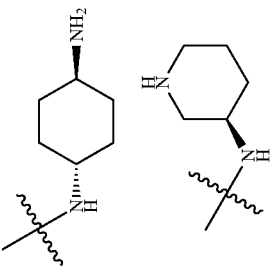 | 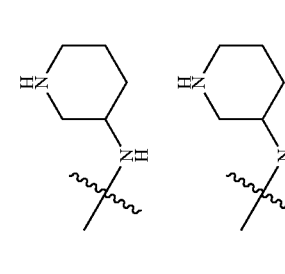 |
| 187 | H | H | Me | 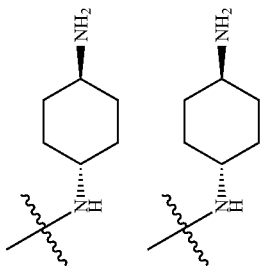 | 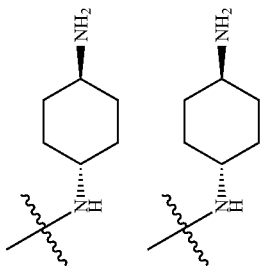 |
| 188 | H | H | Me | 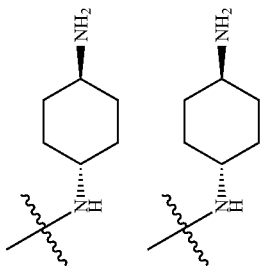 | 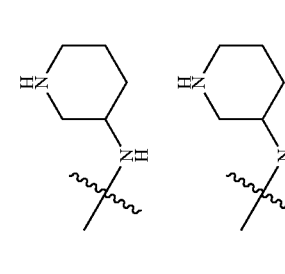 |
| 189 | H | H | Me | 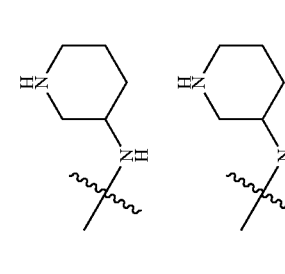 | 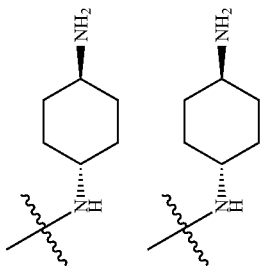 |
| 190 | H | H | Me | 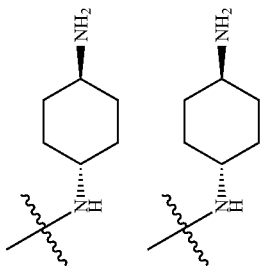 | 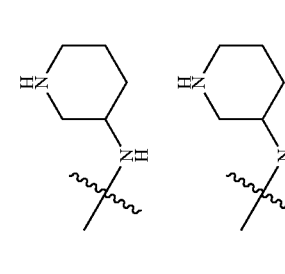 |
| 191 | H | H | Me | 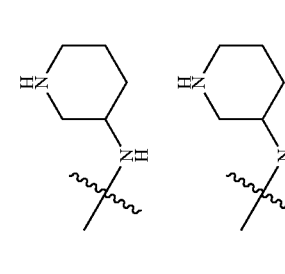 | 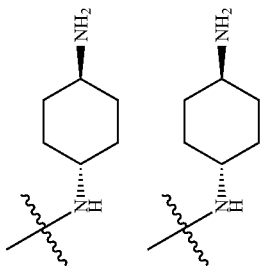 |
| 192 | H | H | Me | 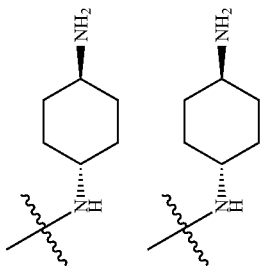 | 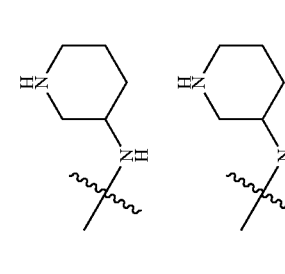 |

TABLE A-continued

| Compound No. | R¹ | R² | R⁴ | R³ | NR⁵R⁶ |
|---|---|---|---|---|---|
| 193 | H | H | Me | 4-OEt-phenyl | 3-aminopiperidinyl (NH linker) |
| 194 | H | H | Me | 4-OEt-phenyl | 3-(2-oxoazepanyl)amino |
| 195 | H | H | Me | 4-OEt-phenyl | trans-4-aminocyclohexylamino |
| 196 | H | H | Me | 4-OH-phenyl | trans-4-aminocyclohexylamino |
| 197 | H | H | Me | 4-(OCH(CH₃)₂)-phenyl | trans-4-aminocyclohexylamino |
| 198 | H | H | Me | 4-OEt-phenyl | 3-aminopiperidinyl (NH linker) |

TABLE A-continued
| Compound No. | R¹ | R² | R³ | R⁴ | NR⁵R⁶ |
|---|---|---|---|---|---|
| 199 | H | H | 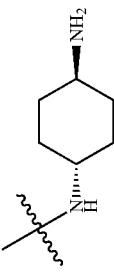 | Me | 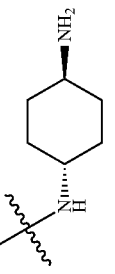 |
| 200 | H | H | 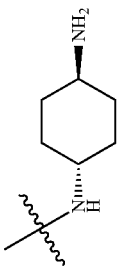 | Me | 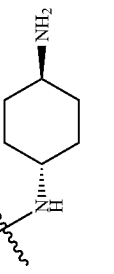 |
| 201 | H | H | 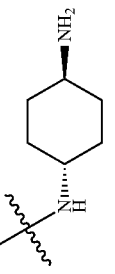 | Me | 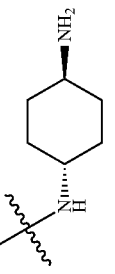 |
| 202 | H | H | 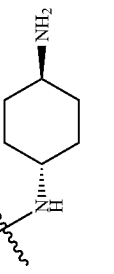 | Me | 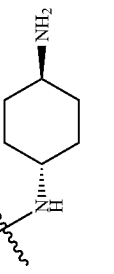 |
| 203 | H | H | 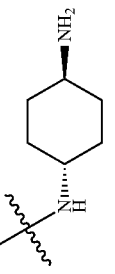 | Me | 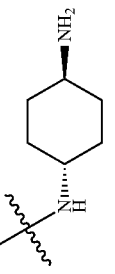 |
| 204 | H | H | 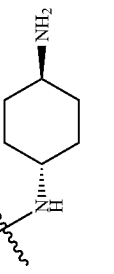 | Me | 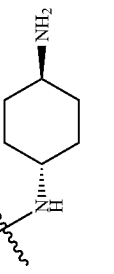 |

| Compound No. | R¹ | R² | R⁴ | R³ | NR⁵R⁶ |
|---|---|---|---|---|---|
| 205 | H | H | Me | 3-NH₂-benzyl ether of 4-substituted phenol | trans-4-aminocyclohexyl-NH- |
| 206 | H | H | Me | 2-NH₂-benzyl ether of 4-substituted phenol | trans-4-aminocyclohexyl-NH- |
| 207 | H | H | Me | 4-OMe-benzyl ether of 4-substituted phenol | trans-4-aminocyclohexyl-NH- |
| 208 | H | H | Me | 3-OMe-benzyl ether of 4-substituted phenol | trans-4-aminocyclohexyl-NH- |

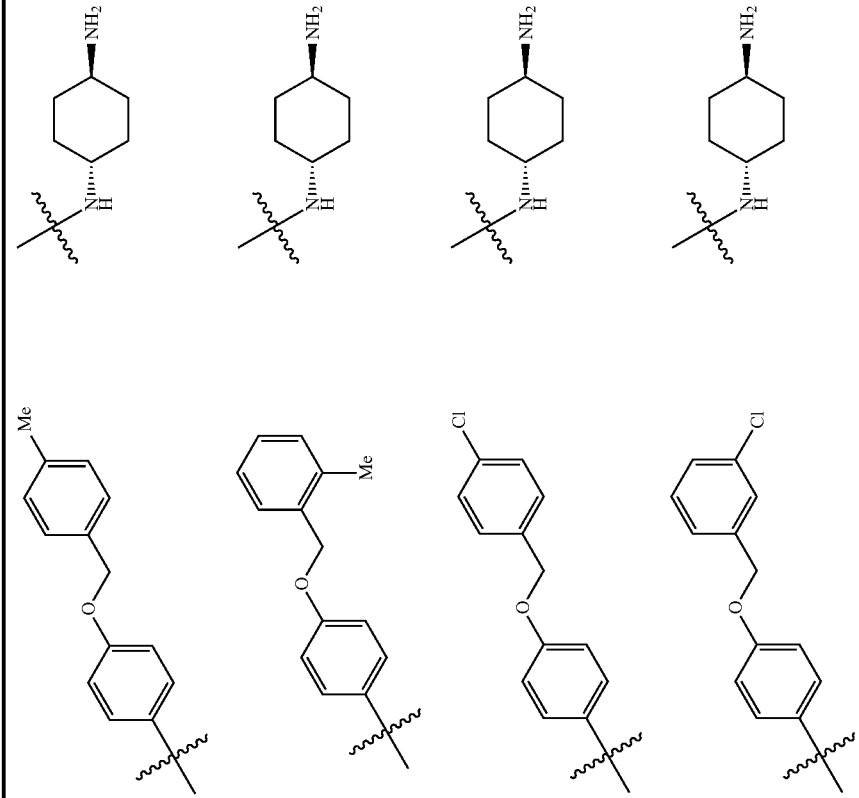

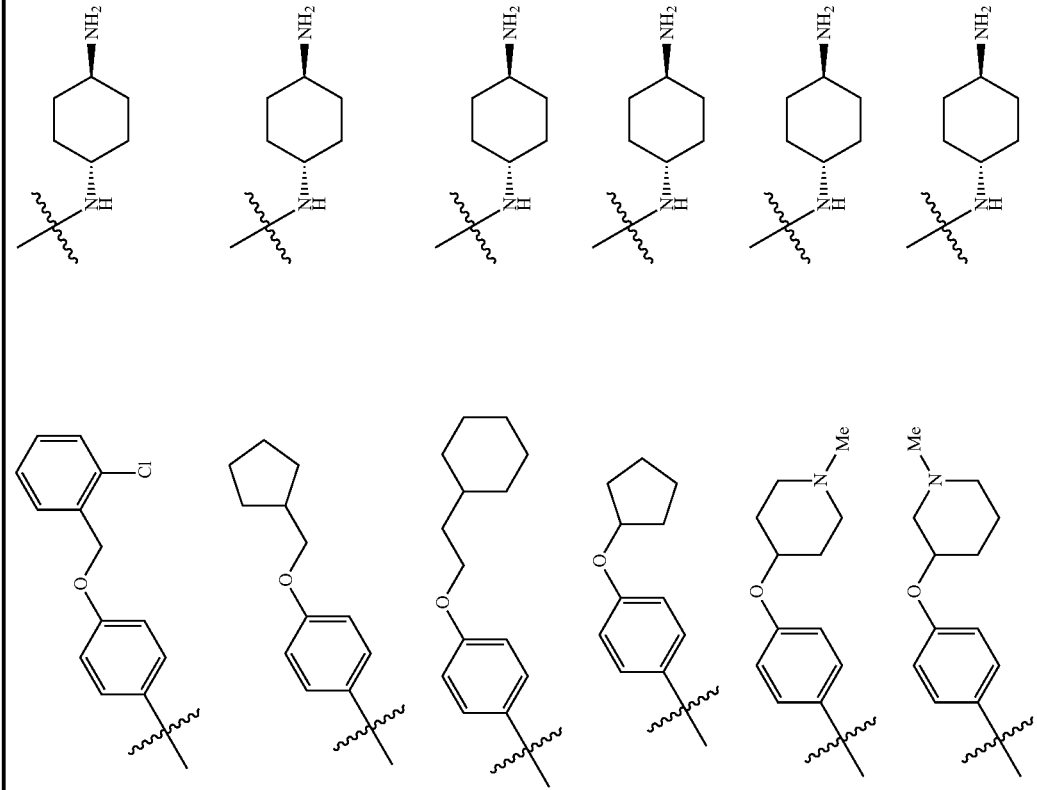

-continued
| Compound No. | R¹ | R² | R³ | R⁴ | NR⁵R⁶ |
|---|---|---|---|---|---|
| 219 | H | H |  | Me |  |
| 220 | H | H |  | Me |  |
| 221 | H | H | 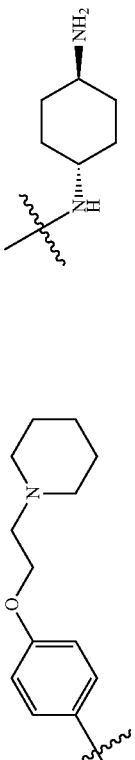 | Me | 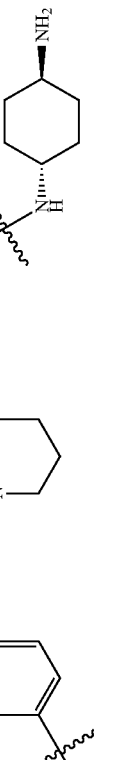 |
| 222 | H | H | 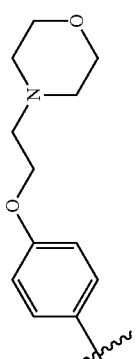 | Me | 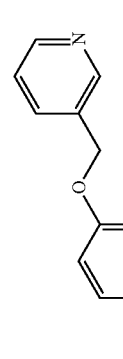 |
| 223 | H | H | 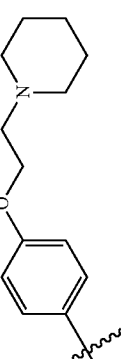 | Me |  |

-continued

| Compound No. | R¹ | R² | R⁴ | R³ | NR⁵R⁶ |
|---|---|---|---|---|---|
| 224 | H | H | Me | 2-pyridyl-CH₂-O-(4-phenyl)- | trans-4-aminocyclohexyl-NH- |
| 225 | H | H | Me | 2-pyridyl-CH₂CH₂-O-(4-phenyl)- | trans-4-aminocyclohexyl-NH- |
| 226 | H | H | Me | (1-methylpiperidin-3-yl)-CH₂-O-(4-phenyl)- | trans-4-aminocyclohexyl-NH- |
| 227 | H | H | Me | (1-methylpiperidin-2-yl)-CH₂-O-(4-phenyl)- | trans-4-aminocyclohexyl-NH- |
| 228 | H | H | Me | 4-pyridyl-CH₂CH₂-O-(4-phenyl)- | trans-4-aminocyclohexyl-NH- |

-continued

| Compound No. | R¹ | R² | R³ | R⁴ | NR⁵R⁶ |
|---|---|---|---|---|---|
| 229 | H | H | 4-(pyrrolidin-3-yloxy)phenyl | Me | trans-4-aminocyclohexylamino |
| 230 | H | H | 4-(2-(piperazin-1-yl)ethoxy)phenyl | Me | trans-4-aminocyclohexylamino |
| 231 | H | H | 4-(2-(piperidin-2-yl)ethoxy)phenyl | Me | trans-4-aminocyclohexylamino |
| 232 | H | H | 4-(piperidin-3-ylmethoxy)phenyl | Me | trans-4-aminocyclohexylamino |
| 233 | H | H | 4-(piperidin-4-ylmethoxy)phenyl | Me | trans-4-aminocyclohexylamino |
| 234 | H | H | 4-(2-(imidazol-1-yl)ethoxy)phenyl | Me | trans-4-aminocyclohexylamino |

| Compound No. | R¹ | R² | R⁴ | R³ | NR⁵R⁶ |
|---|---|---|---|---|---|
| 235 | H | H | Me | 4-(piperidin-3-yloxy)phenyl | trans-4-aminocyclohexylamino |
| 236 | H | H | Me | 4-(piperidin-4-yloxy)phenyl | trans-4-aminocyclohexylamino |
| 237 | H | H | Me | 4-(cyclohexylmethoxy)phenyl | trans-4-aminocyclohexylamino |
| 238 | H | H | Me | 3-(2-cyclohexylethoxy)phenyl | trans-4-aminocyclohexylamino |
| 239 | H | H | Me | 3-(cyclopentyloxy)phenyl | trans-4-aminocyclohexylamino |
| 240 | H | H | Me | 3-(cyclopentylmethoxy)phenyl | trans-4-aminocyclohexylamino |

-continued

| Compound No. | R¹ | R² | R⁴ | R³ | NR⁵R⁶ |
|---|---|---|---|---|---|
| 241 | H | H | Me | 3-(cyclohexyloxy)phenyl | trans-4-aminocyclohexylamino |
| 242 | H | H | Me | 3-(cyclohexylmethoxy)phenyl | trans-4-aminocyclohexylamino |
| 243 | H | H | Me | 3-(benzyloxy)phenyl | trans-4-aminocyclohexylamino |
| 244 | H | H | cyclopentyl | 4-ethoxyphenyl | trans-4-aminocyclohexylamino |
| 245 | H | H | cyclopentyl | 4-ethoxyphenyl | trans-4-aminocyclohexylamino |
| 246 | H | H | Me | 3-((3-aminophenoxy)methyl)phenyl | trans-4-aminocyclohexylamino |

-continued
| Compound No. | R¹ | R² | R³ | R⁴ | NR⁵R⁶ |
|---|---|---|---|---|---|
| 247 | H | H | 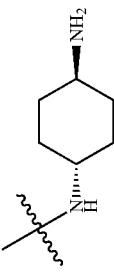 | Me |  |
| 248 | H | H | 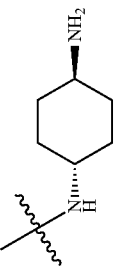 | Me | 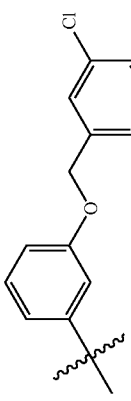 |
| 249 | H | H | 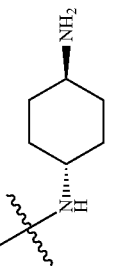 | Me | 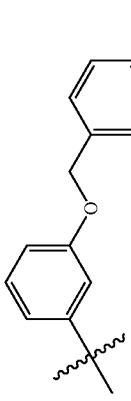 |
| 250 | H | H | 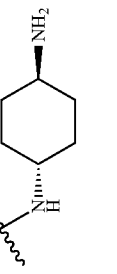 | Me | 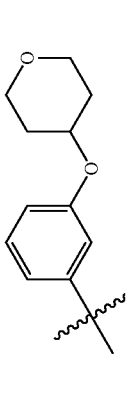 |
| 251 | H | H | 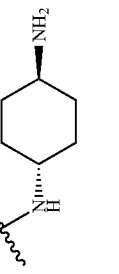 | Me | 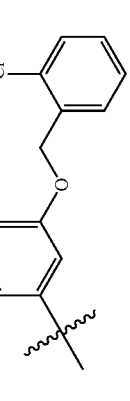 |

-continued
| Compound No. | R¹ | R² | R³ | R⁴ | NR⁵R⁶ |
|---|---|---|---|---|---|
| 252 | H | H | 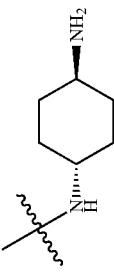 | Me |  |
| 253 | H | H | 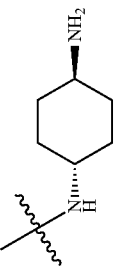 | Me | 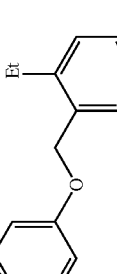 |
| 254 | H | H | 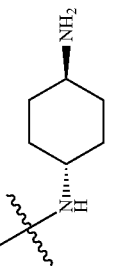 | Me | 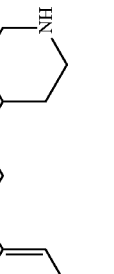 |
| 255 | H | H | 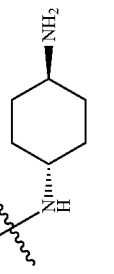 | Me | 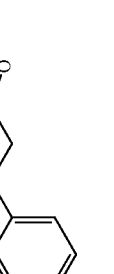 |
| 256 | H | H | 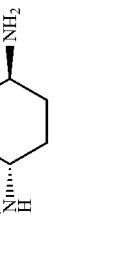 | Me |  |

-continued
| Compound No. | R¹ | R² | R³ | R⁴ | NR⁵R⁶ |
|---|---|---|---|---|---|
| 257 | H | H | 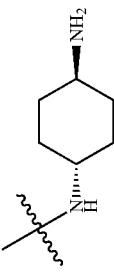 | Me | 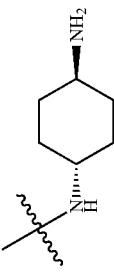 |
| 258 | H | H | 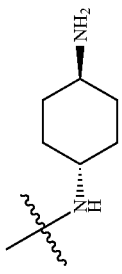 | Me | 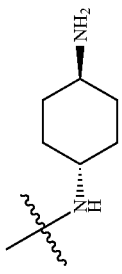 |
| 259 | H | H | 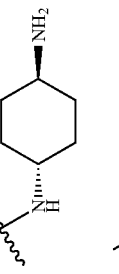 | Me | 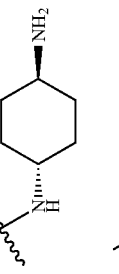 |
| 260 | H | H | 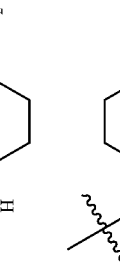 | Me | 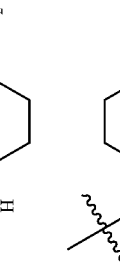 |
| 261 | H | H | 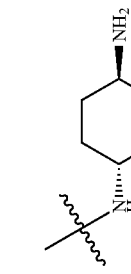 | Me | 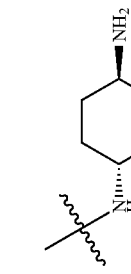 |
| 262 | H | H |  | Me |  |

-continued

| Compound No. | R¹ | R² | R³ | R⁴ | NR⁵R⁶ |
|---|---|---|---|---|---|
| 263 | H | H | 3-(piperidin-2-ylmethoxy)phenyl | Me | trans-4-aminocyclohexylamino |
| 264 | H | H | 3-(2-(piperidin-4-yl)ethoxy)phenyl | Me | trans-4-aminocyclohexylamino |
| 265 | H | H | 3-(piperidin-4-ylmethoxy)phenyl | Me | trans-4-aminocyclohexylamino |
| 266 | H | H | 3-(pyrrolidin-3-yloxy)phenyl | Me | trans-4-aminocyclohexylamino |
| 267 | H | H | 3-(2-(imidazol-1-yl)ethoxy)phenyl | Me | trans-4-aminocyclohexylamino |
| 268 | H | H | 3-((1-methylpiperidin-3-yl)oxy)phenyl | Me | trans-4-aminocyclohexylamino |

-continued

| Compound No. | R¹ | R² | R³ | R⁴ | NR⁵R⁶ |
|---|---|---|---|---|---|
| 269 | H | H | 3-((1-methylpiperidin-2-yl)methoxy)phenyl | Me | trans-4-aminocyclohexylamino |
| 270 | H | H | 3-((1-methylpiperidin-3-yl)methoxy)phenyl | Me | trans-4-aminocyclohexylamino |
| 271 | H | H | 4-ethoxyphenyl | Me | 1-(4-methoxybenzyl)azepan-3-ylamino |
| 272 | H | H | 4-ethoxyphenyl | Me | azepan-3-ylamino |
| 273 | H | H | 3-(pyridin-4-ylmethoxy)phenyl | Me | trans-4-aminocyclohexylamino |
| 274 | H | H | 3-(pyridin-3-ylmethoxy)phenyl | Me | trans-4-aminocyclohexylamino |

-continued

| Compound No. | R¹ | R² | R³ | R⁴ | NR⁵R⁶ |
|---|---|---|---|---|---|
| 275 | H | H | 3-(pyridin-2-ylmethoxy)phenyl | Me | trans-4-aminocyclohexylamino |
| 276 | H | H | 3-(2-aminobenzyloxy)phenyl | Me | trans-4-aminocyclohexylamino |
| 277 | H | H | 3-(2-morpholinoethoxy)phenyl | Me | trans-4-aminocyclohexylamino |
| 278 | H | H | 3-(2-piperidinoethoxy)phenyl | Me | trans-4-aminocyclohexylamino |
| 279 | H | H | 3-(2-(pyridin-4-yl)ethoxy)phenyl | Me | trans-4-aminocyclohexylamino |
| 280 | H | H | 3-(2-(pyridin-2-yl)ethoxy)phenyl | Me | trans-4-aminocyclohexylamino |

-continued

| Compound No. | R¹ | R² | R³ | R⁴ | NR⁵R⁶ |
|---|---|---|---|---|---|
| 281 | H | H | 3-((tetrahydrofuran-3-yl)methoxy)phenyl | Me | trans-4-aminocyclohexylamino |
| 282 | H | H | 3-(2,3-dihydroxypropoxy)phenyl | Me | trans-4-aminocyclohexylamino |
| 283 | H | H | 4-ethoxyphenyl | Me | 4-(piperidin-4-yl)piperidin-1-yl |
| 284 | H | H | biphenyl-4-yl | Me | trans-4-aminocyclohexylamino |
| 285 | H | H | 4'-methoxybiphenyl-4-yl | Me | trans-4-aminocyclohexylamino |

-continued

| Compound No. | R¹ | R² | R⁴ | R³ | NR⁵R⁶ |
|---|---|---|---|---|---|
| 286 | H | H | Me | 4'-(3-methoxyphenyl)phenyl | trans-4-aminocyclohexylamino |
| 287 | H | H | Me | 4'-(2-methoxyphenyl)phenyl | trans-4-aminocyclohexylamino |
| 288 | H | H | Me | 4'-(3-aminophenyl)phenyl | trans-4-aminocyclohexylamino |
| 289 | H | H | Me | 4-(benzothiophen-2-yl)phenyl | trans-4-aminocyclohexylamino |

-continued
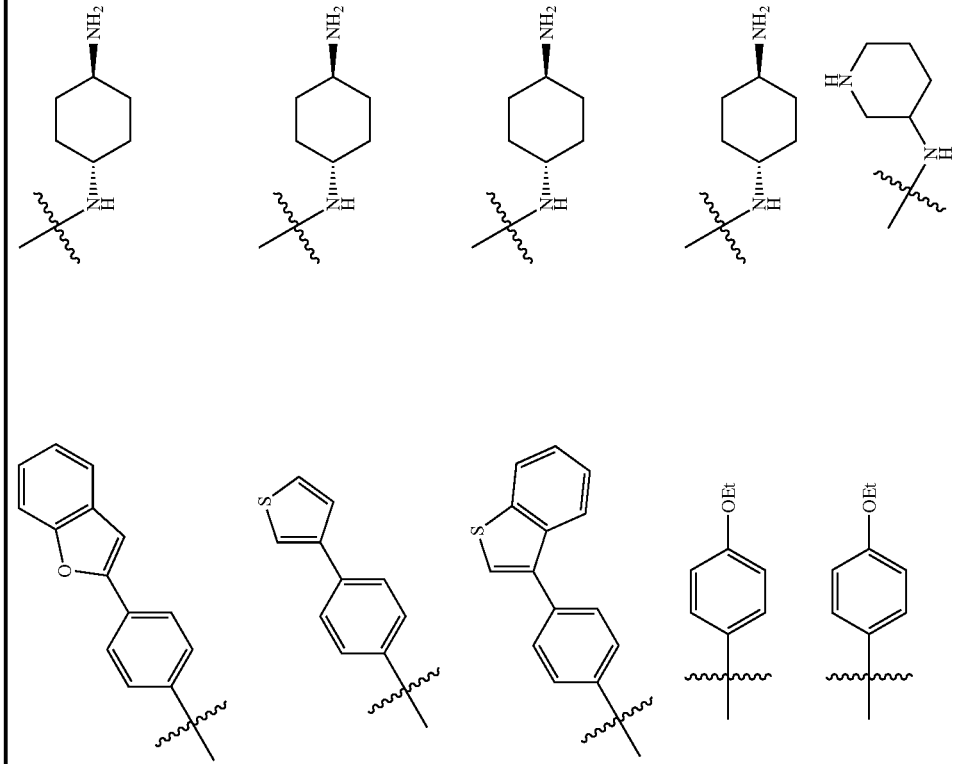
| Compound No. | R¹ | R² | R³ | R⁴ | NR⁵R⁶ |
|---|---|---|---|---|---|
| 290 | H | H | benzofuran-2-yl-phenyl | Me | trans-4-aminocyclohexyl |
| 291 | H | H | thiophen-3-yl-phenyl | Me | trans-4-aminocyclohexyl |
| 292 | H | H | benzothiophen-3-yl-phenyl | Me | trans-4-aminocyclohexyl |
| 293 | H | CN | 4-ethoxyphenyl | Me | trans-4-aminocyclohexyl |
| 294 | H | CN | 4-ethoxyphenyl | Me | piperidin-3-ylamino |

-continued

| Compound No. | R¹ | R² | R⁴ | R³ | NR⁵R⁶ |
|---|---|---|---|---|---|
| 295 | H | CN | Me | 3-Cl, 4-F phenyl | trans-4-aminocyclohexyl |
| 296 | H | H | Me | 4-OEt phenyl | 3-oxopiperidin-2-yl |
| 297 | H | I | H | 3-Cl benzyl | trans-4-aminocyclohexyl |
| 298 | H | H | Me | 4-OEt phenyl | 1-benzylpiperidin-3-yl |
| 299 | H | H | Me | 4-(pyridin-4-yl)phenyl | trans-4-aminocyclohexyl |

-continued
| Compound No. | R¹ | R² | R⁴ | R³ | NR⁵R⁶ |
|---|---|---|---|---|---|
| 300 | H | H | Me | 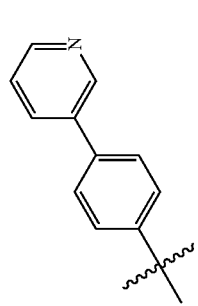 | 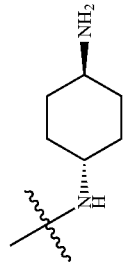 |
| 301 | H | H | Me | 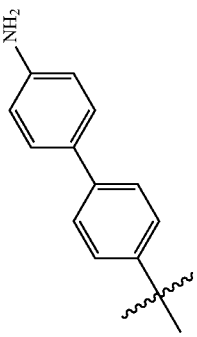 | 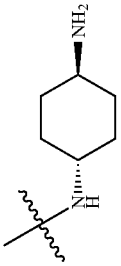 |
| 302 | H | H | Me | 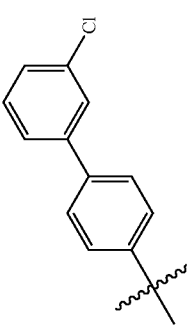 | 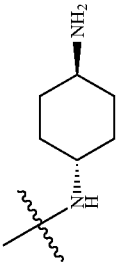 |
| 303 | H | H | Me | 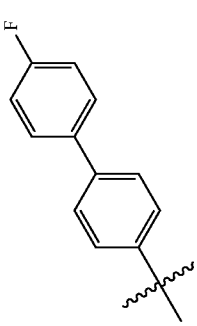 | 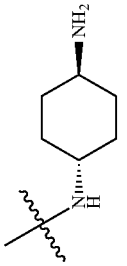 |

-continued

| Compound No. | R¹ | R² | R⁴ | R³ | NR⁵R⁶ |
|---|---|---|---|---|---|
| 304 | H | H | Me | 3'-F-biphenyl | trans-4-aminocyclohexyl-NH- |
| 305 | H | H | Me | 2'-F-biphenyl | trans-4-aminocyclohexyl-NH- |
| 306 | H | H | Me | 4'-OH-biphenyl | trans-4-aminocyclohexyl-NH- |
| 307 | H | H | Me | 3'-OH-biphenyl | trans-4-aminocyclohexyl-NH- |

-continued
| Compound No. | R¹ | R² | R⁴ | R³ | NR⁵R⁶ |
|---|---|---|---|---|---|
| 308 | H | H | Me | 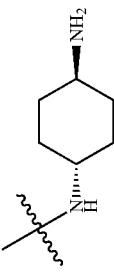 | 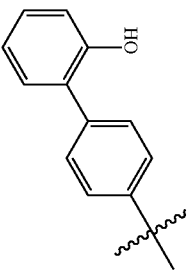 |
| 309 | H | H | Me | 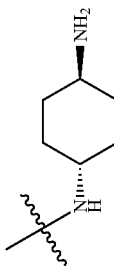 | 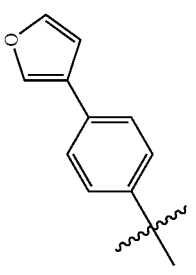 |
| 310 | H | H | Me | 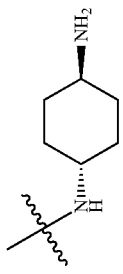 | 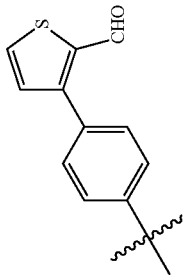 |
| 311 | H | H | Me | 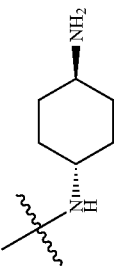 | 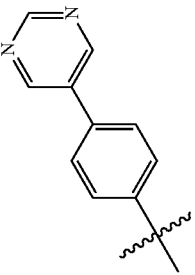 |

-continued
| Compound No. | R¹ | R² | R³ | R⁴ | NR⁵R⁶ |
|---|---|---|---|---|---|
| 312 | H | H | 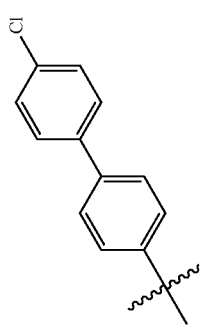 | Me | 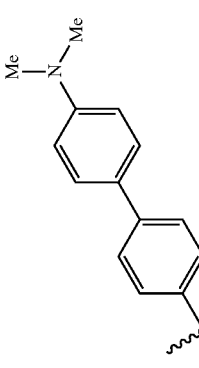 |
| 313 | H | H | 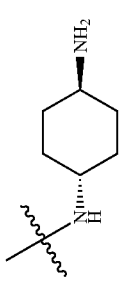 | Me | 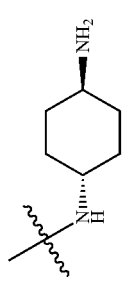 |
| 314 | H | H | 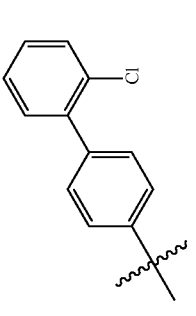 | Me | 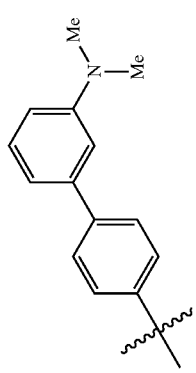 |
| 315 | H | H | 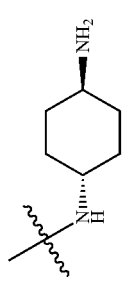 | Me | 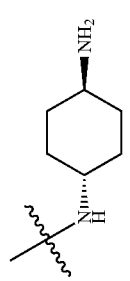 |

-continued
| Compound No. | R¹ | R² | R³ | R⁴ | NR⁵R⁶ |
|---|---|---|---|---|---|
| 316 | H | H | 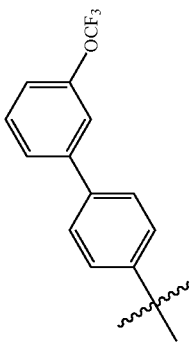 | Me | 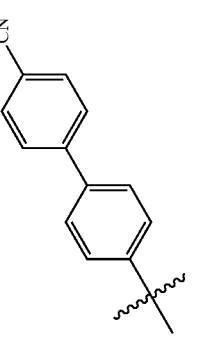 |
| 317 | H | H | 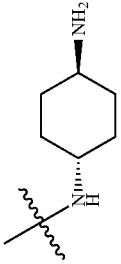 | Me | 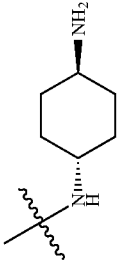 |
| 318 | H | H | 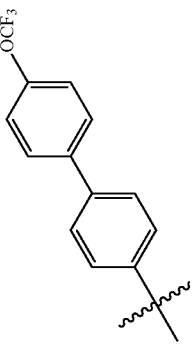 | Me | 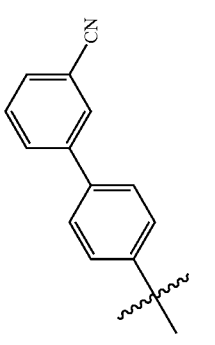 |
| 319 | H | H | 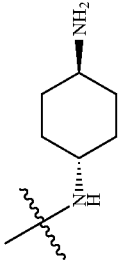 | Me | 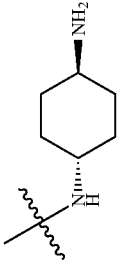 |

-continued
| Compound No. | R¹ | R² | R⁴ | R³ | NR⁵R⁶ |
|---|---|---|---|---|---|
| 320 | H | H | Me | 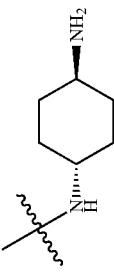 3-Me-biphenyl | 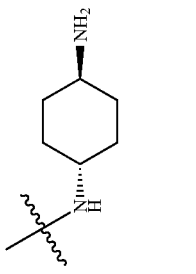 trans-4-aminocyclohexyl-NH- |
| 321 | H | H | Me | 2-Me-biphenyl | trans-4-aminocyclohexyl-NH- |
| 322 | H | H | Me | 4-Me-biphenyl | trans-4-aminocyclohexyl-NH- |
| 323 | H | H | Me | 2-CF₃-biphenyl | trans-4-aminocyclohexyl-NH- |

-continued
| Compound No. | R¹ | R² | R³ | R⁴ | NR⁵R⁶ |
|---|---|---|---|---|---|
| 324 | H | H | 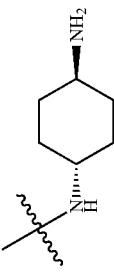 3'-CF₃-biphenyl | Me | 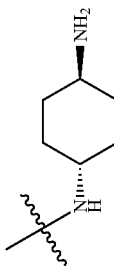 trans-4-aminocyclohexyl |
| 325 | H | 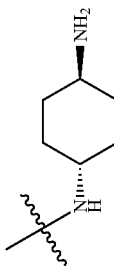 cyclohexyl | 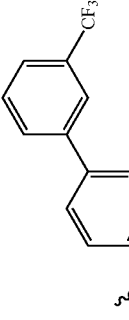 4-OEt-phenyl | Me | 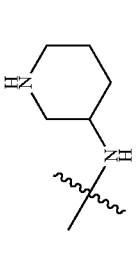 trans-4-aminocyclohexyl |
| 326 | H | 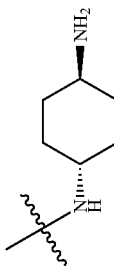 cyclohexyl | 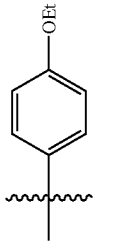 4-OEt-phenyl | Me | 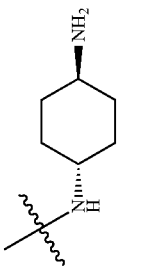 3-aminopiperidinyl |
| 327 | H | COOH | 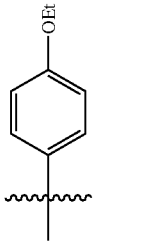 4-OEt-phenyl | Me | 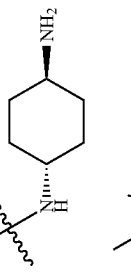 trans-4-aminocyclohexyl |
| 328 | H | 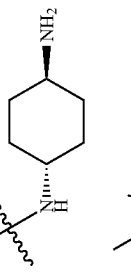 CH(Me)OC(O)- | 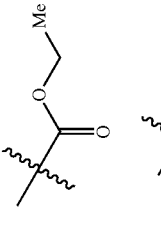 4-OEt-phenyl | Me | trans-4-aminocyclohexyl |
| 329 | H | 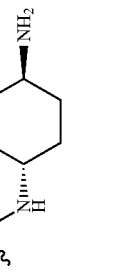 C(O)NH₂ | 4-OEt-phenyl | Me | trans-4-aminocyclohexyl |

-continued
| Compound No. | R¹ | R² | R⁴ | R³ | NR⁵R⁶ |
|---|---|---|---|---|---|
| 330 | H | 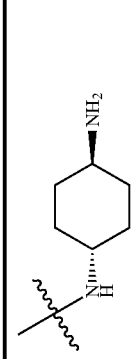 | Me | 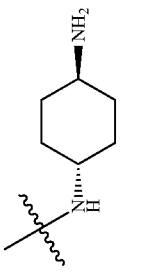 | 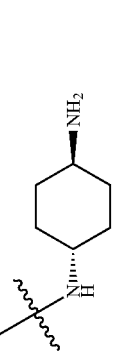 |
| 331 | H | 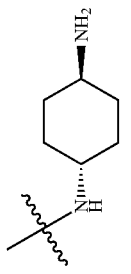 | Me | 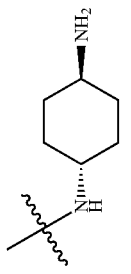 | 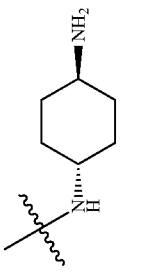 |
| 332 | H | 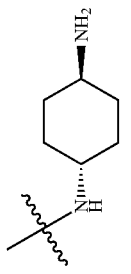 | Me | 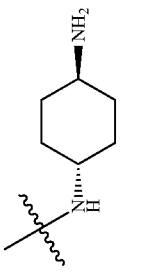 | 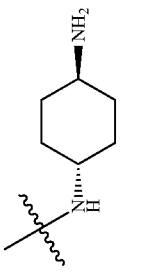 |
| 333 | H | 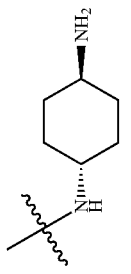 | Me | 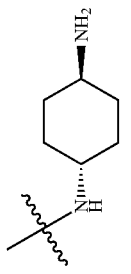 | 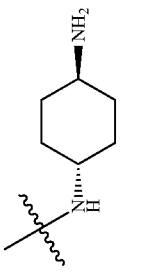 |
| 334 | H | 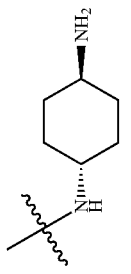 | Me | 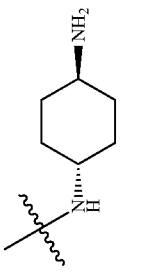 | 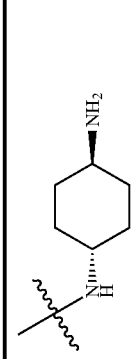 |
| 335 | H | 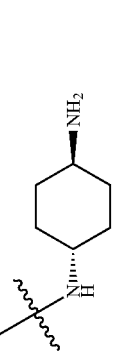 | Me | 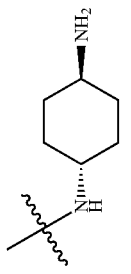 | 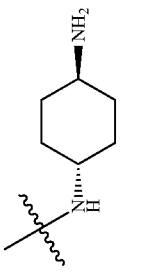 |
| 336 | H | 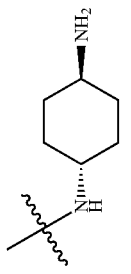 | Me | 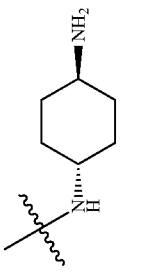 | 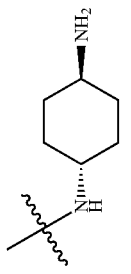 |

-continued

| Compound No. | R¹ | R² | R⁴ | R³ | NR⁵R⁶ |
|---|---|---|---|---|---|
| 337 | H | C(O)N(Me)Me | Me | 4-OEt-phenyl | trans-4-aminocyclohexyl-NH- |
| 338 | H | C(O)-pyrrolidinyl | Me | 4-OEt-phenyl | trans-4-aminocyclohexyl-NH- |
| 339 | H | C(O)NH-cyclopropyl | Me | 4-OEt-phenyl | trans-4-aminocyclohexyl-NH- |
| 340 | H | H | Me | 4-OEt-phenyl | N-Me, 3-piperidinyl |
| 341 | H | H | Me | 4-OEt-phenyl | N-Et, 3-piperidinyl |

-continued

| Compound No. | R¹ | R² | R⁴ | R³ | NR⁵R⁶ |
|---|---|---|---|---|---|
| 342 | H | H | Me | 4-OEt-C₆H₄- | N-benzyl-piperidin-3-yl-amino |
| 343 | H | NH₂ | Me | 4-OEt-C₆H₄- | trans-4-aminocyclohexylamino |
| 344 | H | -N(Me)-CH₂CH₂-N(Me)₂ (acyl) | Me | 4-OEt-C₆H₄- | trans-4-aminocyclohexylamino |
| 345 | H | -NH-CH₂CH₂-(1-methylpyrrolidin-2-yl) (acyl) | Me | 4-OEt-C₆H₄- | trans-4-aminocyclohexylamino |
| 346 | H | -N(Me)-(1-methylpyrrolidin-3-yl) (acyl) | Me | 4-OEt-C₆H₄- | trans-4-aminocyclohexylamino |
| 347 | H | 4-methylpiperazin-1-yl (acyl) | Me | 4-OEt-C₆H₄- | trans-4-aminocyclohexylamino |

-continued

| Compound No. | R¹ | R² | R⁴ | R³ | NR⁵R⁶ |
|---|---|---|---|---|---|
| 348 | H | N(Me)-C(=O)-phenyl | Me | 4-OEt-phenyl | trans-4-aminocyclohexyl-NH- |
| 349 | H | NH-C(=O)-(4-NMe₂-phenyl) | Me | 4-OEt-phenyl | trans-4-aminocyclohexyl-NH- |
| 350 | H | H | Me | 4'-CF₃-biphenyl | trans-4-aminocyclohexyl-NH- |
| 351 | H | H | Me | 4'-(SO₂Et)-biphenyl | trans-4-aminocyclohexyl-NH- |

| Compound No. | R¹ | R² | R³ | R⁴ | NR⁵R⁶ |
|---|---|---|---|---|---|
| 352 | H | H | 4'-(hydroxymethyl)biphenyl-4-yl | Me | trans-4-aminocyclohexylamino |
| 353 | H | H | 3'-(hydroxymethyl)biphenyl-4-yl | Me | trans-4-aminocyclohexylamino |
| 354 | H | H | 3'-(methoxymethyl)biphenyl-4-yl | Me | trans-4-aminocyclohexylamino |
| 355 | H | H | 5-(4-acetylthiophen-2-yl... ) | Me | trans-4-aminocyclohexylamino |

| Compound No. | R¹ | R² | R³ | R⁴ | NR⁵R⁶ |
|---|---|---|---|---|---|
| 356 | H | H | 4'-ethoxybiphenyl-4-yl | Me | trans-4-aminocyclohexylamino |
| 357 | H | H | 5-(4-methylthiophen-2-yl)phenyl | Me | trans-4-aminocyclohexylamino |
| 358 | H | -C(O)NH-CH₂CH₂-(pyrrolidin-1-yl) | 4-ethoxyphenyl | Me | trans-4-aminocyclohexylamino |
| 359 | H | -C(O)NH-(pyridin-2-yl) | 4-ethoxyphenyl | Me | trans-4-aminocyclohexylamino |
| 360 | H | -C(O)NH-(pyridin-3-yl) | 4-ethoxyphenyl | Me | trans-4-aminocyclohexylamino |
| 361 | H | -C(O)NH-(pyridin-4-yl) | 4-ethoxyphenyl | Me | trans-4-aminocyclohexylamino |

-continued

| Compound No. | R¹ | R² | R⁴ | R³ | NR⁵R⁶ |
|---|---|---|---|---|---|
| 362 | H | butyryl (CH₂CH₂CH₂C(=O)–, Me-terminated) | Me | 4-OEt-phenyl | trans-4-aminocyclohexylamino |
| 363 | H | –NHC(=O)CH₂OH | Me | 4-OEt-phenyl | trans-4-aminocyclohexylamino |
| 364 | H | –NHC(=O)CH₂OMe | Me | 4-OEt-phenyl | trans-4-aminocyclohexylamino |
| 365 | H | –NHC(=O)OCH₂Ph | Me | 4-OEt-phenyl | trans-4-aminocyclohexylamino |
| 366 | H | H | Me | 4-OEt-phenyl | –NH-CH(CH(Me)₂)CH₂OH |
| 367 | H | H | Me | 4-OEt-phenyl | –NH-CH(CH₂CH(Me)₂)CH₂OH |
| 368 | H | H | Me | 4-OEt-phenyl | –NH-C(cyclopentyl)(CH₂OH) |

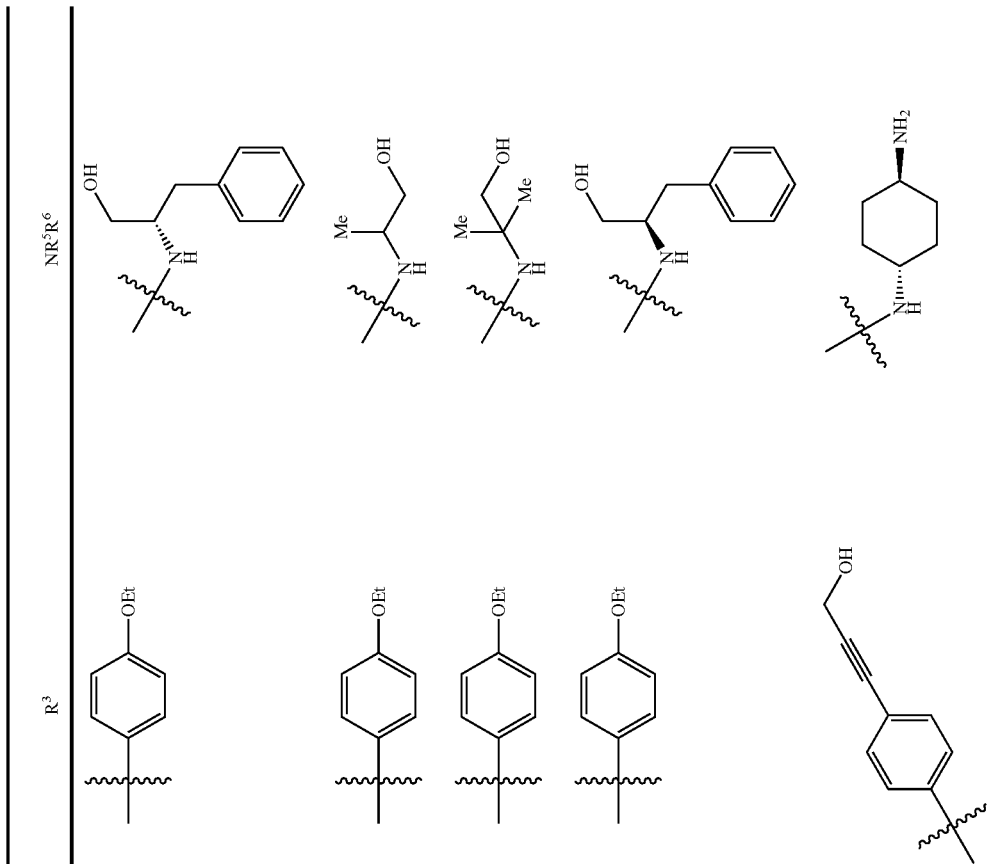

-continued

| Compound No. | R¹ | R² | R⁴ | R³ | NR⁵R⁶ |
|---|---|---|---|---|---|
| 374 | H | H | Me | 4-(3-(methylamino)prop-1-ynyl)phenyl | trans-4-aminocyclohexylamino |
| 375 | H | H | Me | 4-(phenylethynyl)phenyl | trans-4-aminocyclohexylamino |
| 376 | H | H | Me | 4-(3,3-dimethylbut-1-ynyl)phenyl | trans-4-aminocyclohexylamino |
| 377 | H | H | Me | 4-(3-aminoprop-1-ynyl)phenyl | trans-4-aminocyclohexylamino |
| 378 | H | NHC(O)Me | Me | 4-ethoxyphenyl | trans-4-aminocyclohexylamino |

-continued

| Compound No. | R¹ | R² | R⁴ | R³ | NR⁵R⁶ |
|---|---|---|---|---|---|
| 379 | H | -NHC(O)CH₂Me | Me | 4-OEt-phenyl | trans-4-aminocyclohexylamino |
| 380 | H | -NHC(O)-cyclopropyl | Me | 4-OEt-phenyl | trans-4-aminocyclohexylamino |
| 381 | H | -NHC(O)CH₂OC(O)Me | Me | 4-OEt-phenyl | trans-4-aminocyclohexylamino |
| 382 | H | -NHC(O)CH₂CH₂SMe | Me | 4-OEt-phenyl | trans-4-aminocyclohexylamino |
| 383 | H | -NHC(O)Ph | Me | 4-OEt-phenyl | trans-4-aminocyclohexylamino |
| 384 | H | -NHC(O)CH₂Ph | Me | 4-OEt-phenyl | trans-4-aminocyclohexylamino |
| 385 | H | -NHC(O)CF₃ | Me | 4-OEt-phenyl | trans-4-aminocyclohexylamino |

| Compound No. | R¹ | R² | R⁴ | R³ | NR⁵R⁶ |
|---|---|---|---|---|---|
| 386 | H | methanesulfonamide (MeSO₂NH–) | Me | 4-ethoxyphenyl | trans-4-aminocyclohexylamino |
| 387 | H | phenylsulfonamide (PhSO₂NH–) | Me | 4-ethoxyphenyl | trans-4-aminocyclohexylamino |
| 388 | H | N-(2-methylpropyl)urea derivative | Me | 4-ethoxyphenyl | trans-4-aminocyclohexylamino |
| 389 | H | N-phenylurea | Me | 4-ethoxyphenyl | trans-4-aminocyclohexylamino |
| 390 | H | N-methylthiourea | Me | 4-ethoxyphenyl | trans-4-aminocyclohexylamino |
| 391 | H | N-phenylthiourea | Me | 4-ethoxyphenyl | trans-4-aminocyclohexylamino |
| 392 | H | N-methyl-N-methoxyamide (Me,OMe) | Me | 4-ethoxyphenyl | trans-4-aminocyclohexylamino |

-continued
| Compound No. | R¹ | R² | R³ | R⁴ | NR⁵R⁶ |
|---|---|---|---|---|---|
| 393 | H | H | 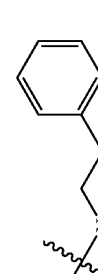 4-OEt-C₆H₄- | Me | 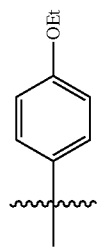 -NH-CH₂CH₂-OH |
| 394 | H | H |  4-OEt-C₆H₄- | Me |  -NH-(CH₂)₃-OH |
| 395 | H | H | 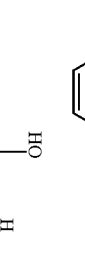 4-OEt-C₆H₄- | Me | 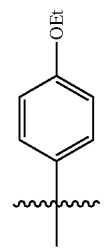 -NH-(CH₂)₄-OH |
| 396 | H | H | 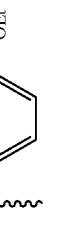 4-OEt-C₆H₄- | Me |  -NH-CH(Ph)-CH₂OH |
| 397 | H | H | 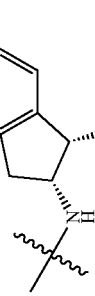 4-OEt-C₆H₄- | Me | 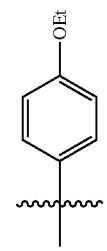 trans-2-aminoindan-1-ol |
| 398 | H | H | 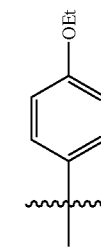 4-OEt-C₆H₄- | Me |  trans-2-aminoindan-1-ol (enantiomer) |
| 399 | H | H | 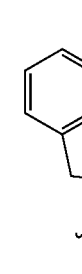 4-OEt-C₆H₄- | Me | 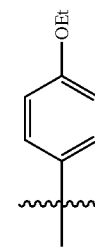 -NH-CH(CH₂OH)(CH₂CH₃) |

-continued

| Compound No. | R¹ | R² | R³ | R⁴ | NR⁵R⁶ |
|---|---|---|---|---|---|
| 400 | H | H | 4-OEt-C₆H₄- | Me | -NH-CH₂CH₂-NH₂ |
| 401 | H | H | 4-OEt-C₆H₄- | Me | -NH-CH(Me)-CH₂-NH₂ |
| 402 | H | H | 4-OEt-C₆H₄- | Me | -NH-CH₂CH₂CH₂-NH₂ |
| 403 | H | H | 4-OEt-C₆H₄- | Me | -NH-C(Me)₂-CH₂-NH₂ |
| 404 | H | H | 4-OEt-C₆H₄- | Me | -NH-(CH₂)₄-NH₂ |
| 405 | H | H | 4-OEt-C₆H₄- | Me | trans-2-aminocyclohexylamino |
| 406 | H | H | 4-OEt-C₆H₄- | Me | trans-2-aminocyclohexylamino |

-continued

| Compound No. | R¹ | R² | R⁴ | R³ | NR⁵R⁶ |
|---|---|---|---|---|---|
| 407 | H | H | Me | 4-OEt-phenyl | 3-aminocyclohexylamino |
| 408 | H | H | Me | 4-OEt-phenyl | 2-hydroxy-3-aminopropylamino |
| 409 | H | H | Me | 2-Me-benzothiazol-5-yl | piperidin-3-ylamino |
| 410 | H | H | Me | 4-OEt-phenyl | (3R)-pyrrolidin-3-ylamino |
| 411 | H | H | Me | 4-OEt-phenyl | 1-benzylpyrrolidin-3-ylamino |
| 412 | H | H | Me | 4-OEt-phenyl | pyrrolidin-3-ylamino |
| 413 | H | Me | Me | 4-OEt-phenyl | trans-4-aminocyclohexylamino |

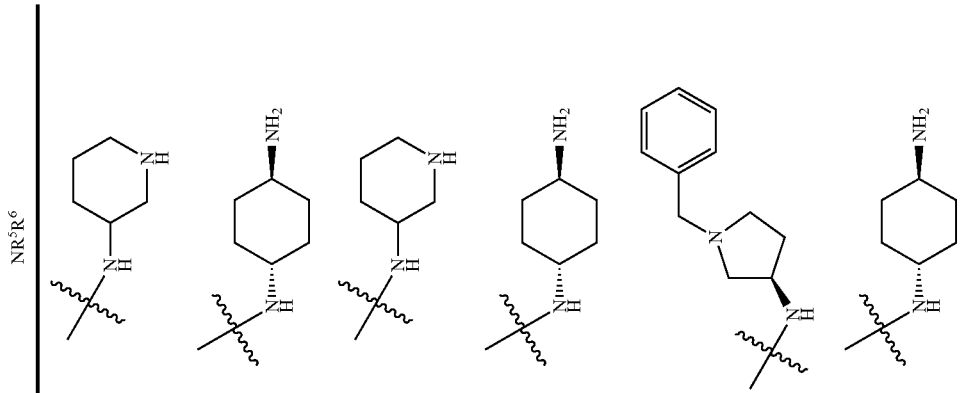

-continued

| Compound No. | R¹ | R² | R³ | R⁴ | NR⁵R⁶ |
|---|---|---|---|---|---|
| 420 | H | H | 2-ethoxyphenyl | Me | trans-4-aminocyclohexylamino |
| 421 | H | H | 4-(3-methylthiophen-4-yl)phenyl | Me | trans-4-aminocyclohexylamino |
| 422 | H | H | 4-(1H-pyrazol-4-yl)phenyl | Me | trans-4-aminocyclohexylamino |
| 423 | H | H | 4-(1H-indol-2-yl)phenyl | Me | trans-4-aminocyclohexylamino |
| 424 | H | H | 4-ethoxyphenyl | Me | (3-hydroxy-1,5,5-trimethylcyclohexyl)methyl-amino |

-continued

| Compound No. | R¹ | R² | R³ | R⁴ | NR⁵R⁶ |
|---|---|---|---|---|---|
| 425 | H | OMe | 4-OEt-phenyl | Me | trans-4-aminocyclohexyl-NH- |
| 426 | H | -C(=O)N(Me)H (α,α-dimethyl) | 4-OEt-phenyl | Me | piperidin-3-yl-NH- |
| 427 | H | -C(=O)N(Me)Me (α,α-dimethyl) | 4-OEt-phenyl | Me | piperidin-3-yl-NH- |
| 428 | H | -C(=O)-pyrrolidin-1-yl (α,α-dimethyl) | 4-OEt-phenyl | Me | piperidin-3-yl-NH- |
| 429 | H | -C(=O)NH-CH₂CH₂-OMe (α,α-dimethyl) | 4-OEt-phenyl | Me | piperidin-3-yl-NH- |
| 430 | H | -C(=O)NH-CH₂CH₂-N(Me)Me (α,α-dimethyl) | 4-OEt-phenyl | Me | piperidin-3-yl-NH- |
| 431 | H | -C(=O)NH-phenyl (α,α-dimethyl) | 4-OEt-phenyl | Me | piperidin-3-yl-NH- |

-continued

| Compound No. | R¹ | R² | R⁴ | R³ | NR⁵R⁶ |
|---|---|---|---|---|---|
| 432 | H | 2-pyridyl-C(O)NH- | Me | 4-OEt-phenyl | piperidin-3-ylamino |
| 433 | H | 3-pyridyl-C(O)NH- | Me | 4-OEt-phenyl | piperidin-3-ylamino |
| 434 | H | 4-pyridyl-C(O)NH- | Me | 4-OEt-phenyl | piperidin-3-ylamino |
| 435 | H | PhCH₂-C(O)NH- | Me | 4-OEt-phenyl | piperidin-3-ylamino |
| 436 | H | PhCH₂-NH- | Me | 4-OEt-phenyl | trans-4-aminocyclohexylamino |
| 437 | H | MeNH- | Me | 4-OEt-phenyl | trans-4-aminocyclohexylamino |
| 438 | H | MeOCH₂CH₂NH- | Me | 4-OEt-phenyl | trans-4-aminocyclohexylamino |

-continued

| Compound No. | R¹ | R² | R⁴ | R³ | NR⁵R⁶ |
|---|---|---|---|---|---|
| 439 | H | -C(=O)OCH₂Me | Me | 4-OEt-phenyl | 3-aminopiperidine |
| 440 | H | COOH | Me | 4-OEt-phenyl | 3-aminopiperidine |
| 441 | H | F | Me | 4-I-phenyl | trans-4-aminocyclohexylamine |
| 442 | H | H | Me | 4-(4-aminophenyl)phenyl | 3-aminopiperidine |
| 443 | H | H | Me | 4-(thiophen-3-yl)phenyl | 3-aminopiperidine |
| 444 | H | H | Me | 4-(3-aminophenyl)phenyl | 3-aminopiperidine |

-continued

| Compound No. | R¹ | R² | R⁴ | R³ | NR⁵R⁶ |
|---|---|---|---|---|---|
| 445 | H | H | Me | 3'-(hydroxymethyl)biphenyl-4-yl | piperidin-3-ylamino |
| 446 | H | H | Me | biphenyl-3-yl | trans-4-aminocyclohexylamino |
| 447 | H | H | Me | 4'-aminobiphenyl-3-yl | trans-4-aminocyclohexylamino |
| 448 | H | H | Me | 3'-aminobiphenyl-3-yl | trans-4-aminocyclohexylamino |

-continued
| Compound No. | R¹ | R² | R⁴ | R³ | NR⁵R⁶ |
|---|---|---|---|---|---|
| 449 | H | H | Me | 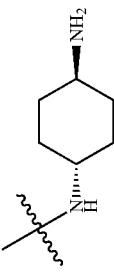 | 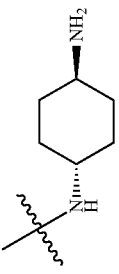 |
| 450 | H | H | Me | 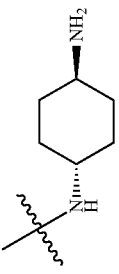 | 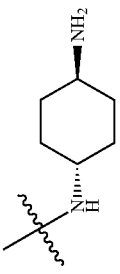 |
| 451 | H | H | Me | 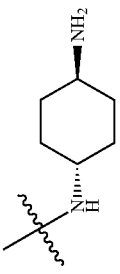 | 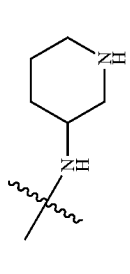 |
| 452 | H | H | Me | 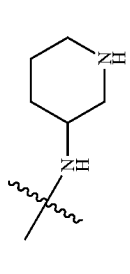 |  |

-continued
| Compound No. | R¹ | R² | R⁴ | R³ | NR⁵R⁶ |
|---|---|---|---|---|---|
| 453 | H | H | Me | 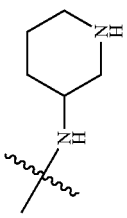 (3-(MeSO₂NH)phenyl) | 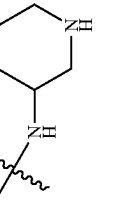 (3-aminopiperidinyl) |
| 454 | H | H | Me | 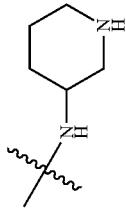 (2,5-difluoro-4-cyanophenyl) | 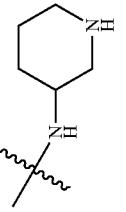 (3-aminopiperidinyl) |
| 455 | H | H | Me | 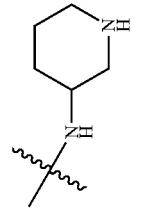 (3,5-dimethoxyphenyl) | 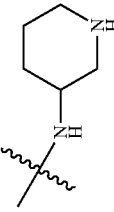 (3-aminopiperidinyl) |
| 456 | H | H | Me | 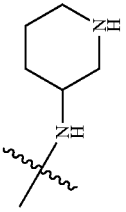 (4-benzoylphenyl) | 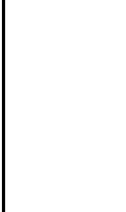 (3-aminopiperidinyl) |

| Compound No. | R¹ | R² | R⁴ | R³ | NR⁵R⁶ |
|---|---|---|---|---|---|
| 457 | H | H | Me | 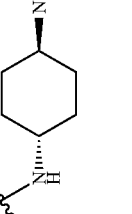 | 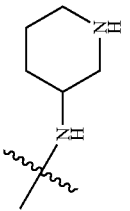 |
| 458 | H | H | Me | 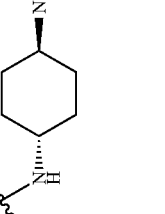 | 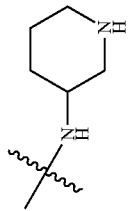 |
| 459 | H | H | Me | 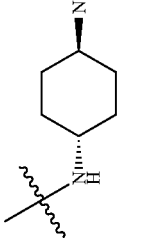 | 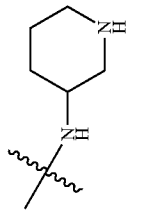 |
| 460 | H | H | Me | 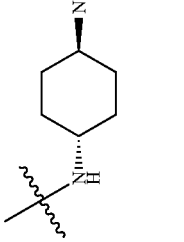 | 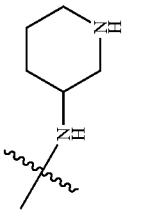 |
| 461 | H | H | Me |  | 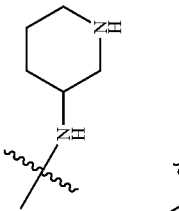 |

-continued

| Compound No. | R¹ | R² | R⁴ | R³ | NR⁵R⁶ |
|---|---|---|---|---|---|
| 462 | H | H | Me | 4-(cyclopropylmethylcarbamoyl)phenyl | trans-4-aminocyclohexylamino |
| 463 | H | H | Me | 4-(cyclopentylcarbamoyl)phenyl | trans-4-aminocyclohexylamino |
| 464 | H | H | Me | 4-(cyclohexylcarbamoyl)phenyl | trans-4-aminocyclohexylamino |
| 465 | H | H | Me | 4-(cyclohexylmethylcarbamoyl)phenyl | trans-4-aminocyclohexylamino |
| 466 | H | H | Me | 4-(2-hydroxyethylcarbamoyl)phenyl | trans-4-aminocyclohexylamino |

-continued

| Compound No. | R¹ | R² | R⁴ | R³ | NR⁵R⁶ |
|---|---|---|---|---|---|
| 467 | H | H | Me | 4-(2-methoxyethylcarbamoyl)phenyl- | trans-4-aminocyclohexylamino- |
| 468 | H | H | Me | 4-((tetrahydrofuran-2-ylmethyl)carbamoyl)phenyl- | trans-4-aminocyclohexylamino- |
| 469 | H | H | Me | 4-(2-(dimethylamino)ethylcarbamoyl)phenyl- | trans-4-aminocyclohexylamino- |
| 470 | H | H | Me | 4-(2-(pyrrolidin-1-yl)ethylcarbamoyl)phenyl- | trans-4-aminocyclohexylamino- |
| 471 | H | H | Me | 4-(2-morpholinoethylcarbamoyl)phenyl- | trans-4-aminocyclohexylamino- |

-continued

| Compound No. | R¹ | R² | R³ | R⁴ | NR⁵R⁶ |
|---|---|---|---|---|---|
| 472 | H | H | 4-(C(O)NH-CH₂CH₂-F)-phenyl | Me | trans-4-aminocyclohexyl-NH- |
| 473 | H | H | 4-(C(O)NH-CH₂CF₃)-phenyl | Me | trans-4-aminocyclohexyl-NH- |
| 474 | H | H | 4-(C(O)NH-CH₂CH₂-Cl)-phenyl | Me | trans-4-aminocyclohexyl-NH- |
| 475 | H | H | 4-(C(O)NH-CH₂CH₂-SMe)-phenyl | Me | trans-4-aminocyclohexyl-NH- |
| 476 | H | H | 4-(C(O)NH-CH₂CH₂-NHC(O)Me)-phenyl | Me | trans-4-aminocyclohexyl-NH- |

-continued
| Compound No. | R¹ | R² | R³ | R⁴ | NR⁵R⁶ |
|---|---|---|---|---|---|
| 477 | H | H | 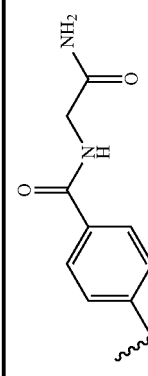 | Me | 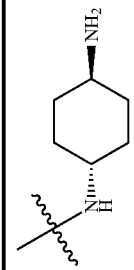 |
| 478 | H | H | 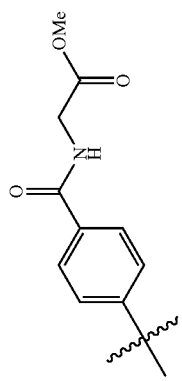 | Me | 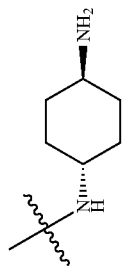 |
| 479 | H | H | 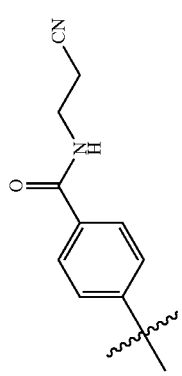 | Me | 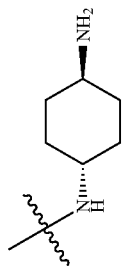 |
| 480 | H | H | 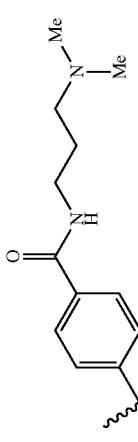 | Me | 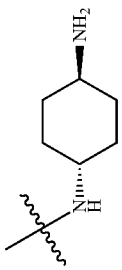 |
| 481 | H | H | 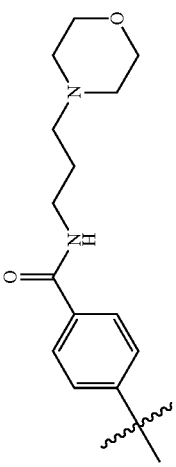 | Me | 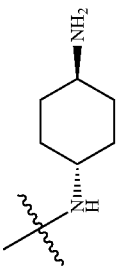 |

-continued

| Compound No. | R¹ | R² | R³ | R⁴ | NR⁵R⁶ |
|---|---|---|---|---|---|
| 482 | H | H | ![1,3-dioxolan-2-ylethyl benzamide] | Me | ![trans-4-aminocyclohexylamino] |
| 483 | H | H | ![3-(1-methoxyethoxy)propyl benzamide] | Me | ![trans-4-aminocyclohexylamino] |
| 484 | H | H | ![N-phenyl benzamide] | Me | ![trans-4-aminocyclohexylamino] |
| 485 | H | H | ![N-(2-hydroxyphenyl) benzamide] | Me | ![trans-4-aminocyclohexylamino] |
| 486 | H | H | ![N-(3-hydroxyphenyl) benzamide] | Me | ![trans-4-aminocyclohexylamino] |

-continued

| Compound No. | R¹ | R² | R³ | R⁴ | NR⁵R⁶ |
|---|---|---|---|---|---|
| 487 | H | H | 4-OH-C₆H₄-NHC(O)-C₆H₄- | Me | trans-4-aminocyclohexyl-NH- |
| 488 | H | H | 2-F-C₆H₄-NHC(O)-C₆H₄- | Me | trans-4-aminocyclohexyl-NH- |
| 489 | H | H | 3-F-C₆H₄-NHC(O)-C₆H₄- | Me | trans-4-aminocyclohexyl-NH- |
| 490 | H | H | 4-F-C₆H₄-NHC(O)-C₆H₄- | Me | trans-4-aminocyclohexyl-NH- |

-continued

| Compound No. | R¹ | R² | R³ | R⁴ | NR⁵R⁶ |
|---|---|---|---|---|---|
| 491 | H | H | ![R3 structure: 4-(benzamide with 2-CN phenyl)] | Me | ![trans-4-aminocyclohexylamino] |
| 492 | H | H | ![R3 structure: 4-(benzamide with 3-CN phenyl)] | Me | ![trans-4-aminocyclohexylamino] |
| 493 | H | H | ![R3 structure: 4-(benzamide with 4-CN phenyl)] | Me | ![trans-4-aminocyclohexylamino] |
| 494 | H | H | ![R3 structure: 4-(benzamide with 2-OMe phenyl)] | Me | ![trans-4-aminocyclohexylamino] |
| 495 | H | H | ![R3 structure: 4-(benzamide with 3-OMe phenyl)] | Me | ![trans-4-aminocyclohexylamino] |

-continued

| Compound No. | R¹ | R² | R³ | R⁴ | NR⁵R⁶ |
|---|---|---|---|---|---|
| 496 | H | H | 4-MeO-C₆H₄-NHC(O)-C₆H₄- | Me | trans-4-aminocyclohexyl-NH- |
| 497 | H | H | (1H-indol-5-yl)-NHC(O)-C₆H₄- | Me | trans-4-aminocyclohexyl-NH- |
| 498 | H | H | (1H-indol-6-yl)-NHC(O)-C₆H₄- | Me | trans-4-aminocyclohexyl-NH- |
| 499 | H | H | (1H-indol-4-yl)-NHC(O)-C₆H₄- | Me | trans-4-aminocyclohexyl-NH- |

-continued

| Compound No. | R¹ | R² | R⁴ | R³ | NR⁵R⁶ |
|---|---|---|---|---|---|
| 500 | H | H | Me | 4-[(2-acetylphenyl)carbamoyl]phenyl | trans-4-aminocyclohexylamino |
| 501 | H | H | Me | 4-[(3-acetylphenyl)carbamoyl]phenyl | trans-4-aminocyclohexylamino |
| 502 | H | H | Me | 4-[(4-propanoylphenyl)carbamoyl]phenyl | trans-4-aminocyclohexylamino |
| 503 | H | H | Me | 4-[(2-carbamoylphenyl)carbamoyl]phenyl | trans-4-aminocyclohexylamino |

-continued
| Compound No. | R¹ | R² | R⁴ | R³ | NR⁵R⁶ |
|---|---|---|---|---|---|
| 504 | H | H | Me |  | 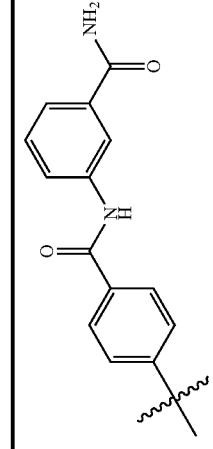 |
| 505 | H | H | Me |  | 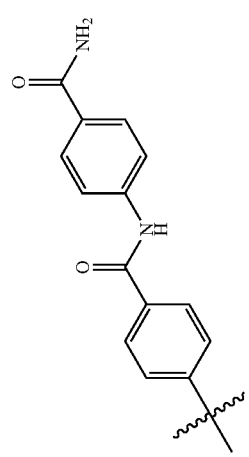 |
| 506 | H | H | Me |  | 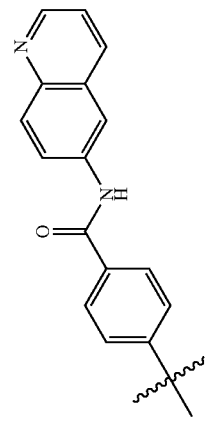 |
| 507 | H | H | Me |  | 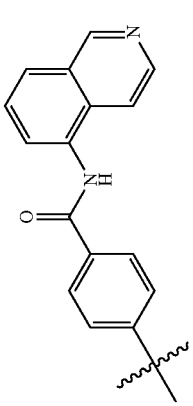 |

-continued

| Compound No. | R¹ | R² | R⁴ | R³ | NR⁵R⁶ |
|---|---|---|---|---|---|
| 508 | H | H | Me | 4-(quinolin-8-ylcarbamoyl)phenyl | trans-4-aminocyclohexylamino |
| 509 | H | H | Me | 4-(quinolin-5-ylcarbamoyl)phenyl | trans-4-aminocyclohexylamino |
| 510 | H | H | Me | 4-(benzylcarbamoyl)phenyl | trans-4-aminocyclohexylamino |
| 511 | H | H | Me | 4-(furan-2-ylmethylcarbamoyl)phenyl | trans-4-aminocyclohexylamino |
| 512 | H | H | Me | 4-(thiophen-2-ylmethylcarbamoyl)phenyl | trans-4-aminocyclohexylamino |

| Compound No. | R¹ | R² | R³ | R⁴ | NR⁵R⁶ |
|---|---|---|---|---|---|
| 513 | H | H | 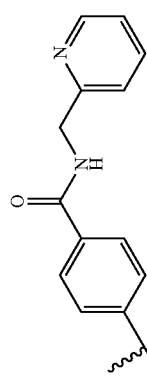 | Me | 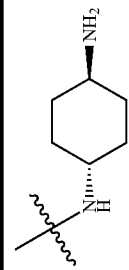 |
| 514 | H | H | 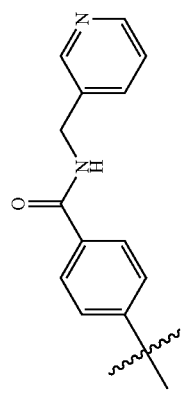 | Me | 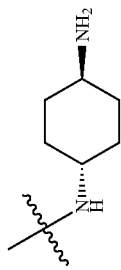 |
| 515 | H | H | 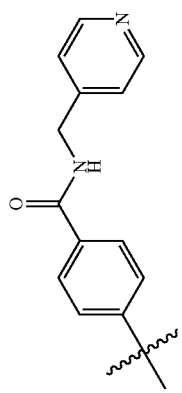 | Me | 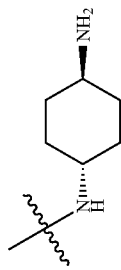 |
| 516 | H | H | 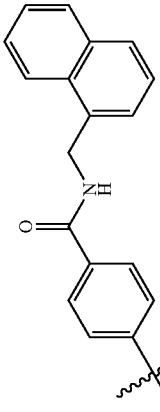 | Me | 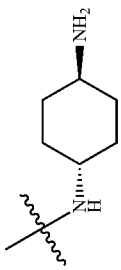 |
| 517 | H | H | 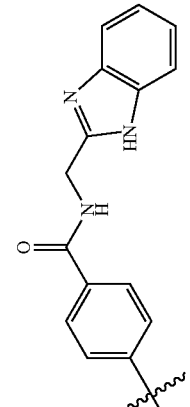 | Me | 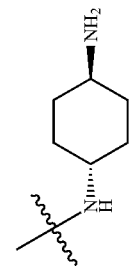 |

-continued

| Compound No. | R¹ | R² | R⁴ | R³ | NR⁵R⁶ |
|---|---|---|---|---|---|
| 518 | H | H | Me | 4-(PhCH₂CH₂NHC(O))-phenyl | trans-4-aminocyclohexylamino |
| 519 | H | H | Me | 4-(3-pyridyl-CH₂CH₂NHC(O))-phenyl | trans-4-aminocyclohexylamino |
| 520 | H | H | Me | 4-(4-pyridyl-CH₂CH₂NHC(O))-phenyl | trans-4-aminocyclohexylamino |
| 521 | H | H | Me | 4-(imidazol-1-yl-CH₂CH₂CH₂NHC(O))-phenyl | trans-4-aminocyclohexylamino |
| 522 | H | H | Me | 4-((1H-imidazol-4-yl)CH₂CH₂NHC(O))-phenyl | trans-4-aminocyclohexylamino |

-continued
| Compound No. | R¹ | R² | R³ | R⁴ | NR⁵R⁶ |
|---|---|---|---|---|---|
| 523 | H | H | 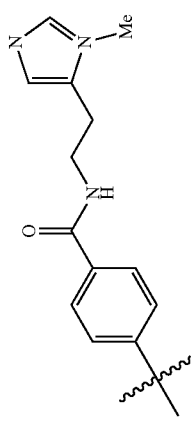 | Me | 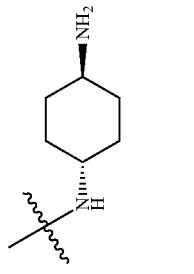 |
| 524 | H | 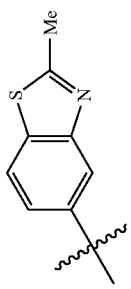 | 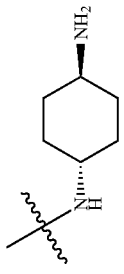 | H | 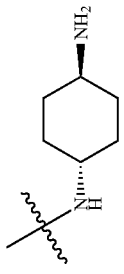 |
| 525 | Me | 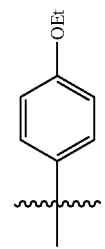 | 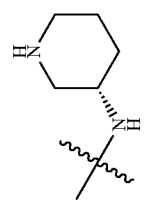 | Me | 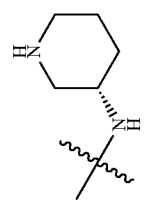 |
| 526 | H | 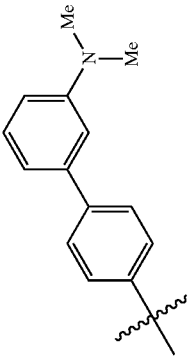 | 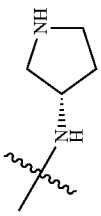 | OMe | 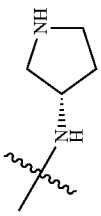 |
| 527 | H | 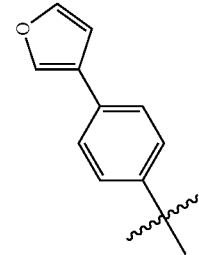 | 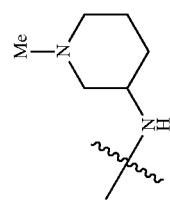 | Et | 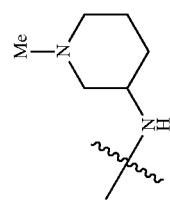 |

-continued

| Compound No. | R¹ | R² | R⁴ | R³ | NR⁵R⁶ |
|---|---|---|---|---|---|
| 528 | H | | | | |
| 529 | H | | | | |
| 530 | H | | | | |
| 531 | H | | Me | | |
| 532 | H | | H | | |
| 533 | H | | Et | | |

-continued
| Compound No. | R¹ | R² | R⁴ | R³ | NR⁵R⁶ |
|---|---|---|---|---|---|
| 534 | H | 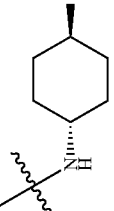 | OMe | 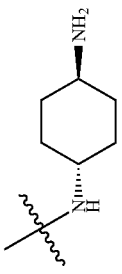 | 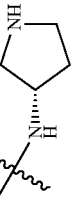 |
| 535 | H | 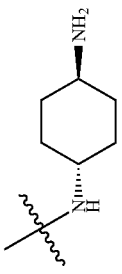 | Me | 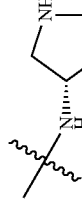 | 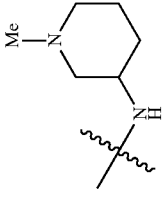 |
| 536 | H | 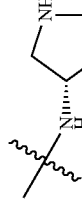 | Me | 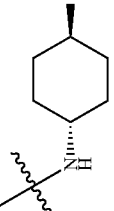 | 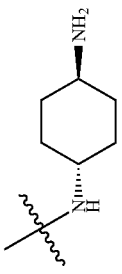 |
| 537 | H | 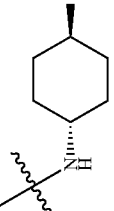 | 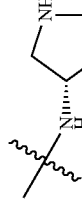 | 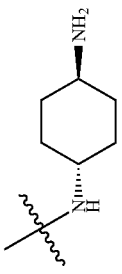 | 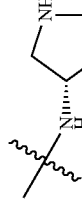 |
| 538 | H | 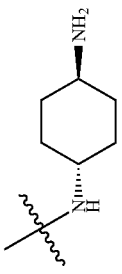 | H | | 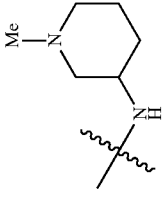 |

-continued

| Compound No. | R¹ | R² | R⁴ | R³ | NR⁵R⁶ |
|---|---|---|---|---|---|
| 539 | H | furan-2-ylmethoxy | Et | isobenzofuran-1(3H)-one-5-yl | trans-4-aminocyclohexylamino |
| 540 | H | (1-methyl-1H-pyrrol-3-yl)methoxy | cyclopentyl | cyclopropylmethyl | trans-4-aminocyclohexylamino |
| 541 | H | 2-methoxyethylamino | Me | thiophen-3-ylmethyl | piperidin-3-ylamino |
| 542 | H | pyrrolidin-1-yl | Et | 2-methylbenzothiazol-6-ylmethyl | pyrrolidin-3-ylamino |
| 543 | Me | dibenzylamino | OMe | 1H-indol-5-ylmethyl | trans-4-aminocyclohexylamino |
| 544 | H | benzylamino | H | 5-(methoxycarbonyl)-1,4-dimethyl-1H-pyrrol-3-ylmethyl | piperidin-3-ylamino |

-continued
| Compound No. | R¹ | R² | R⁴ | R³ | NR⁵R⁶ |
|---|---|---|---|---|---|
| 545 | H | 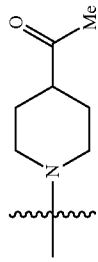 | Me | 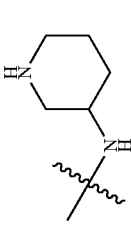 | 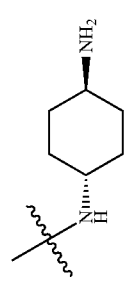 |
| 546 | H | 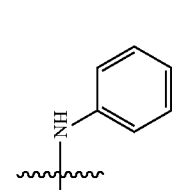 | 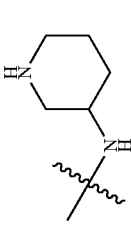 | 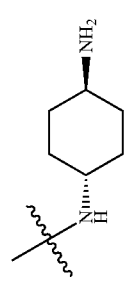 | 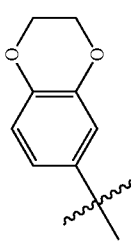 |
| 547 | H | 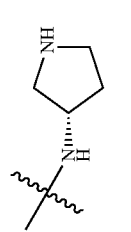 | H | 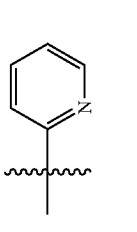 | 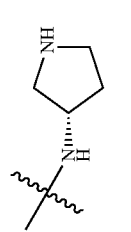 |
| 548 | H | 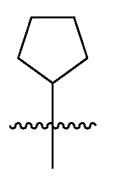 | H | 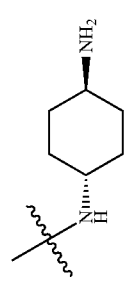 | 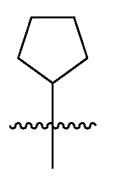 |
| 549 | H | 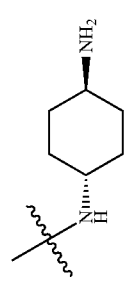 |  |  |  |
| 550 | H |  | Et |  |  |

-continued
| Compound No. | R¹ | R² | R⁴ | R³ | NR⁵R⁶ |
|---|---|---|---|---|---|
| 551 | H | 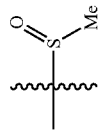 | H | 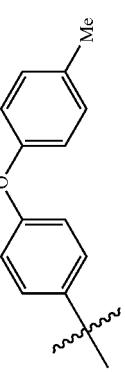 | 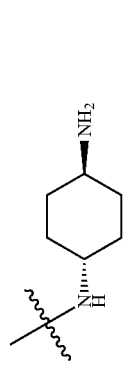 |
| 552 | H | 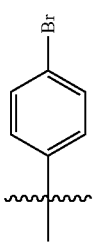 | Et | 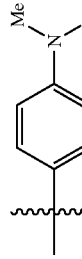 | 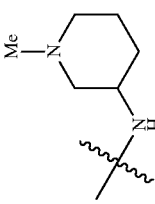 |
| 553 | H | 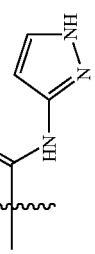 | OMe | 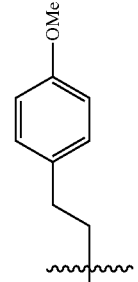 | 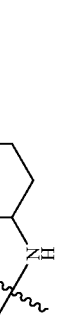 |
| 554 | H | 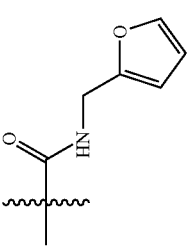 | H | 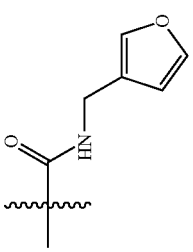 | 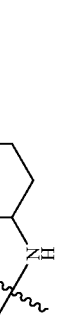 |
| 555 | H | 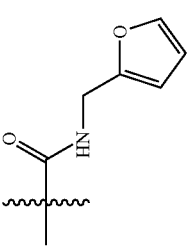 | Et | 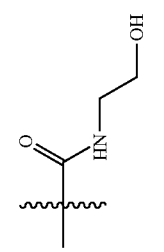 | 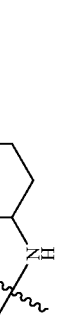 |

-continued
| Compound No. | R¹ | R² | R⁴ | R³ | NR⁵R⁶ |
|---|---|---|---|---|---|
| 556 | H | 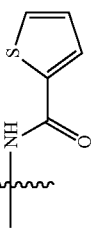 | Me | 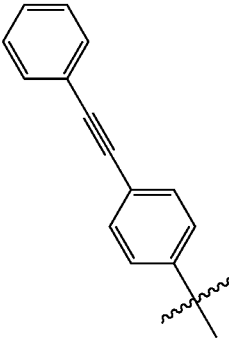 | 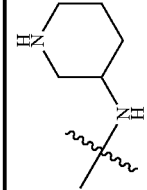 |
| 557 | H | 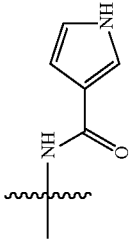 | Me | 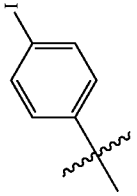 | 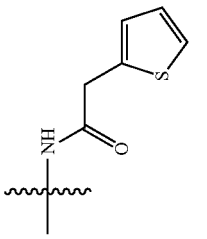 |
| 558 | Me | 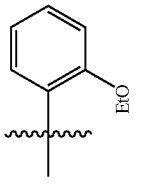 | OMe | 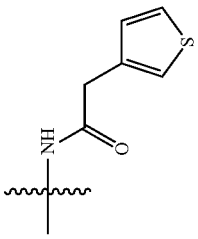 | 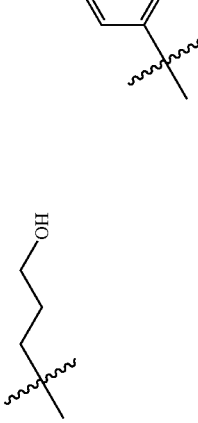 |
| 559 | H | | | | |

-continued

| Compound No. | R¹ | R² | R⁴ | R³ | NR⁵R⁶ |
|---|---|---|---|---|---|
| 560 | H | -NH-C(O)-CH₂-N(Me)Me | Et | 2-acetyl-5-(phenyl)thiophene | 1-Me-piperidin-3-yl-NH- |
| 561 | H | -NH-C(O)-NH-(thiophen-2-yl) | cyclopentyl | 3-chloro-4-fluorobenzyl | trans-4-aminocyclohexyl-NH- |
| 562 | H | -NH-C(O)-NH-(thiophen-3-yl) | Me | 3,4,5-trimethoxyphenyl | piperidin-3-yl-NH- |
| 563 | H | 1-phenyl-imidazolidin-2-on-3-yl | H | 4-(COOEt)phenyl | pyrrolidin-3-yl-NH- |
| 564 | H | CF₃ | Me | 4-(aminomethyl)phenyl | piperidin-3-yl-NH- |

-continued

| Compound No. | R¹ | R² | R⁴ | R³ | NR⁵R⁶ |
|---|---|---|---|---|---|
| 565 | H | OCF₃ | H | 3-(indol-3-yl)propyl | trans-4-aminocyclohexylamino |
| 566 | H | 1,3-dithiolan-2-yl | Me | 2-methyl-1H-indol-5-yl | (3R)-piperidin-3-ylamino |
| 567 | H | 1,3-dithian-2-yl | Et | 2-fluorophenyl | trans-4-aminocyclohexylamino |
| 568 | H | 2-oxopyrrolidin-1-yl | H | Ph | (3S)-pyrrolidin-3-ylamino |
| 569 | H | H | Me | 2-(methylthio)benzothiazol-6-yl | trans-4-aminocyclohexylamino |
| 570 | H | H | Me | 2-methylbenzoxazol-6-yl | (3R)-piperidin-3-ylamino |

-continued

| Compound No. | R¹ | R² | R⁴ | R³ | NR⁵R⁶ |
|---|---|---|---|---|---|
| 571 | H | F | 4-MeO-C₆H₄- | 1H-benzotriazol-5-yl | trans-4-aminocyclohexylamino |
| 572 | H | Br | H | 2-mercaptobenzothiazol-6-yl | (R)-pyrrolidin-3-ylamino |
| 573 | H | -NHC(O)CH₂CH₂OMe | Me | 2-phenylbenzothiazol-6-yl | piperidin-3-ylamino |
| 574 | H | F | Et | 2-(acetylamino)benzothiazol-6-yl | piperidin-3-ylamino |
| 575 | H | H | Me | 2-(benzoylamino)benzothiazol-6-yl | trans-4-aminocyclohexylamino |
| 576 | H | -NHC(O)CH₂-(pyridin-4-yl) | -(CH₂)₃OH | 1-methyl-1H-indazol-5-yl | 2-aminoethylamino |

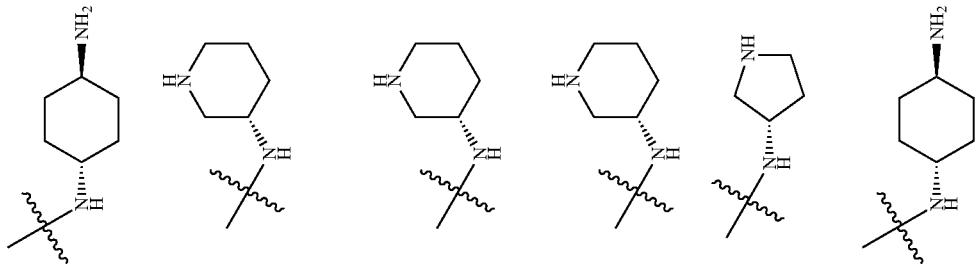

-continued
| Compound No. | R¹ | R² | R⁴ | R³ | NR⁵R⁶ |
|---|---|---|---|---|---|
| 583 | H | 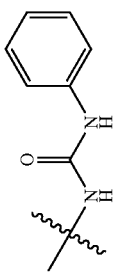 | H | 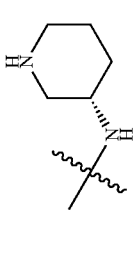 | 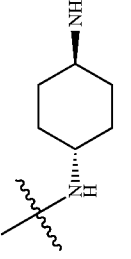 |
| 584 | H | F | H | 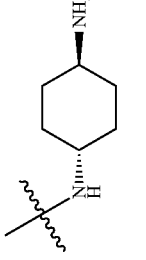 |  |
| 585 | H | F | OMe | 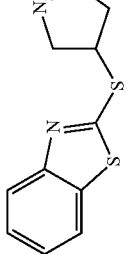 | 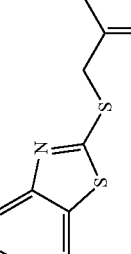 |
| 586 | H | Me | H | 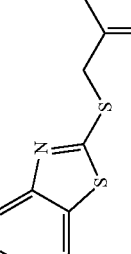 | 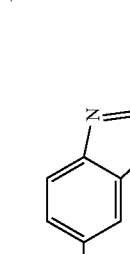 |
| 587 | H | F | Me | 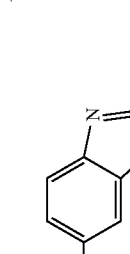 | 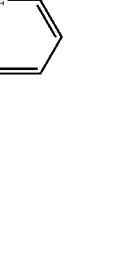 |

-continued

| Compound No. | R¹ | R² | R⁴ | R³ | NR⁵R⁶ |
|---|---|---|---|---|---|
| 588 | H | PhNHC(O)NH- | H | 6-(3-aminophenyl)benzothiazol-2-yl | (3R)-pyrrolidin-3-ylamino |
| 589 | H | F | OMe | 2-(cyclopropanecarbonylamino)benzothiazol-6-yl | trans-4-aminocyclohexylamino |
| 590 | H | H | 5-hydroxypentyl | 2-(phenylacetylamino)benzothiazol-6-yl | trans-4-aminocyclohexylamino |
| 591 | H | CF₃C(O)NH- | Me | 2-(trifluoroacetylamino)benzothiazol-6-yl | trans-4-aminocyclohexylamino |
| 592 | H | F | cyclopentyl | 2-(phenylsulfonylamino)benzothiazol-6-yl | (3R)-pyrrolidin-3-ylamino |
| 593 | H | F | H | 2-(3-methylureido)benzothiazol-6-yl | trans-4-aminocyclohexylamino |

-continued
| Compound No. | R¹ | R² | R³ | R⁴ | NR⁵R⁶ |
|---|---|---|---|---|---|
| 594 | H | Me | 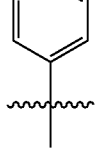 | 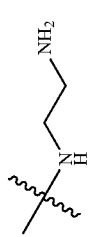 | 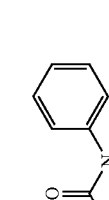 |
| 595 | H |  | 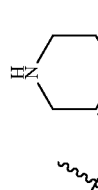 | Me | 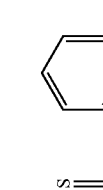 |
| 596 | H | F |  | H |  |
| 597 | H | F |  | H |  |
| 598 | H | F |  | H | |
| 599 | H | H | | OMe | |

| Compound No. | R¹ | R² | R⁴ | R³ | NR⁵R⁶ |
|---|---|---|---|---|---|
| 600 | H | (amide-CH₂CH₂-OMe) | Me | thiazol-2-yl | trans-4-aminocyclohexylamino |
| 601 | H | F | Me | 4,5-dihydrooxazol-2-yl | piperidin-3-ylamino |
| 602 | H | F | Me | 1H-pyrazol-3-yl | 2-aminoethylamino |
| 603 | H | (amide-NH-pyridin-4-yl) | H | thien-2-yl | piperidin-3-ylamino |
| 604 | H | H | Me | furan-2-yl | trans-4-aminocyclohexylamino |
| 605 | H | F | Me | 5-phenyl-1H-pyrazol-3-yl | pyrrolidin-3-ylamino |
| 606 | H | F | Me | 4-phenylthiazol-2-yl | piperidin-3-ylamino |

-continued

| Compound No. | R¹ | R² | R⁴ | R³ | NR⁵R⁶ |
|---|---|---|---|---|---|
| 607 | H | F | H | 3-chloro-4-(pyrrolidin-3-yloxy)phenyl | trans-4-aminocyclohexylamino |
| 608 | H | H | Et | 4-(2-aminopyrimidin-5-yl)phenyl | (piperidin-3-yl)amino |
| 609 | H | NHC(O)CF₃ | H | 5-acetylthiophen-2-yl (3-chloro-4-phenyl) | (piperidin-3-yl)amino |
| 610 | H | NH₂ | cyclopentyl | 4-(2-aminopyrimidin-5-yl)-3-chlorophenyl | trans-4-aminocyclohexylamino |
| 611 | H | F | Me | 3-chloro-4-ethoxyphenyl | (pyrrolidin-3-yl)amino |
| 612 | H | NHC(O)NHPh | Me | 4-ethoxy-3-methylphenyl | (piperidin-3-yl)amino |

-continued
| Compound No. | R¹ | R² | R⁴ | R³ | NR⁵R⁶ |
|---|---|---|---|---|---|
| 613 | H | F | H |  | |
| 614 | H | Me | Me | 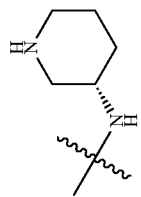 | |
| 615 | H | F | H | 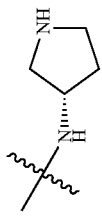 | |
| 616 | H | H | Me | 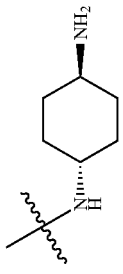 | |
| 617 | H | H | Me | 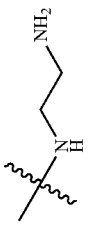 | |
| 618 | H | H | 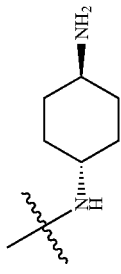 | | |

-continued

| Compound No. | R¹ | R² | R³ | R⁴ | NR⁵R⁶ |
|---|---|---|---|---|---|
| 619 | H | H | 4-(pyrrolidin-3-ylcarboxamido)phenyl | Me | (3R)-piperidin-3-ylamino |
| 620 | H | F | 4-((piperidin-2-yl)acetamido)phenyl | Me | trans-4-aminocyclohexylamino |
| 621 | H | NH₂ | 4-((piperidin-2-yl)methylcarbamoyl)phenyl | H | trans-4-aminocyclohexylamino |
| 622 | H | F | 3-((morpholin-4-yl)methyl)phenylamino | Et | piperidin-3-ylamino |

-continued
| Compound No. | R¹ | R² | R⁴ | R³ | NR⁵R⁶ |
|---|---|---|---|---|---|
| 623 | H | H | Me | 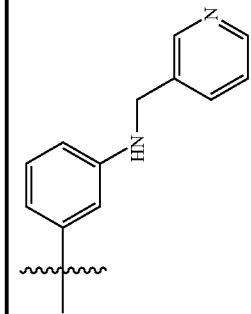 | 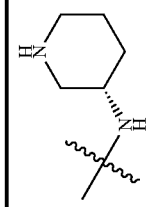 |
| 624 | H | NH₂ | H | 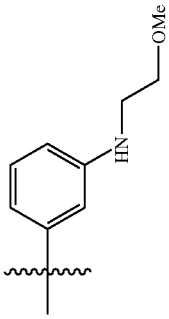 | 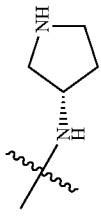 |
| 625 | H | F | 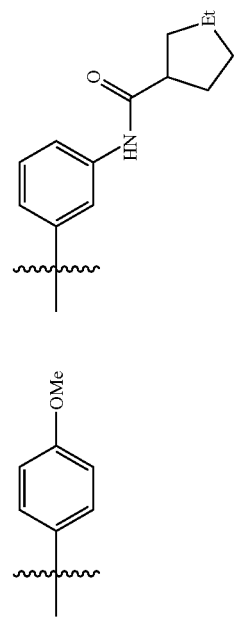 | | 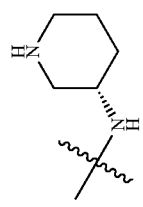 |
| 626 | H | 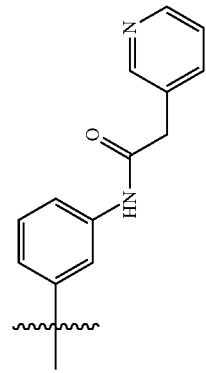 | H | | 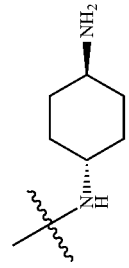 |

-continued
| Compound No. | R¹ | R² | R³ | R⁴ | NR⁵R⁶ |
|---|---|---|---|---|---|
| 627 | H | Br | 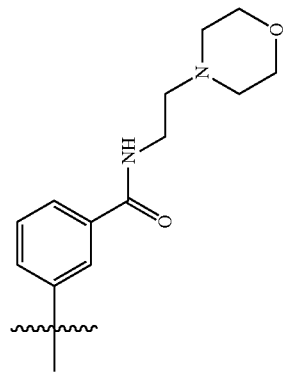 | Me | 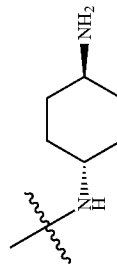 |
| 628 | H | H | 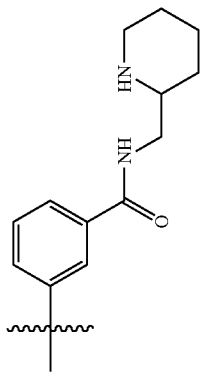 | 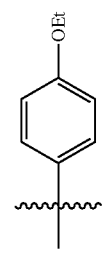 | 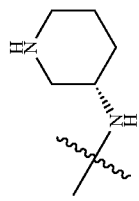 |
| 629 | H | H | 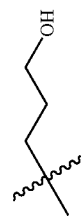 | Me | 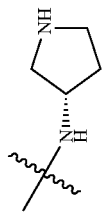 |
| 630 | H | H | 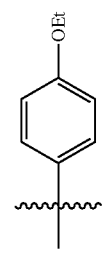 | Me | 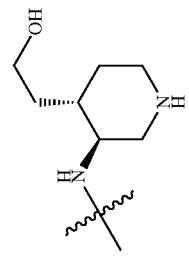 |

-continued

| Compound No. | R¹ | R² | R⁴ | R³ | NR⁵R⁶ |
|---|---|---|---|---|---|
| 631 | H | H | Me | 4-OEt-phenyl | (3-NH-, 4-CH₂CH₂OH)-piperidinyl |
| 632 | H | H | Me | 4-OEt-phenyl | (3-NH-, 4-CH₂C(O)OMe)-piperidinyl |
| 633 | H | H | Me | 4-OEt-phenyl | (3-NH-, 4-CH₂C(O)OMe)-piperidinyl |
| 634 | H | H | Me | 4-OEt-phenyl | (3-NH-, 4-CH₂C(O)OH)-piperidinyl |

-continued
| Compound No. | R¹ | R² | R⁴ | R³ | NR⁵R⁶ |
|---|---|---|---|---|---|
| 635 | H | H | Me | 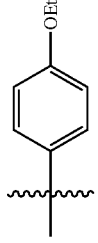 | 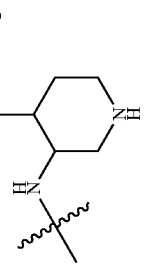 |
| 636 | H | H | Me | 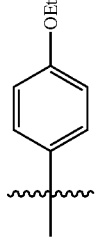 | 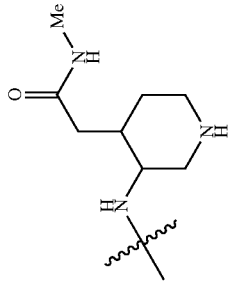 |
| 637 | H | H | Me | 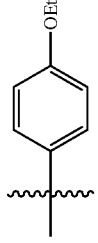 | 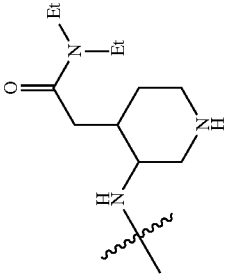 |
| 638 | H | H | Me | 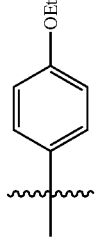 | 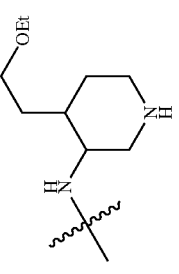 |

| Compound No. | R¹ | R² | R⁴ | R³ | NR⁵R⁶ |
|---|---|---|---|---|---|
| 639 | H | H | Me | 4-OEt-phenyl | 4-(hydroxymethyl)-3-(NH-)piperidine |
| 640 | H | H | Me | 4-OEt-phenyl | 4-carboxy-3-(NH-)piperidine |
| 641 | H | H | Me | 4-OEt-phenyl | 4-(CO-OMe)-3-(NH-)piperidine |
| 642 | H | H | Me | 4-OEt-phenyl | 4-(CO-NH₂)-3-(NH-)piperidine |

-continued

| Compound No. | R¹ | R² | R⁴ | R³ | NR⁵R⁶ |
|---|---|---|---|---|---|
| 643 | H | H | Me | 4-OEt-phenyl | 3-(methylcarbamoyl)piperidin-3-ylamino (Me-NH-C(O)- on piperidine C4, NH-linker on C3) |
| 644 | H | H | Me | 4-OEt-phenyl | 3-(N,N-dimethylcarbamoyl)piperidin-3-ylamino |
| 645 | H | H | Me | 4-OEt-phenyl | 3-(methoxymethyl)piperidin-3-ylamino |
| 646 | H | H | Me | 2-methylbenzothiazol-6-yl | 3-methylpiperidin-3-ylamino |

| Compound No. | R¹ | R² | R⁴ | R³ | NR⁵R⁶ |
|---|---|---|---|---|---|
| 647 | H | H | Me | 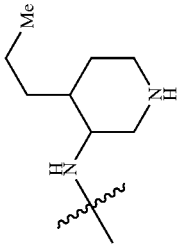 | 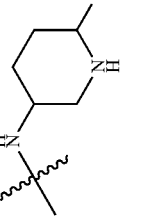 |
| 648 | H | H | Me | 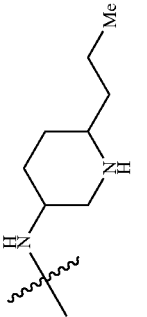 | 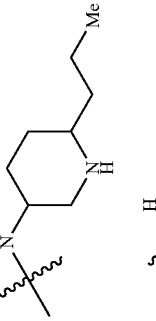 |
| 649 | H | H | Me | 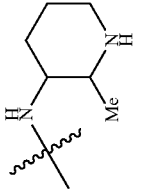 | 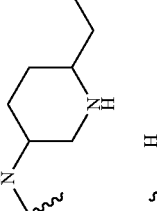 |
| 650 | H | F | Me | 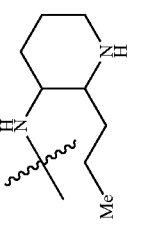 | 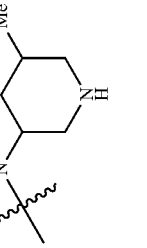 |
| 651 | H | F | Me | 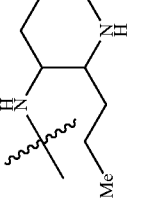 | 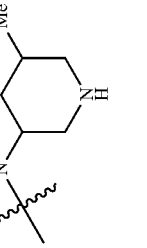 |
| 652 | H | H | Et | 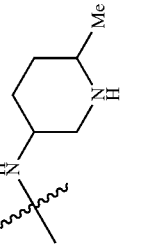 |  |

-continued
| Compound No. | R¹ | R² | R⁴ | R³ | NR⁵R⁶ |
|---|---|---|---|---|---|
| 653 | H | H | Me |  | 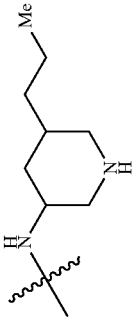 |
| 654 | H | H | Me | 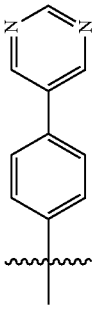 | 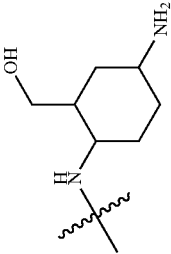 |
| 655 | H | H | Me | 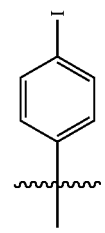 | 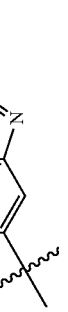 |
| 656 | H | H | Me | 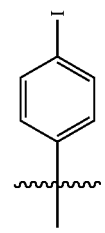 | 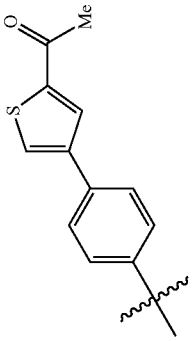 |
| 657 | H | F | Me | 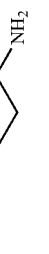 | 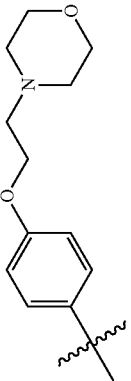 |

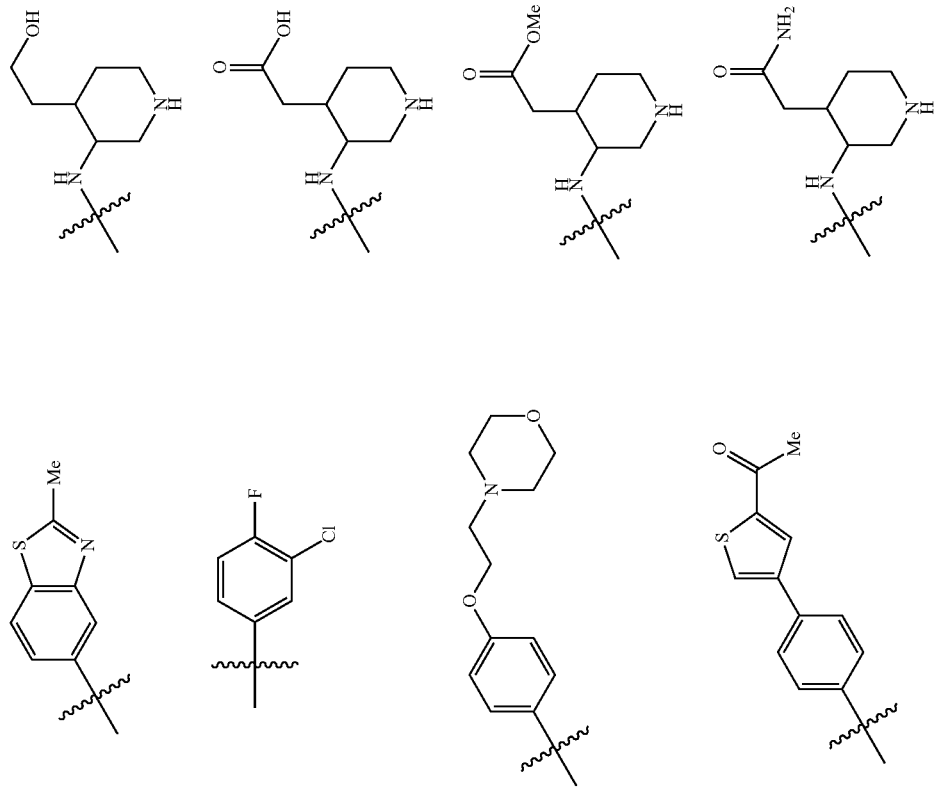

-continued
| Compound No. | R¹ | R² | R⁴ | R³ | NR⁵R⁶ |
|---|---|---|---|---|---|
| 662 | H | F | Me | 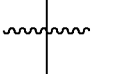 | 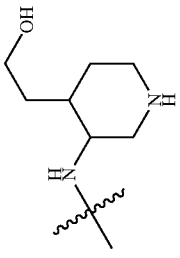 |
| 663 | H | H | Me | 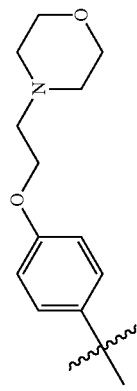 | 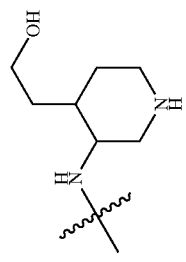 |
| 664 | H | F | Me | 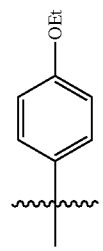 | 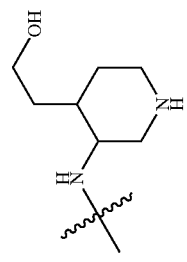 |
| 665 | H | F | Me | 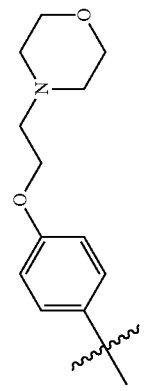 | 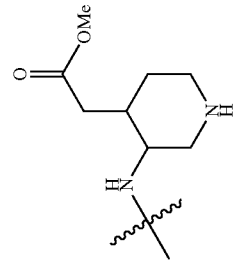 |

-continued
| Compound No. | R¹ | R² | R⁴ | R³ | NR⁵R⁶ |
|---|---|---|---|---|---|
| 666 | H | F | Et | 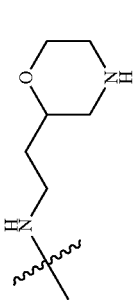 | 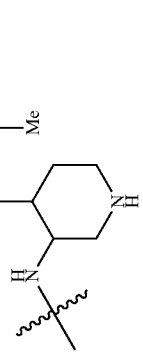 |
| 667 | H | H | Me | 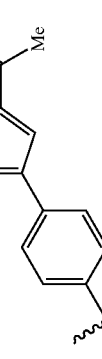 | 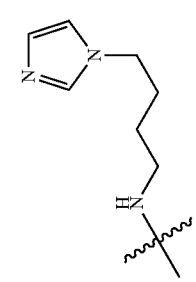 |
| 668 | H | F | Me | 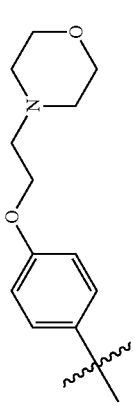 | 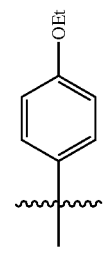 |
| 669 | H | H | Me |  | 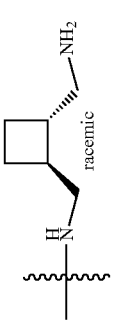 |
| 670 | H | H | Me |  | 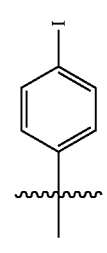 |

| Compound No. | R¹ | R² | R⁴ | R³ | NR⁵R⁶ |
|---|---|---|---|---|---|
| 671 | H | F | Me |  | 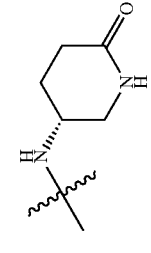 |
| 672 | H | H | Me | 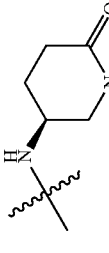 | 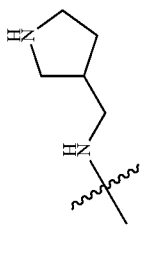 |
| 673 | H | F | Me |  | 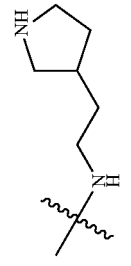 |
| 674 | H | H | Me | 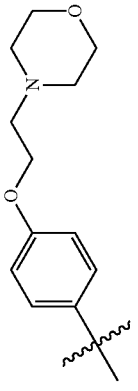 | 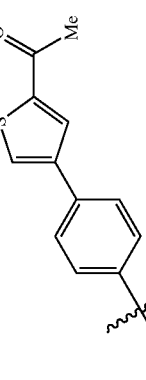 |
| 675 | H | H | Me | 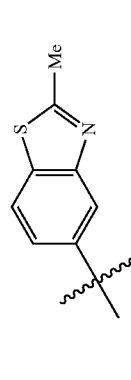 | 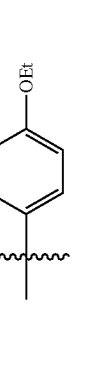 |
| 676 | H | H | Me | 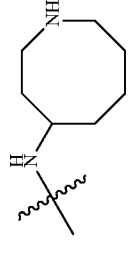 |  |

-continued
| Compound No. | R¹ | R² | R⁴ | R³ | NR⁵R⁶ |
|---|---|---|---|---|---|
| 677 | H | H | Me | 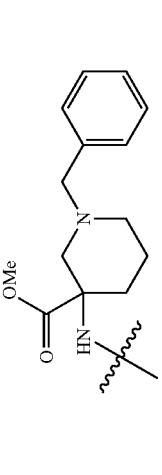 | 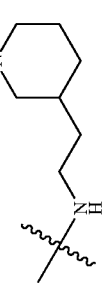 |
| 678 | H | F | Me | 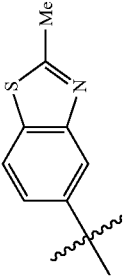 | 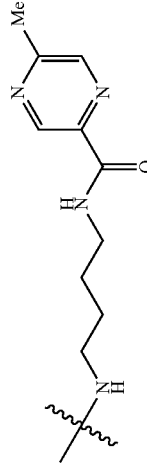 |
| 679 | H | H | Me | 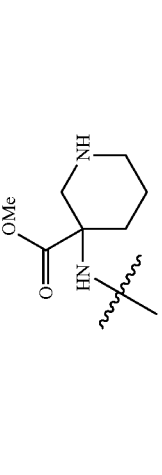 | 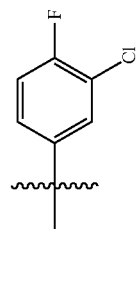 |
| 680 | H | H | Me | 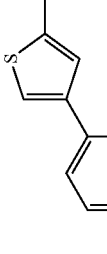 | 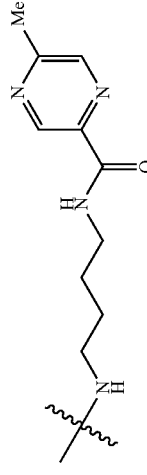 |
| 681 | H | H | Me |  | 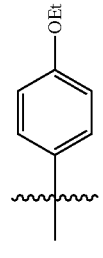 |

-continued

| Compound No. | R¹ | R² | R⁴ | R³ | NR⁵R⁶ |
|---|---|---|---|---|---|
| 682 | H | H | Me | 4-(2-morpholinoethoxy)phenyl | 2,3,4,5-tetrahydro-1H-benzo[b]azepin-5-ylamino |
| 683 | H | F | Me | 4-iodophenyl | methyl 2-(piperidin-4-yl)-2-aminoacetate |
| 684 | H | H | Me | 4-ethoxyphenyl | 4-methylpyrrolidin-3-ylamino |
| 685 | H | H | Me | 4-(pyrimidin-5-yl)phenyl | 3-(hydroxymethyl)pyrrolidin-3-ylamino |
| 686 | H | H | Me | 2-methylbenzo[d]thiazol-5-yl | methyl 4-aminopyrrolidine-2-carboxylate |

-continued
| Compound No. | R¹ | R² | R⁴ | R³ | NR⁵R⁶ |
|---|---|---|---|---|---|
| 687 | H | H | Me | 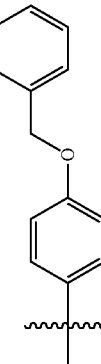 | 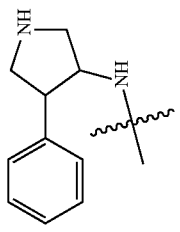 |
| 688 | H | H | Me | 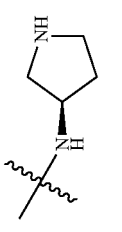 | 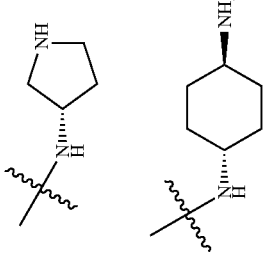 |
| 689 | H | H | Me | 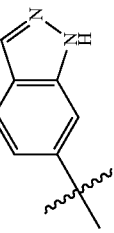 | 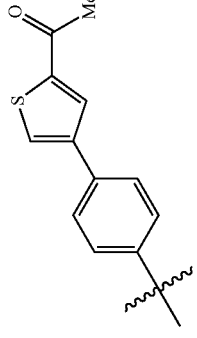 |
| 690 | H | H | Me | 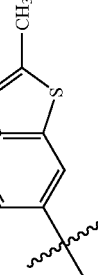 | 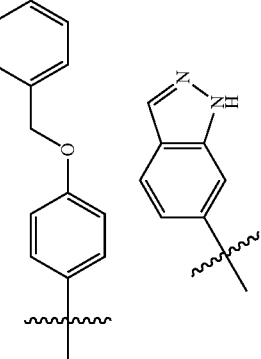 |
| 691 | H | F | Me | 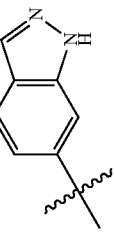 | 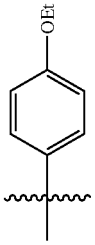 |
| 692 | H | H | Me | 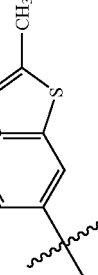 | 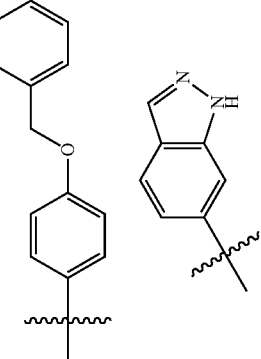 |

-continued
| Compound No. | R¹ | R² | R⁴ | R³ | NR⁵R⁶ |
|---|---|---|---|---|---|
| 693 | H | F | Et | 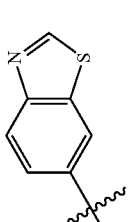 | 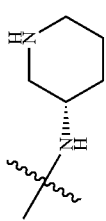 |
| 694 | H | H | Me | 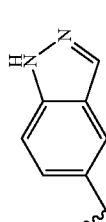 | 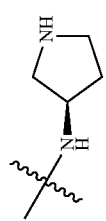 |
| 695 | H | F | Me | 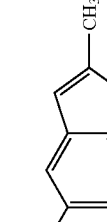 | 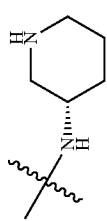 |
| 696 | H | H | Me |  | 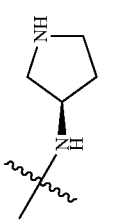 |
| 697 | H | F | Me | 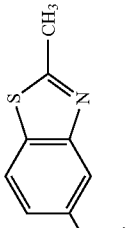 | 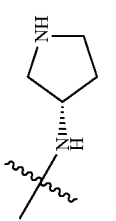 |
| 698 | H | H | Me | 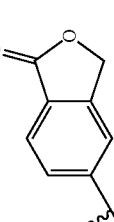 | 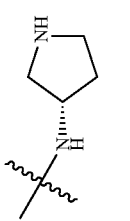 |

-continued
| Compound No. | R¹ | R² | R⁴ | R³ | NR⁵R⁶ |
|---|---|---|---|---|---|
| 699 | H | F | Me | 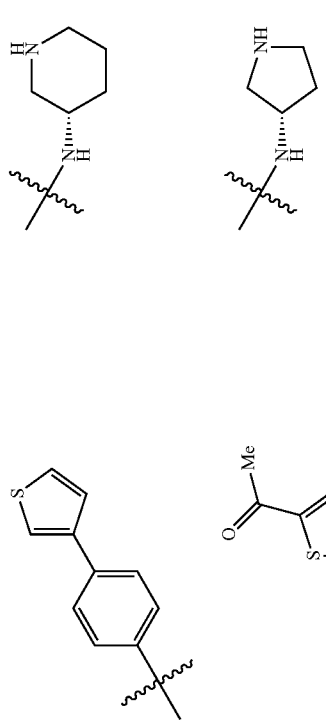 | 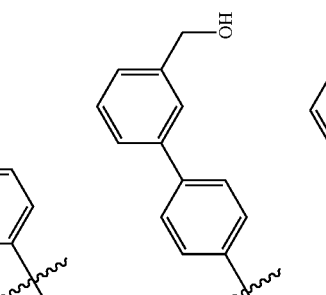 |
| 700 | H | H | Me | 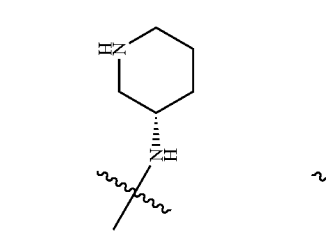 | 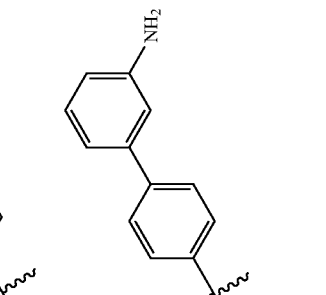 |
| 701 | H | F | Me | 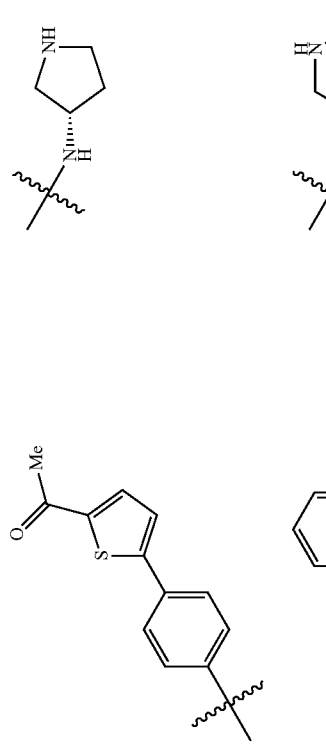 | 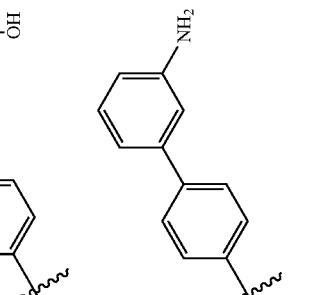 |
| 702 | H | H | Et | 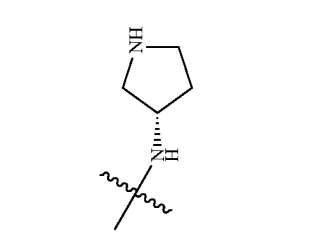 | 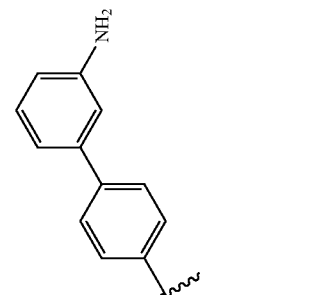 |

-continued

| Compound No. | R¹ | R² | R⁴ | R³ | NR⁵R⁶ |
|---|---|---|---|---|---|
| 703 | H | F | Me | 5-(pyrimidinyl)phenyl | trans-4-aminocyclohexylamino |
| 704 | H | H | Me | 4-(2-morpholinoethoxy)phenyl | (3R)-pyrrolidin-3-ylamino |
| 705 | H | F | Et | 4-(pyridin-3-ylmethoxy)phenyl | pyrrolidin-3-ylamino |
| 706 | H | H | Me | 4-(2-(pyridin-2-yl)ethoxy)phenyl | (3S)-pyrrolidin-3-ylamino |
| 707 | H | F | Me | 4-(pyrrolidin-3-yloxy)phenyl | trans-4-aminocyclohexylamino |

-continued

| Compound No. | R¹ | R² | R⁴ | R³ | NR⁵R⁶ |
|---|---|---|---|---|---|
| 708 | H | (3-pyridyl-NH-C(O)-C(CH₃)₂-) | Me | (4-(tetrahydrofuran-2-ylmethoxy)phenyl-C(CH₃)₂-) | (pyrrolidin-3-yl-NH-) |
| 709 | H | Cl | H | (2-chlorobenzyl-C(CH₃)₂-) | (4-aminocyclohexyl-NH-) |
| 710 | H | Cl | H | (3-phenylpropyl-) | (trans-4-aminocyclohexyl-NH-) |
| 711 | H | Cl | H | (4-fluoro-3-chlorobenzyl-C(CH₃)₂-) | (HOCH₂-CH(CH(CH₃)₂)-NH-) |
| 712 | H | Cl | H | (2-chlorobenzyl-CH(CH₃)-) | (HOCH₂-C(CH₃)₂-NH-) |

-continued
| Compound No. | R¹ | R² | R³ | R⁴ | NR⁵R⁶ |
|---|---|---|---|---|---|
| 713 | H | Cl | 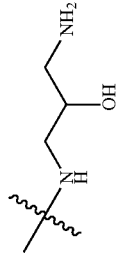 | H | 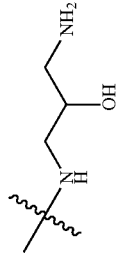 |
| 714 | H | Cl | 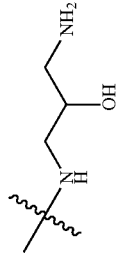 | H | 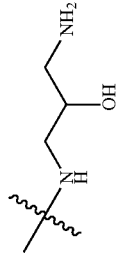 |
| 715 | H | Cl | 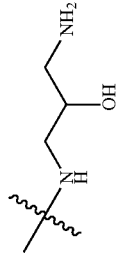 | H | 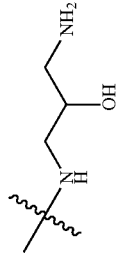 |
| 716 | H | Cl | 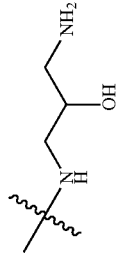 | Me | 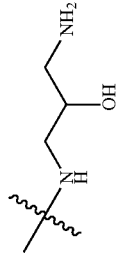 |
| 717 | H | Cl | (see above) | H | (see above) |

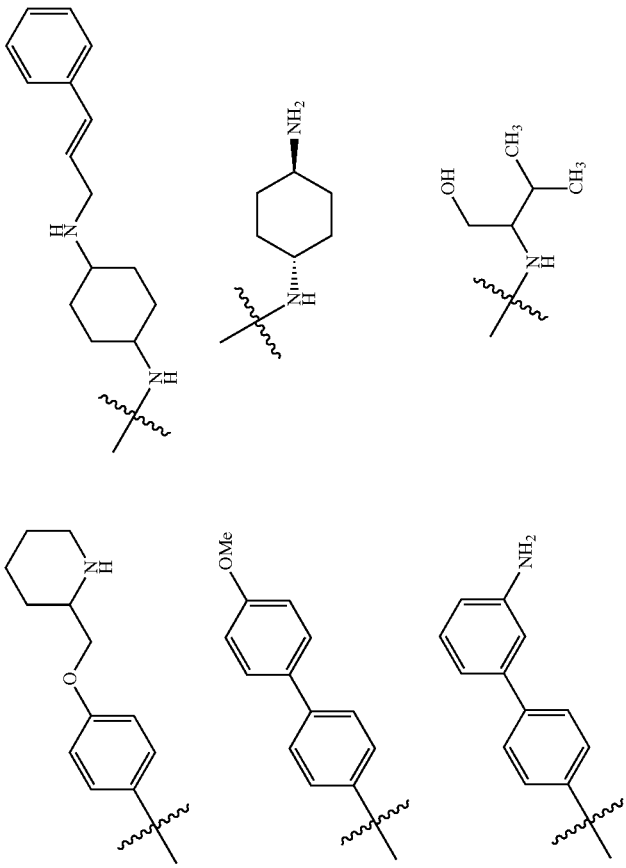

-continued

| Compound No. | R¹ | R² | R⁴ | R³ | NR⁵R⁶ |
|---|---|---|---|---|---|
| 723 | H | Br | H | thiophen-3-yl-phenyl | NH-C(CH₃)-CH₂OH |
| 724 | H | Br | H | 4-(methoxycarbonyl)phenyl | NH-C(CH₃)₂-CH₂OH |
| 725 | H | Br | H | 2-chlorobenzyl | NH-CH₂-CH(OH)-CH₂-NH₂ |
| 726 | H | Br | H | 4-(pyrimidin-5-yl)phenyl | N(Me)-piperidin-3-yl |
| 727 | H | I | H | 3-(methylsulfonylamino)phenyl | NH-(trans-4-aminocyclohexyl) |

-continued
| Compound No. | R¹ | R² | R⁴ | R³ | NR⁵R⁶ |
|---|---|---|---|---|---|
| 728 | H | I | H | 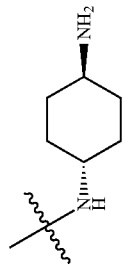 | 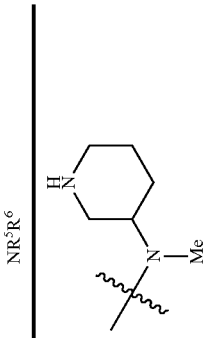 |
| 729 | H | I | H | 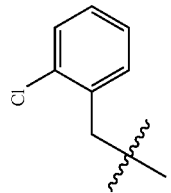 | 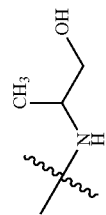 |
| 730 | H | I | H | 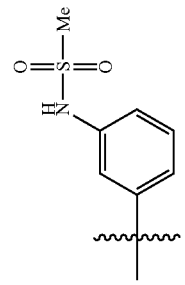 | 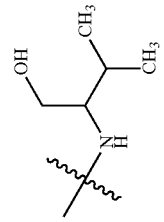 |
| 731 | H | I | H | 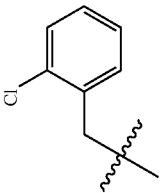 | 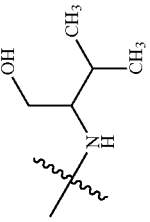 |
| 732 | H | 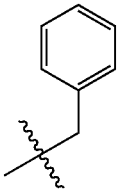 | H | 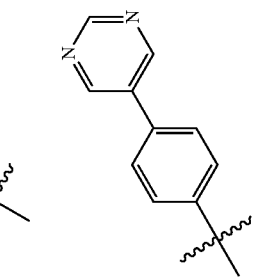 | |

-continued

| Compound No. | R¹ | R² | R⁴ | R³ | NR⁵R⁶ |
|---|---|---|---|---|---|
| 733 | H | benzyl | H | 3-(MeSO₂NH)phenyl | trans-4-aminocyclohexyl |
| 734 | H | Me | H | 2-chlorobenzyl | trans-4-aminocyclohexyl |
| 735 | H | Me | H | 4-(pyrimidin-5-yl)phenyl | 3-amino-2,2-dimethylpropyl |
| 736 | H | cyclohexyl | H | 3-(MeSO₂NH)phenyl | 1-methyl-2-hydroxyethyl |
| 737 | H | cyclohexyl | H | 4-(pyrimidin-5-yl)phenyl | trans-4-aminocyclohexyl |

-continued

| Compound No. | R¹ | R² | R⁴ | R³ | NR⁵R⁶ |
|---|---|---|---|---|---|
| 738 | H | cyclohexyl | H | 2-chlorobenzyl | trans-4-aminocyclohexyl |
| 739 | H | CN | H | 4'-methoxybiphenyl-4-yl | 2-hydroxy-1,1-dimethylethylamino (2-amino-2-methylpropan-1-ol) |
| 740 | H | CN | H | 3-(methanesulfonamido)phenyl | 1-hydroxy-3-methylbutan-2-yl (3-methyl-2-amino-butan-1-ol) |
| 741 | H | CN | H | 4-(pyrimidin-5-yl)phenyl | trans-4-aminocyclohexyl |
| 742 | H | CN | H | methyl 4-benzoate | 1-hydroxypropan-2-yl |

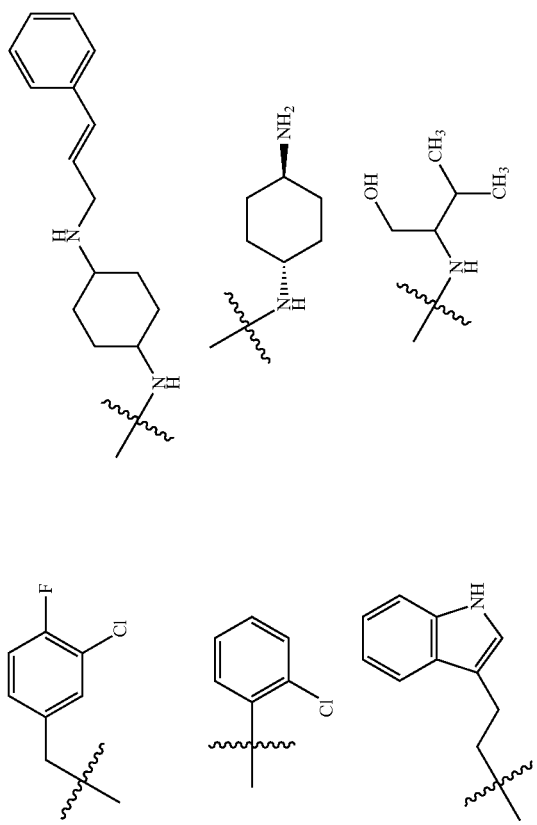

-continued

| Compound No. | R¹ | R² | R⁴ | R³ | NR⁵R⁶ |
|---|---|---|---|---|---|
| 748 | H | N-cyclopropyl amide (connected via C(=O)NH-cyclopropyl) | H | 4'-OMe-biphenyl-4-yl (via gem-dimethyl) | trans-4-aminocyclohexyl-NH- |
| 749 | H | N-(pyridin-4-yl) amide | H | 3-chlorobenzyl (via gem-dimethyl) | trans-4-aminocyclohexyl-NH- |
| 750 | H | SMe | H | 4-(pyrimidin-5-yl)phenyl (via gem-dimethyl) | trans-4-aminocyclohexyl-NH- |
| 751 | H | SMe | H | 3-(methylsulfonylamino)phenyl (via gem-dimethyl) | -NH-CH(CH₃)-CH₂OH |
| 752 | H | SMe | H | 4-hydroxyphenyl (via gem-dimethyl) | trans-4-aminocyclohexyl-NH- |

-continued

| Compound No. | R¹ | R² | R⁴ | R³ | NR⁵R⁶ |
|---|---|---|---|---|---|
| 753 | H | SMe | H | 2-pyridylmethoxy-phenyl | 1-hydroxymethyl-2-methylpropylamino |
| 754 | H | SMe | H | 2-piperidinylmethoxy-phenyl | 1-hydroxymethylethylamino |
| 755 | H | SMe | H | 4-(methoxycarbonyl)phenyl | 4-(cinnamylamino)cyclohexylamino |
| 756 | H | SMe | H | 3'-aminobiphenyl-4-yl | N-methyl-piperidin-3-ylamino |
| 757 | H | SMe | H | 4-(thiophen-3-yl)phenyl | 2-hydroxy-1,1-bis(hydroxymethyl)... |

-continued
| Compound No. | R¹ | R² | R⁴ | R³ | NR⁵R⁶ |
|---|---|---|---|---|---|
| 758 | H | OMe | H | 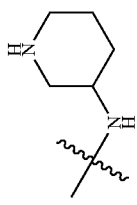 | 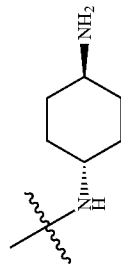 |
| 759 | H | H | Me | 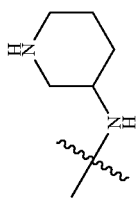 | 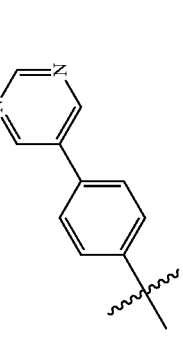 |
| 760 | H | H | Me | 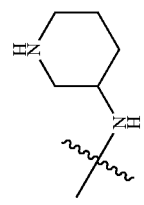 | 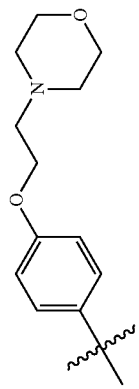 |
| 761 | H | H | Me | 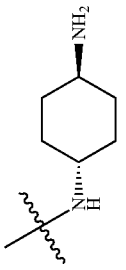 | 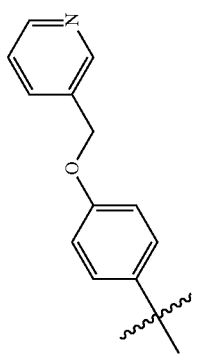 |
| 762 | H | 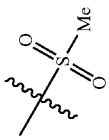 | Me | 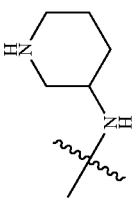 | 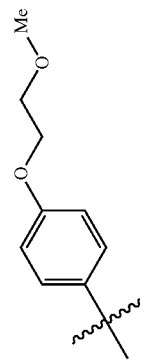 |
| 763 | H | 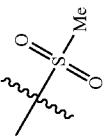 | Me | | 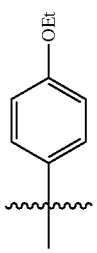 |

-continued

| Compound No. | R¹ | R² | R⁴ | R³ | NR⁵R⁶ |
|---|---|---|---|---|---|
| 764 | H | pyrazol-3-yl-NH-C(O)- | Me | 4-OEt-phenyl | trans-4-aminocyclohexyl-NH- |
| 765 | H | imidazol-2-yl-NH-C(O)- | Me | 4-OEt-phenyl | trans-4-aminocyclohexyl-NH- |
| 766 | H | 1,2,4-triazol-3-yl-NH-C(O)- | Me | 4-OEt-phenyl | trans-4-aminocyclohexyl-NH- |
| 767 | H | tetrazol-5-yl-NH-C(O)- | Me | 4-OEt-phenyl | trans-4-aminocyclohexyl-NH- |
| 768 | H | HOCH₂CH₂-NH-C(O)- | Me | 4-OEt-phenyl | trans-4-aminocyclohexyl-NH- |
| 769 | H | HOCH₂CH₂CH₂-NH-C(O)- | Me | 4-OEt-phenyl | trans-4-aminocyclohexyl-NH- |

-continued

| Compound No. | R¹ | R² | R⁴ | R³ | NR⁵R⁶ |
|---|---|---|---|---|---|
| 770 | H | (acyl-NH-CH₂CH₂-OH) | Me | 4-OEt-phenyl | 3-aminopiperidinyl-NH- |
| 771 | H | (acyl-NH-CH₂CH₂CH₂-OH) | Me | 4-OEt-phenyl | 3-aminopiperidinyl-NH- |
| 772 | H | H | Me | 4-OEt-phenyl | 4-carboxypyrrolidin-3-yl-NH- |
| 773 | H | H | Me | 5-acetyl-thiophen-2-yl-phenyl | 3-aminopiperidinyl-NH- |
| 774 | H | H | Me | 4-(methoxycarbonyl)phenyl | trans-4-aminocyclohexyl-NH- |

| Compound No. | R¹ | R² | R³ | R⁴ | NR⁵R⁶ |
|---|---|---|---|---|---|
| 775 | H | H | 3-(MeSO₂NH)-phenyl | Me | trans-4-aminocyclohexylamino |
| 776 | H | H | 4-(PhNHC(O))-phenyl | Me | trans-4-aminocyclohexylamino |
| 777 | H | H | 3,5-dimethoxyphenyl | Me | trans-4-aminocyclohexylamino |
| 778 | H | H | 4-(PhC(O))-phenyl | Me | trans-4-aminocyclohexylamino |

-continued
| Compound No. | R¹ | R² | R⁴ | R³ | NR⁵R⁶ |
|---|---|---|---|---|---|
| 779 | H | H | Me | 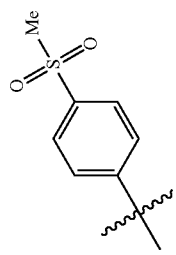 | 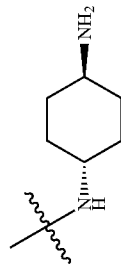 |
| 780 | H | H | Me | 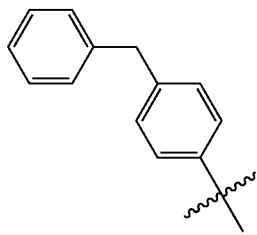 | 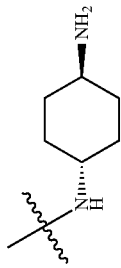 |
| 781 | H | H | Me | 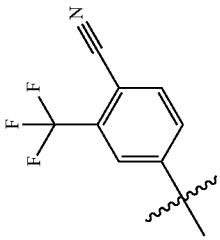 | 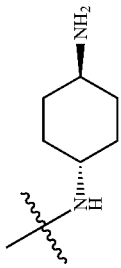 |
| 782 | H | H | Me | 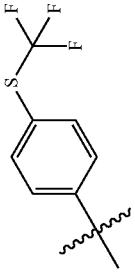 | 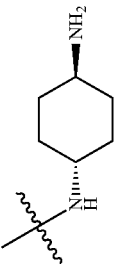 |
| 783 | H | H | Me | 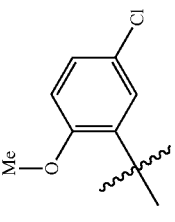 | 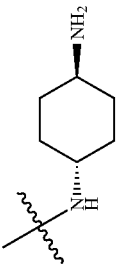 |

-continued

| Compound No. | R¹ | R² | R⁴ | R³ | NR⁵R⁶ |
|---|---|---|---|---|---|
| 784 | H | H | Me | 9-ethylcarbazol-3-yl | trans-4-aminocyclohexylamino |
| 785 | H | H | Me | 3-chloro-4-(trifluoromethoxy)phenyl | trans-4-aminocyclohexylamino |
| 786 | H | H | Me | 4-((4-methoxyphenyl)amino)phenyl | trans-4-aminocyclohexylamino |

-continued
| Compound No. | R¹ | R² | R⁴ | R³ | NR⁵R⁶ |
|---|---|---|---|---|---|
| 787 | H | H | Me | 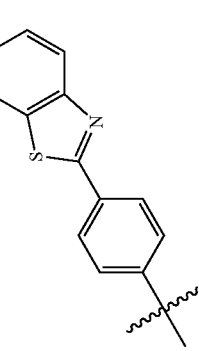 | 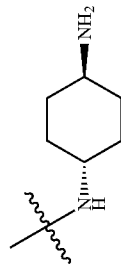 |
| 788 | H | H | Me | 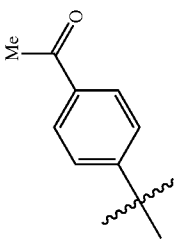 | 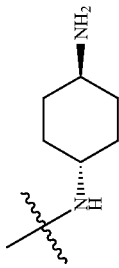 |
| 789 | H | H | Me | 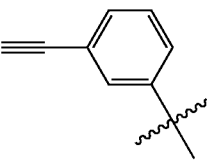 | 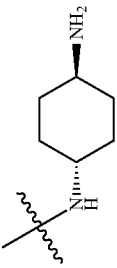 |
| 790 | H |  | Me | 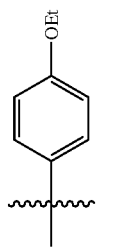 | 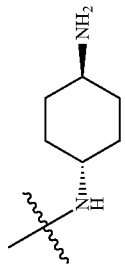 |
| 791 | H |  | Me | 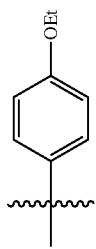 | 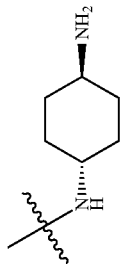 |

-continued

| Compound No. | R¹ | R² | R³ | R⁴ | NR⁵R⁶ |
|---|---|---|---|---|---|
| 792 | H | H | 4-(pyrrolidin-1-ylcarbonyl)phenyl | Me | trans-4-aminocyclohexylamino |
| 793 | H | H | 4-((2,2-dimethylpropyl)aminocarbonyl)phenyl | Me | trans-4-aminocyclohexylamino |
| 794 | H | H | 4-(N,N-dimethylaminocarbonyl)phenyl | Me | trans-4-aminocyclohexylamino |
| 795 | H | H | 5-cyano-2,4-difluorophenyl | Me | trans-4-aminocyclohexylamino |
| 796 | H | H | 4-(phenylaminocarbonyl)phenyl | Me | piperidin-3-ylamino |

-continued
| Compound No. | R¹ | R² | R⁴ | R³ | NR⁵R⁶ |
|---|---|---|---|---|---|
| 797 | H | H | Me | 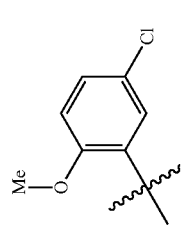 | 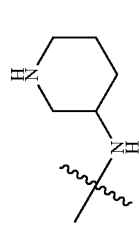 |
| 798 | H | H | Me | 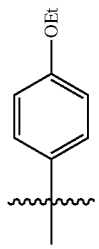 | 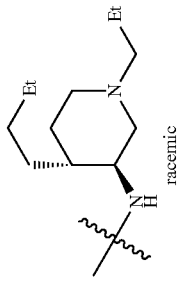 |
| 799 | H | H | Me | 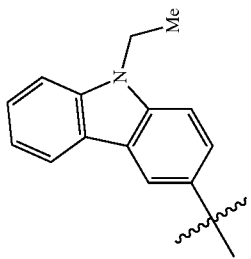 | 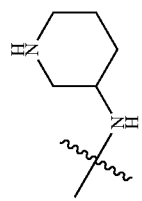 |
| 800 | H | H | Me | 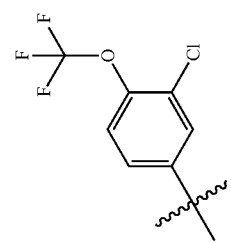 | 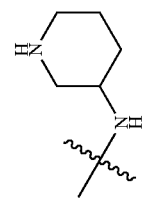 |

-continued
| Compound No. | R¹ | R² | R⁴ | R³ | NR⁵R⁶ |
|---|---|---|---|---|---|
| 801 | H | H | Me | 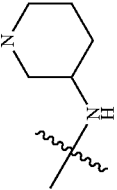 | 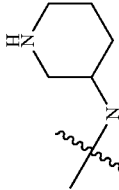 |
| 802 | H | H | Me | 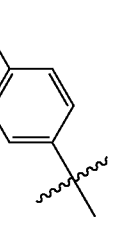 | 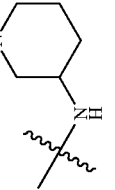 |
| 803 | H | H | Me | 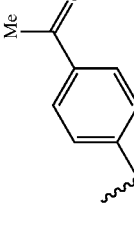 | 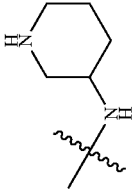 |
| 804 | H | H | Me | | |

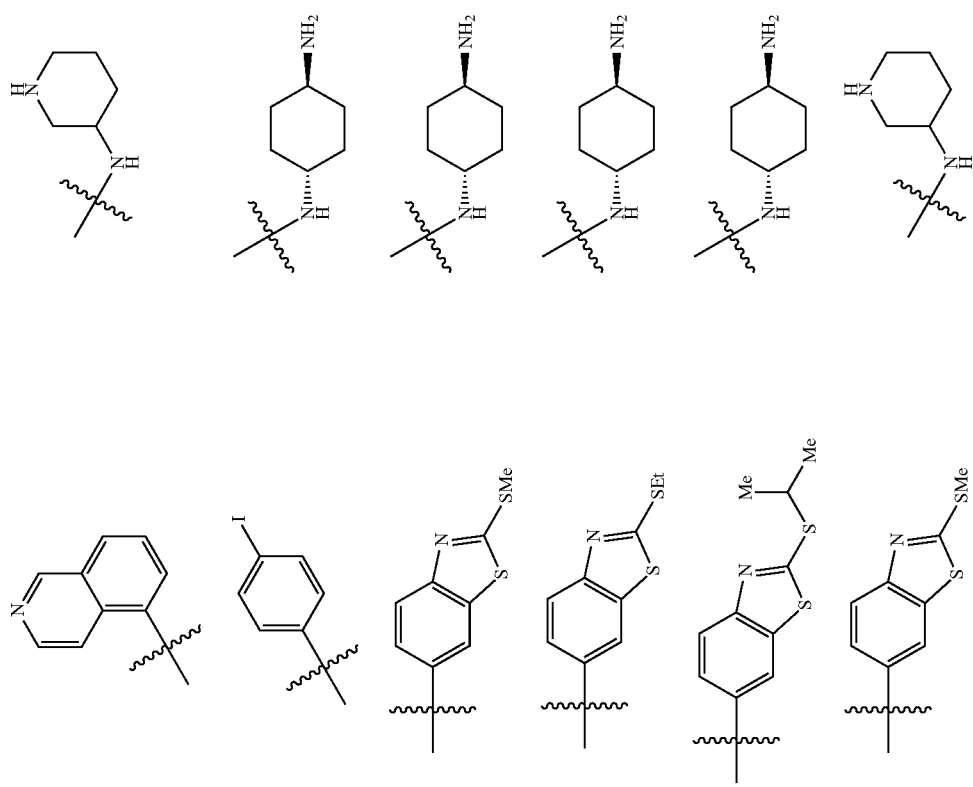

-continued

| Compound No. | $R^1$ | $R^2$ | $R^4$ | $R^3$ | $NR^5R^6$ |
|---|---|---|---|---|---|
| 811 | H | H | Me | 6-(SEt)-benzothiazol-2-yl | piperidin-3-ylamino |
| 812 | H | H | Me | 6-(SCHMe₂)-benzothiazol-2-yl | piperidin-3-ylamino |
| 813 | H | H | Me | 4-(OEt)-phenyl | N-allyl,N-Cbz-piperidin-3,4-diylamino (racemic) |
| 814 | H | H | Me | 4-(OEt)-phenyl | 4-ethyl-piperidin-3-ylamino (racemic) |
| 815 | H | CF₃ | Me | 4-(OEt)-phenyl | trans-4-aminocyclohexylamino |
| 816 | H | CF₃ | Me | 4-(OEt)-phenyl | piperidin-3-ylamino |

-continued

| Compound No. | R¹ | R² | R⁴ | R³ | NR⁵R⁶ |
|---|---|---|---|---|---|
| 817 | H | C(CF₃)₂CF₃ (perfluoro-tert-butyl-like group, with methyl) | Me | 4-OEt-phenyl | trans-4-aminocyclohexyl-NH- |
| 818 | H | C(CF₃)₂CF₃ (perfluoro group with methyl) | Me | 4-OEt-phenyl | piperidin-3-yl-NH- |

In a second aspect, the present invention provides a compound of formula II-26, III-01 and IV which are useful as synthetic intermediates for a compound of formula I:

1) A compound of the formula II-26

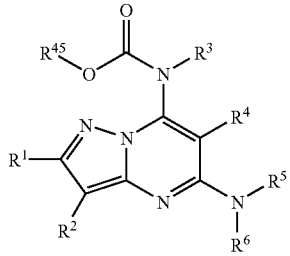

(II-26)

wherein $R^1$-$R^6$ are as defined for formula I above; $R^{45}$ is C1-C8 optionally substituted alkyl or optionally substituted arylalkyl;

with the provisos:

that $R^1$, $R^2$ and $R^4$ are not all H;

$R^{45}$ is preferably tert-butyl or benzyl.

2) A compound of the formula III-01

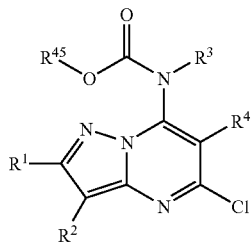

(III-01)

wherein $R^1$-$R^6$ are as defined for formula I above; $R^{45}$ is C1-C8 optionally substituted alkyl or optionally substituted arylalkyl;

with the provisos:

that $R^1$, $R^2$ and $R^4$ are not all H;

$R^{45}$ is preferably tert-butyl or benzyl.

3) A compound of the formula IV

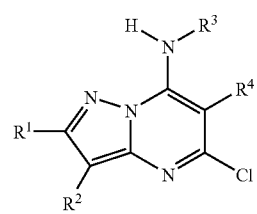

(IV)

wherein $R^1$-$R^6$ are as defined for formula I above;

with the provisos:

that $R^1$, $R^2$ and $R^4$ are not all H;

that $R^4$ is not optionally substituted aryl or optionally substituted heteroaryl.

The pyrazolo[1,5-a]pyrimidine derivatives represented by formula I above exist as tautomers represented by the following formula X and XI:

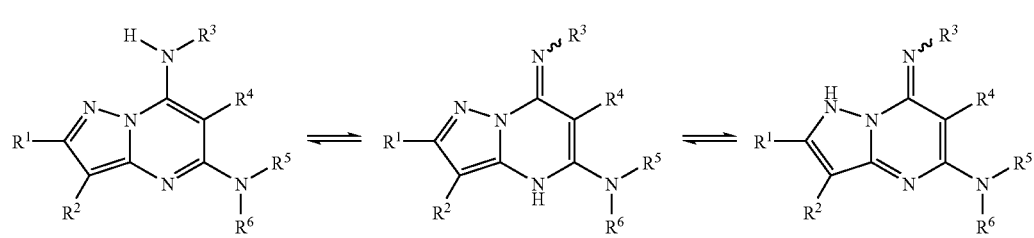

(X)

wherein $R^1$-$R^6$ are as defined for formula I above;

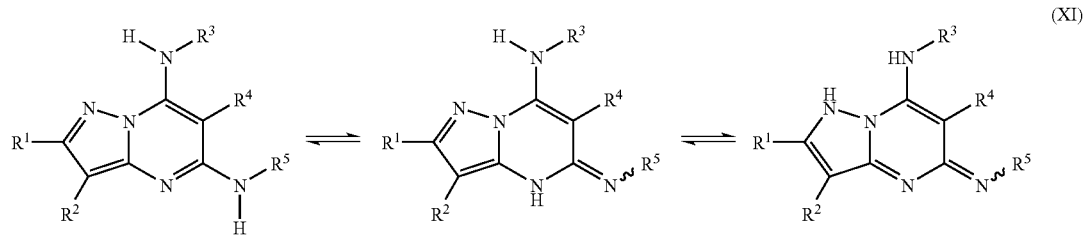

(XI)

wherein $R^1$-$R^6$ are as defined for formula I above;

These tautomers are also encompassed within the scope of the present invention.

In a third aspect, the present invention provides a process for the manufacture of a compound of the invention by reaction of a compound of formula II, III, IV, V, VI, VII, V-01, IV-01, II-01, II-03, II-04, II-06, II-08, II-13, II-15, II-18, II-20, II-22, II24, I-26, I-28 or V-04 as follows, wherein $R^1$-$R^6$ are as defined above:

1) reacting a compound of the formula II

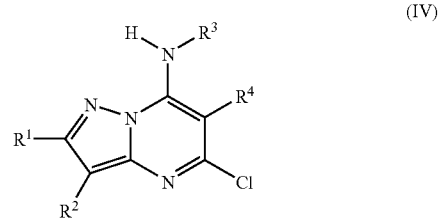

(II)

with acid e.g. trifluoroacetic acid for removal of t-butoxycarbonyl groups of a compound (for example as described in Protective Groups in Organic Synthesis, 3rd Ed, John Wiley & Sons Inc)

2) reacting a compound of the formula III (III)

with a compound of the formula $R^5R^6NH$ either in the absence or presence of transition metal catalyst under e.g. Buchwald conditions (for example as described in J. Am. Chem. Soc. 1994, 116, 7901.)

3) reacting a compound of the formula IV

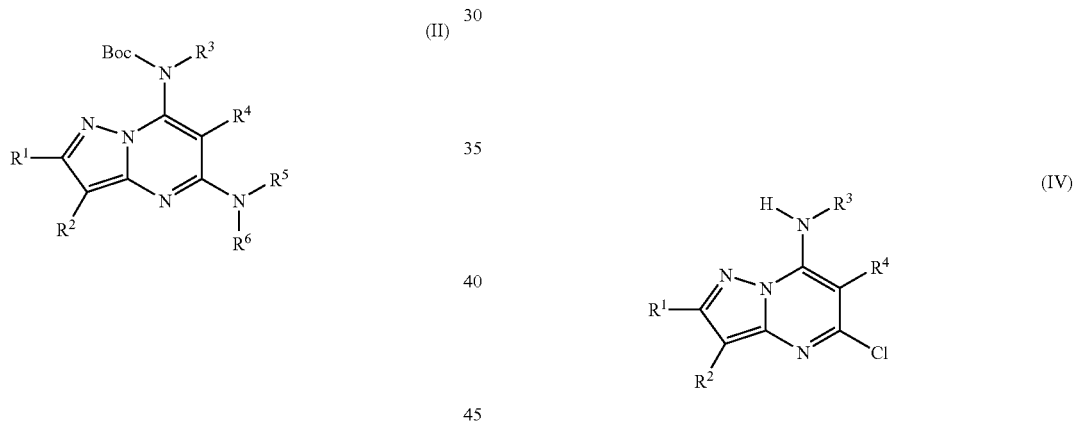

(IV)

with a compound of the formula $R^5R^6NH$ 4) reacting a compound of the formula IV (IV)

with a compound of the formula di t-butyl dicarbonate (for example as described in Protective Groups in Organic Synthesis, 3rd Ed, John Wiley & Sons Inc)

5) reacting a compound of the formula V

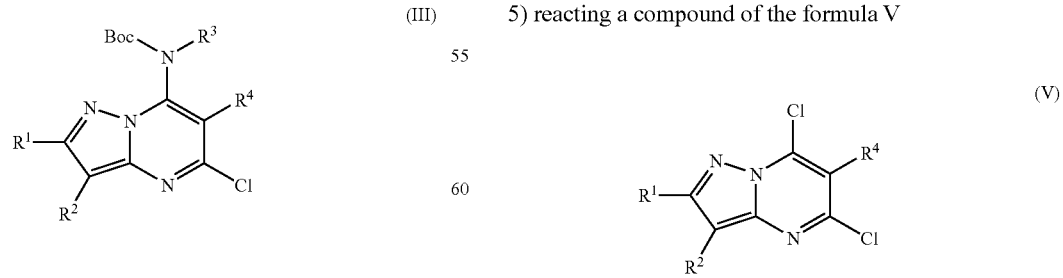

(V)

with a compound of the formula $R^3NH_2$ or $R^3NHAc$ in the presence of base e.g. triethylamine and sodium hydride 6) reacting a compound of the formula VI

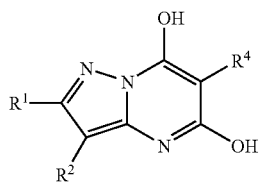

with a halogenating agent e.g. phosphorus oxychloride or phenyl phosphonic dichloride (for example as described in U.S. Pat. No. 3,907,799 (CA 1975, 84, 4998p), J. Med. Chem. 1977, 20, 296, Montash Chem. 1986, 117, 1305.)

7) reacting a compound of the formula VII

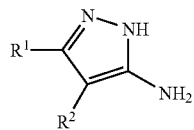

with a compound of the formula $R^4CH(CO_2Me)_2$ or $R^4CH(CO_2Et)_2$ (for example as described in J. Med. Chem 1976, 19, 296 and J. Med. Chem. 1977, 20, 296.)

8) reacting a compound of the formula V-01

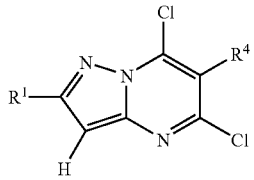

with a halogenating agent e.g. N-chlorosuccinimide, N-bromosuccinimide (for example as described in J. Med. Chem. 1976, 19, 517.) or iodine monochloride 9) reacting a compound of the formula V-01

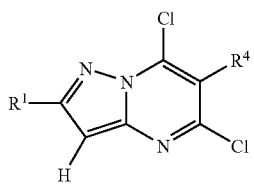

with a thiocyanating agent e.g. combination of potassium thiocyanate and bromine 10) reacting a compound of the formula V-01

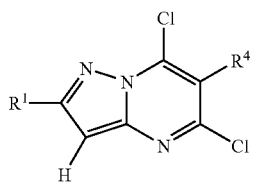

with an acylating agent e.g. dimethyl formamide/phosphorus oxychloride or acetyl chloride/aluminium trichloride 11) reacting a compound of the formula IV-01

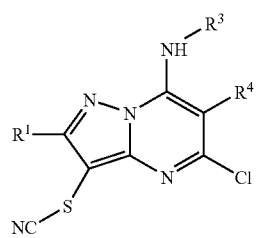

with a Grignard reagent e.g. methyl magnesium chloride 12) reacting a compound of the formula II-01

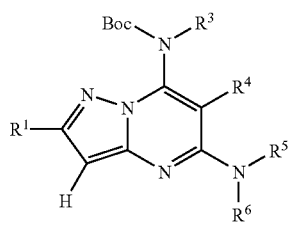

with an acylating agent e.g. trifluoroacetic anhydride 13) reacting a compound of the formula II-01

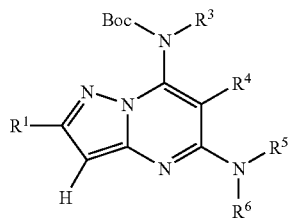

with fluorinating agent e.g. 1-chloromethyl-4-fluoro-1,4-diazoniabicyclo[2.2.2]octane bis(tetrafluoroborate) (J. Chem. Soc. Perkin 1, 1996, 2069.)

14) reacting a compound of the formula II-03

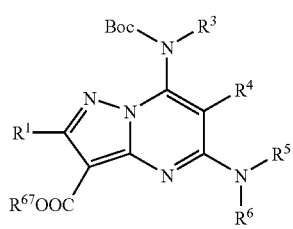
(II-03)

with aqueous sodium hydroxide for the hydrolysis of ester group in compound; $R^{67}$ is methyl or ethyl 15) reacting a compound of the formula II-04

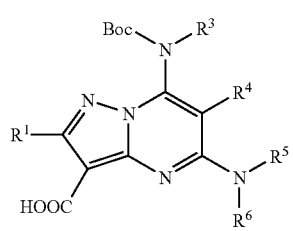
(II-04)

with amine derivatives in the presence of peptide coupling agent e.g. ethyl-3-(3'-dimethylaminopropyl) carbodiimide hydrochloride, N-hydoroxybenzotriazole monohydrate and triethylamine 16) reacting a compound of the formula II-06

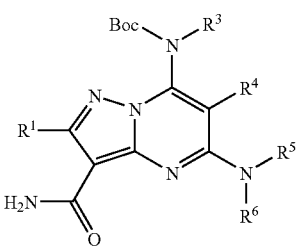
(II-06)

with oxidizing agent e.g. iodosobenzene diacetate for Hofmann rearrangement in the presence of benzyl alcohol (for example as described in J. Org. Chem. 1979, 44, 1746 and Synthesis 1981, 266.), followed by removal of the benzyloxy carbonyl group by hydrogenolysis in the presence of palladium on carbon (for example as described in Protective Groups in Organic Synthesis, 3rd Ed, John Wiley & Sons Inc)

17) reacting a compound of the formula II-08

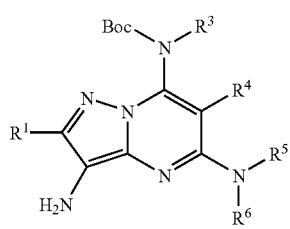
(II-08)

with a compound of the formula $R^{12}COCl$, $R^{12}COOH$, $R^{10}SO_2Cl$, $R^{10}NCO$ or $R^{10}NCS$ 18) reacting a compound of the formula II-13

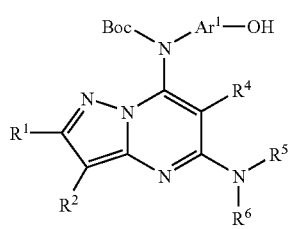
(II-13)

with alcohol derivatives in the presence of e.g. diisopropyl azodicarboxylate and polymer supported triphenylphosphine under e.g. Mitsunobu conditions (for example as described in Synthesis 1981, 1.); $Ar^1$ represents C6-C14 optionally substituted aryl or optionally substituted heteroaryl 19) reacting a compound of the formula II-15

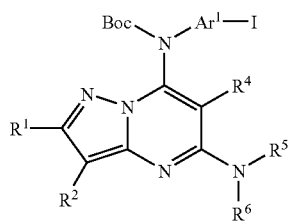
(II-15)

with boronic acid derivatives in the presence of transition metal catalyst under e.g. Suzuki coupling conditions (for example as described in Chem. Rev. 1995, 95, 2457.); $Ar^1$ represents C6-C14 optionally substituted aryl or optionally substituted heteroaryl 20) reacting a compound of the formula II-15

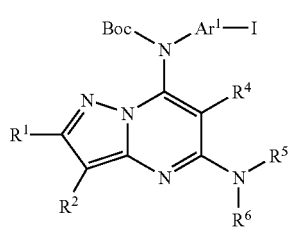
(II-15)

with a 1-alkyne in the presence of transition metal catalyst under Sonogashira coupling conditions (Synthesis 1980, 627, and Comprehensive Organic Synthesis, Vol. 3, p. 521, 1991.); $Ar^1$ represents C6-C14 optionally substituted aryl or optionally substituted heteroaryl 21) reacting a compound of the formula II-18

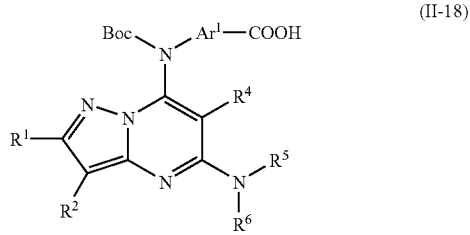

(II-18)

with a compound of the formula $R^{16}R^{17}NH$ in the presence of peptide coupling agent; $Ar^1$ represents C6-C14 optionally substituted aryl or optionally substituted heteroaryl 22) reacting a compound of the formula II-20

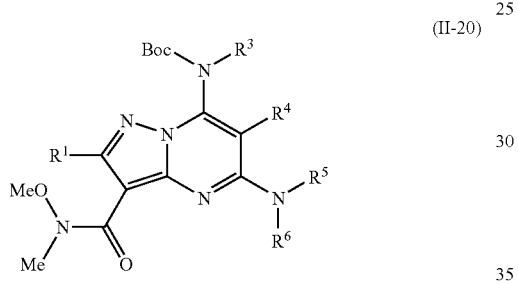

(II-20)

with an alkyl lithium e.g. n-butyl lithium under Weinreb conditions (for example as described in Tetrahedron Lett. 1981, 22, 3815.)

23) reacting a compound of the formula II-22

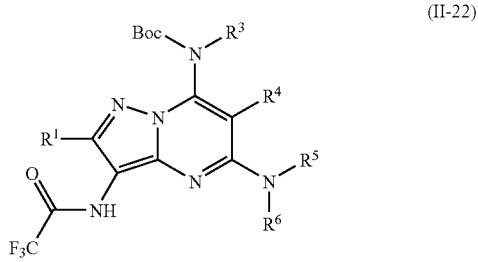

(II-22)

with alkyl halide e.g. methyl iodide in the presence of base, followed by trifluoroacetic acid and sodium hydroxide, respectively, for removal of t-butoxycarbonyl and trifluoroacetyl group from a compound 24) reacting a compound of the formula II-08

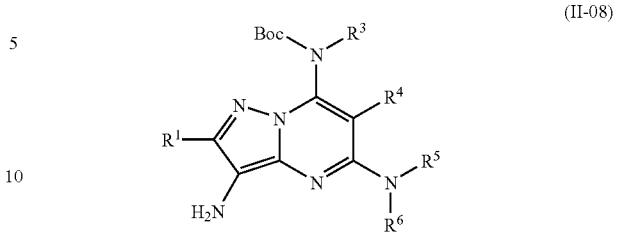

(II-08)

with an aldehyde e.g. benzyl aldehyde in the presence of reducing agent e.g. sodium acetoxyborohydride 25) reacting a compound of the formula II-24

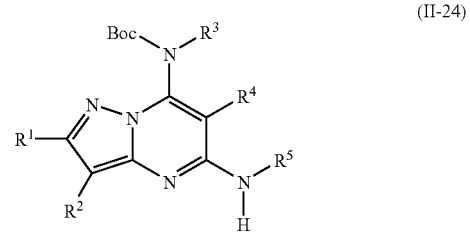

(II-24)

with alkyl halide e.g. methyl iodide in the presence of base e.g. sodium hydride 26) reacting a compound of the formula I-26

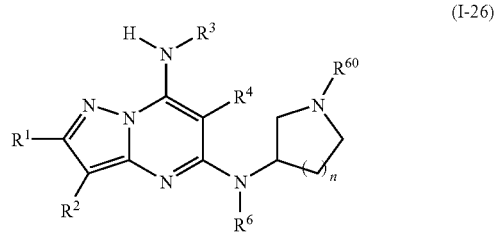

(I-26)

with $H_2$ in the presence of $Pd(OH)_2$—C or alpha-chloroethyl chloroformate followed by methanol for removal of $R^{60}$ group from a compound (for example as described in Protective Groups in Organic Synthesis, 3rd Ed, John Wiley & Sons Inc); $R^{60}$ is benzyl or p-MeO-benzyl; n is 1, 2 or 3

27) reacting a compound of the formula I-28

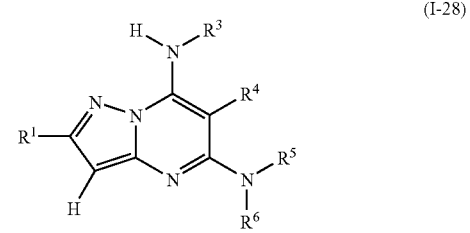

(I-28)

with halogenating agent e.g. iodine monochloride 28) reacting a compound of the formula V-04

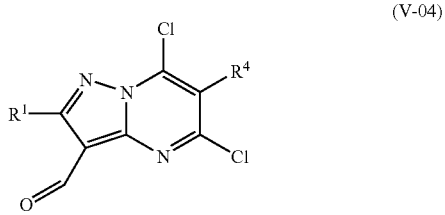

(V-04)

with reducing agent e.g. sodium borohydride or with diol derivative e.g. propane 1,3-diol and ethane 1,2-diol for formation of acetal.

A compound of formula I may undergo one or more further reactions to provide a different compound of formula I. For example, a compound may undergo a reduction, oxidation, elimination, substitution and/or addition reaction.

Figure 2:
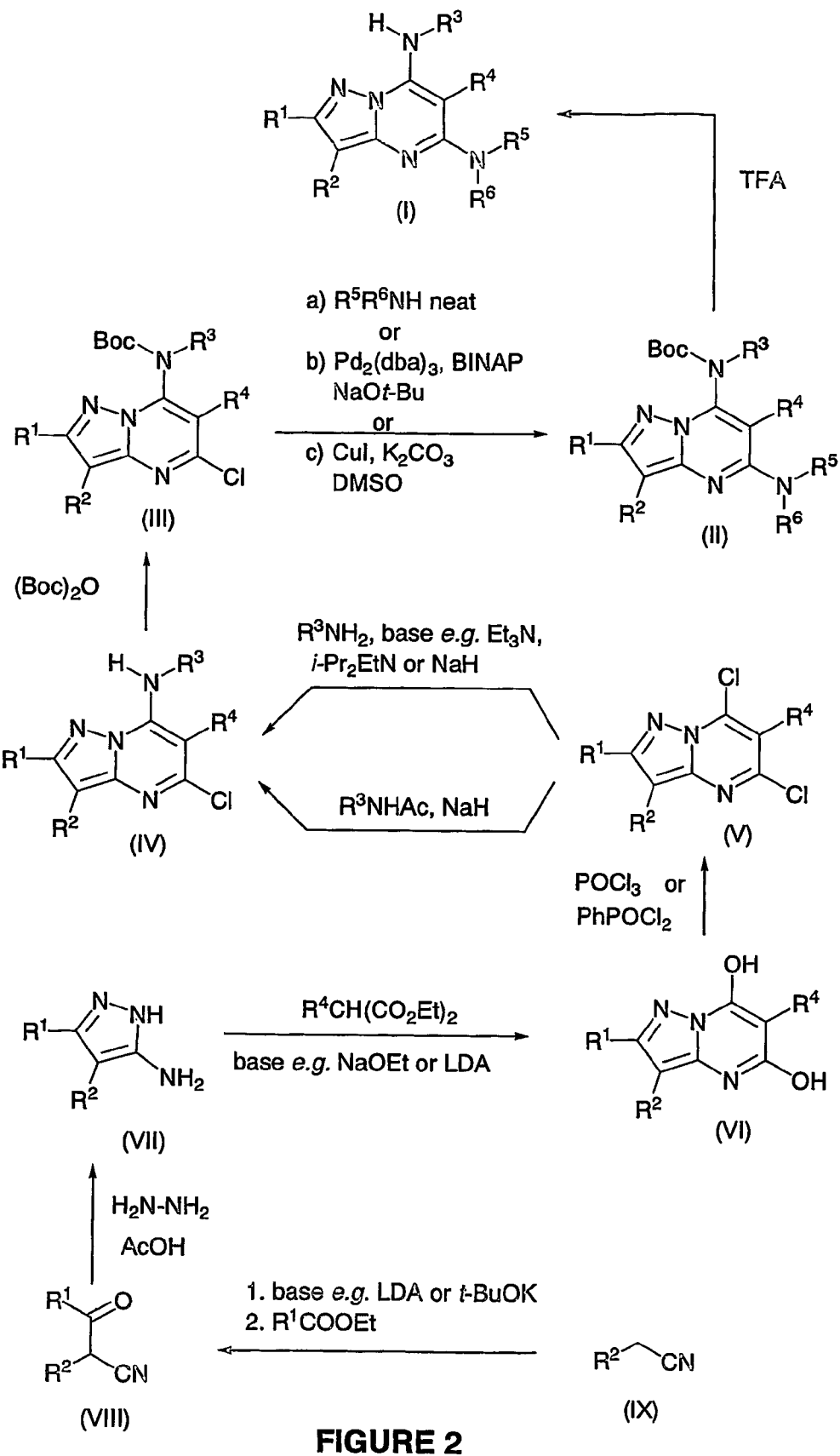
Figure 3:
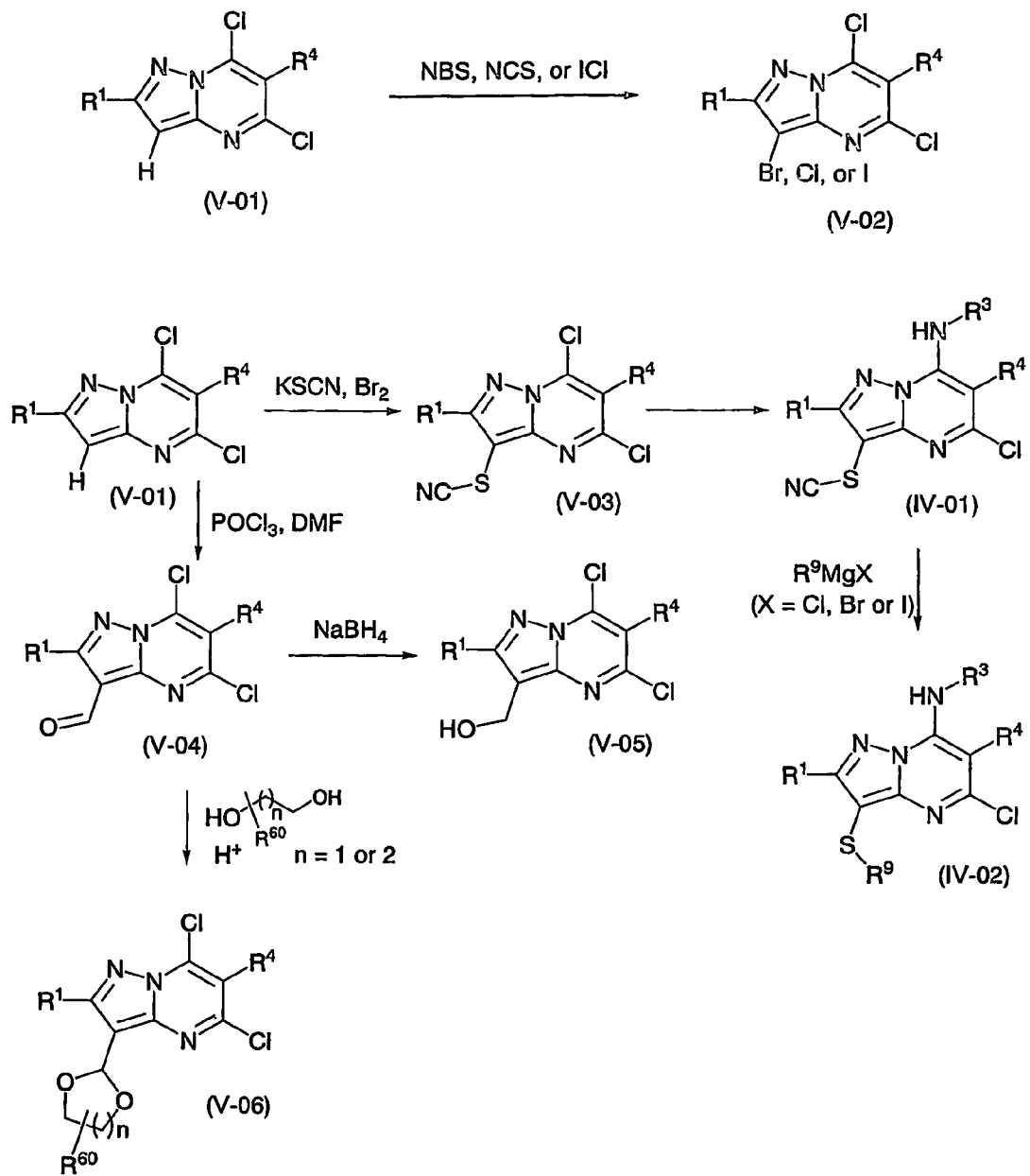
Figure 4:
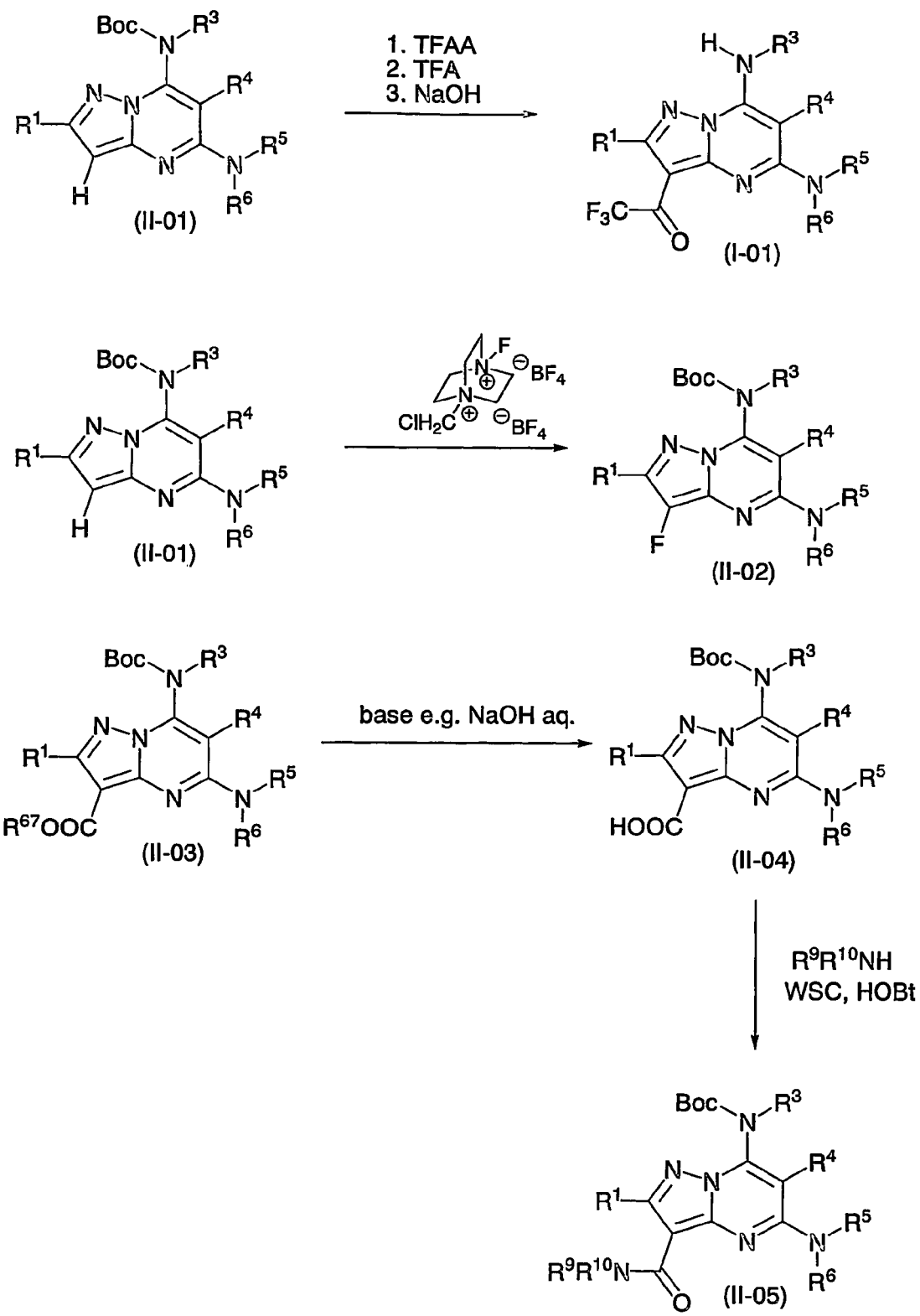
Figure 5:
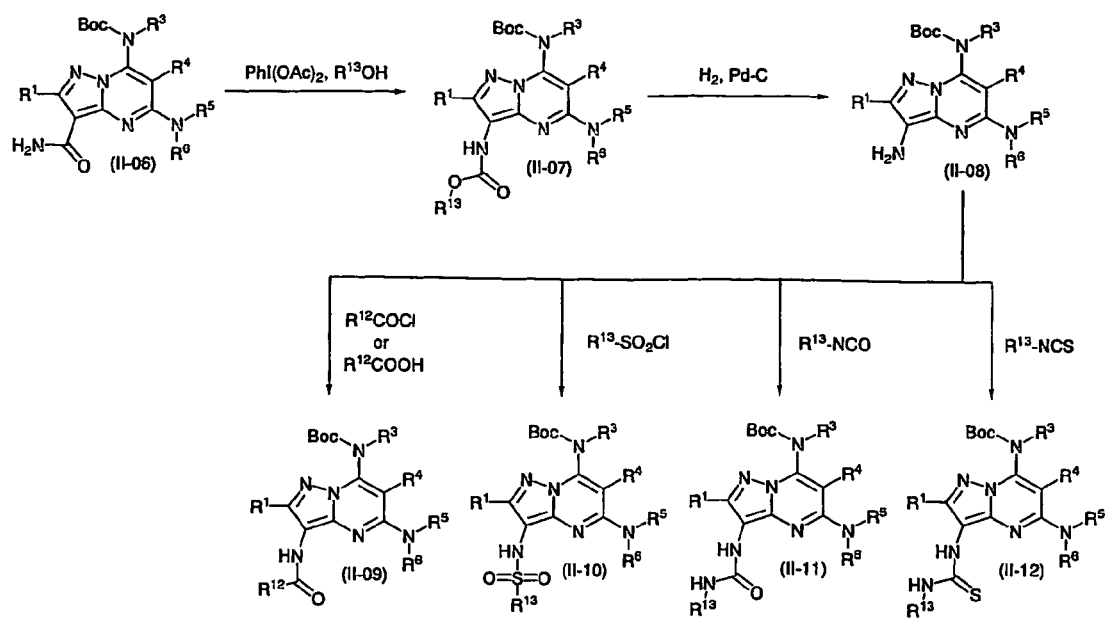
Figure 6:
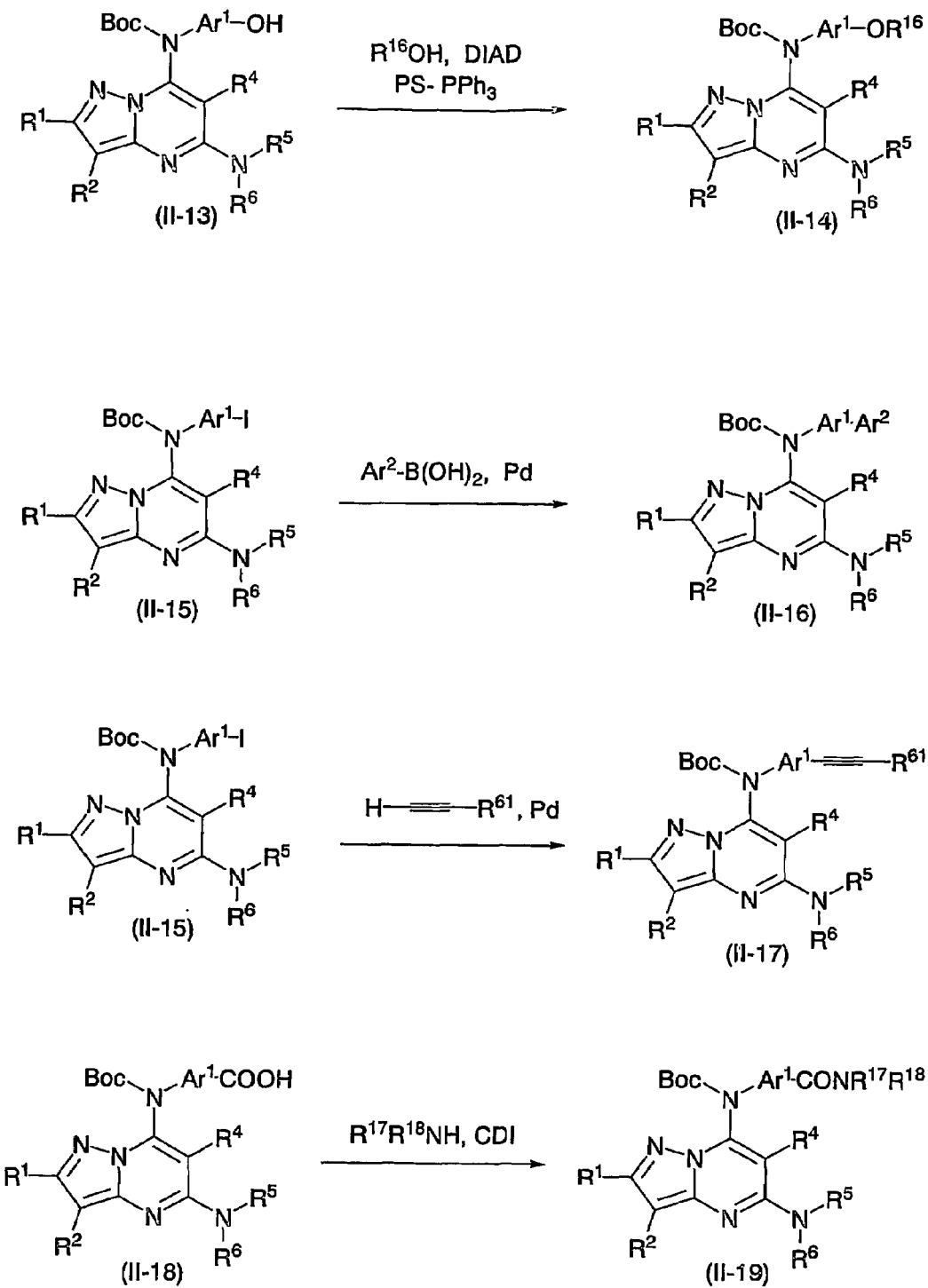
Figure 7:
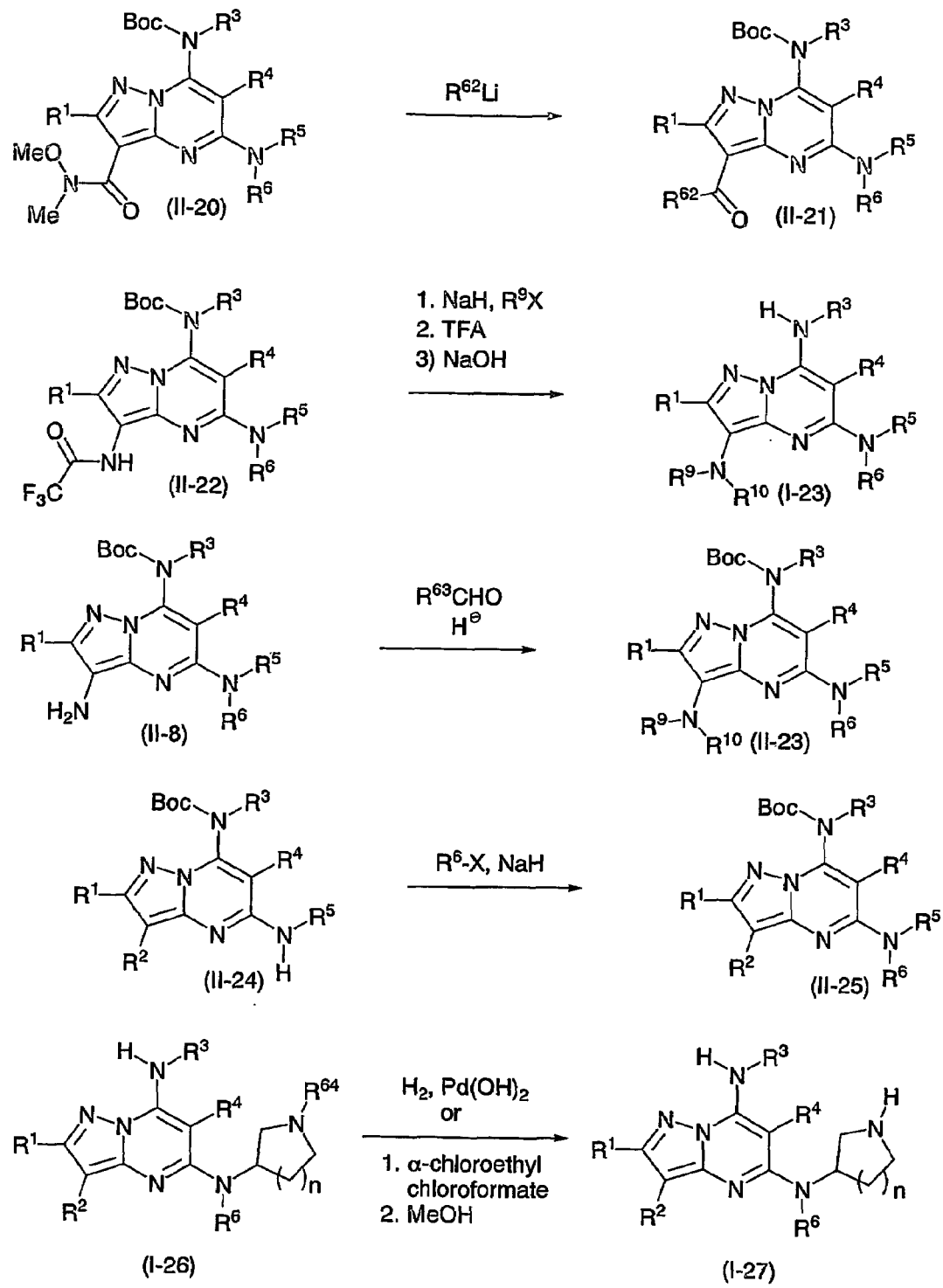

FIG. 2-8 shows a general reaction scheme for the preparation of compounds of Formula I.

The compounds of formula V, VI, VII and VIII are either known or can be prepared by methods analogous to those known for preparing analogous known compounds.

Other methods will be apparent to the chemist skilled in the art, as will the methods for preparing starting materials and intermediates. The Examples also make apparent various methods of preparing compounds of the invention as well as starting materials and intermediates.

In a fourth aspect, the present invention provides a composition comprising a compound of the invention in combination with a pharmaceutically acceptable carrier, diluent or excipient.

The composition may also comprise one or more additional active agents, such as an anti-inflammatory agent (for example a p38 inhibitor, glutamate receptor antagonist, or a calcium channel antagonist), a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

In a fifth aspect, the present invention provides a process for the manufacture of a composition according of the invention which comprises admixing one or more compounds of the invention with one more pharmaceutically acceptable excipients, carriers or diluents. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

In a sixth aspect, the present invention provides a compound or composition of the invention, for use in medicine.

The compounds of the present invention are inhibitors of protein kinases such as mitogen-activated protein kinases, particularly mitogen-activated protein kinase-activated protein kinase 2 (MAPKAP-K2), or cyclin dependent kinases (CDK) e.g., CDK1 and CDK2. Preferably, the compounds of the invention inhibit MAPKAP-K2 or CDK selectively (i.e., the compounds of the present invention show greater activity against one kinase than the other). For the purpose of this invention, an inhibitor is any compound which reduces or prevents the activity of a protein kinase.

The compounds are therefore useful for conditions for which inhibition of protein kinase activity is beneficial. Thus, preferably, this aspect provides a compound of the first aspect, or a composition of the third aspect of the present invention, for the prevention or treatment of a protein kinase-mediated disorder. The compounds of the first aspect of the invention may thus be used for the inhibition of protein kinase.

A "protein kinase-mediated disorder" is any disease or deleterious condition in which protein kinase plays a role. Examples include neurological disorder (including dementia), inflammatory disease, a disorder linked to apoptosis, particularly neuronal apoptosis; stroke, sepsis, autoimmune disease, destructive bone disorder, proliferative disorder, cancer, tumour growth, infectious disease, allergy, ischemia reperfusion injury, heart attack, angiogenic disorder, organ hypoxia, vascular hyperplasia, cardiac hypertrophy and thrombin induced platelet aggregation.

The compounds of the present invention are particularly useful for the prevention or treatment of a neurodegenerative disorder. In particular, the neurodegenerative disorder results from apoptosis and/or inflammation. Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, Sjögren syndrome, psoriatic arthritis, glomerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula I, or a physiologically acceptable salt thereof calculated as the free base, the compound being administered 1 to 4 times per day. Suitably the compounds will be administered for a period of continuous therapy, for example for a week or more.

In a seventh aspect, the present invention provides a method of treating or preventing a protein kinase-mediated disorder in an individual, which method comprises administering to said individual one or more compounds of the invention or a composition of the invention. The active compound is preferably administered in a cumulative effective amount. The individual may be in need of the treatment or prevention. Any of the protein kinase-mediated disorders listed above in relation to the fifth aspect may be the subject of treatment or prevention according to the sixth aspect. One or more other active agent may be administered to the individual simultaneously, subsequently or sequentially to administering the compound. The other active agent may be an anti-inflammatory agent such as a p38 inhibitor, glutamate receptor antagonist, calcium channel antagonist, a chemotherapeutic agent or an antiproliferative agent.

In an eighth aspect, the present invention provides the use of a compound of the invention in the manufacture of a medicament for the prevention or treatment of a protein kinase-mediated disorder. The medicament may be used for treatment or prevention of any of the protein kinase-mediated disorders listed above in relation to the fifth aspect. Again, the compounds of the present invention may be administered simultaneously, subsequently or sequentially with one or more other active agent such as a p38 inhibitor.

In a ninth aspect, the present invention provides an assay for determining the activity of the compounds of the present invention, comprising providing a system for assaying the activity and assaying the activity of the compound. Preferably the assay is for the protein kinase inhibiting activity of the compound. The compounds of the invention may be assayed in vitro, in vivo, in silico, or in a primary cell culture or a cell line. In vitro assays include assays that determine inhibition of the kinase activity of activated protein kinase. Alternatively, in vitro assays may quantitate the ability of a compound to bind protein kinase and may be measured either by radiolabelling the compound prior to binding, then isolating the inhibitor/protein kinase complex and determining the amount of the radiolabel bound or by running a competition experiment where new inhibitors are incubated with protein kinase bound to known radioligands. An example of an assay which may be used is Scintillation Proximity Assay (SPA), preferably using radiolabelled ATP. Another example is ELISA. Any type or isoform of protein kinase may be used in these assays.

In a tenth aspect, the present invention provides a method of inhibiting the activity or function of a protein kinase, which method comprises exposing a protein kinase to a compound or a composition of the invention. The method may be performed in a research model, in vitro, in silico, or in vivo such as in an animal model. A suitable animal model may be a kainic acid model in rat or mice, traumatic brain injury model in rat, or MPTP in mice for neurodegenerative disorder and a collagen induced arthritis model in rat or mice, type II collagen-antibodies induced arthritis in mice, or a LPS induced endotoxin shock model in mice for inflammatory disease.

All features of each of the aspects apply to all other aspects mutatis mutandis.

EXAMPLES

The invention will now be explained in greater detail by the following examples, with the understanding that the scope of the invention is not in any sense restricted by these examples. The numbers assigned to each of the compounds in the examples correspond to the Compound Nos. of the compounds listed as specific examples in Tables A above. Structures of isolated novel compounds were confirmed by $^1$H NMR and/or other appropriate analyses.

Compounds were characterised by mass spectrometry using single quadrupole instrumentation with an electrospray source. M+H indicates values obtained for compound molecular mass (M) with proton (H) capture and M−H compound molecular mass (M) with proton (H) loss. Melting points (mp) are uncorrected; (d) denotes decomposition at or near the melting point. Compounds which were not solids were gums. The 1H-NMR spectra (400 MHz, DMSO-d6 or CDCl3) of selected compounds of the invention were measured. The data for the chemical shifts (d: ppm) and coupling constants (J: Hz) are shown. The "HPLC retention time" data for the compounds synthesized in the examples are the retention time for the compounds in HPLC analysis carried out under the following conditions.

HPLC (High Performance Liquid Chromatography) Conditions
System: Hewlett-Packard 1100 HPLC
Column: Cadenza CD-C18 (Imtakt) 100 mm×4.6 mmf

[Method A]
Solvent: A: H2O/acetonitrile=95/5
   0.05% TFA (trifluoroacetic acid)
  B: H2O/acetonitrile=5/95
   0.05% TFA (trifluoroacetic acid)
Flow rate: 1.0 mL/min
Gradient:
0-1 min, solvent B: 10% solvent A: 90%
1-13 min, solvent B: 10%→70% solvent A: 90%→30%
13-14 min, solvent B: 70%→100% solvent A: 30%→0%
14-16 min, solvent B: 100% solvent A: 0%
16-19 min, solvent B: 100%→10% solvent A: 0%→90%
Calculation of purity: Area % of UV absorption (254 nm)

[Method B]
Solvent: A: H2O/acetonitrile=95/5
   0.05% TFA (trifluoroacetic acid)
  B: H2O/acetonitrile=5/95
   0.05% TFA (trifluoroacetic acid)
Flow rate: 1.0 mL/min
Gradient:
0-1 min, solvent B: 5% solvent A: 95%
1-13 min, solvent B: 5%→55% solvent A: 95%→45%
13-14 min, solvent B; 55%→100% solvent A: 45%→0%
14-17 min, solvent B: 100% solvent A: 0%
17-18 min, solvent B: 100%→5% solvent A: 0%→95%
Calculation of purity: Area % of UV absorption (254 nm)

[Method C]
Solvent: A: H2O/acetonitrile=95/5
   0.05% TFA (trifluoroacetic acid)
  B: H2O/acetonitrile=5/95
   0.05% TFA (trifluoroacetic acid)
Flow rate: 1.5 mL/min
Gradient:
0-1 min, solvent B: 2% solvent A: 98%
1-9 min, solvent B: 2%→30% solvent A: 98%→70%
9-13 min, solvent B: 30%→100% solvent A: 70%→0%
13-16 min, solvent B: 100% solvent A: 0%
16-17.5min, solvent B: 100%→2% solvent A: 0%→98%
Calculation of purity: Area % of UV absorption (254 nm)

[Method D]
Solvent: A: H2O/acetonitrile=95/5
   0.1% NEt3 (triethyl amine)
  B: H2O/acetonitrile=5/95
   0.1% NEt3 (triethyl amine)
Flow rate: 1.5 mL/min
Gradient:
0-1 min, solvent B: 10% solvent A: 90%
1-14 min, solvent B: 10%→100% solvent A: 90%→0%
14-16 min, solvent B: 100% solvent A: 0%
16-17 min, solvent B: 100%→10% solvent A: 0%→90%
17-20min, solvent B: 10 solvent A: 90%
Calculation of purity: Area % of UV absorption (254 nm)

Example 1

[General Procedure for the Synthesis of Pyrazolo[1,5-a]pyrimidines of General Formula (VI)]

To a stirred solution of sodium ethoxide (50 mmol) in ethanol (100 mL) was added the appropriately 2-substituted malonic acid diester (20 mmol) and appropriately substituted 3-aminopyrazole (VII) (20 mmol). The mixture was heated at reflux for 18 h, during which a precipitate formed.* The reaction was cooled to room temperature and the mixture was filtered through an A4 sinter (whilst washing with a minimum of cool ethanol). The residue was dried under vacuum. The dried precipitate was dissolved in water (ca. 100 mL) and the resulting solution was acidified (pH 2) with concentrated HCl. This rendered a pale-white precipitate (VI), which was filtered and dried. Typical unoptimised yields ranged from 20-40%.

* In several cases where the substituent was an alkyl chain, little or no precipitate was formed. In these situations, the ethanol was removed under reduced pressure. The residue was partitioned between water and ethyl acetate. The aqueous phase was acidified (pH 2) with concentrated HCl and back-extracted with ethyl acetate. The organic phase was washed (water and saturated aqueous NaCl) and dried (MgSO$_4$) to give the desired bis-hydroxy compound (VI).

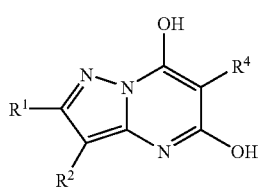

(VI)

| Compound No. | $R^1$ | $R^2$ | $R^4$ | mp (° C.) |
|---|---|---|---|---|
| VI-01 | Me | H | H | 240 (d) |
| VI-02 | H | H | Ph | 285 |
| VI-03 | H | H | Et | 260 |

Example 2

[General Procedure for the Synthesis of Pyrazolo[1,5-a]pyrimidines of General Formula (V)]

To a suspension of bis-hydroxy compound (VI) (2 g) in N,N-dimethylaniline (2 mL) was added phosphorous oxychloride (or phenyl phosphonic dichloride) (20 mL). The mixture was heated at reflux for 18 h, and excess phosphorus oxychloride (or phenyl phosphonic dichloride) was removed in vacuo. The residue was poured onto ice (50 g) and extracted with $CH_2Cl_2$ (5×). The organic phase was adsorbed onto neutral (activity I) alumina and chromatographed (typically using petrol→30% ethyl acetate/petrol as eluent). To gave the appropriately substituted 5,7-dichloropyrazolo[1,5-a]pyrimidine intermediate (V) in yields of ca. 40% values.

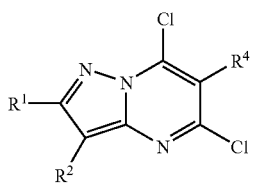
(V)

| Compound No | $R^1$ | $R^2$ | $R^4$ | mp (° C.) or $^1$H-NMR (400 MHz, $CDCl_3$) d (ppm) |
|---|---|---|---|---|
| V-07 | Me | H | H | 92-95 |
| V-08 | H | H | Ph | 182-186 |
| V-09 | H | H | Et | 60-62 |
| V-10 | H | H | Me | 2.55(s, 3H, $CH_3$), 6.7(s, 1H, Het-H), 8.12 (s, 1H, Het-H). |

Example 3

[General Procedure for the Synthesis of Pyrazolo[1,5-a]pyrimidines of General Formula (V-02)]

A solution of the 5,7-dichloropyrazolo[1,5-a]pyrimidine (V-01) (0.01 mol) in chloroform (50 mL) was treated with N-chlorosuccinimide, N-bromosuccinimide or iodine monochloride (0.011 mol) at room temperature. The mixture was boiled under reflux until all solids were dissolved and no starting material remained (by TLC). The mixture was poured onto ice/water and the organic layer was separated, washed with aqueous $Na_2CO_3$, dried over $MgSO_4$, and the solvent removed in vacuo. The residual material was purified by chromatography over silica gel to provide the 3-halo-5,7-dichloropyrazolo[1,5-a]pyrimidine (V-02).

| Compound No. | $R^1$ | $R^2$ | $R^4$ | $^1$H-NMR (400 MHz, $CDCl_3$) d(ppm) |
|---|---|---|---|---|
| V-11 | H | Br | H | 8.2(s, 1H, Het-H), 7.05(s, 1H, Het-H). |
| V-12 | H | I | H | 8.15(s, 1H, Het-H), 2.60(s, 3H, 6-Me). |

Example 4

[General Procedures for the Synthesis of Pyrazolo[1,5-a]pyrimidines of General Formula (V-03)]

Synthesis of {5,7-dichloro(pyrazolo[1,5-a]pyramidin-7-yl)}thiocarbonitrile.

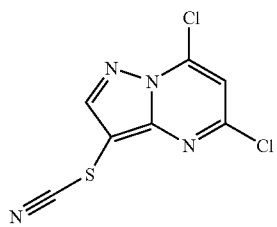

To a solution of powdered potassium thiocyanate (2.66 g) in acetic acid (20 mL) was added slowly a solution of bromine (0.72 mL) in acetic acid (3 mL) whilst maintaining the temperature between 10-15° C. 5,7-Dichloropyrazolo[1,5-a]pyrimidine (2.5 g) in acetic acid (30 mL) was added and the resulting solution was stirred at 15° C. for 30 min and then room temperature for 3 h after which, the solvent was removed under reduced pressure. Water and ethyl acetate were added and the product was extracted with ethyl acetate (3×). The combined organic phase was dried ($Na_2SO_4$), evaporated and subjected to flash chromatography to give the title compound (780 mg, 73% pure by $^1$H-NMR); $^1$H-NMR (400 MHz, $CDCl_3$) d(ppm): 8.27 (1H, s, 2-H), 7.10 (1H, s, 6-H).

Example 5

[General Procedures for the Synthesis of Pyrazolo[1,5a]pyrimidines of General Formula (V-04)]

Synthesis of 5,7-dichloro-6-methylpyrazolo[1,5-a]pyrimidine-3-carbaldehyde.

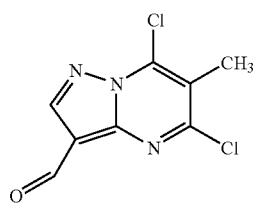

To N,N-dimethyl formamide (9 mL) under nitrogen at room temperature was added $POCl_3$ (3 mL) and the resulting slurry was stirred for 5 min. 5,7-Dichloro-6-methylpyrazolo[1,5-a]pyrimidine (5 g) was slowly added and resulting thick mixture was heated at 70° C. for 3 h. The mixture was poured onto ice and basified with sodium hydroxide (5 g). The residue was filtered and the dried precipitate chromatographed on silica gel (eluting with $CH_2Cl_2$→20% ethyl acetate/$CH_2Cl_2$) to give the title compound (3.74 g); mp 137-139° C.

Example 6

[General Procedures for the Synthesis of Pyrazolo[1,5-a]pyrimidines of General Formula (V-05)]

Synthesis of {5,7-dichloro-6-methyl(pyrazolo[1,5-a]pyrimidin-3-yl)}methanol.

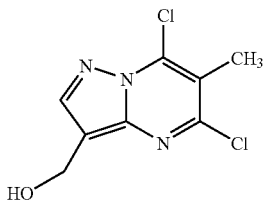

To 5,7-dichloro-6-methylpyrazolo[1,5-a]pyrimidine-3-carbaldehyde (200 mg) in ethanol (20 mL) was added sodium borohydride (70 mg) and the reaction mixture was stirred at room temperature for 15 min. Saturated aqueous $NH_4Cl$ (1 mL) was added and the reaction mixture was stirred for a further 10 min then the solvent was removed under reduced pressure. Water and ethyl acetate were added and the product was extracted with ethyl acetate (3×). The combined organic phase was washed (water, saturated aqueous NaCl) and dried ($MgSO_4$) to give the title compound (150 mg); $^1$H-NMR (400 MHz, $CDCl_3$) d(ppm): 8.22 (1H, s, 2-H), 4.90 (1H, s, $CH_2OH$).

Example 7

[General Procedures for the Synthesis of Pyrazolo[1,5-a]pyrimidines of General Formula (V-06)]

Synthesis of 2-{5,7-dichloro-6-methyl(pyrazolo[1,5-a]pyrimidin-3-yl)}-1,3-dioxane.

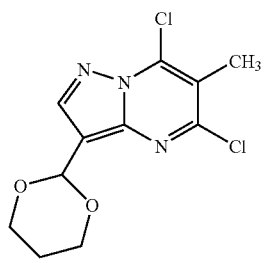

To 5,7-dichloro-6-methylpyrazolo[1,5-a]pyrimidine-3-carbaldehyde (290 mg) in toluene (40 mL) was added pyridinium p-toluenesulfonate (60 mg) and propan-1,3-diol. The mixture was then heated under reflux for 2 h, with azeotropic removal of water. The solution was cooled and evaporated under reduced pressure. The residue was chromatographed on silica gel using ethyl acetate/petroleum ether ⅔ as eluent to give the title compound (310 mg) as a white solid; $^1$H-NMR (400 MHz, $CDCl_3$) d(ppm): 8.32 (1H, s, 2-H), 5.97 (1H, s, $CHO_2R$), 4.25 (2H, br dd, $OCH_{eq}$), 4.05 (2H, br t, $OCH_{ax}$), 2.50 (3H, s, 6-Me), 2.25 (1H, m, $CCH_{eq}HC$), 1.48 (1H, br d, $CCHH_{ax}C$).

Example 8

[General Procedures for the Synthesis of Pyrazolo[1,5-a]pyrimidines of General Formula (IV) and (IV-01)]

a) To a solution of (appropriately substituted) 5,7-dichloropyrazolo[1,5-a]pyrimidine (V) or {5,7-dichloro(pyrazolo[1,5-a]pyramidin-7-yl)}thiocarbonitrile and triethylamine (2 equivalents) in 2-propanol (20 mL) was added the amine $R^3NH_2$ (1 or 1.1 equivalents) and the mixture was stirred at room temperature overnight. The mixture was concentrated in vacuo and the residue was then partitioned between water and $CH_2Cl_2$. The organic phase was washed twice with water and the combined aqueous phases back-extracted with $CH_2Cl_2$. The organic layer was combined, washed with saturated aqueous NaCl and dried over $Na_2SO_4$. Removal of the solvent in vacuo yielded the precursor (IV). [Purification performed—normally the products did not require any further purification, if they did, they were recrystallised. Analysis performed—$^1$H-NMR, HPLC and MS].

Should the above room-temperature reaction not occur satisfactorily, the following may be applied:

b) To a solution of the 5,7-dichloropyrazolo[1,5-a]pyrimidine (V) (2 g) in 2-propanol (25 mL) containing N,N-diisopropylethylamine (2 equivalents) was added the amine $R^3NH_2$ (1.2 equivalents). The reaction was heated overnight at 80° C. and the solvent removed in vacuo. The residue was partitioned between water and $CH_2Cl_2$ and the organic phase was washed with water, saturated aqueous NaCl and dried over $MgSO_4$. Removal of the solvent in vacuo yielded the product (IV).

c) To a stirred suspension of sodium hydride (50 mmol) in N,N-dimethylformamide (30 mL) was added appropriately substituted aniline derivative (25 mmol) and then appropriately substituted 5,7-dichloropyrazolo[1,5-a]pyrimidine (V) (25 mmol) in tetrahydrofuran (50 mL). The resulting mixture was stirred at 50° C. for 2 h. The reaction was quenched with saturated aqueous $NH_4Cl$. After extraction with ethyl acetate, the combined organic layer was washed with saturated aqueous NaCl and dried over $MgSO_4$. The solvent was removed in vacuo to give the crude title compound (IV). Typical unoptimised yields for d) 60-80%.

d) To a solution of 2-chloroacetanilide (2.2 mmol) in toluene (3 mL) at room temperature was added sodium hydride (3 mmol) after the addition the mixture was heated until effervescence ceased and the solution became homogenous. The appropriately substituted 5,7-dichloropyrazolo[1,5-a]pyrimidine (V) (1 mmol) was added and the mixture heated at reflux for 5 h. (The solution became heterogeneous during this time). Upon cooling, acetic acid (1 mL) and water (1 mL) were cautiously added and the mixture was stirred for 15 min. The solvent was removed in vacuo and the residual acetic acid removed by azeotropic evaporation with toluene (3×). The residue was partitioned between water and ethyl acetate. The organic phase was washed (water and saturated aqueous NaCl) and dried. The solvent was removed in vacuo and the residue was chromatographed to afford the desired compound (IV). Typical unoptimised yields for c) 50-70%. The Rf of starting material (V) and product (IV) are chromatographically indistinguishable, making complete reaction difficult to determine. It appears that at least 5 h is required for significant reaction to occur.

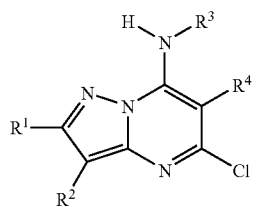

(IV)

| Compound No. | R¹ | R² | R⁴ | R³ | mp (° C.) or ¹H-NMR (400 MHz) d (ppm) |
|---|---|---|---|---|---|
| IV-03 | H | H | Me | 2-chlorophenyl | (CDCl₃) 1.91(s, 3H, CH₃), 6.5(s, 1H, Het-H), 7.05(d, 1H, ArH), 7.15(t, 1H, ArH), 7.27(t, 1H, ArH), 7.45(d, 1H, ArH). |
| IV-04 | H | Cl | H | 3-chloro-4-fluorophenyl | 184-186 |
| IV-05 | H | COOEt | CH₃ | 4-ethoxyphenyl | (DMSO-d6) 1.27-1.35(m, 6H), 1.78(s, 3H), 4.02(q, J=6.84Hz, 2H), 4.27(q, J=7.08Hz, 2H), 6.92(d, J=8.80Hz, 2H), 7.15(d, J=8.80Hz, 2H), 8.62(s, 1H), 9.95(s, 1H). |
| IV-06 | H | CN | H | 3-chloro-4-fluorophenyl | (CDCl₃) 8.31(s, 1H), 7.48(dd, J=2.44, 6.24Hz, 1H), 7.35(m, 1H), 6.33(s, 1H). |
| IV-07 | H | H | CH₃ | 4-(benzyloxy)phenyl | (CDCl₃) 8.07(s, 1H), 8.00(d, J=2.2Hz, 1H), 7.46-7.35(m, 5H), 7.12(d, J=9.04Hz, 2H), 7.00(d, J=9.04Hz, 2H), 6.49(d, J=2.2Hz, 1H), 5.09(s, 2H), 1.90(s, 3H). |
| IV-08 | H | H | CH₃ | 3-chloro-4-fluorophenyl | (CDCl₃) 8.01(d, J=2.2Hz, 1H), 7.98(brs, 1H), 7.18(m, 2H), 7.01(m, 1H), 6.54(d, J=2.2Hz, 1H), 1.96(s, 3H). |
| IV-09 | H | CN | CH₃ | 4-ethoxyphenyl | (CDCl₃) 8.25(s, 1H), 8.16(brs, 1H), 7.14(d, J=8.8Hz, 2H), 6.94(d, J=8.8Hz, 2H), 4.07(q, J=7.08Hz, 2H), 1.89(s, 3H), 1.45(t, J=6.84Hz, 3H). |

Example 9

[General Procedure for the Synthesis of Pyrazolo[1,5-a]pyrimidines of General Formula (IV-02)]

Synthesis of (3-chloro-4-fluorophenyl) {5-chloro-3-methylthio(pyrazolo[1,5-a]pyrimidin-7-yl)}amine.

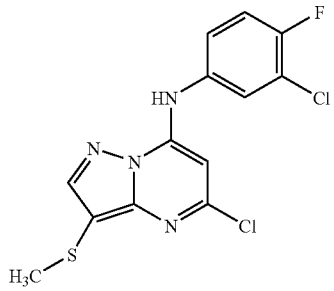

Methyl magnesium chloride (0.25 mL, 3M solution) was added cautiously to a solution of {5-chloro-7-[(3-chloro-4-fluorophenyl)amino]-6-methyl(pyrazolo[1,5-a]pyrimidin-3-yl)}thiocarbonitrile (100 mg) in dry tetrahydrofuran (5 mL) while maintaining the temperature between 0-4° C. for 2 h. Acetic acid (2 equivalents.) was added and the solvent was removed under reduced pressure. Water and ethyl acetate were added and the product was extracted with ethyl acetate (3×). The combined organic phase was dried ($Na_2SO_4$) and evaporated to give the title compound (98 mg); mp 156-158° C.

Example 10

[General Procedure for the Synthesis of Pyrazolo[1,5-a]pyrimidines of General Formula (III)]

To a solution of the precursor (IV) formed above (2 g) in 1,4-dioxane (10 mL) was added di-tert-butyl dicarbonate (2 equivalents) in 1,4-dioxane (10 mL) followed by a catalytic amount of 4-dimethylaminopyridine. The reaction was stirred at room temperature overnight and if starting material was detected by TLC, the reaction was left for longer. The mixture was concentrated in vacuo and the residue was then partitioned between water and $CH_2Cl_2$. The organic phase was washed with 10% citric acid, water and saturated aqueous NaCl and then dried over $MgSO_4$. Removal of the solvent in vacuo gave the Boc protected intermediate (III). [Purification performed—filter column to remove any residual 4-dimethylaminopyridine. Analysis performed—$^1$H-NMR, HPLC and MS].

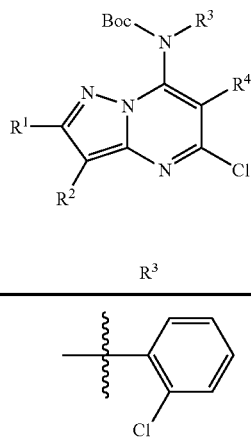

(III)

| Compound No. | $R^1$ | $R^2$ | $R^4$ | $R^3$ | mp (° C.) or $^1$H-NMR (400 MHz) d (ppm) |
|---|---|---|---|---|---|
| III-01 | H | H | Me | 2-chlorophenyl | (CDCl$_3$) 1.94(br s, 9H, C(CH$_3$)$_3$), 2.55(s, 3H, CH$_3$), 6.68(s, 1H, Het-H), 7.05(d, 1H, ArH), 7.15(t, 1H, ArH), 7.24(t, 1H, ArH), 7.5(d, 1H, ArH), 8.12(s, 1H, Het-H). |
| III-02 | H | Br | H | 3-chloro-4-fluorophenyl | 136-138 |
| III-03 | H | Cl | H | 3-chloro-4-fluorophenyl | 130-132 |
| III-04 | H | COOEt | CH$_3$ | 4-ethoxyphenyl | (DMSO-d6) 1.10-1.50(m, 15H), 2.22(s, 3H), 3.98(q, J=7.08Hz, 2H), 4.30(q, J=7.08Hz, 2H), 6.87(d, J=8.80Hz, 2H), 7.22(d, J=9.04Hz, 2H), 8.68 (brs, 1H). |

-continued (III)

Structure: Pyrazolo[1,5-a]pyrimidine core with Boc-N(R³) at 7-position, R⁴ at 6-position, Cl at 5-position, R¹ at 2-position, R² at 3-position.

| Compound No. | R¹ | R² | R⁴ | R³ | mp (° C.) or ¹H-NMR (400 MHz) d (ppm) |
|---|---|---|---|---|---|
| III-05 | H | H | CH₃ | 2-(methylthio)benzothiazol-6-yl | (CDCl₃) 8.12(d, J=2.2Hz, 1H), 7.78(d, J=8.8Hz, 1H), 7.73 (br, 1H), 7.31(br, 1H), 6.69(d, J=2.2Hz, 1H), 2.78(s, 3H), 2.31(brs, 3H), 1.35(brs, 9H). |
| III-06 | H | H | CH₃ | 2-(ethylthio)benzothiazol-6-yl | (CDCl₃) 8.12(d, J=2.2Hz, 1H), 7.78(d, J=8.8Hz, 1H), 7.71(br, 1H), 7.31(br, 1H), 6.69(d, J=2.2Hz, 1H), 3.34(q, J=7.56Hz, 1H), 2.31(brs, 3H), 1.47 (t, J=7.32Hz, 3H), 1.35(brs, 9H). |
| III-07 | H | H | CH₃ | 2-(isopropylthio)benzothiazol-6-yl | (CDCl₃) 8.12(d, J=2.2Hz, 1H), 7.79(d, J=8.8Hz, 1H), 7.82(br, 1H), 7.31(br, 1H), 6.69(d, J=2.2Hz, 1H), 4.06 (sevenfold, J=6.84Hz, 1H), 2.32(brs, 3H), 1.49(d, J=6.84Hz, 6H), 1.35 (brs, 9H). |
| III-08 | H | CH₃ | CH₃ | 4-ethoxyphenyl | (CDCl₃) 7.94(s, 1H), 7.17(d, J=9.04Hz, 2H), 6.80(d, 2H), 3.98(q, J=7.08Hz, 2H), 2.35(brs, 3H), 2.29(brs, 3H), 1.38(t, J=7.08Hz, 3H), 1.25(brs, 9H). |
| III-09 | H | H | CH₃ | 4-(methoxycarbonyl)phenyl | (CDCl₃) 8.09(d, J=2.44Hz, 1H), 7.98(d, J=9.04Hz, 2H), 7.27(d, J=8.53Hz, 2H), 6.69(d, 1H), 3.89(s, 3H), 2.24 (s, 3H), 1.36(s, 9H). |

Example 11

[General Procedures for the Synthesis of Pyrazolo[1,5-a]pyrimidines of General Formula (II)]

a) An intimate mixture (III) (100 mg) and amine (HNR⁵R⁶) (1.5 g) were heated together at 80-85° C. for 18 h, then cooled. The crude material was then partitioned between ethyl acetate and saturated aqueous NaHCO₃. The organic phase was then separated, washed with water and dried over MgSO₄ and concentrated in vacuo. The crude material was then subjected to column chromatography over silica gel. CH₂Cl₂ was used as eluent, then gradient elution up to 95% CH₂Cl₂+5% (10 M NH₃ in methanol). Typical purified yield 20 mg.

b) A solution of the Boc intermediate (III) (0.248 mmol), the amine (HNR⁵R⁶) (0.496 mmol), copper iodide (0.496 mmol), and potassium carbonate (0.496 mmol) in DMSO (0.8 mL) was stirred at 85° C. for 2 days. The reaction mixture was cooled to room temperature, followed by quenched with saturated aqueous NH₄Cl. The mixture was extracted with Et₂O. The combined extract was washed with saturated aqueous NaCl, dried over Na₂SO₄, filtered, and evaporated. The residue was purified by column chromatography (5~10% MeOH—CH₂Cl₂) to give the title compound (II).

c) Synthesis of 4-{7-[tert-Butoxycarbonyl-(4-ethoxy-phenyl)-amino]-6-methyl-pyrazolo[1,5-a]pyrimidin-5-ylamino}-pyrrolidine-1,2-dicarboxylic acid 1-tert-butyl ester

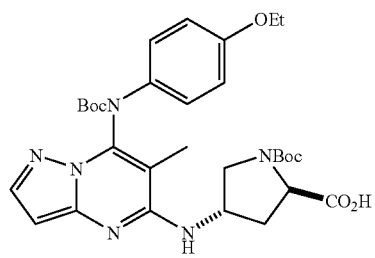

A solution of the Boc intermediate (0.248 mmol), the (S)-4-amino L-proline (114 mg, 0.496 mmol), copper iodide (94.4 mg, 0.496 mmol) and potassium carbonate (68.5 mg, 0.496 mmol) in DMSO (0.8 mL) was stirred at 85° C. for 2 days. The reaction mixture was cooled to room temperature, followed by quenched with saturated aqueous NH₄Cl. The mixture was extracted with Et₂O. The combined extract was washed with saturated aqueous NaCl, dried over Na₂SO₄, filtered, and evaporated. The residue was purified by column chromatography (5~10% MeOH—CH₂Cl₂) to give coupling compound (66.0 mg, 44.6%). The title compound was obtained.

The ¹H-NMR for this compound was shown bellow.
¹H-NMR (400 MHz, CD₃OD) d(ppm): 1.25 (t, J=7.1 Hz, 3H), 1.34 (s, 18H), 1.95 (m, 1H), 2.56 (m, 1H), 3.44 (m, 1H), 3.69 (m, 1H), 3.89 (q, J=7.1 Hz, 2H), 4.16 (m, 1H), 6.05 (m, 1H, 6.74 (d, J=7.1 Hz, 2H), 7.14 (d, J=8.5 Hz, 2H), 7.68 (s, 1H).

vacuo, and the resultant residue was dissolved in N,N-dimethylformamide (1 mL), filtered and purified by preparative HPLC to give the product (I). [Analysis performed—LC/MS)].

Example 13

[General Procedure for the Synthesis of Pyrazolo[1,5-a]pyrimidines of General Formula (I-01)]

Synthesis of 1-{5-[(trans-4-aminocyclohexyl)amino]-7-[(4-iodophenyl)amino]-6-methyl(pyrazolo[1,5-a]pyrimidin-3-yl)}-2,2,2-trifluoroethan-1-one (Compound NO: 417).

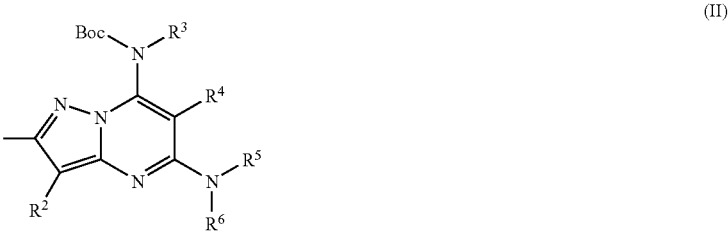

(II)

| Compound No. | R¹ | R² | R⁴ | R³ | NR⁵R⁶ | ¹H-NMR (400 MHz) d (ppm) |
|---|---|---|---|---|---|---|
| II-26 | H | COOEt | CH₃ | —C₆H₄—OEt | HN—(cyclohexyl)—NH₂ | (DMSO-d6) 1.03-1.51(m, 19H), 1.74-2.08(m, 7H), 2.50-2.58(m, 1H), 3.96(q, J=7.08Hz, 2H), 4.01-4.13(m, 1H), 4.19(q, J=7.08Hz, 2H), 6.85 (d, J=9.04Hz, 2H), 6.91(d, J=7.32Hz, 1H), 7.18(d, J=8.56Hz, 2H), 8.17(brs, 1H). |

Example 12

[General Procedures for the Synthesis of Pyrazolo[1,5-a]pyrimidines of General Formula (I)]

a) An intimate mixture of the Boc intermediate (III) (100 mg) and the amine (HNR⁵R⁶) (1.5 g) were heated together at 80-85° C. for 90 min, then cooled. The crude material was then partitioned between CH₂Cl₂ and saturated aqueous NaHCO₃. The organic phase was then separated and washed with water, dried over MgSO₄ and concentrated in vacuo. The crude material dissolved in CH₂Cl₂ (10 mL) and trifluoroacetic acid (5 mL). The mixture was stirred for 1 h at room temperature, then evaporated in vacuo. The residue was partitioned between saturated aqueous NaHCO₃ and CH₂Cl₂, the organic phase was separated, dried over MgSO₄ then subjected to column chromatography over silica gel. CH₂Cl₂ was used as eluent, then gradient elution up to 95% CH₂Cl₂+5% (10 M NH₃ in methanol). Typical purified yield 20 mg.

b) The Boc intermediate (III) (0.1 mmol) was dissolved in toluene (1 ml) and the amine (HNR⁵R⁶) (1.2 equivalents) was added. Tris(dibenzylideneacetone)dipalladium (0) (2 mol %), 2,2'-bis(diphenylphosphino)-1,1'-binaphtyl (4 mol %) and sodium tert-butoxide (1.2 equivalents) were added sequentially under an atmosphere of nitrogen. The reaction was heated and agitated overnight at 80° C. following which the reaction was filtered through a 0.45 micron filter. The solvent was removed in vacuo and the residue was resuspended in CH₂Cl₂ (0.2 mL). Trifluoroacetic acid (0.8 mL) was added and the reactions allowed to stand for 1 h at room temperature. The mixture was evaporated to dryness, in

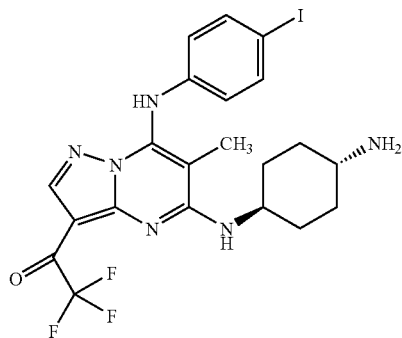

To a solution of N-{5-[(trans-4-aminocyclohexyl)amino]-6-methyl(pyrazolo[1,5-a]pyrimidin-7-yl)}(tert-butoxy)-N-(4-iodophenyl)carboxamide (50 mg) in 1,2-dichloroethane (1.8 mL) was added trifluoroacetic anhydride (1.8 mL). The resulting mixture was stirred at 45° C. for 3 h and then the solvent was removed in vacuo. The residue was dissolved in CH₂Cl₂ (1.25 mL). To this stirred solution was added trifluoroacetic acid (0.53 mL). The resulting mixture was stirred at room temperature for 3 h, and then the solvent was removed in vacuo. The residue was dissolved in tetrahydrofuran (1.6 mL) and methanol (0.18 mL). To this stirred solution was added 2 mol/L aqueous NaOH (0.18 mL). The resulting mixture was stirred at room temperature for 15 h. The reaction was quenched with aqueous 1N HCl. After extraction with CH$_2$Cl$_2$, the combined organic layer was washed with saturated aqueous NaCl, dried over Na$_2$SO$_4$ and then the solvent was removed in vacuo. The residue was purified by preparative HPLC to give the title compound (33.0 mg, yield 41% as 3 trifluoroacetic acids salt) as a white solid. The $^1$H-NMR, HPLC retention time and ESI/MS data for this compound are shown below.

$^1$H-NMR (400 MHz, DMSO-d$_6$) d(ppm): 1.38-1.56 (m, 4H), 1.79 (s, 3H), 1.97-2.12(m, 4H), 3.04(brs, 1H), 4.09(brs, 1H), 6.73(d, J=8.52 Hz, 2H), 7.11(d, J=7.32 Hz, 1H), 7.57(d, J=8.04 Hz, 2H), 7.86(brs, 3H), 8.34(s, 1H), 9.27(s, 1H).

HPLC retention time (method A): 14.7 min.

ESI/MS: 559.3 (M+H, C$_{21}$H$_{22}$F$_3$IN$_6$O).

Example 14

[General Procedure for the Synthesis of Pyrazolo[1,5-a]pyrimidines of General Formula (I-02)]

Synthesis of {5-[(trans-4-aminocyclohexyl)amino]-3-fluoro-6-methyl(pyrazolo[1,5-a]pyrimidin-7-yl)}(4-iodophenyl)amine (Compound NO: 441).

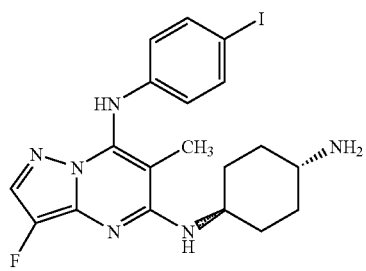

N-{5-[(trans-4-aminocyclohexyl)amino]-6-methyl(pyrazolo[1,5-a]pyrimidin-7-yl)}(tert-butoxy)-N-(4-iodophenyl)carboxamide (20 mg) was dissolved in tetrahydrofuran (300 µL). To this solution was added 1-chloromethyl-4-fluoro-1,4-diazoniabicyclo[2,2,2]octane bis(tetrafluoroborate) (63 mg). The resulting mixture was stirred for 19 h at 40° C. The reaction was quenched with saturated aqueous NaHCO$_3$. After extraction with CH$_2$Cl$_2$, the combined organic layer was washed with saturated aqueous NaCl, dried over Na$_2$SO$_4$, and the solvent was removed in vacuo to give the crude Boc protected intermediate. This crude product was used in the next reaction without further purification.

The crude product was dissolved in CH$_2$Cl$_2$ (2.0 mL). To this solution was added trifluoroacetic acid (0.2 mL). After stirring for 4 h, the solvent was removed in vacuo. The residue was purified on preparative TLC to give the title compound (1.5 mg, 9% yield). The $^1$H-NMR, HPLC retention time and ESI/MS data for this compound are shown below.

$^1$H-NMR (400 MHz, CDCl$_3$) d(ppm): 1.25(m, 2H), 1.36 (m, 2H), 1.72(s, 3H), 1.99(m, 2H), 2.22(m, 2H), 2.72(m, 1H), 4.14(m, 1H), 6.73(m, 2H), 7.32(brs, 1H), 7.60(m, 2H), 7.69 (d, J=3.40 Hz, 1H).

HPLC retention time (method A): 12.9 min.

ESI/MS: 481.4 (M+H, C$_{19}$H$_{23}$FIN$_6$).

Example 15

[General Procedure for the Synthesis of Pyrazolo[1,5-a]pyrimidines of General Formula (II-04)]

Synthesis of 5-({trans-4-[(tert-butoxy)carbonylamino]cyclohexyl}amino)-7-[(tert-butoxy)-N-(4-ethoxyphenyl)carbonylamino]-6-methylpyrazolo[1,5-a]pyrimidine-3-carboxylic acid.

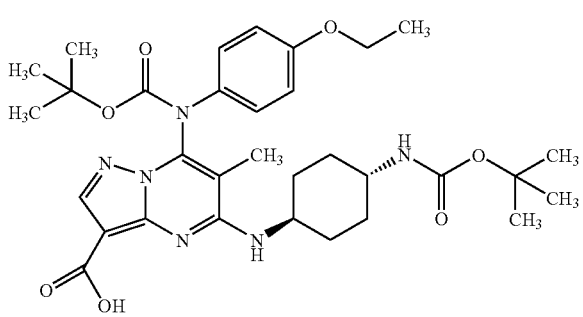

To a stirred suspension of ethyl 5-({trans-4-[(tert-butoxy)carbonylamino]cyclohexyl}amino)-7-[(tert-butoxy)-N-(4-ethoxyphenyl)carbonylamino]-6-methylpyrazolo[1,5-a]pyrimidine-3-carboxylate (5.55 g) in 2-propanol (136 mL) was added 2 mol/L aqueous NaOH (34 mL). The resulting mixture was stirred at 50° C. for 40 h, and then at 80° C. for 4 h. The mixture was acidified (pH 4) with 1 mol/L aqueous HCl and concentrated in vacuo. The residue was suspended in water (150 mL) and slowly stirred for 1 h. The precipitate was filtered and dried in vacuo to give the title compound (5.35 g, yield 78%) as a white solid. The $^1$H-NMR and ESI/MS data for this compound are shown below.

$^1$H-NMR (400 MHz, DMSO-d$_6$) d(ppm): 1.19-1.28(br, 4H), 1.29(t, J=7.08 Hz, 3H), 1.38(s, 18H), 1.73-1.86(br, 2H), 1.86-2.04(br, 5H), 3.15-3.33(m, 1H), 3.97(q, J=7.08 Hz, 2H), 4.02-4.08(m, 1H), 6.43(brs, 1H), 6.82(d, J=8.80 Hz, 1H), 6.86(d, J=8.76 Hz, 2H), 7.20(d, J=7.80 Hz, 2H), 7.93(brs, 1H).

ESI/MS: 625.5 (M+H, C$_{32}$H$_{44}$N$_6$O$_7$).

Example 16

[General Procedure for the Synthesis of Pyrazolo[1,5-a]pyrimidines of General Formula (II-05)]

Synthesis of 5-({trans-4-[(tert-butoxy)carbonylamino]cyclohexyl}amino)-7-[(tert-butoxy)-N-(4-ethoxyphenyl)carbonylamino]-6-methylpyrazolo[1,5-a]pyrimidine-3-carboxamide.

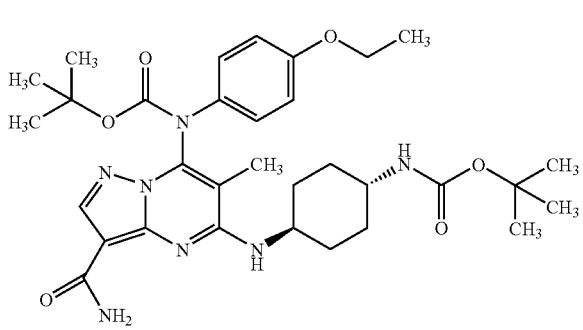

To a stirred solution of 5-({trans-4-[(tert-butoxy)carbonylamino]cyclohexyl}amino)-7-[(tert-butoxy)-N-(4-ethoxyphenyl)carbonylamino]-6-methylpyrazolo[1,5-a]pyrimidine-3-carboxylic acid (1.25 g) in N,N-dimethylformamide (20 mL) were added ethyl-3-(3'-dimethylaminopropyl)carbodiimide hydrochloride (1.92 g), N-hydoroxybenzotriazole monohydrate (0.31 g), triethylamine (2.8 mL) and ammonia (5.0 mL, 2.0 mol/L in methanol). The resulting mixture was stirred at room temperature for 24 h. The reaction was quenched with saturated aqueous NaCl. After extraction with $CH_2Cl_2$, the combined organic layer was washed with water, dried over $MgSO_4$, and the solvent was removed in vacuo to give the crude title compound (1.25 g) as a white solid. This crude product was used in the next reaction without further purification. ESI/MS data for this compound are shown below.

ESI/MS: 624.6 (M+H, $C_{32}H_{45}N_7O_6$).

Example 17

[General Procedure for the Synthesis of Pyrazolo[1,5a]pyrimidines of General Formula (II-07)]

Synthesis of N-[5-({trans-4-[(tert-butoxy)carbonylamino]cyclohexyl}amino)-7-[(tert-butoxy)-N-(4-ethoxyphenyl)carbonylamino]-6-methyl(pyrazolo[1,5-a]pyrimidin-3-yl)](phenylmethoxyl)carboxamide.

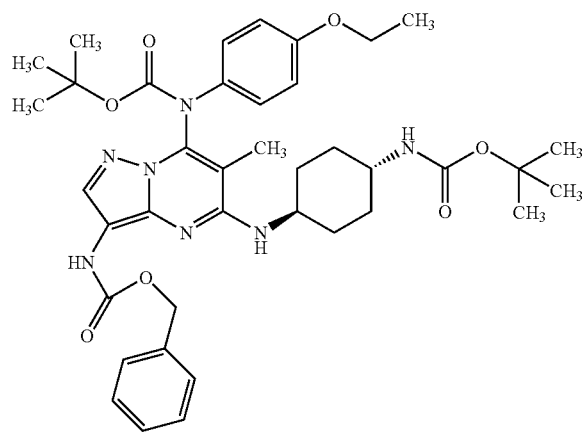

To a stirred solution of crude 5-({trans-4-[(tert-butoxy)carbonylamino]cyclohexyl}amino)-7-[(tert-butoxy)-N-(4-ethoxyphenyl)carbonylamino]-6-methylpyrazolo[1,5-a]pyrimidine-3-carboxamide (1.25 g) in benzyl alcohol (5.0 mL) was added potassium tert-butoxide (0.561 g). The resulting mixture was stirred at room temperature for 10 min. and then at 0° C. for 10 min. To this stirred solution was added iodobenzene diacetate (0.773 g), stirred at 0° C. for 10 min., and allowed to warm room temperature. The resulting mixture was stirred at room temperature for 12 h. The reaction was quenched with saturated aqueous NaCl. After extraction with $CH_2Cl_2$, the combined organic layer was dried over $MgSO_4$, and solvent was removed in vacuo to give the crude title compound (1.46 g) as pale red oil. This crude product was used in the next reaction without further purification. The $^1$H-NMR and ESI/MS data for this compound are shown below.

$^1$H-NMR (400 MHz, DMSO-$d_6$) d(ppm): 1.18-1.30(brs, 4H), 1.29(t, J=7.08 Hz, 3H), 1.38(s, 18H), 1.75-1.86(m,2H), 1.87-1.97(m, 2H), 2.00(brs, 3H), 3.15-3.28(m, 1H), 3.97(t, J=7.08 Hz, 2H), 3.85-4.10(m, 1H), 5.12(s, 2H), 6.43-6.53(m, 1H), 6.75(d, J=7.56 Hz, 2H), 6.86(d, J=8.80 Hz, 2H), 7.15-7.50(m, 7H), 7.83(brs, 1H), 8.86(brs, 1H).

ESI/MS: 730.7 (M+H, $C_{39}H_{51}N_7O_7$).

Example 18

[General Procedure for the Synthesis of Pyrazolo[1,5-a]pyrimidines of General Formula (II-08)]

Synthesis of N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide.

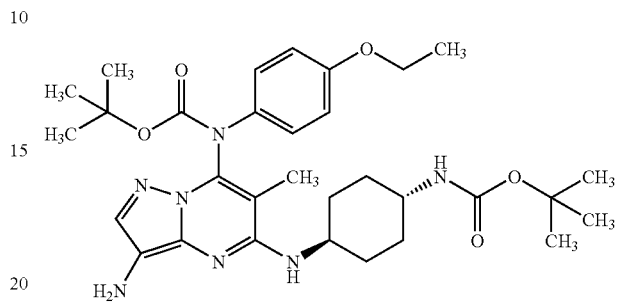

To a stirred solution of the crude N-[5-({trans-4-[(tert-butoxy)carbonylamino]cyclohexyl}amino)-7-[(tert-butoxy)-N-(4-ethoxyphenyl)carbonylamino]-6-methyl(pyrazolo[1,5-a]pyrimidin-3-yl)](phenylmethoxyl)carboxamide (1.46 g) in ethanol (100 mL) and acetic acid (0.46 mL) was added Pd/C (0.29 g, 10% on carbon). The resulting mixture was stirred at room temperature for 2 days under hydrogen atmosphere, and Pd/C was filtered off. The solvent was removed in vacuo. The residue was purified by silica gel column chromatography (elute with ethyl acetate/n-hexane=3/1) to give the title compound (0.560 g, yield 47% for 2 steps) as a pale yellow solid. The $^1$H-NMR and ESI/MS data for this compound are shown below.

$^1$H-NMR (400 MHz, DMSO-$d_6$) d(ppm): 1.20-1.35(brs, 4H), 1.29(t, J=7.08 Hz, 3H), 1.38(s, 18H), 1.75-1.90(brs, 3H), 1.90-2.05(m, 4H), 3.22(brs, 1H), 3.92-4.00(m, 3H), 6.21 (brs, 1H), 6.77(d, J=8.04 Hz, 1H), 6.83-6.87(m, 3H), 7.20 (brs, 3H), 7.45(brs, 1H).

ESI/MS: 596.6 (M+H, $C_{31}H_{45}N_7O_5$).

Example 19

[General Procedure for the Synthesis of Pyrazolo[1,5-a]pyrimidines of General Formula (I-09)]

Synthesis of N-{5-[(trans-4-aminocyclohexyl)amino]-7-[(4-ethoxyphenyl)amino]-6-methyl(pyrazolo[1,5-a]pyrimidin-3-yl)}acetamide (Compound NO: 378).

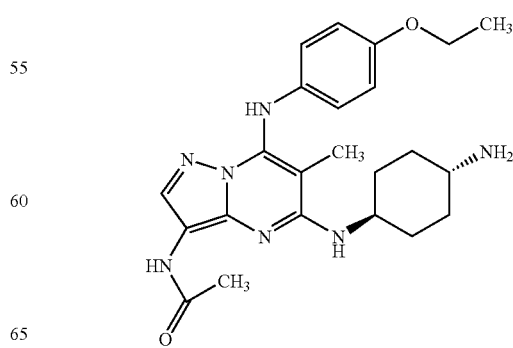

To acetyl chloride (7.1 μL) were added N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide (14.9 mg) in CH$_2$Cl$_2$ (250 μL) and triethylamine (13.9 μL). The resulting mixture was stirred at room temperature for 1 h. The reaction was quenched with saturated aqueous NaCl. After extraction with CH$_2$Cl$_2$, the solvent was removed in vacuo to give the crude di-Boc protected intermediate. This crude product was used in the nest reaction without further purification.

The crude product was dissolved in CH$_2$Cl$_2$ (175 μL). To this solution was added trifluoroacetic acid (75 μL). The resulting mixture was stirred at room temperature for 2 h, and then the solvent was removed in vacuo. The residue was purified by preparative HPLC to give the title compound (9.04 mg, yield 46% as 3 trifluoroacetic acids salt) as a white solid. The $^1$H-NMR, HPLC retention time and ESI/MS data for this compound are shown below.

$^1$H-NMR (400 MHz, DMSO-d$_6$) d(ppm): 1.30(t, J=6.84 Hz, 3H), 1.32-1.55 (m, 4H), 1.63 (s, 3H), 1.85-2.05(m, 4H), 2.05(s, 3H), 3.00(brs, 1H), 3.97(q, J=6.80 Hz, 2H), 4.05(brs, 1H), 6.24(brs, 1H), 6.85(d, J=9.00 Hz, 2H), 6.90(d, J=8.80 Hz, 2H), 7.78(brs, 3H), 8.00(s, 1H), 8.54(brs, 1H), 9.40(brs, 1H).

HPLC retention time (method A): 8.4 min.
ESI/MS: 438.4 (M+H, C$_{23}$H$_{31}$N$_7$O$_2$).

Example 20

[General Procedure for the Synthesis of Pyrazolo[1,5-a]pyrimidines of General Formula (I-10)]

Synthesis of {5-[(trans-4-aminocyclohexyl)amino]-7-[(4-ethoxyphenyl)amino]-6-methyl(pyrazolo[1,5-a]pyrimidin-3-yl)}(methylsulfonyl)amine (Compound No: 386).

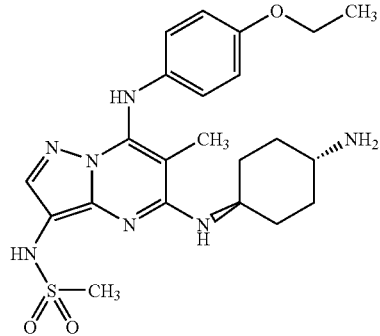

To methanesulfonyl chloride (11.5 mg) were added N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide (14.9 mg) in CH$_2$Cl$_2$ (250 μL) and triethylamine (13.9 μL). The resulting mixture was stirred at room temperature for 1 h. The reaction was quenched with saturated aqueous NaCl. After extraction with CH$_2$Cl$_2$, the solvent was removed in vacuo to give the crude di-Boc protected intermediate. This crude product was used in the next reaction without further purification.

The crude product was dissolved in CH$_2$Cl$_2$ (175 μL). To this solution was added trifluoroacetic acid (75 μL). The resulting mixture was stirred at room temperature for 2 h, and then the solvent was removed in vacuo. The residue was purified by preparative HPLC to give the title compound (2.43 mg, yield 12% as 3 trifluoroacetic acids salt) as a white solid. The $^1$H-NMR, HPLC retention time and ESI/MS data for this compound are shown below.

$^1$H-NMR (400 MHz, DMSO-d$_6$) d(ppm): 1.26(t, J=7.08 Hz, 3H), 1.30-1.45 (m, 4H), 1.60 (s, 3H), 1.87-2.03(m, 4H), 2.93(brs, 1H), 3.06(s,3H), 3.85-3.98(m, 3H), 6.24(d, J=7.32 Hz, 1H), 6.81(d, J=9.28 Hz, 2H), 6.86(d, J=9.04 Hz, 2H), 7.68(s, 1H), 7.72(brs, 3H), 8.56(s, 1H), 8.75(s, 1H).

HPLC retention time (method A): 10.5 min.
ESI/MS: 474.4 (M+H, C$_{22}$H$_{31}$N$_7$O$_3$S).

Example 21

[General Procedure for the Synthesis of Pyrazolo[1,5-a]pyrimidines of General Formula (I-11)]

Synthesis of N-{5-[(trans-4-aminocyclohexyl)amino]-7-[(4-ethoxyphenyl)amino]-6-methyl(pyrazolo[1,5-a]pyrimidin-3-yl)}(phenylamino)carboxamide (Compound NO: 389).

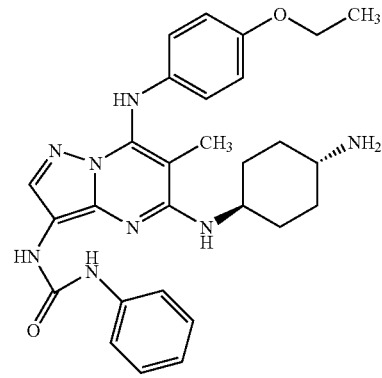

To phenyl isocyanate (11.9 mg) were added N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide (14.9 mg) in CH$_2$Cl$_2$ (250 μL) and triethylamine (13.9 μL). The resulting mixture was stirred at room temperature for 1 h. The reaction was quenched with saturated aqueous NaCl. After extraction with CH$_2$Cl$_2$, the solvent was removed in vacuo to give the crude di-Boc protected intermediate. This crude product was used in the next reaction without further purification.

The crude product was dissolved in CH$_2$Cl$_2$ (175 μL). To this stirred solution was added trifluoroacetic acid (75 μL). The resulting nature was stirred at room temperature for 2 h, and then the solvent was removed in vacuo. The residue was purified by preparative HPLC to give the title compound (6.59 mg, yield 31% as 3 trifluoroacetic acids salt) as a white solid. The $^1$H-NMR, HPLC retention time and ESI/MS data for this compound are shown below.

$^1$H-NMR (400 MHz, DMSO-d$_6$) d(ppm): 1.30(t, J=7.08 Hz, 3H), 1.36-1.47(m, 4H), 1.65(s, 3H), 1.90-2.10(m, 4H), 2.98(brs, 1H), 3.97(q, J=7.08 Hz, 2H, 4.03(brs, 1H), 6.13(brs, 1H), 6.82-6.96(m, 5H), 7.25(t, J=8.28 Hz, 2H), 7.45(d, J=7.60 Hz, 2H), 7.76(brs, 3H), 7.86(brs, 1H), 7.95(s, 1H), 8.58(brs, 1H), 8.76(brs, 1H).

HPLC retention time (method A): 10.9 min.
ESI/MS: 515.6 (M+H, C$_{28}$H$_{34}$N$_8$O$_2$).

Example 22

[General Procedure for the Synthesis of Pyrazolo[1,5-a]pyrimidines of General Formula (I-12)]

Synthesis of ({5-[(trans-4-aminocyclohexyl)amino]-7-[(4-ethoxyphenyl)amino]-6-methyl(pyrazolo[1,5-a]pyrimidin-3-yl)}amino)(methylamino)methane-1-thione (Compound No: 390).

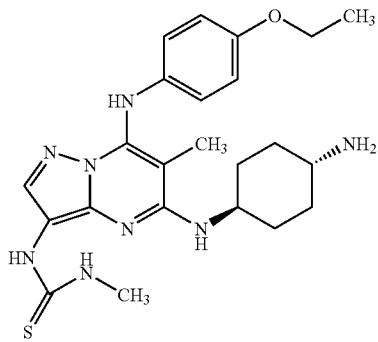

To methyl thioisocyanate (7.3 mg) were added N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide (14.9 mg) in CH$_2$Cl$_2$ (250 μL) and triethylamine (13.9 μL). The resulting mixture was stirred at room temperature for 1 h. The reaction was quenched with saturated aqueous NaCl. After extraction with CH$_2$Cl$_2$, the solvent was removed in vacuo to give the crude di-Boc protected intermediate. This crude product was used in the next reaction without further purification.

The crude product was dissolved in CH$_2$Cl$_2$ (175 μL). To this stirred solution was added trifluoroacetic acid (75 μL). The resulting mixture was stirred at room temperature for 2 h, and then the solvent was removed in vacuo. The residue was purified by preparative HPLC to give the title compound (8.32 mg, yield 41% as 3 trifluoroacetic acids salt) as a white solid. The $^1$H-NMR, HPLC retention time and ESI/MS data for this compound are shown below.

$^1$H-NMR (400 MHz, DMSO-d$_6$) d(ppm): 1.30(t, J=6.84 Hz, 3H), 1.33-1.50(m, 4H), 1.64(s, 3H), 1.88-2.05(m, 4H), 2.91(d, J=4.40 Hz, 3H), 2.98(brs, 1H), 3.88(brs, 1H), 3.97(q, J=6.80 Hz, 2H), 6.27(d, J=7.08 Hz, 1H), 6.80-6.95(m, 4H), 7.67(s, 1H), 7.70-7.90(m, 4H), 8.61(s, 1H), 9.06(s, 1H).

HPLC retention time (method A): 10.3 min.

ESI/MS: 469.4 (M+H, C$_{23}$H$_{32}$N$_8$OS).

Example 23

[General Procedure for the Synthesis of Pyrazolo[1,5-a]pyrimidines of General Formula (I-14)]

Synthesis of {5-[(trans-4-aminocyclohexyl)amino]-6-methyl(pyrazolo[1,5-a]pyrimidin-7-yl)}[4-(methylethoxy)phenyl]amine (Compound NO: 197).

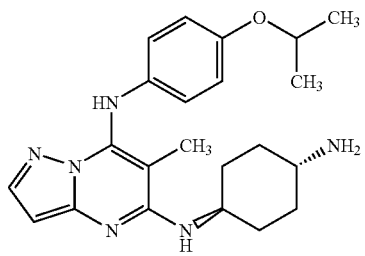

A solution of N-{5-[(4-aminocyclohexyl)amino]-6-methyl(8-hydropyrazolo[1,5-a]pyrimidin-7-yl)}(tert-butoxy)-N-[4-(phenylmethoxy)phenyl]carboxamide (3.68 g) and Pd/C (0.78 g, 10% on carbon) in methanol (140 mL) was stirred under hydrogen atmosphere for 23 h. The catalyst was filtered off and the solvent was removed in vacuo to give the crude intermediate (2.93 g) as a pale brown solid. This crude intermediate was used in the next reaction without further purification.

A suspension of crude intermediate (22.7 mg), 2-propanol (19 μL) and polymer-supported triphenylphosphine resin (3.0 mmol/g, 83.5 mg) in CH$_2$Cl$_2$ (1.0 mL) was shaken for 0.5 h at room temperature. To this suspension was added a solution of diisopropylazodicarboxylate (39.3 μL) in CH$_2$Cl$_2$ (1.1 mL) and then shaken at room temperature for 10 h. The reaction mixture was filtrated and the residual resin was washed with CH$_2$Cl$_2$ (3×1.0 mL). The combined filtrate was evaporated in vacuo to give the crude Boc protected intermediate. This crude product was used in the next reaction without further purification.

The crude product was dissolved in CH$_2$Cl$_2$ (1.0 mL). To this solution was added trifluoroacetic acid (0.87 mL). The resulting mixture was stirred at room temperature for 2.3 h and the solvent was removed in vacuo. The residue was purified by preparative HPLC to give the title compound (7.3 mg, 37% yield as 3 trifluoroacetic acids salt). The HPLC retention time and ESI/MS data for this compound are shown below.

HPLC retention time (method A): 7.6 min.

ESI/MS: 395.0 (M+H, C$_{22}$H$_{30}$N$_6$O).

Synthesis of {5-[(trans-4-aminocyclohexyl)amino]-6-methyl(pyrazolo[1,5-a]pyrimidin-7-yl)}[3-(2-piperazinylethoxy)phenyl]amine (Compound NO: 259)

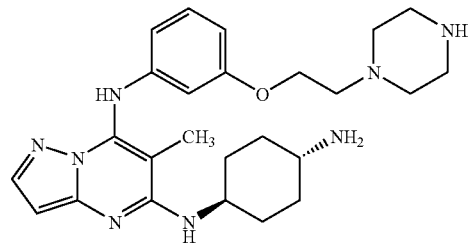

A solution of N-{5-[(4-aminocyclohexyl)amino]-6-methyl(8-hydropyrazolo[1,5-a]pyrimidin-7-yl)}(tert-butoxy)-N-[3-(phenylmethoxy)phenyl]carboxamide (11.6 g) and Pd/C (0.62 g, 10% on carbon) in methanol (150 mL) was stirred under hydrogen atmosphere for 23 h. The catalyst was filtered off and the solvent was removed in vacuo to give the crude intermediate (10.7 g) as a pale brown solid. This crude intermediate was used in the next reaction without further purification.

A suspension of crude intermediate (33.9 mg), 4-(2-hydroxyethyl)piperazinecarboxylate (86.4 mg) and polymer-supported triphenylphosphine resin (3.0 mmol/g, 125 mg) in $CH_2Cl_2$ (1.75 mL) was shaken for 0.5 h at room temperature. To this suspension was added a solution of diisopropylazodicarboxylate (59.0 μL) in $CH_2Cl_2$ (1.0 mL) and then shaken at room temperature for 17.5 h. The reaction mixture was filtrated and the residual resin was washed with $CH_2Cl_2$ (3×1.0 mL). The combined filtrate was evaporated in vacuo to give the crude Boc protected intermediate. This crude product was used in the next reaction without further purification.

The crude product was dissolved in $CH_2Cl_2$ (1.0 mL). To this solution was added trifluoroacetic acid (0.87 mL). The resulting mixture was stirred at room temperature for 2.3 h and the solvent was removed in vacuo. The residue was purified by preparative HPLC to give the title compound (20.6 mg, 34% yield as 3 trifluoroacetic acids salt). The HPLC retention time and ESI/MS data for this compound are shown below.

HPLC retention time (method B): 2.3 min.
ESI/MS: 465.7 (M+H, $C_{25}H_{36}N_8O$).

Example 24

[General Procedure for the Synthesis of Pyrazolo[1,5-a]pyrimidines of General Formula (I-16)]

Synthesis of {5-[(trans-4-aminocyclohexyl)amino]-6-methyl(pyrazolo[1,5-a]pyrimidin-7-yl)}(4-phenylphenyl)amine (Compound NO: 284).

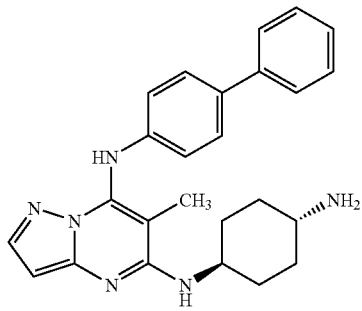

A mixture of N-{5-[(trans-4-aminocyclohexyl)amino]-6-methyl(pyrazolo[1,5-a]pyrimidin-7-yl)}(tert-butoxy)-N-(4-iodophenyl)carboxamide (30 mg), phenylboronic acid (7.2 mg), $Na_2CO_3$ (67.8 mg), palladium (II) acetate (3.6 mg) and triphenylphosphine (12.5 mg) in it-propanol (1.08 mL) and $H_2O$ (0.217 mL) was stirred for 19.3 h at 80° C. The reaction mixture was filtrated and the filtrate was evaporated in vacuo to give the crude Boc protected intermediate. This crude product was used in the next reaction without further purification.

The crude product was dissolved in $CH_2Cl_2$ (1.0 mL). To this solution was added trifluoroacetic acid (0.87 mL). The resulting mixture was stirred for 1.8 h, the solvent was removed in vacuo. The residue was purified by preparative HPLC to give the title compound (9.1 mg, 23% yield as 3 trifluoroacetic acids salt). The HPLC retention time and ESI/MS data for this compound are shown below.

HPLC retention time (method B): 10.8 min.
ESI/MS: 413.3 (M+H, $C_{25}H_{28}N_6$).

Synthesis of {5-[(trans-4-aminocyclohexyl)amino]-6-methyl(pyrazolo[1,5-a]pyrimidin-7-yl)}(3-(3-pyridyl)phenyl)amine (Compound NO: 450).

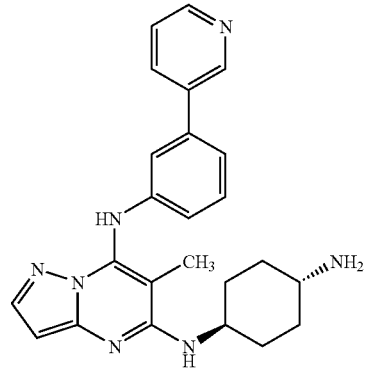

The title compound and Boc protected intermediate were synthesised in the same manner as above using N-{5-[(trans-4-aminocyclohexyl)amino]-6-methyl(pyrazolo[1,5-a]pyrimidin-7-yl)}(tert-butoxy)-N-(3-iodophenyl)carboxamide, pyridine-3-boronic acid, $Na_2CO_3$ palladium (II) acetate and triphenylphosphine. The title compound (6.1 mg, 15% yield as 3 trifluoroacetic acids salt) was obtained. The HPLC retention time and ESI/MS data for this compound are shown below.

HPLC retention time (method A): 6.0 min.
ESI/MS: 414.1 (M+H, $C_{24}H_{27}N_7$).

Example 25

[General Procedure for the Synthesis of Pyrazolo[1,5-a]pyrimidines of General Formula (I-17)]

Synthesis of {5-[(trans-4-aminocyclohexyl)amino]-6-methyl(pyrazolo[1,5-a]pyrimidin-7-yl)}[4-(2-phenylethynyl)phenyl]amine (Compound NO: 375).

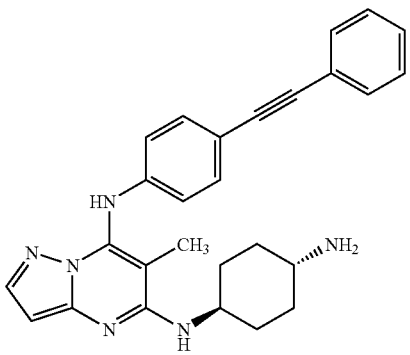

To a mixture of N-{5-[(trans-4-aminocyclohexyl)amino]-6-methyl(pyrazolo[1,5-a]pyrimidin-7-yl)}(tert-butoxy)-N-(4-iodophenyl)carboxamide (30 mg), palladium (II) acetate (6.0 mg), triphenylphosphine (7.0 mg) in tetrahydrofuran (0.5 mL) was added ethynylbenzene (17.6 μL) and triethylamine (26 μL). The resulting mixture was stirred for 15 min. To this mixture was added cupper (I) iodide (3.0 mg) and stired for 1 h at 50° C. The reaction mixture was filtrated and the filtrate was evaporated in vacuo to give the crude Boc protected intermediate. This crude product was used in the next reaction without further purification.

The crude product was dissolved in $CH_2Cl_2$ (1.0 mL). To this solution was added trifluoroacetic acid (0.87 mL). After

Example 26

[General Procedure for the Synthesis of Pyrazolo[1,5-a]pyrimidines of General Formula (I-19)]

Synthesis of 4-({5-[(trans-4-aminocyclohexyl)amino]-6-methyl(pyrazolo[1,5-a]pyrimidin-7-yl)}amino)phenyl pyrrolidinyl ketone (Compound No.792).

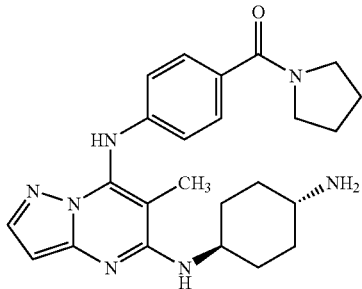

To a stirred solution of 4-{(tert-butoxy)-N-[5-({trans-4-[(tert-butoxy)carbonylamino]cyclohexyl}amino)-6-methyl(pyrazolo[1,5-a]pyrimidin-7-yl)]carbonylamino}benzoic acid (50 mg) in N,N-dimethylformamide (1.0 mL) was added carbonyldiimidazole (69 mg) and stirred at room temperature for 30 minutes. The resulting mixture was added to pyrrolidine (100 µL) and stirred at room temperature for 15 h. The reaction was quenched with saturated aqueous NaCl. After extraction with $CH_2Cl_2$, the solvent was removed in vacuo to give the crude di-Boc protected intermediate. This crude product was used in the next reaction without further purification.

The crude product was dissolved in $CH_2Cl_2$ (700 µL). To this stirred solution was added trifluoroacetic acid (300 µL). The resulting mixture was stirred at room temperature for 2 h, and then the solvent was removed in vacuo. The residue was purified by preparative HPLC to give the title compound (39.43 mg, yield 59% as 3 trifluoroacetic acids salt) as a white solid. The $^1$H-NMR, HPLC retention time and ESI/MS data for this compound are shown below.

$^1$H-NMR (400 MHz, DMSO-$d_6$) d(ppm): 1.37-1.53 (m, 4H), 1.73-1.88 (m, 7H), 1.92-2.07 (m, 4H), 2.95-3.05 (m, 1H), 3.43 (t, J=6.60 Hz, 4H), 3.89-4.00 (m, 1H), 6.07 (s, 1H), 6.49 (brs, 1H), 6.86 (d, J=8.28 Hz, 2H), 7.45 (d, J=8.56 Hz, 2H), 7.73-7.91 (m, 4H), 9.18 (brs, 1H).

HPLC retention time (method A): 6.9 min.

ESI/MS: 434.1 (M+H, $C_{24}H_{31}N_7O$).

Example 27

[General Procedure for the Synthesis of Pyrazolo[1,5-a]pyrimidines of General Formula (I-21)]

Synthesis of 1-{5-[(trans-4-aminocyclohexyl)amino]-7-[(4-ethoxyphenyl)amino]-6-methyl(pyrazolo[1,5-a]pyridin-3-yl)}pentan-1-one (Compound NO:362).

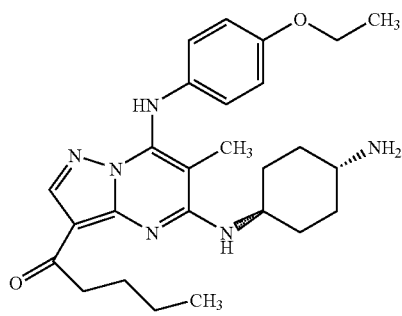

(tert-Butoxy)-N-[5-({trans-4-[(tert-butoxy)carbonylamino]cyclohexyl}amino)-3-(N-methoxy-N-methylcarbamoyl)-6-methyl(pyrazolo[1,5-a]pyrimidin-7-yl)]-N-(4-ethoxyphenyl)carboxamide (33.4 mg) was dissolved in tetrahydrofuran (500 µL) and stirred at -7° C. for 5 min under nitrogen atmosphere. To this stirred solution was added n-butyl lithium (61.5 µL, 2.44 M in n-hexane). The resulting mixture was stirred at -78° C. for 1 h, allowed to warm at room temperature and then stirred at room temperature for 23 h. The reaction was quenched with saturated aqueous $NH_4Cl$. After extraction with ethyl acetate, the combined organic layer was washed with saturated aqueous NaCl, dried over $Na_2SO_4$ and then the solvent was removed in vacuo to give the crude di-Boc protected intermediate. This crude product was used in the next reaction without further purification.

The crude product was dissolved in $CH_2Cl_2$ (175 µL). To this stirred solution was added trifluoroacetic acid (75 µL). The resulting mixture was stirred at room temperature for 2 h, and then the solvent was removed in vacuo. The residue was purified by preparative HPLC to give the title compound (2.93 mg, yield 6% for 2 steps as 3 trifluoroacetic acids salt) as a white solid. The $^1$H-NMR, HPLC retention time and ESI/MS data for this compound are shown below.

$^1$H-NMR (400 MHz, DMSO-$d_6$) d(ppm): 0.91(t, J=7.32 Hz, 3H), 1.30(t, J=7.04 Hz, 3H), 1.32-1.52(m, 6H), 1.57-1.67 (m, 5H), 1.90-2.15(m, 4H), 2.96-3.06(m, 3H), 3.92-4.03(m, 3H), 6.57(d, J=7.32 Hz, 1H), 6.85(d, J=9.04 Hz, 2H), 6.92(d, J=9.00 Hz, 2H), 7.75-7.90(m, 3H), 8.14(s, 1H), 8.78(s, 1H).

HPLC retention time (method A): 14.2 min.

ESI/MS: 465.2 (M+H, $C_{26}H_{36}N_6O_2$).

Example 28

[General Procedure for the Synthesis of Pyrazolo[1,5-a]pyrimidines of General Formula (I-23)]

Synthesis of {5-[(trans-4-aminocyclohexyl)amino]-6-methyl-[3-benzylamino](pyrazolo[1,5-a]pyrimidin-7-yl)}(4-ethoxyphenyl)amine (Compound No. 436).

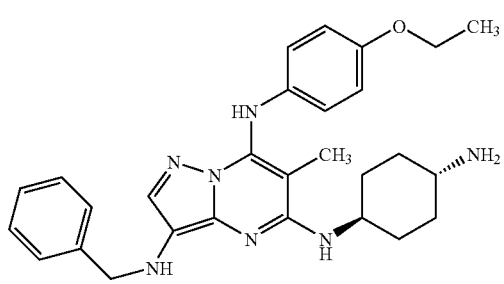

stirring for 4 h, the solvent was removed in vacuo. The residue was purified by preparative HPLC to give the title compound (11.4 mg, 27% yield as 3 trifluoroacetic acids salt). The HPLC retention time and ESI/MS data for this compound are shown below.

HPLC retention time (method A): 12.7 min.

ESI/MS: 437.2 (M+H, $C_{27}H_{28}N_6$).

To sodium hydride (1.2 mg) was added N-[5-({trans-4-[(tert-butoxy)carbonylamino]cyclohexyl}amino)-7-[(tert-butoxy)-N-(4-ethoxyphenyl)carbonylamino]-6-methyl(pyrazolo[1,5-a]pyrimidin-3-yl)]-2,2,2-trifluoroacetamide (20.8 mg) in tetrahydrofuran (300 μL). The resulting mixture was stirred at room temperature for 1 h, to this solution was added benzyl bromide (4.3 μL) and then stirred at room temperature for 15 h. The reaction was quenched with saturated aqueous NaCl. After extraction with $CH_2Cl_2$, the solvent was removed in vacuo. The residue was dissolved in $CH_2Cl_2$ (210 μL). To this stirred solution was added trifluoroacetic acid (90 μL). The resulting mixture was stirred at room temperature for 2 h, and then the solvent was removed in vacuo. The residue was dissolved in methanol (300 μL). To this stirred solution was added aqueous 2 mol/L NaOH (75 μL). The resulting mixture was stirred at room temperature for 2 h. The reaction was quenched with saturated aqueous NaCl. After extraction with $CH_2Cl_2$, the solvent was removed in vacuo. The residue was purified by preparative HPLC to give the title compound (12.79 mg, yield 52% as 3 trifluoroacetic acids salt) as a white solid. The $^1$H-NMR, HPLC retention time and ESI/MS data for this compound are shown below.

$^1$H-NMR (400 MHz, DMSO-$d_6$) d(ppm): 1.30(t, J=7.08 Hz, 3H), 1.38-1.55(m, 4H), 1.65(s, 3H), 1.95-2.13(m, 4H), 3.02(brs, 1H), 3.92-4.05(m, 3H), 4.62(s, 2H), 6.50(d, J=7.02 Hz, 1H), 6.85(d, J=9.28 Hz, 2H), 6.89(d, J=9.28 Hz, 2H), 7.38-7.46(m, 5H), 7.80(s, 1H), 7.88-7.97(m, 3H), 8.73(s, 1H).

HPLC retention time (method A): 11.2 min.

ESI/MS: 486.4 (M+H, $C_{28}H_{35}N_7O$).

Synthesis of [5-[(trans-4-aminocyclohexyl)amino]-3-({[3-(difluoromethoxy)phenyl]methyl}amino)-6-methyl(pyrazolo[1,5-a]pyrimidin-7-yl)](4-ethoxyphenyl)amine (Compound No. 791).

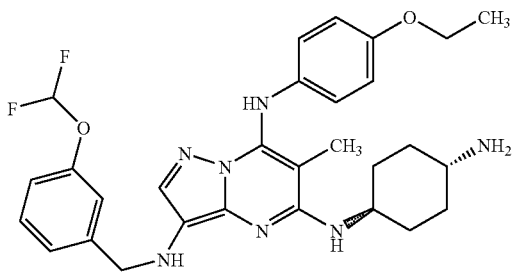

To a solution of 3-(difluoromethoxy)benzaldehyde (5.1 mg) in 1,2-dichloroethane (340 μL) and acetic acid (35 μL) were added N-[3-amino-5-({trans-4-[(tert-butoxy)carbonylamino]cyclohexyl}amino)-6-methyl(pyrazolo[1,5-a]pyrimidin-7-yl)](tert-butoxy)-N-(4-ethoxyphenyl)carboxamide (22.4 mg). The resulting mixture was stirred at 70° C. for 30 min. To this solution was added sodium tetrahydroborate (20 mg) and stirred at room temperature for 10 min. The reaction was quenched with water. After extraction with $CH_2Cl_2$, the combined organic layer was washed with saturated aqueous NaCl and the solvent was removed in vacuo to give the crude di-Boc protected intermediate. This crude product was used in the next reaction without further purification.

The crude product was dissolved in $CH_2Cl_2$ (280 μL). To this stirred solution was added trifluoroacetic acid (120 μL). The resulting mixture was stirred at room temperature for 2 h, and then the solvent was removed in vacuo. The residue was purified by preparative HPLC to give the title compound (15.58 mg, yield 46% as 3 trifluoroacetic acids salt) as a white solid. The $^1$H-NMR, HPLC retention time and ESI/MS data for this compound are shown below.

$^1$H-NMR (400 MHz, DMSO-$d_6$) d(ppm): 1.30(t, J=6.84 Hz, 3H), 1.35-1.52(m, 4H), 1.65(s, 3H), 1.95-2.12(m, 4H), 3.01(m, 1H), 3.92-4.00(m, 3H), 4.63(s, 2H), 6.40-6.47(m, 1H), 6.82-6.90(m, 4H), 7.16-7.30(m, 4H), 7.45(t, J=8.04 Hz, 1H), 7.76(brs, 1H), 7.85(brs, 3H), 8.69(brs, 1H).

HPLC retention time (method A): 10.9 min.

ESI/MS: 552.1 (M+H, $C_{29}H_{35}F_2N_7O_2$).

Example 29

[General Procedure for the Synthesis of Pyrazolo[1,5a-]pyrimidines of General Formula (I-25)]

Synthesis of {7-[(4-ethoxyphenyl)amino]-6-methyl(pyrazolo[1,5-a]pyrimidin-5-yl)}methyl-3-piperidylamine (Compound NO: 340).

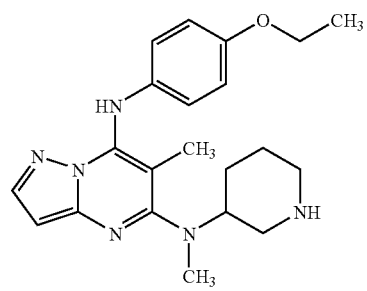

To a solution of tert-butyl 3-({7-[(tert-butoxy)-N-(4-ethoxyphenyl)carbonylamino]-6-methyl(pyrazolo[1,5-a]pyrimidin-5-yl)}methylamino)piperidinecarboxylate (22.3 mg) in N,N-dimethylformamide (0.5 mL) was added sodium hydride (>60% w/w in oil, 3.1 mg). The resulting mixture was stirred at room temperature for 10 min. To this solution was added methyl iodide (3.7 μL) and the resulting mixture was stirred for further 15 h. The reaction was quenched with water. After extraction with $CH_2Cl_2$, the combined organic layer was washed with saturated aqueous NaCl, dried over $Na_2SO_4$, and the solvent was removed in vacuo to give the crude di-Boc protected intermediate. This crude product was used in the next reaction without further purification.

The crude product was dissolved in $CH_2Cl_2$ (1.0 mL). To this solution was added trifluoroacetic acid (0.87 mL) and stirred for 5.5 h. The solvent was removed in vacuo. The residue was purified on preparative TLC to give the title compound (14.6 mg, 64% yield). The $^1$H-NMR, HPLC retention time and ESI/MS data for this compound are shown below.

$^1$H-NMR (400 MHz, DMSO-$d_6$) d(ppm): 1.42(t, 3H), 1.78 (s, 3H), 1.81(m, 3H), 1.96(m, 1H), 2.57(m, 1H), 2.86(s, 3H), 2.89(m, 1H), 3.08(m, 1H), 3.24(m, 1H), 3.49(m, 1H), 3.99(q, 2H), 5.30(brs, 1H), 6.24(d, J=2.2 Hz, 1H), 6.91(m, 2H), 6.98 (m, 2H), 7.68(brs, 1H), 7.85(d, J=2.2 Hz, 1H) HPLC retention time (method A): 9.8 min.

ESI/MS: 381.2 (M+H, $C_{21}H_{28}N_6O$).

Example 30

[General Procedure for the Synthesis of Pyrazolo[1,5a-]pyrimidines of General Formula (I-27)]

Synthesis of {5-[((3S)(3-piperidyl))amino]-6-methyl(pyrazolo[1,5-a]pyrimidin-7-yl)}(4-ethoxyphenyl)amine (Compound NO: 193).

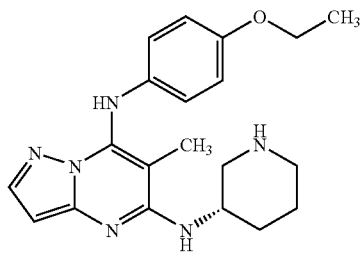

To a stirred solution of N-(5-{[(3S)-1-benzyl(3-piperidyl)]amino}-6-methyl(pyrazolo[1,5-a]pyrimidin-7-yl))(tert-butoxy)-N-(4-ethoxyphenyl)carboxamide (272 mg) in CH2Cl2 (2 mL) was added trifluoroacetic acid (2 mL). After stirring at room temperature for 3 h, the reaction mixture was poured into the saturated aqueous NaHCO$_3$ and extracted with CH$_2$Cl$_2$. The combined extract was washed with saturated aqueous NaCl, dried over Na$_2$SO$_4$, filtered, and the solvent was removed in vacuo. The residue was purified by silica gel column chromatography (96% CH$_2$Cl$_2$+4% (2 M NH$_3$ in methanol) was used as eluent, then gradient elution up to 90% CH$_2$Cl$_2$+10% (2.0 M NH$_3$ in methanol)) to give the intermediate (237 mg).

A solution of this intermediate in ethanol (2 mL) was hydrogenated under hydrogen atmosphere in the presence of Pd(OH)$_2$/C (125 mg, 10% on carbon). After stirring for 5 h, the reaction mixture was filtered, and evaporated in vacuo. The crude residue was purified by column chromatography (96% CH$_2$Cl$_2$+4% (2.0 M NH$_3$ in methanol)) to give the title compound (107 mg, 60%). The 1H-NMR, HPLC retention time and ESI/MS data for this compound are shown below.

1H-NMR (400 MHz, CDCl3) d(ppm): 7.76 (d, J=2.2 Hz, 1H), 7.49 (s, 1H), 7.00 (d, J=9.0 Hz, 2H), 6.85 (d, J=8.8 Hz, 2H), 6.11 (d, J=2.2 Hz, 1H), 4.95 (m, 1H), 4.27 (m, 1H), 4.02 (q, J=7.1 Hz, 2H), 3.20 (m, 1H), 2.83 (m, 2H), 2.71 (dd, J=6.2 Hz, 11.4 Hz, 1H), 1.87 (m, 1H), 1.71 (m, 2H), 1.71 (s, 3H), 1.56 (m, 1H), 1.49 (t, J=7.1 Hz, 3H).

HPLC retention time (method A): 8.0 min.
ESI/MS: 367.4 (M+H, C$_{20}$H$_{26}$N$_6$O).

Synthesis of [5-(azaperhydroepin-3-ylamino)-6-methyl(pyrazolo[1,5-a]pyrimidin-7-yl)](4-ethoxyphenyl)amine (Compound No: 272).

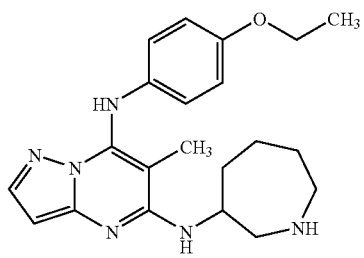

To a solution of (tert-butoxy)-N-(4-ethoxyphenyl)-N-(6-mrthyl-5-{[1-benzylazaperhydoepin-3-yl]amino}(pyrazolo[1,5-a]pyrimidine-7-yl))carboxamide (6.6 mg) in CH$_2$Cl$_2$ (0.5 mL) was added trifluoroacetic acid (0.3 mL) at 0° C. After stirring for 16 h at room temperature, the reaction mixture was poured into saturated aqueous NaHCO$_3$ and extracted with ethyl acetate. The combined organic layer was washed with saturated aqueous NaCl, dried over Na$_2$SO$_4$, filtered, and evaporated in vacuo. The residue was purified on preparative TLC to give the intermediate (5.0 mg, 91%).

To a stirred solution of this intermediate (2.0 mg) in CH$_2$Cl$_2$ (0.3 mL) was added α-chloroethyl chloroformate (2 μL) at 0° C. After stirring for 0.5 h, to the reaction mixture was added saturated aqueous NaHCO$_3$ and then extracted with ethyl acetate. The combined organic layer was washed with saturated aqueous NaCl, dried over Na$_2$SO$_4$, filtered, and evaporated in vacuo. The residue was dissolved in methanol (0.5 mL). After reflux for 4 h, the reaction mixture was cooled to room temperature and then evaporated in vacuo. The residue was purified on preparative TLC (90% CH$_2$Cl$_2$+10% (2.0 M NH$_3$ in methanol)) to give the title compound (0.9 mg, 59%). The HPLC retention time and ESI/MS data for this compound are shown below.

HPLC retention time (method A): 4.4 min.
ESI/MS: 381.4 (M+H, C$_{21}$H$_{28}$N$_6$O).

Example 31

[General Procedure for the Synthesis of Pyrazolo[1,5-a]pyrimidines of General Formula (I-29)]

Synthesis of {5-[(trans-4-aminocyclohexyl)amino]-3-iodo(pyrazolo[1,5-a]pyrimidin-7-yl)}[(3-chlorophenyl)methyl]amine (Compound NO: 297).

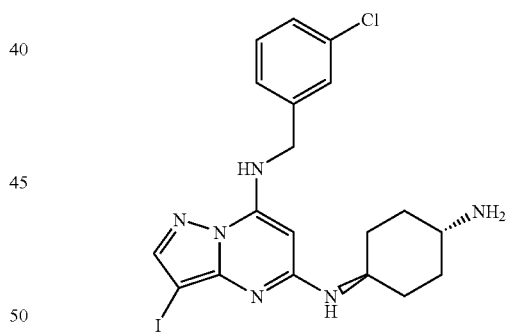

To a stirred solution of {5-[(trans-4-aminocyclohexyl)amino](pyrazolo[1,5-a]pyrimidin-7-yl)}[(3-chlorophenyl)methyl]amine (41.8 mg) in CH$_2$Cl$_2$ (565 μL) was added ICl (169 μL, 1.0 M in CH$_2$Cl$_2$), and the resulting mixture was stirred at room temperature for 4 h in the dark. The reaction was quenched with saturated aqueous Na$_2$S$_2$O$_3$. The resulting precipitate was collected by filtration. After extraction of filtrate by CH$_2$Cl$_2$, the combined organic layer was washed with saturated aqueous NaCl. To this solution, the precipitate collected above was dissolved, and the solvent was removed in vacuo. The residue was purified by preparative HPLC, and the fraction contained the title compound was basified (pH 9) with saturated aqueous NaHCO$_3$. After extraction with CH$_2$Cl$_2$, combined organic layer was dried over Na$_2$SO$_4$. The solvent was removed in vacuo, and the title compound (23.11 mg, 41% yield) was obtained as a white solid. The ¹H-NMR, HPLC retention time and ESI/MS data for this compound are shown below.

¹H-NMR (270 MHz, DMSO-d₆) d(ppm): 1.00-1.40(m, 4H), 1.70-2.00(m, 4H), 2.71(m, 1H), 3.65(m, 1H), 4.44(brs, 2H), 5.10(s, 1H), 6.76(d, J=7.83 Hz, 1H), 7.10-7.50(m, 4H), 7.81(s, 1H), 8.05(brs, 1H).

HPLC retention time (method A): 7.6 min.

ESI/MS: 497.4 (M+H, $C_{19}H_{22}ClIN_6$).

Example 32

[General Procedure for the Synthesis of Pyrazolo[1,5-a]pyrimidines of General Formula (I-31)]

To a solution of pyrazolo[1,5-a]pyrimidine (I-30) (50 mg) in tetrahydrofuran (5 ml) was added cyclohexanone (1.1 equivalents) and the reaction was heated for 16 h at 60° C. To the cooled mixture was then added sodium cyanoborohydride (5 equivalents) and stirred at room temperature for 2 h. The mixture was evaporated to dryness, in vacuo, and the resultant residue dissolved in water and ethyl acetate. The organic layer was separated, dried over MgSO₄ then subjected to column chromatography over silica gel. The eluent was CH₂Cl₂, then gradient elution up to 95% CH₂Cl₂+5% (10 M NH₃ in methanol) to give pyrazolo[1,5-a]pyrimidine of General Formula (I-31).

Example 33

Synthesis of 7-N-(4-Ethoxy-phenyl)-6-methyl-5-N-(4-propyl-piperidin-3-yl)-pyrazolo[1,5-a]pyrimidine-5,7-diamine (Compound NO:814)

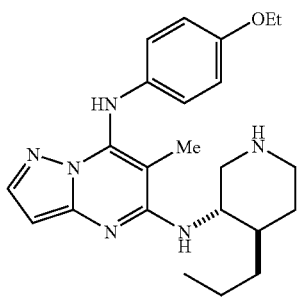

To a stirred solution of 4-allyl 3-oxopiperidine (3.39 g, 12.4 mmol) in tetrahydrofuran (31 mL) was added a solution of lithium tris sec-buyul hydrobororate in tetrahydrofuran (15 mL; 1M solution) at −78° C. After stirring at −78° C. for 3 h, the mixture was acidified with 1 N HCl and extracted with AcOEt. The combined extract was washed with saturated aqueous NaHCO₃, followed by saturated aqueous NaCl. The organic layer was dried over Na₂SO₄, filtered and evaporated in vacuo. The residue was purified by column chromatography (20% AcOEt-hexane) to give 4-Allyl-3-hydroxy-piperidine-1-carboxylic acid benzyl ester (3.12 g).

¹H-NMR (400 MHz, CDCl₃) d(ppm): 7.35 (m, 5H), 5.79 (m, 1H), 5.13 (m, 2H), 5.09 (m, 1H, 5.04 (m, 1H), 4.22 (br, 2H), 3.83 (m, 1H), 2.92 (m, 1H), 2.77 (br, 1H), 2.21 (m, 1H), 2.05 (m, 1H), 1.57 (m, 2H), 1.48 (br, 1H).

To a stirred solution of 4-Allyl-3-hydroxy-piperidine-1-carboxylic acid benzyl ester (293 mg, 1.06 mmol) were added triphenyl phosphine(362 mg, 1.38 mmol), a solution of diethyl azodicarboxylate in toluene (0.6 ml, 1.38 immol; 40% solution) and DPPA (297 µL, 1.38 mmol). After stirring for 4 h, the mixture was evaporated and the residue was purified by column chromatography (15% AcOEt-hexane)to give 4-Allyl-3-azido-piperidine-1-carboxylic acid benzyl ester.

To a stirred solution of above residue in tetrahydrofuran (3.5 mL)-H₂O (0.35 mL) was added triphenyl phosphine (417 mg, 1.59 mmol). The mixture was stirred under reflux for 16 h, added NaSO₄, filtered and evaporated. The crude mixture was purified by column chromatography to give 4-Allyl-3-amino-piperidine-1-carboxylic acid benzyl ester (118 mg, 41% in 2 steps).

¹H-NMR (400 MHz, CD₃OD) d(ppm): 7.2 (m, 5H), 5.71 (m, 1H), 5.00 (s, 2H), 4.99 (m, 1H), 4.93 (m, 1H), 4.05 (m, 1H), 3.96 (m, 1H), 2.70 (br, 1H), 2.47 (br, 1H), 2.39 (m, 1H), 2.30 (m, 1H), 1.84 (m, 1H), 1.66 (m, 1H), 1.24 (m, 1H), 1.04 (m, 1H).

4-Allyl-3-[7-(4ethoxy-phenylamino)-6-methyl-pyrazolo[1,5-a]pyrimidin-5-ylamino]-piperidine-1-carboxylic acid benzyl ester was prepared by Example 12.

A solution of 4-Allyl-3-[7-(4-ethoxy-phenylamino)-6-methyl-pyrazolo[1,5-a]pyrimidin-5-ylamino]-piperidine-1-carboxylic acid benzyl ester (3.1 mg) in EtOH (1.5 mL) was hydrogenated in the presence of 10% palladium on carbon (7.5 mg) for 45 min. The mixture was filtered through a pad of Celite and evapotrated. The residue was purified on preparative TLC to give the title compound (1.4 mg).

¹H-NMR (400 MHz, CDCl₃) d(ppm): 7.77 (d, J=2.2 Hz, 1H), 7.51 (s, 1H), 7.01 (d, J=8.8 Hz, 2H), 6.86 (d, J=9.04 Hz, 2H), 6.10 (d, J=2.2 Hz, 1H), 4.45 (br, 1H), 4.05 (m, 1H), 4.02 (q, J=6.84 Hz, 2H), 3.47 (dd, 1H), 3.09 (m, 1H), 2.68 (m, 1H), 2.48 (m, 1H), 2.02 (m, 1H), 1.91-1.43 (m, 3H), 1.69 (s, 3H), 1.42 (t, J=6.84 Hz, 3H), 1.26 (m, 2H), 0.89 (t, J=7.08 Hz, 3H).

Example 34

The compounds of the invention listed in Table B below were synthesized according to the respective methods in Examples 1 to 33 using the corresponding starting materials and reagents. The numbers assigned to each of the compounds in Table B correspond to the Compound Nos. of the compounds listed as specific examples in Table A above. Compounds were characterised by mass spectrometry using single quadrupole instrumentation with an electrospray source. M+H indicates values obtained for compound molecular mass (M) with proton (H) capture and M−H compound molecular mass (M) with proton (H) loss. Melting points (mp) are uncorrected; (d) denotes decomposition at or near the melting point. Compounds which were not solids were gums. The. ¹H-NMR spectra (400 MHz, DMSO-d₆ or CDCl₃) of selected compounds of the invention were measured. The data for the chemical shifts (d: ppm) and coupling constants (J: Hz) are shown in Table B. The "HPLC retention time" are the retention time for the compounds in HPLC analysis carried out under the condition of the Method A, B, C or D above. The "method of preparation" in Table B are the example numbers of the corresponding methods in witch the compounds were synthesized.

TABLE B

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 1 | 400.2 | | 9.5 | A | | (DMSO-d6) 8.31(s, 1H), 7.61(dd, 1H), 7.49(t, 1H), 7.39(m, 1H), 7.27(d, 1H), 5.59(s, 1H), 3.94(m, 1H), 2.49(m, 1H), 1.88(m, 2H), 1.76(m, 2h), 1.15(m, 4H). | 12 |
| 2 | 455 | | 10.2 | A | 222-225 | | 12 |
| 3 | 389 | | | | 102-105(d) | | 12 |
| 4 | 431 | | | | 102-105(d) | | 12 |
| 5 | 451 | | | | 198-200(d) | | 12 |
| 6 | 469 | | 12.1 | A | 224-226(d) | | 12 |
| 7 | 409 | | 11.2 | A | 227-230(d) | | 12 |
| 8 | 509 | | | | 234-237(d) | | 12 |
| 9 | 447 | | | | 221-223 | | 12 |
| 10 | 389 | | 9.4 | A | 229-232 | | 12 |
| 11 | 417 | | 10.3 | A | 196-198 | ((DMSO-d6) 7.76(s, 1H), 7.31(t, 1H), 6.95(d, 1H), 6.71(m, 1H), 6.30(d, 2H), 6.09(s, 1H), 4.05(m, 1H), 2.60(m, 2H), 2.52(m, 2H), 1.95(m, 2H), 1.85(m, 2H), 1.45(m, 4H), 1.20(m, 2H), 0.90(t, 2H). | 12 |
| 12 | 451 | | 10.9 | A | Gum | | 12 |
| 13 | 469 | 467 | 10.5 | A | Gum | | 12 |
| 14 | 495 | | 13.2 | A | 188-191 | | 12 |
| 15 | 371 | | 9.1 | A | 87-92(d) | (CDCl$_3$) 7.79(s, 1H), 7.42(d, 2H), 7.15(t, 1H), 6.98(t, 1H), 6.80(d, 1H), 6.25(s, 1H), 4.35(m, 1H), 4.18(m, 1H), 2.71(m, 1H), 2.21(m, 2H), 1.92(m, 1H), 1.72(s, 3H), 1.35(m, 2H), 1.25(m, 2H). | 12 |
| 16 | 385 | 383 | 9.4 | A | 174-176(d) | (CDCl$_3$) 7.79(s, 1H), 7.41(d, 1H), 7.15(t, 1H), 6.98(t, 1H), 7.87(d, 1H), 6.13(s, 1H), 4.42(d, 1H), 4.10(m, 1H), 2.70(m, 1H), 2.28(q, 2H), 2.20(m, 2H), 1.19(m, 2H), 3.37(m, 2H), 1.25(m, 2H), 1.00(t, 3H). | 12 |
| 17 | 397 | | 9.9 | A | 153-155 | | 12 |
| 18 | 469 | 467 | | | 213-216 | | 12 |
| 19 | 415 | 413 | 10.3 | A | 176-178 | (CDCl$_3$) 7.75(s, 1H), 7.55(bs, 1H), 7.10(m, 2H), 6.92(m, 1H), 6.13(s, 1H), 5.65(m, 1H), 5.18(d, 1H), 5.15(d, 1H), 4.62(d, 1H), 4.02(m, 1H), 3.00(d, 2H), 2.70(m, 1H), 2.18(m, 2H), 1.90(m, 2H), 1.45(bs, 2H), 1.32(m, 2H), 1.10(m, 2H). | 12 |
| 20 | 449 | | | | 220-222 | | 12 |
| 21 | 337 | | | | Gum | | 12 |
| 22 | 447 | | 11.3 | A | Gum | | 12 |
| 23 | 403 | 401 | 9.5 | A | Gum | | 12 |
| 24 | 465 | 463 | 10.9 | A | Gum | (CDCl$_3$) 7.80(s, 1H), 7.49(s, 1H), 7.25(m, 3H), 7.09(m, 3H), 6.90(m, 2H), 6.18(s, 1H), 4.21(d, 1H), 3.90(m, 1H), 2.55(m, 1H), 2.03(s, 2H), 1.97(d, 2H), 1.80(d, 2H), 1.28(m, 1H), 1.25(m, 2H), 0.85(m, 2H). | 12 |
| 25 | 369 | 367 | 7.7 | A | Gum | (CDCl$_3$) 7.88(s, 1H), 7.15(m, 2H), 7.04(m, 2H), 6.95(m, 1H), 6.12(s, 1H), 4.40(d, 2H), 4.10(m, 1H), 2.71(m, 1H), 2.28(q, 2H), 2.20(d, 2H), 1.90(d, 2H), 1.20~1.50(m, 6H), 0.90(t, 3H). | 12 |
| 26 | 385 | 383 | 8.9 | A | Gum | (CDCl$_3$) 7.87(s, 1H), 7.25(d, 2H), | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 27 | 380 | | 7.7 | A | 202-204 | 6.95(d, 2H), 6.12(s, 1H), 4.40(m, 1H), 4.10(m, 1H), 2.70(m, 1H), 2.25(q, 2H), 2.20(d, 2H), 2.05(d, 1H), 1.96(d, 2H), 1.53(bs, 2H), 1.45~1.15(m, 4H), 0.97(t, 3H). (CDCl$_3$) 7.75(s, 1H), 7.28(d, 1H), 7.20(t, 1H), 6.65(m, 2H), 6.59(s, 1H), 6.12(s, 1H), 4.40(m, 1H), 4.10(m, 1H), 3.80(s, 3H), 2.71(m, 1H), 2.32(q, 2H), 2.21(d, 2H), 1.95(d, 2H), 1.58~1.18(m, 6H), 1.02(t, 3H). | 12 |
| 28 | 381 | | 7.9 | A | Gum | (CDCl$_3$) 7.75(s, 1H), 7.42(bs, 1H), 7.11(d, 2H), 6.82(d, 2H), 6.12(s, 1H), 4.31(d, 1H), 4.08(m, 1H), 3.81(s, 3H), 2.70(m, 1H), 2.20(m, 3H), 1.92(m, 2H), 1.60(bs, 2H), 1.35(m, 2H), 1.20(m, 2H), 0.90(t, 3H). | 12 |
| 29 | 365 | | 8.4 | A | 176-178 | (CDCl$_3$) 7.75(s, 1H), 7.21(d, 1H), 7.18(s, 1H), 7.12(m, 1H), 7.03(d, 1H), 6.10(s, 1H), 4.30(d, 1H), 4.09(m, 1H), 2.70(m, 1H), 2.35(s, 3H), 2.21(m, 2H), 2.11(q, 2H), 1.92(d, 2H), 1.40(bs, 2H), 1.35(m, 2H), 1.21(m, 2H), 0.85(t, 3H). | 12 |
| 30 | 379 | | 10.5 | A | Gum | | 12 |
| 31 | 395 | | 9.8 | A | 131-133 | | 12 |
| 32 | 381 | | 9.0 | A | 163-165 | | 12 |
| 33 | 443 | | 11.2 | A | 147-149 | (CDCl$_3$) 7.75(s, 1H), 7.50(bs, 1H), 7.30(t, 2H), 7.1(m, 3H), 7.02(d, 2H), 6.98(d, 2H), 6.11(s, 1H), 4.35(d, 1H), 4.11(m, 1H), 2.70(m, 1H), 2.29(q, 2H), 2.25(m, 2H), 1.95(m, 2H), 1.50(bs, 2H), 1.35(m, 2H), 1.25(m, 2H), 0.95(t, 3H). | 12 |
| 34 | 394 | | 6.1 | A | 60-62 | (CDCl$_3$) 7.75(s, 1H), 7.35(s, 1H), 7.12(t, 1H), 6.49(d, 1H), 6.39(m, 2H), 6.12(s, 1H), 4.35(d, 1H), 4.08(m, 1H), 2.92(s, 6H), 2.70(m, 1H), 2.29(q, 2H), 2.20(m, 2H), 1.90(m, 2H), 1.46(bs, 2H), 1.36(m, 2H), 1.22(m, 2H), 0.95(t, 3H). | 12 |
| 35 | 457 | | 11.3 | A | 120-122 | (CDCl$_3$) 7.78(s, 1H), 7.48~7.29(m, 5H), 7.10(d, 2H), 6.90(d, 2H), 6.12(s, 1H), 5.30(s, 1H), 5.05(s, 2H), 4.30(d, 1H), 4.10(m, 1H), 2.70(m, 1H), 2.20(m, 4H), 1.80(m, 2H), 1.35(m, 4H), 1.25(m, 2H), 0.90(t, 3H). | 12 |
| 36 | 397 | | 9.5 | A | 190-192 | (CDCl$_3$) 7.75(s, 1H), 7.35(bs, 1H), 7.20(d, 2H), 6.98(d, 2H), 6.12(s, 1H), 4.41(d, 1H), 4.15(m, 1H), 2.72(m, 1H), 2.49(s, 3H), 2.24(m, 4H), 1.95(d, 2H), 1.50(bs, 2H), 1.40(m, 2H), 1.27(m, 2H), 0.96(t, 3H). | 12 |
| 37 | 385 | | 7.5 | A | 183-184 | | 12 |
| 38 | 399 | | 9.8 | A | 63-65 | | 12 |
| 39 | 379 | | | | 127-129 | | 12 |
| 40 | 417 | | 9.4 | A | Gum | | 12 |
| 41 | 315 | | 6.5 | A | Gum | | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 42 | 381 | | | | Gum | | 12 |
| 43 | 389 | 387 | 10.7 | A | Gum | (CDCl$_3$) 7.76(s, 1H), 7.20(s, 1H), 7.10(m, 2H), 6.95(m, 1H), 6.12(s, 1H), 4.30(br, 1H), 3.12(m, 1H), 2.85(m, 2H), 2.75(m, 1H), 2.32(q, 2H), 1.90~1.50(m, 6H), 1.03(t, 3H). | 12 |
| 44 | 389 | 387 | 9.2 | A | 148-154 | | 12 |
| 45 | 371 | 369 | | | Gum | | 12 |
| 46 | 329 | 327 | 7.8 | A | 91-93 | | 12 |
| 47 | 483 | 481 | 10.5 | A | Gum | | 12 |
| 48 | 493 | 491 | 9.4 | A | 240-241 | | 12 |
| 49 | | 499 | | | 153-155 | | 12 |
| 50 | 441-444 | 437-439 | 11.4 | A | Gum | | 12 |
| 51 | 411 | 409 | 7.2 | A | 65-68 | | 12 |
| 52 | 441 | 439 | | | 162-165 | (CDCl$_3$) 7.76(s, 1H), 7.40(s, 1H), 6.78(d, 1H), 6.70(s, 1H), 6.68(d, 1H), 6.11(s, 1H), 5.55(m, 1H), 4.05(m, 1H), 3.88(s, 3H), 3.82(s, 3H), 3.41(m, 1H), 2.69(m, 1H), 2.32(m, 2H), 2.18(m, 2H), 2.0(m, 2H), 1.92(m, 2H), 1.45(t, 2H), 1.40~1.15(m, 6H). | 12 |
| 53 | 453 | 451 | 10.2 | A | 116-118 | | 12 |
| 54 | 441 | 439 | | | 166-168 | | 12 |
| 55 | 415 | 413 | | | 189-192 | (CDCl$_3$) 7.75(s, 1H), 7.39(s, 1H), 7.14(s, 1H), 7.02(d, 1H), 6.87(d, 1H), 6.12(s, 1H), 4.32(d, 1H), 4.10(m, 1H), 3.90(s, 3H), 2.71(m, 1H), 2.20(m, 4H), 1.94(d, 2H), 1.45~1.15(m, 6H), 0.92(t, 3H). | 12 |
| 56 | 423 | 421 | 11.9 | A | 144-148 | | 12 |
| 57 | 457 | 455 | | | 102-104 | | 12 |
| 58 | 411 | 409 | | | 181-185 | | 12 |
| 59 | 429-432 | 427-430 | 9.7 | A | 197-199 | (CDCl$_3$) 7.76(s, 1H), 7.32(s, 1H), 7.21(d, 1H), 7.15(d, 1H), 6.95(d, 1H), 6.15(s, 1H), 4.41(d, 1H), 4.10(m, 1H), 2.75(m, 1H), 2.27(q, 2H), 2.22(m, 2H), 1.93(m, 2H), 1.42(br, 2H), 1.40~1.20(m, 4H), 1.00(t, 3H). | 12 |
| 60 | 477 | 475 | 9.5 | A | 199-201 | (CDCl$_3$) 7.76(s, 1H), 7.49(bs, 1H), 7.35(d, 1H), 7.30(s, 1H), 7.00~6.90(m, 2H), 6.15(s, 1H), 4.42(d, 1H), 4.08(m, 1H), 2.71(m, 1H), 2.32(q, 2H), 2.20(m, 2H), 1.92(m, 2H), 1.55(bs, 2H), 1.42~1.20(m, 4H), 1.01(t, 3H). | 12 |
| 61 | 395 | 393 | | | 150-152 | (CDCl$_3$) 7.76(s, 1H), 7.32(s, 1H), 7.17(t, 1H), 6.60(d, 1H), 6.55(s, 1H), 6.13(s, 1H), 4.38(d, 1H), 4.08(m, 1H), 3.98(q, 2H), 2.70(m, 1H), 2.31(q, 2H), 2.20(m, 2H), 1.92(m, 2H), 1.46(br, 2H), 1.38(q, 3H), 1.38~1.19(m, 4H), 0.95(q, 3H). | 12 |
| 62 | 397 | | | | Gum | | 12 |
| 63 | 443 | | | | Gum | (CDCl$_3$) 7.77(s, 1H), 7.33(s, 1H), 7.15(d, 2H), 7.05(d, 2H), 6.95(d, 2H), 6.90(d, 2H), 6.13(s, 1H), 5.19(br, 1H), 4.28(m, 1H), 3.19(dd, 1H), 2.83(m, 1H), 2.72(m, 2H), 2.31(s, 3H), 2.30(q, 2H), 1.90~1.50(m, 5H), 0.97(t, 3H). | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 64 | 392.3 | | 6.4 | A | | (CDCl₃) 8.00(s, 1H), 7.53(br, 1H), 7.23(d, 2H), 6.96(d, 2H), 5.29(s, 1H), 4.65(m, 1H), 4.06(q, 2H), 3.71(s, 3H), 2.67(m, 1H), 2.06(m, 2H), 1.89(m, 2H), 1.56(br, 2H), 1.45(t, 3H), 1.28~1.14(m, 4H). | 12 |
| 65 | 383 | | 8.5 | A | 185-187 | (CDCl₃) 7.80(s, 1H), 7.50(s, 1H), 7.25(d, 2H), 6.98(d, 2H), 6.15(s, 1H), 4.30(m, 1H), 4.10(m, 1H), 2.75(m, 1H), 2.50(s, 3H), 2.22(m, 2H), 1.92(m, 2H), 1.72(s, 3H), 1.48~1.18(m, 6H). | 12 |
| 66 | 438 | 436 | | | Gum | | 12 |
| 67 | 409 | | 8.7 | A | Gum | | 12 |
| 68 | 409 | 407 | | | 59-60 | | 12 |
| 69 | 452 | | | | Gum | | 12 |
| 70 | 423 | | | | Gum | (CDCl₃) 7.95(d, 2H), 7.75(s, 1H), 7.40(bs, 1H), 6.95(d, 2H), 6.15(s, 1H), 4.45(d, 1H), 4.35(q, 2H), 4.10(q, 2H), 2.86(m, 1H), 2.30(q, 2H), 2.25(m, 2H), 2.18(bs, 2H), 2.03(s, 3H), 1.95(m, 2H), 1.37(m, 4H), 1.28(t, 3H), 1.00(t, 3H). | 12 |
| 71 | 423 | | | | Gum | (CDCl₃) 7.78(s, 1H), 7.77(d, 1H), 7.65(s, 1H), 7.38(t, 1H), 7.25(s, 1H), 7.20(d, 1H), 6.13(s, 1H), 4.41(m, 1H), 4.40(q, 2H), 4.10(m, 1H), 2.71(m, 1H), 2.21(m, 4H), 1.12(m, 2H), 1.51(bs, 2H), 1.39(t, 3H), 1.39~1.20(m, 4H), 1.98(t, 3H). | 12 |
| 72 | 365 | | | | Gum | (DMSO-d6) 8.35(bs, 1H), 7.65(s, 1H), 7.08(t, 1H), 6.65(d, 1H), 6.60(s, 1H), 6.52(d, 1H), 6.18(d, 1H), 5.95(s, 1H), 3.95(m, 1H), 2.41(m, 2H), 2.20(s, 3H), 1.86(m, 2H), 1.78(m, 2H), 1.40(m, 2H), 1.18(m, 2H), 0.90(t, 3H). | 12 |
| 73 | 433 | | | | Gum | | 12 |
| 74 | 457 | | | | Gum | | 12 |
| 75 | 443 | | | | Gum | | 12 |
| 76 | 365 | | 9.0 | A | 148-149 | (CDCl₃) 7.77(s, 1H), 7.48(s, 1H), 7.07(d, 1H), 6.82(s, 1H), 6.76(d, 1H), 6.14(s, 1H), 4.25(d, 1H), 4.10(m, 1H), 2.72(m, 1H), 2.23(s, 3H), 2.21(m, 2H), 1.90(m, 2H), 1.70(s, 3H), 1.45(br, 2H), 1.45~1.20(m, 4H). | 12 |
| 77 | 415 | | 9.0 | A | 215-216 | (CDCl₃) 7.78(s, 1H), 7.43(s, 1H), 7.19(d, 2H), 7.10(s, 1H), 6.90(m, 1H), 6.10(s, 1H), 4.31(d, 1H), 4.10(m, 1H), 2.85(m, 1H), 2.23(m, 2H), 1.92(m, 2H), 1.78(s, 3H), 1.45~1.20(m, 6H). | 12 |
| 78 | 421 | 419 | | | 225-235 | | 12 |
| 79 | 357 | 355 | | | 120-160 | | 12 |
| 80 | 355 | | 7.3 | A | Gum | | 12 |
| 81 | 381 | | | | 146-148 | (CDCl₃) 7.75(s, 1H), 7.50(bs, 1H), 7.18(t, 1H), 6.60(d, 1H), 6.52(d, 1H), 6.50(s, 1H), 6.12(s, 1H), 4.12(m, 1H), 4.05(m, 1H), 4.00(m, 2H), 2.72(bs, 1H), 2.20(m, | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 82 | 366 | | | | Gum | 2H), 1.93(m, 2H), 1.72(s, 3H), 1.49(m, 4H). | 12 |
| 83 | 463 | | 8.7 | A | 134-136 | (CDCl₃) 7.76(s, 1H), 7.42(s, 1H), 7.38(d, 1H), 7.25(s, 1H), 7.02(t, 1H), 6.92(d, 1H), 6.15(s, 1H), 4.32(d, 1H), 4.08(m, 1H), 2.75(m, 1H), 2.23(m, 2H), 1.95(m, 1H), 1.75(s, 3H), 1.60(br, 2H), 1.40(m, 2H), 1.25(m, 2H). | 12 |
| 84 | 405 | 403 | | | 198-200 | (CDCl₃) 7.80(bs, 1H), 7.78(s, 1H), 7.51(d, 2H), 6.92(d, 2H), 6.18(s, 1H), 4.37(d, 1H), 4.10(m, 1H), 2.62(m, 1H), 2.21(m, 2H), 1.95(m, 2H), 1.75(s, 3H), 1.51(bs, 2H), 1.32(m, 2H), 1.28(m, 2H). | 12 |
| 85 | 371 | | 8.5 | A | 209-212 | (CDCl₃) 7.75(s, 1H), 7.46(bs, 1H), 7.25(s, 1H), 7.20(t, 1H), 7.02(d, 1H), 6.92(s, 1H), 6.85(d, 1H), 6.15(s, 1H), 4.31(d, 1H), 4.06(m, 1H), 2.72(m, 1H), 2.20(m, 2H), 1.92(m, 2H), 1.75(s, 3H), 1.52(bs, 2H), 1.32(m, 2H), 1.25(m, 2H). | 12 |
| 86 | 331 | | | | 138-145 | | 12 |
| 87 | 303 | | | | Gum | | 12 |
| 88 | 353 | 351 | 5.9 | A | 145-150 | | 12 |
| 89 | 351 | | 13.4 | B | Gum | (CDCl₃) 7.76(s, 1H), 7.45(s, 1H), 7.27(s, 2H), 7.08(d, 1H), 6.82(s, 1H), 6.72(d, 1H), 6.10(s, 1H), 4.98(m, 1H), 4.3(m, 1H), 3.2(d, 1H), 2.82(m, 2H), 2.71(m, 1H), 2.29(m, 1H), 2.20(s, 3H), 1.83(m, 1H), 1.80~1.50(m, 2H), 1.25(s, 2H). | 12 |
| 90 | 391 | 389 | | | Gum | (CDCl₃) 7.80(s, 1H), 7.55(d, 2H), 7.50(s, 1H), 7.00(d, 2H), 6.15(s, 1H), 5.20(m, 1H), | 12 |
| 91 | 367 | | | | Gum | (CDCl₃) 7.76(s, 1H), 7.42(s, 1H), 7.20(t, 1H), 6.61(d, 1H), 6.60(m, 2H), 6.50(s, 1H), 6.12(s, 1H), 4.25(d, 1H), 4.05(m, 1H), 3.78(s, 3H), 2.75(m, 1H), 2.22(m, 2H), 1.95(m, 2H), 1.75(s, 3H), 1.50~1.12(m, 6H). | 12 |
| 92 | 411 | | | | 101-104 | | 12 |
| 93 | 468 | | | | Gum | | 12 |
| 94 | 467 | 465 | | | 120-130 | | 12 |
| 95 | 367 | | 5.3 | A | 200-202 | (DMSO-d6) 7.50(s, 1H), 7.00(d, 2H), 6.65(d, 2H), 5.75(d, 2H), 5.53(s, 1H), 5.51(s, 1H), 4.82(bs, 1H), 4.20(s, 2H), 3.75(m, 1H), 3.00(br, 2H), 2.35(m, 1H), 2.30(s, 2H), 1.71(m, 2H), 1.51(d, 2H), 1.50(s, 3H), 1.15(m, 2H), 0.95(m, 2H). | 12 |
| 96 | | | | | 158-162 | (CDCl₃) 7.76(s, 1H), 7.52(bs, 1H), 7.27(d, 2H), 6.95(d, 2H), 6.15(s, 1H), 4.32(d, 1H), 4.10(m, 1H), 3.82(s, 2H), 2.72(m, 1H), 2.22(m, 2H), 1.95(m, 2H), 1.70(bs, 4H), 1.35(m, 2H), 1.23(m, 2H). | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 97 | 367 | | | | 97-100 | (CDCl$_3$) 7.73(s, 1H), 7.57(bs, 1H), 7.25(t, 1H), 7.02(d, 1H), 6.95(s, 1H), 6.86(d, 1H), 6.13(s, 1H), 4.52(s, 2H), 4.32(d, 1H), 4.05(d, 1H), 2.70(m, 1H), 2.20(m, 2H), 1.90(m, 2H), 1.73(s, 3H), 1.33(m, 2H), 1.20(m, 2H). | 12 |
| 98 | 377 | 375 | 7.4 | A | 205-207 | | 12 |
| 99 | 401 | | | | Gum | | 12 |
| 100 | 317 | | | | Gum | | 12 |
| 101 | 392 | 390 | | | Gum | | 12 |
| 102 | 337 | | 7.1 | A | 96-99 | (CDCl$_3$) 7.80(s, 1H), 7.50(bs, 1H), 7.40(t, 2H), 7.08(t, 1H), 7.00(d, 2H), 6.15(s, 1H), 4.28(d, 1H), 4.09(m, 1H), 2.75(m, 1H), 2.22(m, 2H), 1.98(m, 2H), 1.72(s, 3H), 1.35(m, 2H), 1.25(m, 2H). | 12 |
| 103 | 463 | | 9.2 | A | 105-108 | (CDCl$_3$). 7.78(s, 1H), 7.60(d, 2H), 7.46(bs, 1H), 6.75(d, 2H), 6.15(s, 1H), 4.30(d, 1H), 4.09(m, 1H), 2.78(m, 1H), 2.23(m, 2H), 1.95(m, 2H), 1.87(bs, 2H), 1.75(s, 3H), 1.41(m, 2H), 1.28(m, 2H). | 12 |
| 104 | 449 | | 10.2 | A | Gum | (CDCl$_3$) 7.74(s, 1H), 7.45(s, 1H), 7.38(d, 1H), 7.30(s, 1H), 7.05(t, 1H), 6.95(d, 1H), 6.15(s, 1H), 5.10(m, 1H), 4.30(m, 1H), 3.20(dd, 1H), 2.82(m, 2H), 2.72(m, 1H), 1.90(m, 1H), 1.80(s, 3H), 1.75(m, 2H), 1.43(m, 1H). | 12 |
| 105 | 449 | 447 | | | Gum | | 12 |
| 106 | 357 | | 9.3 | A | Gum | | 12 |
| 107 | 376 | 374 | 7.2 | A | 207-209 | (CDCl$_3$) 8.70(bs, 1H), 7.80(s, 1H), 7.70(bs, 1H), 7.35(s, 1H), 7.20(s, 1H), 6.95(d, 1H), 6.45(s, 1H), 6.15(s, 1H), 4.22(d, 1H), 4.05(m, 1H), 3.45(s, 3H), 2.71(m, 1H), 2.20(d, 2H), 1.90(d, 2H), 1.51(s, 3H), 1.35(m, 2H), 1.24(m, 2H). | 12 |
| 108 | 374 | | | | Gum | | 12 |
| 109 | 388 | | | | Gum | | 12 |
| 110 | 319 | | | | Gum | | 12 |
| 111 | 408 | | | | 95-99 | (CDCl$_3$) 7.78(s, 1H), 7.72(d, 1H), 7.62(s, 1H), 7.57(s, 1H), 7.05(d, 1H), 6.15(s, 1H), 4.25(d, 1H), 4.07(m, 1H), 2.82(s, 3H), 2.70(m, 1H), 2.21(m, 2H), 1.95(m, 2H), 1.75(s, 3H), 1.50(bs, 2H), 1.35(m, 2H), 1.25(m, 2H). | 12 |
| 112 | 394 | | 6.1 | A | 100-108 | | 12 |
| 113 | 449 | 447 | | | 181-183 | | 12 |
| 114 | 409 | | 10.0 | A | Gum | | 12 |
| 115 | 417 | | | | 165-168 | (CDCl$_3$) 7.76(s, 1H), 7.19(bs, 1H), 7.05(m, 2H), 6.90(m, 1H), 6.14(s, 1H), 4.55(d, 1H), 4.10(m, 1H), 3.05(m, 1H), 2.73(m, 2H), 1.95(m, 2H), 1.50(d, 1H), 1.45(m, 2H), 1.30(m, 2H), 1.23(d, 6H), 1.0(dd, 1H). | 12 |
| 116 | 434 | | | | Gum | | 12 |
| 117 | 436 | | | | 140-142 | | 12 |
| 118 | 403 | | | | 210-215 | (CDCl$_3$) 7.80(d, 2H), 7.50(s, 1H), | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| | | | | | | 7.35(d, 2H), 7.25(d, 2H), 6.17(s, 1H), 7.05(d, 2H), 6.15(s, 1H), 4.31(d, 1H), 4.09(m, 1H), 2.71(m, 1H), 2.20(m, 2H), 1.90(m, 2H), 1.75(s, 3H), 1.40(m, 2H), 1.25(m, 4H). | |
| 119 | 338 | | | | Gum | | 12 |
| 120 | 323 | | | | Gum | | 12 |
| 121 | 353 | 351 | | | 100-105 | | 12 |
| 122 | 402 | | | | Gum | | 12 |
| 123 | 378 | 376 | | | 155-156 | | 12 |
| 124 | 449 | 447 | | | Gum | (CDCl$_3$) 7.78(s, 1H), 7.44(s, 1H), 7.08(d, 2H), 6.89(d, 2H), 6.10(s, 1H), 4.30(d, 1H), 4.10(m, 1H), 3.18(m, 3H), 2.71(m, 1H), 2.59(m, 3H), 2.36(s, 3H), 2.19(m, 3H), 1.92(m, 1H), 1.60(br, 2H), 1.34(m, 2H), 1.20(m, 2H), 0.88(t, 3H). | 12 |
| 125 | 434 | 432 | | | Gum | | 12 |
| 126 | 395 | 393 | | | 68-72 | (CDCl3) 7.78(s, 1H), 7.44(s, 1H), 6.80(d, 1H), 6.55(s, 1H), 6.13(d, 1H), 4.24(s, 4H), 4.22(m, 1H), 4.05(m, 1H), 2.72(m, 1H), 2.21(m, 2H), 1.94(m, 2H), 1.71(s, 3H), 1.40~1.15(m, 6H). | 12 |
| 127 | 377 | 375 | | | 60-75 | | 12 |
| 128 | 435 | 433 | | | Gum | | 12 |
| 129 | 420 | 418 | | | 58-66 | (CDCl3) 7.78(s, 1H), 7.50(s, 1H), 6.97(d, 2H), 6.90(d, 2H), 6.20(s, 1H), 4.20(d, 1H), 4.07(m, 1H), 3.12(m, 4H), 2.72(m, 1H), 2.20(m, 2H), 1.94(m, 2H), 1.72(m, 2H), 1.64(s, 3H), 1.55(m, 2H), 1.45(m, 2H), 1.35(m, 2H), 1.25(m, 2H). | 12 |
| 130 | 408 | 406 | | | Gum | | 12 |
| 131 | 377 | 375 | | | Gum | (CDCl$_3$) 8.00(s, 1H), 7.79(s, 1H), 7.66(d, 1H), 6.91(d, 1H), 6.89(s, 1H), 7.78(m, 1H), 6.65(m, 1H), 6.15(s, 1H), 5.32(s, 1H), 4.44(d, 1H), 4.12(m, 1H), 3.15(m, 1H), 2.75(m, 1H), 2.15(m, 4H), 1.92(m, 2H), 1.81(s, 3H), 1.35(m, 2H), 1.22(m, 4H). | 12 |
| 132 | 495 | | | | 70-75 | | 12 |
| 133 | 361 | | | | 180-183 | | 12 |
| 134 | 381 | | | | Gum | | 12 |
| 135 | 361 | 359 | | | Gum | | 12 |
| 136 | | 571 | | | 90-93 | | 32 |
| 137 | 457 | 455 | | | Gum | (CDCl$_3$) 7.85(d, 1H), 7.75(s, 1H), 6.95(s, 1H), 6.85(d, 1H), 6.18(s, 1H), 4.50(d, 1H), 4.35(q, 2H), 4.12(m, 1H), 2.73(m, 1H), 2.31(q, 2H), 2.22(m, 2H), 1.92(m, 2H), 1.42(t, H), 1.42~1.1.20(m, 4H), 1.10(t, 3H). | 12 |
| 138 | 395 | | | | 64-67 | | 12 |
| 139 | 418 | 416 | | | Gum | | 12 |
| 140 | 473 | | | | Gum | (CDCl$_3$) 7.75(s, 1H), 7.70(s, 1H), 6.87(d, 2H), 6.64(d, 2H), 6.60(d, 2H), 6.41(d, 2H), 6.15(s, 1H), 4.22(d, 1H), 4.05(m, 1H), 3.90(q, 2H), 3.72(s, 3H), 2.60(m, 1H), 2.08(m, 2H), 1.81(m, 2H), 1.38(t, 3H), 1.25(m, 2H), 1.00(m, 2H). | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 141 | 412 | | | | 70-74 | | 12 |
| 142 | 367 | 365 | | | 80-85 | | 12 |
| 143 | 396 | | | | Gum | | 12 |
| 144 | 396 | | | | Gum | | 12 |
| 145 | 393 | | | | 236-240 | | 12 |
| 146 | 393 | 391 | | | 210-215 | | 12 |
| 147 | 459 | | | | 230-234 | | 12 |
| 148 | 390 | 388 | | | Gum | (CDCl$_3$) 8.02(bs, 1H), 7.78(s, 1H), 7.66(s, 1H), 7.20(d, 1H), 6.88(d, 1H), 6.19(s, 1H), 6.13(s, 1H), 4.20(d, 1H), 4.05(m, 1H), 2.70(m, 1H), 2.44(s, 3H), 2.20(m, 2H), 1.93(m, 2H), 1.60(s, 3H), 1.42(brs, 2H), 1.32(m, 2H), 1.23(m, 2H). | 12 |
| 149 | 376 | | | | Gum | (CDCl$_3$) 8.46(bs, 1H), 7.80(s, 1H), 7.70(s, 1H), 7.22(d, 1H), 7.19(s, 1H), 7.10(t, 1H), 6.68(d, 1H), 6.50(s, 1H), 6.18(s, 1H), 4.25(d, 1H), 4.10(m, 1H), 2.71(m, 1H), 2.21(m, 2H), 1.92(m, 2H), 1.67(s, 3H), 1.52(bs, 2H), 1.38(m, 2H), 1.28(m, 2H). | 12 |
| 150 | 421 | | | | Gum | | 12 |
| 151 | | 392 | | | 206-210 | | 12 |
| 152 | 375 | 373 | | | Gum | | 12 |
| 153 | | 374 | | | 116-125 | (CDCl$_3$) 8.58(bs, 1H), 7.80(s, 1H), 7.70(s, 1H), 7.55(d, 1H), 7.19(d, 1H), 7.07(s, 1H), 6.90(d, 1H), 6.55(s, 1H), 6.15(s, 1H), 4.25(d, 1H), 4.05(m, 1H), 2.72(m, 1H), 2.20(m, 2H), 1.93(m, 2H), 1.62(s, 3H), 1.60(bs, 2H), 1.40(m, 2H), 1.26(m, 2H). | 12 |
| 154 | 409 | | | | 204-205 | | 12 |
| 155 | 408 | | | | 210-215 | (CDCl$_3$) 7.85(d, 1h), 7.78(s, 1H), 7.65(s, 1H), 7.39(s, 1H), 7.10(d, 1H), 6.15(s, 1H), 4.30(d, 1H), 4.08(m, 1H), 2.80(s, 3H), 2.70(m, 1H), 2.22(m, 2H), 1.92(m, 2H), 1.70(s, 3H), 1.35(m, 2H), 1.25(m, 2H). | 12 |
| 156 | 341 | | | | Gum | (CDCl$_3$) 7.78(s, 1H), 7.40(bs, 1H), 7.13(m, 1H), 7.03(m, 1H), 7.01(m, 1H), 6.89(t, 1H), 6.13(s, 1H), 5.10(m, 1H), 4.28(m, 1H), 3.18(m, 1H), 2.82(m, 2H), 2.72(m, 1H), 1.87(m, 1H), 1.81(s, 3H), 1.75(m, 2H), 1.68(m, 1H), 1.59(m, 1H). | 12 |
| 157 | 363 | | | | 120-123 | | 12 |
| 158 | 395 | | | | 64-65 | | 12 |
| 159 | 429 | | | | 184-187 | (CDCl$_3$) 7.78(s, 1H), 7.15(m, 4H), 6.98(d, 1H), 6.15(s, 1H), 4.40(d, 1H), 4.10(m, 1H), 2.72(m, 1H), 2.28(q, 2H), 2.20(m, 2H), 1.92(m, 2H), 1.40(m, 2H), 1.25(m, 2H), 1.01(t, 3H). | 12 |
| 160 | 415 | | | | Gum | | 12 |
| 161 | 326 | 324 | | | 114-116 | | 12 |
| 162 | 324 | 322 | | | 92-94 | | 12 |
| 163 | 421 | 419 | | | 68-69 | | 12 |
| 164 | 407 | 405 | | | 55-60 | | 12 |
| 165 | 423 | 421 | | | 63-65 | | 12 |
| 166 | 409 | 407 | | | 63-66 | | 12 |
| 167 | 351 | | | | Gum | | 12 |
| 168 | 477 | | | | 104-106 | | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 169 | 497 | | | | Gum | | 12 |
| 170 | 382.2 | | 7.1 | A | | (DMSO-d6) 8.34(s, 1H), 7.66(dd, 1H), 7.52(dd, 1H), 7.47(td, 1H), 7.41(td, 1H), 7.32(d, 1H), 5.06(s, 1H), 3.77(m, 1H), 2.99(m, 1H), 1.94(m, 4H), 1.40(m, 2H), 1.19(m, 2H). | 12 |
| 171 | 391 | | | | Gum | | 12 |
| 172 | 405 | | | | Gum | | 12 |
| 173 | 383 | | | | Gum | (CDCl$_3$) 7.79(s, 1H), 7.52(s, 1H), 7.15(d, 2H), 6.85(d, 2H), 6.10(s, 1H), 5.50(m, 1H), 4.15(m, 1H), 4.05(q, 2H), 3.20(s, 3H), 2.90(m, 1H), 2.75(m, 2H), 2.62(m, 1H), 2.30(m, 1H), 1.95(m, 1H), 1.75~1.53(m, 3H), 1.42(t, 2H). | 12 |
| 174 | 379 | 377 | | | Gum | (CDCl$_3$) 7.85(d, 1H), 7.78(s, 1H), 7.59(bs, 1H), 7.07(d, 1H), 6.93(s, 1H), 5.30(m, 1H), 5.22(s, 2H), 4.35(m, 1H), 3.15(dd, 1H), 2.88(m, 3H), 2.00~1.82(m, 4H), 1.92(s, 3H), 1.62(m, 1H). | 12 |
| 175 | 394 | 392 | | | Gum | (CDCl$_3$) 7.78(s, 1H), 7.70(d, 2H), 7.50(bs, 1H), 6.90(d, 2H), 6.70(m, 1H), 6.15(s, 1H), 4.45(d, 1H), 4.08(m, 1H), 3.15(m, 1H), 2.75(m, 2H), 2.32(q, 2H), 2.22(m, 2H), 1.95(m, 2H), 1.52~1.18(m, 6H), 1.03(t, 3H). | 12 |
| 176 | 443.3 | | 8.9 | A | | (DMSO-d6) 7.80(s, 1H), 7.45~7.32(m, 5H), 6.95(s, 1H), 6.05(s, 1H), 5.06(s, 2H), 3.90(m, 1H), 2.98(m, 1H), 1.98(m, 4H), 1.62(s, 3H), 1.43(t, 4H). | 12 |
| 177 | 393.3 | | 9.0 | A | | | 12 |
| 178 | 380.3 | | 5.8 | B | | | 12 |
| 179 | 421.3 | | 8.1 | A | | | 12 |
| 180 | 385.3 | | 7.6 | A | | | 12 |
| 181 | 315.3 | | 5.9 | A | | | 12 |
| 182 | 319.4 | | 7.4 | B | | | 12 |
| 183 | 331.4 | | 7.4 | A | | | 12 |
| 184 | 351.3 | | 6.7 | A | | | 12 |
| 185 | 372.3 | | 5.2 | B | | | 12 |
| 186 | 381.3 | | 11.4 | B | | | 12 |
| 187 | 367.3 | | 6.6 | B | | | 12 |
| 188 | 357.3 | | 8.6 | B | | | 12 |
| 189 | 381.3 | | 9.6 | B | | | 12 |
| 190 | 395.3 | | 10.7 | B | | (CDCl$_3$) 7.72(d, 1H), 7.11(d, 2H), 6.83(dd, 2H), 6.05(d, 1H), 5.82(t, 1H), 4.12(d, 1H). 4.04(m, 1H), 3.78(s, 3H), 3.68(q, 2H), 2.89(t, 2H), 2.70(m, 1H), 2.19(m, 1H), 2.17(m, 1H), 2.04(s, 3H), 1.93(m, 1H), 1.90(m, 1H), 1.52(br, 2H), 1.34(m, 2H), 1.23(m, 2H). | 12 |
| 191 | 375.2 | | 12.7 | B | | | 12 |
| 192 | 381.3 | | 10.8 | B | | | 12 |
| 194 | 395.7 | | 8.9 | B | | | 12 |
| 195 | 382.7 | | 8.1 | B | | | 12 |
| 196 | 353.3 | | 5.0 | B | | (DMSO-d6) 9.33(br, 1H), 7.83(s, 1H), 6.89(d, 2H), 6.71(d, 2H), 6.08(bs, 1H), 3.88(m, 1H), 2.98(m, 1H), 1.97(m, 4H), 1.58(s, 3H), 1.43(m, 4H). | 23 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 198 | 367.3 | | 7.4 | A | | | 12 |
| 199 | 415.2 | | 7.1 | A | | | 23 |
| 200 | 411.3 | | 5.9 | A | | | 23 |
| 201 | 395.3 | | 7.9 | A | | | 23 |
| 202 | 435.3 | | 9.1 | A | | | 23 |
| 203 | 367.3 | | 5.9 | A | | | 23 |
| 204 | 458.3 | | 4.8 | A | | | 23 |
| 205 | 458.3 | | 5.2 | A | | | 23 |
| 206 | 458.3 | | 6.4 | A | | | 23 |
| 207 | 473.3 | | 7.6 | A | | | 23 |
| 208 | 473.2 | | 8.6 | A | | | 23 |
| 209 | 457.3 | | 8.1 | A | | | 23 |
| 210 | 457.2 | | 7.9 | A | | | 23 |
| 211 | 477.2 | | 9.5 | A | | | 23 |
| 212 | 477.2 | | 9.4 | A | | | 23 |
| 213 | 477.2 | | 9.3 | A | | | 23 |
| 214 | 435.3 | | 9.6 | A | | | 23 |
| 215 | 463.3 | | 10.9 | A | | | 23 |
| 216 | 421.3 | | 8.6 | A | | | 23 |
| 217 | 450.3 | | 5.4 | C | | | 23 |
| 218 | 450.3 | | 5.4 | C | | | 23 |
| 219 | 437.3 | | 6.4 | A | | | 23 |
| 220 | 444.2 | | 4.4 | B | | | 23 |
| 221 | 466.3 | | 3.8 | B | | | 23 |
| 222 | 444.2 | | 4.3 | B | | | 23 |
| 223 | 464.2 | | 4.3 | B | | | 23 |
| 224 | 444.2 | | 4.8 | B | | | 23 |
| 225 | 458.2 | | 4.4 | B | | | 23 |
| 226 | 464.2 | | 4.6 | B | | | 23 |
| 227 | 464.2 | | 4.4 | B | | | 23 |
| 228 | 458.1 | | 4.5 | B | | | 23 |
| 229 | 422.7 | | 4.7 | C | | | 23 |
| 230 | 465.7 | | 3.9 | C | | | 23 |
| 231 | 464.8 | | 6.3 | C | | | 23 |
| 232 | 450.7 | | 6.1 | C | | | 23 |
| 233 | 450.7 | | 6.3 | C | | | 23 |
| 234 | 447.7 | | 5.2 | C | | | 23 |
| 235 | 436.7 | | 5.3 | C | | | 23 |
| 236 | 436.7 | | 5.3 | C | | | 23 |
| 237 | 449.7 | | 14.1 | C | | | 23 |
| 238 | 463.3 | | 10.1 | B | | | 23 |
| 239 | 421.3 | | 8.0 | B | | | 23 |
| 240 | 435.3 | | 8.9 | B | | | 23 |
| 241 | 435.3 | | 8.6 | B | | | 23 |
| 242 | 449.3 | | 9.6 | B | | | 23 |
| 243 | 443.3 | | 8.2 | B | | | 23 |
| 244 | 435.4 | | 8.2 | B | | | 12 |
| 245 | 421.4 | | 9.2 | B | | | 12 |
| 246 | 458.4 | | 5.3 | B | | | 23 |
| 247 | 477.3 | | 9.1 | B | | | 23 |
| 248 | 477.3 | | 9.1 | B | | | 23 |
| 249 | 437.4 | | 6.2 | B | | | 23 |
| 250 | 477.3 | | 8.9 | B | | | 23 |
| 251 | 450.7 | | 6.3 | C | | | 23 |
| 252 | 473.2 | | 8.2 | B | | | 23 |
| 253 | 457.2 | | 8.6 | B | | | 23 |
| 254 | 457.2 | | 8.4 | B | | | 23 |
| 255 | 464.8 | | 7.0 | C | | | 23 |
| 256 | 437.7 | | 9.1 | C | | | 23 |
| 257 | 427.7 | | 5.9 | C | | | 23 |
| 258 | 436.7 | | 3.9 | B | | | 23 |
| 260 | 464.7 | | 4.7 | B | | | 23 |
| 261 | 450.7 | | 4.5 | B | | | 23 |
| 262 | 436.7 | | 4.0 | B | | | 23 |
| 263 | 450.7 | | 4.1 | B | | | 23 |
| 264 | 464.7 | | 4.8 | B | | | 23 |
| 265 | 450.7 | | 4.5 | B | | | 23 |
| 266 | 422.7 | | 3.4 | B | | | 23 |
| 267 | 447.7 | | 3.9 | B | | | 23 |
| 268 | 450.7 | | 3.9 | B | | | 23 |
| 269 | 464.7 | | 4.3 | B | | | 23 |
| 270 | 464.7 | | 4.5 | B | | | 23 |
| 271 | 501.7 | | 5.4 | A | | | 12 |

TABLE B-continued

| Compound No. | ESI/MS M+H | M−H | HPLC Retention Time (min.) | HPLC Method | Mp(° C.) | 1H-NMR(400 MHz) d(ppm) | Method of Preparation |
|---|---|---|---|---|---|---|---|
| 273 | 444.7 | | 6.8 | C | | | 23 |
| 274 | 444.7 | | 7.0 | C | | | 23 |
| 275 | 444.7 | | 7.6 | C | | | 23 |
| 276 | 458.7 | | 5.1 | B | | | 23 |
| 277 | 466.7 | | 5.9 | C | | | 23 |
| 278 | 464.7 | | 6.8 | C | | | 23 |
| 279 | 458.7 | | 7.1 | C | | | 23 |
| 280 | 458.7 | | 7.0 | C | | | 23 |
| 281 | 437.7 | | 10.4 | C | | | 23 |
| 282 | 427.7 | | 6.9 | C | | | 23 |
| 283 | 435.7 | | 7.2 | A | | | 12 |
| 285 | 443.3 | | 11.1 | B | | | 24 |
| 286 | 443.3 | | 11.1 | B | | | 24 |
| 287 | 443.3 | | 11.1 | B | | | 24 |
| 288 | 428.3 | | 6.8 | B | | | 24 |
| 289 | 469.2 | | 12.8 | B | | | 24 |
| 290 | 453.2 | | 12.2 | B | | | 24 |
| 291 | 419.2 | | 10.6 | B | | | 24 |
| 292 | 469.2 | | 12.5 | B | | | 24 |
| 293 | 406.3 | | 12.7 | B | | | 12 |
| 294 | 392.3 | | 11.9 | B | | | 12 |
| 295 | 414.2 | | 11.8 | B | | | 12 |
| 296 | 381.3 | | 9.6 | A | | | 12 |
| 298 | 457.3 | | 9.8 | A | | | 12 |
| 299 | 414.4 | | 5.3 | B | | | 24 |
| 300 | 414.4 | | 5.5 | B | | | 24 |
| 301 | 428.3 | | 6.4 | B | | | 24 |
| 302 | 447.2 | | 11.8 | B | | | 24 |
| 303 | 431.3 | | 11.0 | B | | | 24 |
| 304 | 431.3 | | 11.0 | B | | | 24 |
| 305 | 431.3 | | 10.8 | B | | | 24 |
| 306 | 429.2 | | 8.6 | B | | | 24 |
| 307 | 429.2 | | 8.9 | B | | | 24 |
| 308 | 429.2 | | 9.3 | B | | | 24 |
| 309 | 403.3 | | 9.7 | B | | | 24 |
| 310 | 447.2 | | 9.1 | D | | | 24 |
| 311 | 415.3 | | 5.9 | D | | | 24 |
| 312 | 447.3 | | 11.8 | B | | | 24 |
| 313 | 447.3 | | 11.1 | B | | | 24 |
| 314 | 456.3 | | 7.5 | B | | | 24 |
| 315 | 456.4 | | 7.3 | B | | | 24 |
| 316 | 497.3 | | 12.4 | B | | | 24 |
| 317 | 497.3 | | 12.3 | B | | | 24 |
| 318 | 438.3 | | 9.8 | B | | | 24 |
| 319 | 438.3 | | 9.9 | B | | | 24 |
| 320 | 427.4 | | 11.5 | B | | | 24 |
| 321 | 427.4 | | 11.2 | B | | | 24 |
| 322 | 427.4 | | 11.5 | B | | | 24 |
| 323 | 481.3 | | 11.6 | B | | | 24 |
| 324 | 481.3 | | 12.0 | B | | | 24 |
| 325 | 463.4 | | 9.4 | A | | | 12 |
| 326 | 449.4 | | 11.5 | A | | | 12 |
| 327 | 425.3 | | 8.3 | A | | | 15 |
| 328 | 453.3 | | 9.6 | A | | | 12 |
| 329 | 424.2 | | 7.9 | A | | | 16 |
| 330 | 438.3 | | 8.1 | A | | | 16 |
| 331 | 452.3 | | 8.4 | A | | | 16 |
| 332 | 482.3 | | 8.4 | A | | | 16 |
| 333 | 495.3 | | 7.2 | A | | | 16 |
| 334 | 481.3 | | 7.9 | A | | | 16 |
| 335 | 500.3 | | 10.0 | A | | | 16 |
| 336 | 514.3 | | 9.5 | A | | | 16 |
| 337 | 452.3 | | 7.3 | A | | | 16 |
| 338 | 478.3 | | 7.6 | A | | | 16 |
| 339 | 464.3 | | 8.4 | A | | | 16 |
| 341 | 395.2 | | 11.1 | A | | | 29 |
| 342 | 457.2 | | 12.7 | A | | | 29 |
| 343 | 501.2 | | 9.3 | A | | | 18 |
| 344 | 509.3 | | 9.5 | A | | | 16 |
| 345 | 535.4 | | 10.1 | A | | | 16 |
| 346 | | | | | | | 16 |
| 347 | 507.3 | | 9.5 | A | | | 16 |
| 348 | 514.3 | | 12.1 | A | | | 16 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 349 | 543.3 | | 10.6 | A | | | 16 |
| 350 | 481.3 | | 10.0 | A | | | 24 |
| 351 | 505.3 | | 7.2 | A | | | 24 |
| 352 | 443.3 | | 6.6 | A | | | 24 |
| 353 | 443.3 | | 6.8 | A | | | 24 |
| 354 | 457.3 | | 8.4 | A | | | 24 |
| 355 | 461.3 | | 7.5 | A | | | 24 |
| 356 | 457.4 | | 9.2 | A | | | 24 |
| 357 | 433.3 | | 10.5 | D | | | 24 |
| 358 | 521.3 | | 9.8 | A | | | 16 |
| 359 | 501.2 | | 11.5 | A | | | 16 |
| 360 | 501.2 | | 10.6 | A | | | 16 |
| 361 | 501.2 | | 10.6 | A | | | 16 |
| 363 | 454.3 | | 8.6 | A | | | 19 |
| 364 | 468.2 | | 9.5 | A | | | 19 |
| 365 | 530.2 | | 13.2 | A | | | 17 |
| 366 | 370.3 | | 14.1 | A | | | 12 |
| 367 | 384.2 | | 15.2 | A | | | 12 |
| 368 | 382.2 | | 14.0 | A | | | 12 |
| 369 | 418.2 | | 13.8 | A | | | 12 |
| 370 | 342.3 | | 11.2 | A | | | 12 |
| 371 | 356.2 | | 12.6 | A | | | 12 |
| 372 | 418.2 | | 14.8 | A | | | 12 |
| 373 | 391.2 | | 7.3 | A | | | 25 |
| 374 | 404.3 | | 5.3 | A | | | 25 |
| 376 | | | | | | | 25 |
| 377 | 390.3 | | 4.6 | A | | | 25 |
| 379 | 452.2 | | 9.2 | A | | | 19 |
| 380 | 464.2 | | 9.6 | A | | | (DMSO-d6) 9.66(brs, 1H), 8.65(brs, 1H), 7.94(s, 1H), 7.76(brs, 3H), 6.87(d, 2H9, 6.81(d, 2H), 4.07~3.87(m, 3H), 2.96(brs, 1H), 2.05~1.80(m, 4H), 1.59(s, 3H), 1.50~1.35(m, 4H), 1.26(t, 3H), 0.79~0.65(m, 4H). | 19 |
| 381 | 496.2 | | 9.5 | A | | | 19 |
| 382 | 498.2 | | 9.3 | A | | | 19 |
| 383 | 500.2 | | 10.7 | A | | | (DMSO-d6) 9.76(brs, 1H), 8.67(brs, 1H), 7.97-8.03(m, 3H), 7.72(brs, 3H), 7.46-7.63(m, 3H), 6.82-6.96(m, 4H), 3.92-4.03(m, 3H), 2.97(brs, 1H), 1.90-2.08(m, 4H), 1.66(s, 3H), 1.35-1.48(m, 4H), 1.31(t, 3H). | 19 |
| 384 | 514.2 | | 10.5 | A | | | (DMSO-d6) 9.44(brs, 1H), 8.56(brs, 1H), 7.94(s, 1H), 7.76(brs, 3H), 7.18-7.35(m, 5H), 6.78-6.87(m, 4H), 6.13(brs, 1H), 4.02(brs, 1H), 3.93(q, 2H), 3.64(s, 2H), 2.96(brs, 1H), 1.89-2.03(m, 4H), 1.60(s, 3H), 1.32-1.48(m, 4H), 1.26(t, 3H). | 19 |
| 385 | 492.1 | | 11.8 | A | | | 19 |
| 387 | 536.1 | | 12.3 | A | | | 20 |
| 388 | 481.2 | | 9.3 | A | | | (DMSO-d6) 8.66(brs, 1H), 7.70-7.80(m, 4H), 6.78-6.90(m, 2H), 6.30(brs, 1H), 3.82-3.97(m, 3H), 2.90-3.05(m, 3H), 1.88-2.02(m, 4H), 1.58(s, 3H), 1.32-1.46(m, 6H), 1.26(t, 3H), 0.82(t, 3H). | 21 |
| 391 | 531.1 | | 12.3 | A | | | 22 |
| 392 | 468.2 | | 9.7 | A | | | 16 |
| 393 | 328.3 | | 9.5 | A | | | 12 |
| 394 | 342.3 | | 9.7 | A | | | 12 |
| 395 | 356.2 | | 10.2 | A | | | 12 |
| 396 | 404.2 | | 13.3 | A | | | 12 |
| 397 | 416.3 | | 13.6 | A | | | 12 |
| 398 | 416.3 | | 13.2 | A | | | 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 399 | 356.3 | | 10.8 | A | | | 12 |
| 400 | 327.2 | | 9.0 | A | | | 12 |
| 401 | 341.2 | | 9.0 | A | | | 12 |
| 402 | 341.2 | | 8.4 | A | | | 12 |
| 403 | 369.2 | | 10.3 | A | | | 12 |
| 404 | 355.3 | | 8.0 | A | | | 12 |
| 405 | 381.2 | | 10.2 | A | | | 12 |
| 406 | 381.2 | | 11.0 | A | | | 12 |
| 407 | 381.2 | | 9.1 | A | | | 12 |
| 408 | 357.2 | | 8.1 | A | | | 12 |
| 409 | 394.2 | | 8.6 | A | | | 30 |
| 410 | 353.3 | | 9.1 | A | | | 30 |
| 411 | 443.2 | | 12.9 | A | | | 12 |
| 412 | 353.3 | | 8.9 | A | | | 30 |
| 413 | 395.3 | | 8.7 | A | | (CDCl₃) 8.25(s, 1H), 8.21(bs, 1H), 7.61(s, 1H), 7.06(d, 2H), 6.88(d, 2H), 4.23(m, 1H), 4.02(q, 2H), 3.11(m, 1H), 2.15(s, 3H), 2.11(m, 4H), 1.62(s, 3H), 1.61(m, 4H), 1.41(t, 3H). | 12 |
| 414 | 381.3 | | 9.9 | A | | (CDCl₃) 10.3(br, 1H), 10.1(br, 1H), 8.32(s, 1H), 7.68(s, 1H), 7.06(d, 2H), 6.91(d, 2H), 4.95(m, 1H), 4.05(q, 2H), 3.48(m, 2H), 3.28(m, 1H), 2.94(m, 1H), 2.35(s, 3H), 2.05(m, 2H), 1.99(m, 2H), 1.68(s, 3H), 1.44(t, 3H). | 12 |
| 415 | 471.3 | | 12.4 | A | | (CDCl₃) 8.21(br, 2H), 8.14(s, 1H), 7.51(s, 1H), 7.22(s, 2H), 7.21(s, 2H), 7.13(m, 1H), 7.02(d, 2H), 6.87(d, 2H), 4.13(m, 1H), 4.01(q, 2H), 3.99(s, 2H), 3.09(m, 1H), 2.07(m, 4H), 1.61(m, 1H), 1.60(s, 3H), 1.44(m, 1H), 1.41(t, 3H). | 12 |
| 416 | 457.2 | | 1.7 | A | | (CDCl₃) 10.2(br, 1H), 9.91(br, 1H), 8.26(s, 1H), 7.58(s, 1H), 7.43(br, 1H), 7.31-7.16(m, 5H), 7.05(d, 2H), 6.89(d, 2H), 4.92(m, 1H), 4.22(s, 2H), 4.03(q, 2H), 3.44(m, 2H), 3.22(m, 1H), 2.98(m, 1H), 2.35(s, 2H), 2.06-1.99(m, 4H), 1.68(s, 3H), 1.42(t, 3H). | 12 |
| 418 | 443.2 | | 12.4 | A | | | 12 |
| 419 | 457.2 | | 12.0 | A | | | 24 |
| 420 | 457.2 | | 11.0 | A | | | 24 |
| 421 | 433.2 | | 11.3 | A | | | 24 |
| 422 | 403.3 | | 6.5 | A | | | 24 |
| 423 | 452.2 | | 11.0 | A | | | 24 |
| 424 | 438.3 | | 14.3 | A | | | 12 |
| 425 | 411.2 | | 9.0 | A | | (CDCl₃) 7.61(1H, s), 7.42(brs, 1H), 6.97(m, 2H), 6.85(m, 2H), 4.14(m, 1H), 4.02(q, 2H), 3.98(s, 3H), 2.73(m, 1H), 2.22(m, 2H), 1.94(m, 2H), 1.65(s, 3H), 1.42(t, 3H), 1.35(m, 2H), 1.23(m, 2H). | 12 |
| 426 | 424.5 | | 10.4 | A | | (DMSO-d6) 8.93(s, 1H), 8.74(brs, 2H), 8.12(s, 1H), 7.73(d, 1H), 6.95(d, 2H), 6.86(d, 2H), 6.69(d, 1H), 4.39(brs, 1H), 3.98(q, 2H), 3.38~3.47(m, 1H), 3.21~3.30(m, 1H), 2.93~3.03(m, 1H), 2.82~3.03(m, 4H), 1.99~2.09(m, 1H), 1.88~1.97(m, 1H), 1.57~1.83(m, 4H), 1.31(t, 3H). | 16 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 427 | 438.6 | | 10.9 | A | | | 16 |
| 428 | 464.6 | | 13.1 | A | | | 16 |
| 429 | 468.5 | | 11.4 | A | | | 16 |
| 430 | 481.6 | | 9.0 | A | | | 16 |
| 431 | 486.6 | | 14.4 | A | | (DMSO-d6) 9.05(s, 1H), 8.70~8.90(m, 2H), 8.26(s, 1H), 7.68(d, 2H), 7.37(t, 2H), 7.09(t, 1H), 6.99(d, 2H), 6.88(d, 2H), 6.81(d, 1H), 4.45~4.55(m, 1H), 3.99(q, 2H), 3.37~3.45(m, 1H), 3.15~3.30(m, 2H), 2.87~2.98(m, 1H), 2.18~2.27(m, 1H), 1.88~2.00(m, 1H), 1.55~1.82(m, 5H), 1.31(t, 3H). | 16 |
| 432 | 487.5 | | 12.7 | A | | | 16 |
| 433 | 487.5 | | 11.0 | A | | ((DMSO-d6) 9.07(s, 1H), 8.85(d, 1H), 8.72(brs, 2H), 8.35(dd, 1H), 8.25~8.32(m, 2H), 7.47~7.52(m, 1H), 6.99(d, 2H), 6.88(d, 2H), 6.82(d, 1H), 4.48~4.60(m, 1H), 3.99(q, 2H), 3.33~3.42(m, 1H), 3.12~3.30(m, 2H), 2.85~2.97(m, 1H), 2.17~2.25(m, 1H), 1.89~2.00(m, 1H), 1.57~1.80(m, 5H), 1.31(t, 3H). | 16 |
| 434 | 487.6 | | 10.0 | A | | ((DMSO-d6) 9.14(s, 1H), 8.68~8.82(m, 2H), 8.65(d, 2H), 8.39(s, 1H), 8.00(d, 2H), 6.98(d, 2H), 6.83~6.92(m, 3H), 4.48~4.58(m, 1H), 3.99(q, 2H), 3.36~3.45(m, 1H), 3.15~3.25(m, 2H), 2.89~3.01(m, 1H), 2.12~2.21(m, 1H), 1.88~1.98(m, 1H), 1.62~1.77(m, 5H), 1.31(t, 3H). | 16 |
| 435 | 500.6 | | 12.4 | A | | ((DMSO-d6) 8.96(s, 1H), 8.54~8.75(m, 2H), 8.27~8.34(m, 1H), 8.16(s, 1H), 7.30~7.35(m, 4H), 7.22~7.29(m, 1H), 6.96(d, 2H), 6.87(d, 2H), 6.68(d, 1H), 4.77(dd, 1H), 4.41(dd, 1H), 4.25~4.35(m, 1H), 3.98(q, 2H), 2.98~3.27(m, 3H), 2.79~2.92(m, 1H), 1.83~1.92(m, 1H), 1.38~1.75(m, 6H), 1.31(t, 3H). | 16 |
| 437 | 410.6 | | 10.1 | A | | | 28 |
| 438 | 454.6 | | 9.9 | A | | | 28 |
| 439 | 439.6 | | 14.8 | A | | 59Db0011 ((DMSO-d6) 8.65~8.90(m, 3H), 8.19(s, 1H), 6.94(d, 2H), 6.87(d, 2H), 6.63(d, 1H), 4.36~4.46(m, 1H), 4.16~4.26(m, 2H), 3.99(q, 2H), 3.40~3.48(m, 1H), 3.06~3.24(m, 2H), 2.85~2.97(m, 1H), 1.86~2.10(m, 2H), 1.62~1.78(m, 5H), 1.27~1.35(m, 6H). | 12 |
| 440 | 411.6 | | 11.1 | A | | 59Db0021 ((DMSO-d6) 8.87~8.97(brs, 1H), 8.58~8.78(m, 2H), 8.16(s, 1H), 6.82~6.97(m, 4H), 6.70(d, 1H), 4.31~4.45(m, 1H), 3.98(q, 2H), 3.35~3.45(m, 1H), 2.74~3.25(m, 3H), 1.86~2.03(s, 3H), 1.60~1.77(m, 5H), 1.31(t, 3H). | 15 |
| 442 | 414.1 | | 7.0 | A | | | 24 |
| 443 | 405 | | 13.1 | A | | | 24 |
| 444 | 414.1 | | 7.9 | A | | | 24 |
| 445 | 429.1 | | 9.8 | A | | | 24 |
| 446 | 413.1 | | 11.1 | A | | | 24 |
| 447 | 428.1 | | 7.3 | A | | | 24 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 448 | 428.1 | | 7.6 | A | | | 24 |
| 449 | 414.1 | | 5.7 | A | | | 24 |
| 451 | 461 | | 10.1 | A | | | 24 |
| 452 | 381.1 | | 9.3 | A | | | 12 |
| 453 | 416 | | 7.5 | A | | | 12 |
| 454 | 384.1 | | 9.5 | A | | | 12 |
| 455 | 383.1 | | 10.2 | A | | | 12 |
| 456 | 427.1 | | 10.8 | A | | | 12 |
| 457 | 413.1 | | 12.8 | A | | | 12 |
| 458 | 416 | | 10.9 | A | | | 12 |
| 459 | 423 | | 12.2 | A | | | 12 |
| 460 | 394.1 | | 6.0 | B | | | Ex. 26 |
| 462 | 420 | | 7.2 | B | | | Ex. 26 |
| 463 | 448 | | 9.9 | B | | | Ex. 26 |
| 465 | 476.1 | | 13.0 | B | | | Ex. 26 |
| 466 | 424.1 | | 4.6 | A | | | Ex. 26 |
| 467 | 438 | | 7.0 | B | | | Ex. 26 |
| 468 | 464 | | 8.7 | B | | | Ex. 26 |
| 469 | 451.1 | | 5.5 | B | | | Ex. 26 |
| 470 | 477.1 | | 6.5 | B | | | Ex. 26 |
| 471 | 493.1 | | 6.1 | B | | | Ex. 26 |
| 472 | 426 | | 7.8 | B | | | Ex. 26 |
| 473 | 462 | | 10.2 | B | | | Ex. 26 |
| 474 | 442 | | 8.7 | B | | | Ex. 26 |
| 475 | 454 | | 9.6 | B | | | Ex. 26 |
| 476 | 465 | | 6.3 | B | | | Ex. 26 |
| 477 | 437.1 | | 6.1 | B | | | Ex. 26 |
| 478 | 452 | | 7.5 | B | | | Ex. 26 |
| 480 | 465.1 | | 5.9 | B | | | Ex. 26 |
| 481 | 507.1 | | 5.9 | B | | | Ex. 26 |
| 483 | 480.1 | | 10.6 | B | | | Ex. 26 |
| 488 | 474 | | 11.5 | B | | | Ex. 26 |
| 489 | 474 | | 12.0 | B | | | Ex. 26 |
| 490 | 474 | | 12.3 | B | | | Ex. 26 |
| 492 | 481.1 | | 11.8 | B | | | Ex. 26 |
| 493 | 481.1 | | 11.8 | B | | | Ex. 26 |
| 494 | 486.1 | | 12.4 | B | | | Ex. 26 |
| 495 | 486.1 | | 11.2 | B | | | Ex. 26 |
| 496 | 486.1 | | 10.8 | B | | | Ex. 26 |
| 503 | 499.1 | | 9.9 | B | | | Ex. 26 |
| 504 | 499.1 | | 7.4 | B | | | Ex. 26 |
| 505 | 499.1 | | 7.9 | B | | | Ex. 26 |
| 506 | 507 | | 8.1 | B | | | Ex. 26 |
| 510 | 470.1 | | 9.3 | A | | | Ex. 26 |
| 511 | 460 | | 9.4 | B | | | Ex. 26 |
| 512 | 476 | | 10.3 | B | | | Ex. 26 |
| 513 | 471.1 | | 4.3 | A | | | Ex. 26 |
| 514 | 471 | | 6.2 | B | | | Ex. 26 |
| 515 | 471 | | 5.8 | B | | | Ex. 26 |
| 518 | 484 | | 12.3 | B | | | Ex. 26 |
| 519 | 485 | | 6.5 | B | | | Ex. 26 |
| 520 | 485 | | 6.5 | B | | | Ex. 26 |
| 521 | 488.1 | | 6.1 | B | | | Ex. 26 |
| 522 | 474.1 | | 6.3 | B | | | Ex. 26 |
| 759 | 452.1 | | 5.5 | A | | | Ex. 23 |
| 760 | 430 | | 6.5 | A | | | Ex. 23 |
| 761 | 397 | | 9.4 | A | | | Ex. 23 |
| 762 | 459 | | 10.9 | A | | (CDCl$_3$) 8.04(s, 1H), 7.87(brs, 2H), 7.54(brs, 1H), 6.99(d, J=8.8Hz, 2H), 6.85(d, J=9.0Hz, 2H), 4.02(q, J=7.0Hz, 2H), 3.60~4.30(m, 3H), 3.26(s, 3H), 3.15~3.30(m, 1H), 2.10~2.30(m, 4H), 1.50~1.75(m, 2H), 1.60(s, 3H), 1.42(t, J=6.9Hz, 3H), 1.30~1.50(m, 2H). | Ex. 12 |
| 763 | 445.1 | | 11.7 | A | | (CDCl$_3$) 9.33(brs, 1H), 8.80(brs, 1H), 8.07(s, 1H), 7.63(brs, 1H), 7.03(d, J=8.8Hz, 2H), 6.89(d, J=8.8Hz, 2H), 5.20~5.60(m, 1H), 4.52(brs, 1H), 4.04(q, | Ex. 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| | | | | | | J=7.0Hz, 2H), 3.60~3.70(m, 1H), 3.20(s, 3H), 3.15~3.30(m, 3H), 2.00~2.15(m, 2H), 1.80~2.00(m, 2H), 1.65(s, 3H), 1.43(t, J=7.0Hz, 3H). | |
| 764 | 490 | | 12.0 | A | | | Ex. 16 |
| 765 | 490 | | 10.7 | A | | | Ex. 16 |
| 766 | 491 | | 11.2 | A | | | Ex. 16 |
| 767 | 492 | | 12.8 | A | | | Ex. 16 |
| 768 | 468.1 | | 11.9 | A | | | Ex. 16 |
| 769 | 482.1 | | 10.7 | A | | | Ex. 16 |
| 770 | 454 | | 11.2 | A | | | Ex. 16 |
| 771 | 468.1 | | 11.1 | A | | | Ex. 16 |
| 772 | 397 | | 10.0 | A | | (CDCl₃) 8.42(s, 1H), 7.84(s, 1H), 7.74(m, 1H), 7.11(d, J=8.8Hz, 2H), 6.91(d, J=8.8Hz, 2H), 6.36(s, 1H), 5.06(m, 1H), 4.48(m, 1H), 4.04(q, J=6.84, 2H), 3.87(m, 1H), 3.63(m, 1H), 2.98(m, 1H), 2.42(m, 1H), 1.42(t, J=6.86Hz, 3H). | Ex. 12 |
| 773 | 447 | | 10.0 | A | | | Ex. 24 |
| 774 | 395.1 | | 9.4 | A | | | Ex. 12 |
| 775 | 430 | | 6.3 | A | | | Ex. 12 |
| 776 | 456 | | 11.1 | B | | | Ex. 26 |
| 777 | 397 | | 8.4 | A | | | Ex. 12 |
| 778 | 441 | | 10.0 | A | | | Ex. 12 |
| 779 | 415 | | 5.5 | A | | | Ex. 12 |
| 780 | 427.1 | | 11.8 | A | | | Ex. 12 |
| 781 | 430 | | 9.4 | A | | | Ex. 12 |
| 782 | 437 | | 12.6 | A | | | Ex. 12 |
| 783 | 401.1 | | 10.2 | A | | | Ex. 12 |
| 784 | 454.2 | | 11.2 | A | | | Ex. 12 |
| 785 | 455 | | 11.4 | A | | | Ex. 12 |
| 786 | 458.1 | | 10.7 | A | | | Ex. 12 |
| 787 | 484 | | 12.1 | A | | | Ex. 12 |
| 788 | 379.1 | | 6.7 | A | | | Ex. 12 |
| 789 | 361.1 | | 8.6 | A | | | Ex. 12 |
| 790 | 516.1 | | 10.2 | A | | | Ex. 28 |
| 791 | 552.1 | | 10.9 | A | | | Ex. 28 |
| 792 | 434.1 | | 6.9 | A | | | Ex. 26 |
| 793 | 450.1 | | 10.5 | B | | | Ex. 26 |
| 794 | 408.1 | | 7.2 | B | | | Ex. 26 |
| 795 | 398 | | 8.4 | A | | | Ex. 12 |
| 796 | 442.1 | | 11.1 | A | | | Ex. 12 |
| 797 | 387.1 | | 11.9 | A | | | Ex. 12 |
| 798 | 437.2 | | 12.6 | A | | | Ex. 12 |
| 799 | 440.2 | | 12.0 | A | | | Ex. 12 |
| 800 | 441.0 | | 12.6 | A | | | Ex. 12 |
| 801 | 444.1 | | 10.9 | A | | | Ex. 12 |
| 802 | 470.1 | | 12.8 | A | | | Ex. 12 |
| 803 | 365.2 | | 8.1 | A | | | Ex. 12 |
| 804 | 347.1 | | 9.8 | A | | | Ex. 12 |
| 805 | 374.1 | | 4.5 | A | | | Ex. 12 |
| 806 | 498.9 | | 15.1 | A | | (CD₃OD) 7.61~7.58(m, 2H), 7.38~7.29(m, 2H), 4.05~4.00(m, 1H), 3.09~3.07(m, 1H), 2.21~2.18(m, 2H), 2.13~2.09(m, 2H), 1.99(s, 3H), 1.58~1.49(m, 2H), 1.43~1.34(m, 2H). | Ex. 14 |
| 807 | 440.0 | | 8.722 | A | | (CD₃OD) 7.96(s, 1H), 7.82(d, 1H), 7.71(d, 1H), 7.32(dd, 1H), 3.92(m, 2H), 3.16(m, 2H), 2.81(s, 3H), 2.15(m, 4H), 1.68(s, 3H), 1.66(m, 4H). | Ex. 12 |
| 808 | 454.0 | | 10.3 | A | | (CD₃OD) 7.96(s, 1H), 7.83(d, 1H), 7.71(d, 1H), 7.32(dd, 1H), 3.84(m, 2H), 3.38(q, 2H), 3.16(m, 2H), | Ex. 12 |

TABLE B-continued

| Compound No. | ESI/MS M+H | ESI/MS M−H | HPLC Retention Time (min.) | HPLC Method | Mp(° C.) | 1H-NMR(400 MHz) d(ppm) | Method of Preparation |
|---|---|---|---|---|---|---|---|
| 809 | 468.0 | | 11.8 | A | | 2.16(m, 4H), 1.68(s, 3H), 1.66(m, 4H), 1.49(t, 3H). (CD₃OD) 7.96(s, 1H), 7.84(d, 1H), 7.71(d, 1H), 7.32(dd, 1H), 4.09(m, 1H), 3.92(m, 2H), 3.16(m, 2H), 2.81(s, 3H), 2.15(m, 4H), 1.68(s, 3H), 1.66(m, 4H). | Ex. 12 |
| 810 | 426.0 | | 9.6 | A | | (CD₃OD) 7.84(s, 1H), 7.75(d, 1H), 7.46(d, 1H), 7.16(dd, 1H), 4.42(m, 1H), 3.64(m, 1H), 3.38(m, 1H), 3.30(m, 2H), 2.97(m, 1H), 2.79(s, 3H), 2.16(m, 1H), 2.07(m, 1H), 1.89(m, 1H), 1.80(s, 3H). | Ex. 12 |
| 811 | 440.0 | | 10.7 | A | | (CD₃OD) 7.87(s, 1H), 7.77(d, 1H), 7.50(d, 1H), 7.19(dd, 1H), 4.39(m, 1H), 3.64(m, 1H), 3.38(m, 1H), 3.36(q, 2H), 3.30(m, 2H), 2.98(m, 1H), 2.79(s, 3H), 2.17(m, 1H), 2.08(m, 1H), 1.89(m, 1H), 1.78(s, 3H), 1.47(t, 3H). | Ex. 12 |
| 812 | 454.0 | | 11.9 | A | | (CD₃OD) 7.88(s, 1H), 7.79(d, 1H), 7.51(d, 1H), 7.20(dd, 1H), 4.39(m, 1H), 4.04(m, 1H), 3.65(m, 1H), 3.38(m, 1H), 3.00(m, 2H), 2.98(m, 1H), 2.17(m, 1H), 2.09(m, 1H), 1.92(m, 1H), 1.78(s, 3H), 1.49(d, 6H). | Ex. 12 |
| 813 | 541.2 | | 16.1 | A | | (CDCl₃) 7.79(d, J=2.2Hz, 1H), 7.54(s, 1H), 7.37~7.29(m, 5H), 7.00(d, J=8.8Hz, 2H), 6.86(d, J=9.04Hz, 2H), 6.09(brs, 1H), 5.79(m, 1H), 5.14(d, J=2.72Hz, 2H), 5.04(s, 1H), 5.01(m, 1H), 4.44(br, 1H), 4.26(br, 1H), 4.12(br, 1H), 4.02(q, J=6.84Hz, 2H), 2.94(br, 1H), 2.76(br, 1H), 2.41(m, 1H), 2.06(m, 1H), 1.83(br, 1H), 1.64(s, 3H), 1.42(t, J=7.08Hz, 3H). | Ex. 12 |
| 815 | 449.4 | | 13.9 | A | | | Ex. 12 |
| 816 | 435.5 | | 13.7 | A | | | Ex. 12 |
| 817 | 499.3 | | 15.6 | A | | | Ex. 12 |
| 818 | 485.2 | | 14.9 | A | | | Ex. 12 |

Example 35

[General Procedure for Measurement of MAPKAP-K2 Enzyme Activity Inhibition]

(Compound Preparation)

Compounds were dissolved in DMSO at a concentration of 10 mM and stored in aliquots at −20° C. Compounds in DMSO from these stock aliquots were diluted in DMSO to produce the required range of 30× stock solutions. These stock solutions were then subjected to 1:3, dilutions in order to prepare the required range of 10× stock solutions and 5 μL of each solution was used per 50 μL reaction. A final DMSO concentration of 3% was maintained throughout all compound dilution series to maximise compound solubility. Compounds were routinely tested at final concentrations ranging from 300 μM to 0.001 μM, but may have been tested at lower concentrations depending upon their activity.

(MAPKAP-K2 Assay)

The kinase reaction was conducted in a round-bottomed polypropylene 96-well plate. MAPKAP-Kinase 2 was diluted to 0.5 mU/μL in diluent buffer (50 mM Tris/HCl. pH7.5, 0.1 mM EGTA, 0.1% (v/v) β-mercaptoethanol, 1 mg/mL BSA). 5 μL compound or 30% DMSO was added to each well followed by 25 μL substrate cocktail (final concentration: 10 μM ATP, 30 μM peptide (KKLNRTLSVA), 0.5 μCi 33P-γ-ATP in 50 mM Tris pH7.5, 0.1 mM EGTA, 10 mM Mg-acetate and 0.1% β-mercaptoethanol). The reaction was initiated with the addition of 20 μL enzyme solution per well or 20 μL diluent buffer without enzyme. The plate was shaken for 10 seconds and then left at room temperature for 30 minutes. The reaction was terminated with 50 μL 150 mM phosphoric acid. 90 μL of the reaction mixture was then transferred into a 96-well P81 filter plate (Whatmann) and incubated at room temperature for 5 minutes. The filter plate was then washed 4 times with 200 μL 75 mM phosphoric acid per well on a plate vacuum manifold (Millipore) and dried in an oven for 2-3 hours. Packard MicroScint '0' (30 μL) was then added to each well, the plate was mixed for 30 minutes and subjected to liquid scintillation counting on a Packard TopCount.

After adding 25 μL of peptide substrate solution [60 μM substrate peptide, 20 μM ATP, 50 mM Tris buffer (pH 7.5), 0.1 mM EGTA, 0.1% β-mercaptoethanol, 20 mM magnesium acetate, 0.1 μCi [γ-33P]ATP (specific activity: approximately 110 TBq/mmol)] to 5 μL of the test compound using 5% dimethylsulfoxide as the solvent, reaction was initiated by further addition of 20 μL of a MAPKAP-K2 enzyme solution [10 mU recombinant human MAPKAP-K2, 50 mM Tris buffer (pH 7.5), 0.1 mM EGTA, 0.1 % β-mercaptoethanol, 0.1% BSA]. After conducting the reaction for 30 minutes at room temperature, an equivalent volume of a 200 mM phosphoric acid solution was added to suspend the reaction, and 90 μL of the reaction product was adsorbed onto a Multi-Screen PH plate (Millipore) and rinsed with a 100 mM phosphoric acid solution. After drying the plate, 30 μL of MicroScint-O (Packard BioScience) was added, and the cpm was measured with a scintillation counter to determine the inhibiting activity. Substrate peptide is Lys-Lys-Leu-Asn-Arg-Thr-Leu-Ser-Val-Ala.

(Interpretation)
% Control=(X−B)/(Tot−B)×100
% Inhibition=100−% Contr
X=cpm of the test compound wells
B=cpm of wells without enzyme
Tot=cpm of wells with DMSO vehicle only (MAPKAP-K2 Inhibitory Activity)

The efficacy of the compounds in Table A against MAPKAP-K2 is shown in Table C below.

(The activity is presented as +, ++, or +++ representing active, more active and very active based on assays conducted at typically 1-100 μM).

TABLE C

| Compound No | activity |
|---|---|
| 1 | ++ |
| 2 | ++ |
| 7 | ++ |
| 10 | +++ |
| 11 | +++ |
| 12 | +++ |
| 13 | + |
| 14 | ++ |
| 15 | +++ |
| 16 | +++ |
| 17 | +++ |
| 18 | ++ |
| 19 | +++ |
| 20 | ++ |
| 21 | ++ |
| 22 | ++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |

TABLE C-continued

| Compound No | activity |
|---|---|
| 36 | +++ |
| 37 | +++ |
| 38 | ++ |
| 39 | ++ |
| 40 | ++ |
| 41 | ++ |
| 42 | ++ |
| 43 | +++ |
| 44 | ++ |
| 45 | ++ |
| 46 | ++ |
| 47 | ++ |
| 48 | ++ |
| 49 | ++ |
| 50 | ++ |
| 51 | +++ |
| 52 | +++ |
| 53 | +++ |
| 54 | ++ |
| 55 | +++ |
| 56 | +++ |
| 57 | +++ |
| 58 | ++ |
| 59 | +++ |
| 60 | +++ |
| 61 | +++ |
| 62 | ++ |
| 63 | +++ |
| 64 | +++ |
| 65 | +++ |
| 66 | ++ |
| 67 | +++ |
| 68 | +++ |
| 69 | ++ |
| 70 | +++ |
| 71 | ++ |
| 72 | +++ |
| 73 | ++ |
| 74 | ++ |
| 75 | ++ |
| 76 | +++ |
| 77 | +++ |
| 79 | ++ |
| 80 | +++ |
| 81 | +++ |
| 82 | ++ |
| 83 | +++ |
| 84 | +++ |
| 85 | +++ |
| 86 | ++ |
| 87 | ++ |
| 88 | +++ |
| 89 | +++ |
| 90 | +++ |
| 91 | ++ |
| 93 | ++ |
| 94 | ++ |
| 95 | +++ |
| 96 | +++ |
| 97 | +++ |
| 98 | +++ |
| 100 | ++ |
| 102 | +++ |
| 103 | +++ |
| 104 | +++ |
| 105 | +++ |
| 106 | +++ |
| 107 | +++ |
| 110 | + |
| 111 | +++ |
| 112 | +++ |
| 113 | ++ |
| 114 | +++ |
| 115 | +++ |
| 116 | ++ |
| 117 | ++ |
| 118 | +++ |

TABLE C-continued

| Compound No | activity |
|---|---|
| 119 | + |
| 120 | ++ |
| 121 | ++ |
| 122 | ++ |
| 124 | ++ |
| 125 | ++ |
| 126 | +++ |
| 127 | + |
| 128 | ++ |
| 129 | +++ |
| 130 | ++ |
| 131 | +++ |
| 135 | + |
| 137 | +++ |
| 139 | + |
| 140 | +++ |
| 141 | ++ |
| 142 | + |
| 145 | ++ |
| 146 | ++ |
| 148 | +++ |
| 149 | +++ |
| 150 | +++ |
| 151 | ++ |
| 152 | ++ |
| 153 | +++ |
| 155 | +++ |
| 156 | +++ |
| 157 | ++ |
| 159 | +++ |
| 160 | ++ |
| 167 | ++ |
| 168 | ++ |
| 169 | ++ |
| 170 | +++ |
| 171 | ++ |
| 172 | ++ |
| 173 | +++ |
| 174 | +++ |
| 175 | +++ |
| 176 | +++ |
| 177 | ++ |
| 178 | +++ |
| 179 | +++ |
| 180 | ++ |
| 181 | ++ |
| 182 | + |
| 183 | ++ |
| 184 | ++ |
| 187 | ++ |
| 190 | + |
| 191 | +++ |
| 192 | ++ |
| 193 | +++ |
| 195 | + |
| 196 | +++ |
| 197 | +++ |
| 198 | +++ |
| 199 | +++ |
| 200 | +++ |
| 201 | +++ |
| 202 | +++ |
| 203 | +++ |
| 204 | ++ |
| 205 | +++ |
| 206 | ++ |
| 207 | ++ |
| 208 | +++ |
| 209 | ++ |
| 210 | ++ |
| 211 | +++ |
| 212 | ++ |
| 213 | +++ |
| 214 | +++ |
| 215 | ++ |
| 216 | +++ |
| 217 | ++ |

TABLE C-continued

| Compound No | activity |
|---|---|
| 218 | +++ |
| 219 | +++ |
| 220 | ++ |
| 221 | +++ |
| 222 | +++ |
| 223 | +++ |
| 224 | +++ |
| 225 | +++ |
| 226 | +++ |
| 227 | ++ |
| 228 | +++ |
| 229 | +++ |
| 230 | +++ |
| 231 | ++ |
| 232 | +++ |
| 233 | ++ |
| 234 | +++ |
| 235 | ++ |
| 236 | ++ |
| 237 | ++ |
| 238 | ++ |
| 239 | ++ |
| 240 | ++ |
| 241 | ++ |
| 242 | ++ |
| 243 | ++ |
| 244 | ++ |
| 245 | +++ |
| 246 | ++ |
| 247 | ++ |
| 248 | ++ |
| 249 | ++ |
| 250 | ++ |
| 251 | +++ |
| 252 | ++ |
| 253 | +++ |
| 254 | +++ |
| 255 | ++ |
| 256 | +++ |
| 257 | ++ |
| 258 | ++ |
| 259 | ++ |
| 260 | ++ |
| 261 | ++ |
| 262 | ++ |
| 263 | ++ |
| 264 | ++ |
| 265 | ++ |
| 266 | ++ |
| 267 | ++ |
| 268 | ++ |
| 269 | ++ |
| 270 | ++ |
| 272 | ++ |
| 273 | ++ |
| 274 | ++ |
| 275 | ++ |
| 276 | ++ |
| 277 | ++ |
| 278 | ++ |
| 279 | ++ |
| 280 | ++ |
| 281 | ++ |
| 282 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | ++ |
| 293 | +++ |
| 294 | ++ |
| 295 | +++ |
| 297 | ++ |

TABLE C-continued

| Compound No | activity |
|---|---|
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | ++ |
| 311 | +++ |
| 312 | +++ |
| 313 | ++ |
| 314 | +++ |
| 315 | +++ |
| 316 | +++ |
| 317 | +++ |
| 318 | +++ |
| 319 | +++ |
| 320 | +++ |
| 321 | +++ |
| 322 | +++ |
| 323 | ++ |
| 324 | +++ |
| 325 | + |
| 327 | +++ |
| 329 | + |
| 330 | ++ |
| 331 | + |
| 332 | ++ |
| 333 | + |
| 335 | ++ |
| 336 | + |
| 337 | + |
| 338 | + |
| 340 | + |
| 341 | + |
| 343 | ++ |
| 347 | + |
| 349 | + |
| 350 | +++ |
| 351 | +++ |
| 352 | +++ |
| 353 | +++ |
| 354 | +++ |
| 355 | +++ |
| 356 | +++ |
| 357 | +++ |
| 358 | + |
| 359 | ++ |
| 360 | ++ |
| 361 | +++ |
| 362 | ++ |
| 364 | + |
| 365 | + |
| 373 | +++ |
| 374 | +++ |
| 375 | +++ |
| 376 | +++ |
| 377 | +++ |
| 378 | + |
| 379 | + |
| 381 | + |
| 382 | + |
| 383 | + |
| 384 | ++ |
| 385 | ++ |
| 386 | + |
| 387 | + |
| 389 | ++ |
| 391 | + |
| 393 | + |
| 394 | + |
| 400 | ++ |
| 401 | ++ |

TABLE C-continued

| Compound No | activity |
|---|---|
| 402 | ++ |
| 403 | ++ |
| 404 | ++ |
| 406 | + |
| 407 | + |
| 408 | ++ |
| 409 | +++ |
| 410 | +++ |
| 411 | ++ |
| 412 | ++ |
| 413 | ++ |
| 414 | ++ |
| 415 | + |
| 417 | + |
| 418 | ++ |
| 419 | +++ |
| 420 | ++ |
| 421 | +++ |
| 422 | +++ |
| 423 | +++ |
| 424 | + |
| 427 | + |
| 428 | + |
| 429 | ++ |
| 430 | + |
| 431 | ++ |
| 432 | ++ |
| 433 | + |
| 434 | ++ |
| 435 | ++ |
| 436 | + |
| 437 | + |
| 438 | ++ |
| 440 | +++ |
| 441 | +++ |
| 442 | +++ |
| 443 | +++ |
| 444 | +++ |
| 445 | +++ |
| 446 | +++ |
| 447 | +++ |
| 448 | +++ |
| 449 | +++ |
| 450 | +++ |
| 451 | +++ |
| 452 | +++ |
| 453 | +++ |
| 454 | ++ |
| 455 | ++ |
| 456 | +++ |
| 457 | +++ |
| 458 | ++ |
| 459 | +++ |
| 460 | +++ |
| 462 | +++ |
| 463 | +++ |
| 465 | +++ |
| 466 | +++ |
| 467 | +++ |
| 468 | +++ |
| 469 | +++ |
| 470 | +++ |
| 471 | +++ |
| 472 | +++ |
| 473 | +++ |
| 474 | +++ |
| 475 | +++ |
| 476 | +++ |
| 477 | +++ |
| 478 | +++ |

TABLE C-continued

| Compound No | activity |
|---|---|
| 480 | +++ |
| 481 | +++ |
| 483 | +++ |
| 488 | +++ |
| 489 | +++ |
| 490 | +++ |
| 492 | +++ |
| 493 | +++ |
| 494 | +++ |
| 495 | +++ |
| 496 | +++ |
| 503 | +++ |
| 504 | ++ |
| 505 | +++ |
| 506 | +++ |
| 510 | +++ |
| 511 | +++ |
| 512 | +++ |
| 513 | +++ |
| 514 | +++ |
| 515 | +++ |
| 518 | +++ |
| 519 | +++ |
| 520 | +++ |
| 521 | +++ |
| 522 | +++ |
| 759 | +++ |
| 760 | +++ |
| 761 | +++ |
| 764 | ++ |
| 765 | ++ |
| 766 | + |
| 767 | ++ |
| 768 | + |
| 769 | ++ |
| 772 | ++ |
| 773 | +++ |
| 774 | +++ |
| 775 | +++ |
| 776 | +++ |
| 777 | ++ |
| 778 | +++ |
| 779 | +++ |
| 780 | +++ |
| 781 | ++ |
| 782 | +++ |
| 783 | ++ |
| 784 | +++ |
| 785 | +++ |
| 786 | +++ |
| 787 | +++ |
| 788 | +++ |
| 789 | +++ |
| 790 | + |
| 792 | +++ |
| 793 | +++ |
| 794 | +++ |
| 795 | ++ |
| 797 | ++ |
| 799 | +++ |
| 800 | +++ |
| 801 | +++ |
| 802 | +++ |
| 803 | +++ |
| 804 | +++ |
| 805 | ++ |
| 806 | + |
| 807 | +++ |
| 808 | +++ |
| 809 | +++ |
| 810 | +++ |
| 811 | +++ |
| 812 | +++ |
| 814 | ++ |

Example 36

[General Procedure for Measurement of CDK-1 Enzyme Activity Inhibition]

(Compound Preparation)

Compounds were dissolved in DMSO at a concentration of 10 mM and stored in aliquots at −20° C. Compounds in DMSO from these stock aliquots were diluted in DMSO to produce the required range of 30× stock solutions. These stock solutions were then subjected to 1:3 dilutions in order to prepare the required range of 10× stock solutions and 5 µL of each solution was used per 50 µL reaction. A final DMSO concentration of 3% was maintained throughout all compound dilution series to maximise compound solubility. Compounds were routinely tested at final concentrations ranging from 300 µM to 0.001 µM, but may have been tested at lower concentrations depending upon their activity.

(CDK-1 Assay)

The kinase reaction was conducted in a round-bottomed polypropylene 96-well plate. CDK-1 was diluted to 0.5 U/µL in diluent buffer (50 mM Tris/HCl. pH7.5, 0.1 mM EGTA, 0.1% (v/v) β-mercaptoethanol, 1 mg/mL BSA). 5 µL compound or 30% DMSO was added to each well followed by 25 µL substrate cocktail (final concentration: 10 µM ATP, 50 µM peptide (HSTPPKKKAK), 0.5 µCi $^{33}$P-γ-ATP in 50 mM Tris-HCl (pH 7.5), 1 mM EGTA, 2 mM DTT, 10 mM $MgCl_2$, 0.01% Brij-35). The reaction was initiated with the addition of 20 µL enzyme solution per well or 20 µL of diluent buffer without enzyme. The plate was shaken for 10 seconds and then left at room temperature for 15 minutes. The reaction was terminated with 50 µL 150 mM phosphoric acid. 90 µL of the reaction mixture was then transferred into a 96-well P81 filter plate (Whatmann) and incubated at room temperature for 5 minutes. The filter plate was then washed 4 times with 200 µL 75 mM phosphoric acid per well on a plate vacuum manifold (Millipore) and dried in an oven for 2-3 hours. Packard MicroScint '0' (30 µL) was then added to each well, the plate was miffed for 30 minutes and subjected to liquid scintillation counting on a Packard TopCount.

(Interpretation)
% Control=(X−B)/(Tot−B)×100
% Inhibition=100−% Control
X=cpm of the test compound wells
B=cpm of wells without enzyme
Tot=cpm of wells with DMSO vehicle only (CD K-1 Inhibitory Activity)

Compounds that inhibit CDK-1 ($IC_{50}$<100 µM) are; 2, 7, 9, 10, 11, 12, 14, 15, 16, 17, 18, 19, 23, 24, 26, 27, 28, 29, 30, 31, 32, 33, 35 and 36.

Example 37

[General Procedure for Measurement of CDK-2 Enzyme Activity Inhibition]

(Compound Preparation)

Compounds were dissolved in DMSO at a concentration of 10 mM and stored in aliquots at −20° C. Compounds in DMSO from these stock aliquots were diluted in DMSO to produce the required range of 30× stock solutions. These stock solutions were then subjected to 1:3 dilutions in order to prepare the required range of 10× stock solutions and 5 µL of each solution was used per 50 µL reaction. A final DMSO concentration of 3% was maintained throughout all compound dilution series to maximise compound solubility. Compounds were routinely tested at final concentrations ranging from 300 μM to 0.001 μM, but may have been tested at lower concentrations depending upon their activity.

(CDK-2 Assay)

a) The kinase reaction was conducted in a round-bottomed polypropylene 96-well plate. CDK-2 was diluted to 0.5 ng/μL in diluent buffer (50 mM Tris/HCl. pH7.5, 0.1 mM EGTA, 0.1% (v/v) β-mercaptoethanol, 1 mg/ml BSA). 5 μL compound or 30% DMSO was added to each well followed by 25 μL substrate cocktail (final 10 μM ATP, 0.1 mg/ml Histone type III-S, 0.2 μCi $^{33}$P-γ-ATP in 50 mM Tris-HCl (pH 7.5), 1 mM EGTA, 2 mM DTT, 10 mM MgCl$_2$, 0.01% Brij-35). The reaction was initiated with the addition of 20 μL enzyme solution per well or 20 μL of diluent buffer without enzyme. The plate was shaken for 10 seconds and then left at room temperature for 60 minutes. The reaction was terminated with 50 μL 150 mM phosphoric acid. 90 μL of the reaction mixture was then transferred into a 96-well P81 filter plate (Whatmann) and incubated at room temperature for 5 minutes. The filter plate was then washed 4 times with 200 μL 75 mM phosphoric acid per well on a plate vacuum manifold (Millipore) and dried in an oven for 2-3 hours. Packard MicroScint '0' (30 μL) was then added to each well, the plate was mixed for 30 minutes and subjected to liquid scintillation counting on a Packard TopCount.

After adding 25 μL of substrate solution [0.2 mg/ml Histone type III-S, 20 μM ATP, 100 mM Tris buffer (pH 7.5), 2 mM EGTA, 4 mM DTT, 0.02% polyoxyethylene lauryl ether (23 Lauryl Ether; Brij 35), 20 mM magnesium chloride, 0.2 μCi [γ-$^{33}$P]ATP (specific activity: approximately 110 TBq/mmol)] to 5 μL of the test compound using 5% dimethylsulfoxide as the solvent, reaction was initiated by fulrther addition of 20 μL of a CDK2 enzyme solution [2.5 mU recombinant human CDK2/cyclin A, 50 mM Tris buffer (pH 7.5), 0.1 mM EGTA, 0.1% β-mercaptoethanol, 0.1% BSA]. After conducting the reaction for 15 minutes at room temperature, an equivalent volume of a 70% trichloroacetic acid (TCA) solution was added to suspend the reaction, and 90 μL of the reaction product was adsorbed onto a MultiScreen HV plate (Millipore) and rinsed with a 25% TCA solution. After drying the plate, 30 μL of MicroScint-O (Packard Bio-Science) was added, and the cpm was measured with a scintillation counter to determine the inhibiting activity.

(Interpretation)
% Control=(X−B)/(Tot−B)×100
% Inhibition=100−% Control
X=cpm of the test compound wells
B=cpm of wells without enzyme
Tot=cpm of wells with DMSO vehicle only (CDK-2 Inhibitory Activity)

Compounds that inhibit CDK-2 (IC$_{50}$<100 μM) are; 1, 2, 6, 7, 10, 11, 12, 13, 14, 15, 16, 23, 28, 31, 32, 35, 37, 38, 41, 42, 43, 44, 46, 47, 48, 49, 50, 51, 52, 53, 55, 56, 57, 58, 59, 60, 61, 63, 64, 65, 68, 70, 71, 72, 74, 75, 76, 77, 78, 80, 81, 83, 84, 85, 86, 87, 88, 89, 91, 92, 93, 95, 97, 98, 102, 103, 105, 107, 111, 112, 113, 114, 115, 116, 118, 125, 126, 128, 129, 131, 137, 140, 148, 149, 151, 152, 153, 154, 155, 156, 157, 158, 159, 160, 163, 164, 165, 166, 167, 168, 169, 170, 171, 172, 173, 175, 176, 178, 179, 191, 193, 196, 197, 198, 199, 200, 201, 202, 203, 204, 205, 203, 211, 212, 213, 214, 215, 216, 217, 219, 221, 222, 223, 224, 225, 226, 228, 229, 231, 234, 237, 238, 239, 240, 243, 246, 247, 248, 250, 251, 252, 253, 254, 256, 267, 274, 282, 284, 285, 286, 287, 288, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 333, 335, 340, 341, 343, 350, 351, 352, 353, 354, 355, 356, 357, 359, 360, 361, 362, 366, 368, 371, 410, 411, 412, 417, 418, 419, 420, 421, 422, 423, 425, 437, 441, 442, 443, 444, 445, 460, 463, 511, 514, 762, 764, 765, 772, 773, 776, 778 and 785.

INDUSTRIAL APPLICABILITY

The Pyrazolo[1,5-a]pyrimidine derivatives represented by formula I and their pharmaceutically acceptable salts exhibit excellent kinase inhibiting activity (particularly MAPKAP-K2 inhibiting activity). Drugs comprising the compounds as effective ingredients are therefore expected to be useful as therapeutic or prophylactic agents for a protein kinase mediated disorder in which kinase is implicated, such as such as inflammatory disease, autoimmune disease, destructive bone disorder, cancer and/or tumour growth.

The invention claimed is:
1. A compound of formula I:

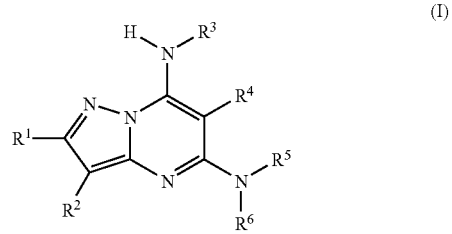

(I)

wherein R$^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^2$ is hydrogen, halogen, —CN, —NO$_2$, —CHO, -G-R$^7$ (G is a bond, —C(=O)— or —O—C(=O)—; and R$^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^8$ (R$^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —NR$^9$R$^{10}$ (R$^9$ is as defined for R$^8$; R$^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl; provided that when R$^7$ is C6-C14 optionally substituted aryl or optionally substituted heteroaryl, then G is not a bond), —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^{13}$, which may be the same or different, are as defined for R$^8$), —SR$^9$ (R$^9$ is as defined for R$^8$) or —S(O)$_m$R$^9$ (R$^9$ is as defined for R$^8$; m is 1 or 2);

R$^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl (having as a substituent one or more selected from the group consisting of halogen, —CN, —NO$_2$, —CHO, -G-R$^{15}$ {G is a bond, —C(=O)— or —O—C(=O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X is O, S, N—CN or NH), —NR$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) or —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)), unsubstituted heterocyclyl, substituted heterocyclyl (having as a substituent one or more selected from the group consisting of halogen, —CN, —NO$_2$, —CHO, -G-R$^{23}$ {G is a bond, —C(=O)— or —O—C(=O)—; R$^{23}$ is as defined for R$^{15}$}, —NR$^{24}$C(=O)R$^{25}$ (R$^{24}$ is as defined for R$^8$; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), —NR$^{24}$C(=X)NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$R$^{24}$ (R$^{24}$ is as defined for R$^8$; m is 0, 1 or 2) and —SO$_2$NR$^{28}$R$^{29}$ (R$^{28}$ and R$^{29}$, which may be the same or different, are as defined for R$^8$; R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)), optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ is as defined for R$^8$), —SR$^{30}$ (R$^{30}$ is as defined for R$^8$), —NR$^{30}$R$^{31}$ (R$^{30}$ and R$^{31}$, which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$(R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$SO$_2$R$^{31}$ (R$^{30}$ and R$^{31}$, which may be the same or different, are as defined for R$^8$);

R$^5$ is C1-C8 substituted alkyl, C2-C8 optionally substituted alkenyl, C2-C8 optionally substituted alkynyl, C3-C8 substituted cycloalkyl (having as a substituent one or more selected from the group consisting of halogen, —CN, —NO$_2$, —CHO, -G-R$^{34}$ {G is a bond, —C(=O)— or —O—C(=O)—; R$^{34}$ is as defined for R$^{15}$}, —NR$^{35}$C(=O)R$^{36}$ (R$^{35}$ is as defined for R$^8$; R$^{36}$ is as defined for R$^{12}$), —NR$^{35}$C(=X)OR$^{37}$ (R$^{35}$ and R$^{37}$, which may be the same or different, are as defined for R$^8$; X is O, S, N—CN or NH), —NR$^{35}$C(=X)NR$^{37}$R$^{38}$ (R$^{35}$, R$^{37}$ and R$^{38}$, which may be the same or different, are as defined for R$^8$; X is O, S, N—CN or NH) and NR$^{35}$SO$_2$R$^{37}$ (R$^{35}$ and R$^{37}$, which may be the same or different, are as defined for R$^8$)), unsubstituted heterocyclyl, substituted heterocyclyl (having as a substituent one or more selected from the group consisting of halogen, —CN, —NO$_2$, —CHO, -G-R$^{39}$ {G is a bond, —C(=O)— or —O—C(=O)—; R$^{39}$ is as defined for R$^{15}$}, —NR$^{40}$C(=O)R$^{41}$ (R$^{40}$ is as defined for R$^8$; R$^{41}$ is as defined for R$^{12}$), —NR$^{40}$C(=X)OR$^{42}$ (R$^{40}$ and R$^{42}$, which may be the same or different, are as defined for R$^8$; X is O, S, N—CN or NH), —NR$^{40}$C(=X)NR$^{42}$R$^{43}$ (R$^{40}$, R$^{42}$ and R$^{43}$, which may be the same or different, are as defined for R$^8$; X is O, S, N—CN or NH) and —NR$^{40}$SO$_2$R$^{42}$ (R$^{40}$ and R$^{42}$, which may be the same or different, are as defined for R$^8$)), optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl or —NR$^{44}$R$^{45}$ (R$^{44}$ and R$^{45}$, which may be the same or different, are C1-C8 optionally substituted alkyl; R$^{44}$ and R$^{45}$ together may be taken together with the nitrogen to which they are attached to form a mono heterocycle with 5-7 members and optionally containing, in addition to the nitrogen, one or two additional heteroatoms selected from N, O and S, the said mono heterocycle may optionally be substituted with one or more substituents);

$R^6$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl;

with the provisos:

that $R^1$, $R^2$ and $R^4$ are not all H;

that $R^4$ is not pentafluorophenyl;

that $R^5$ not a group represented as the following (a):

(a) C1-C6 alkyl or C3-C6 cycloalkyl, in which an alkyl group or a cycloalkyl group optionally may be substituted by phenyl or by one or more fluoro substituents;

or a pharmaceutically acceptable salt thereof.

2. A compound of formula I-b:

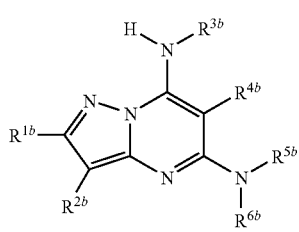

wherein $R^{1b}$ is hydrogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl;

$R^{2b}$ is hydrogen, halogen, —CN, —NO$_2$, —CHO or -G-$R^{52}$ {G is a bond, —C(O)— or —O—C(═O)—; and $R^{52}$ is C1-C6 optionally substituted alkyl, C2-C6 optionally substituted alkenyl, C2-C6 optionally substituted alkynyl, C3-C8 optionally substituted cycloalkyl, optionally substituted arylalkyl, optionally substituted heteroarylalkyl, optionally substituted arylalkenyl, optionally substituted heteroarylalkenyl, optionally substituted arylalkynyl, optionally substituted heteroarylalkynyl, —OR$^{53}$ (R$^{53}$ is hydrogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl), —NR$^{54}$R$^{55}$, —NR$^{54}$C(═O)R$^{55}$, —SR$^{54}$, optionally substituted aryl or optionally substituted heteroaryl; provided that when $R^{52}$ is optionally substituted aryl or optionally substituted heteroaryl then G is not a bond; wherein R$^{54}$ and R$^{55}$, which may be the same or different, are as defined for R$^{53}$; or wherein R$^{54}$ and R$^{55}$ together form an optionally substituted ring that optionally contains one or more heteroatoms selected from N, O and S};

$R^{3b}$ is C1-C8 optionally substituted alkyl, C2-C8 optionally substituted alkenyl, C2-C8 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl or optionally substituted heteroarylalkynyl;

$R^{4b}$ is hydrogen, halogen, C1-C6 optionally substituted alkyl, C2-C6 optionally substituted alkenyl, C2-C6 optionally substituted alkynyl, C3-C8 optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl, optionally substituted heteroarylalkynyl, —OR$^{56}$, —SR$^{56}$, —NR$^{56}$R$^{57}$ or —NR$^{56}$C(═O)R$^{57}$; wherein R$^{56}$ and R$^{57}$, which may be the same or different, are as defined for R$^{53}$; or wherein R$^{56}$ and R$^{57}$ together form an optionally substituted ring which optionally contains one or more heteroatoms;

$R^{5b}$ is C1-C6 substituted alkynyl, C2-C6 optionally substituted alkenyl, C2-C6 optionally substituted alkynyl, C3-C8 substituted cycloalkyl, optionally substituted heterocyclyl or optionally substituted heterocyclylalkyl;

$R^6$ is hydrogen, C1-C6 optionally substituted alkyl, C2-C6 optionally substituted alkenyl, C2-C6 optionally substituted alkynyl or C3-C8 optionally substituted cycloalkyl;

with the provisos:

that $R^{1b}$, $R^{2b}$ and $R^{4b}$ are not all H;

that $R^{4b}$ is not pentafluorophenyl;

that $R^{5b}$ is not a group represented as the following (a):

(a) C1-C6 alkyl or C3-C6 cycloalkyl, in which an alkyl group optionally may be substituted by phenyl or by one or more fluoro substituents; or a pharmaceutically acceptable salt thtereof.

3. The compound as claimed in claim 1 wherein $R^1$ is hydrogen or C1-C8 optionally substituted alkyl.

4. The compound as claimed in claim 1 wherein $R^1$ is hydrogen.

5. The compound as claimed in claim 1 wherein $R^2$ is —NO$_2$, —OC(═O)R$^7$, —CO$_2$R$^8$ or —CONR$^9$R$^{10}$; wherein $R^7$, $R^8$, $R^9$ and $R^{10}$ are as defined in claim 1.

6. The compound as claimed in claim 1 wherein $R^2$ is —NR$^9$C(═O)R$^{12}$, —NR$^9$C(═X)OR$^{13}$, —NR$^9$C(═X)NR$^{13}$R$^{14}$, —NR$^9$SO$_2$R$^{13}$, —SR$^9$ or —S(O)$_m$R$^9$; wherein $R^9$, $R^{12}$, $R^{13}$, $R^{14}$ and X are as defined in claim 1; m is 1 or 2.

7. The compound as claimed in claim 1 wherein $R^2$ is C1-C8 optionally substituted alkyl, C3-C8 optionally substituted cycloalkyl or optionally substituted arylalkyl.

8. The compound as claimed in claim 1 wherein $R^2$ is hydrogen, halogen, —CN or —SCH$_3$.

9. The compound as claimed in claim 1 wherein $R^2$ is halogen.

10. The compound as claimed in claim 1 wherein $R^2$ is F.

11. The compound as claimed in claim 1 wherein $R^2$ is hydrogen.

12. The compound as claimed in claim 1 wherein $R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl, unsubstituted heteroaryl, substituted heteroaryl, optionally substituted arylalkyl or optionally substituted heteroarylalkyl.

13. The compound as claimed in claim 1 wherein $R^3$ is C6-C14 substituted aryl.

14. The compound as claimed in claim 1 wherein $R^3$ is C6-C14 substituted aryl {having as a substituent one or more selected from the group consisting of halogen, —CN, —$NO_2$, -G-$R^{15}$, —$NR^{17}C(=O)R^{19}$ and —$S(O)mR^{17}$; wherein $R^{15}$, $R^{17}$, $R^{19}$ or G are as defined in claim 1; m is 0, 1 or 2}.

15. The compound as claimed in claim 1 wherein $R^3$ is C6-C14 substituted aryl (having as a substituent one or more selected from the group consisting of halogen, —CN, —$NO_2$, -G-$R^{15}$ {G is a bond or —C(=O)—; $R^{15}$ is C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl, —$OR^{16}$ or —$NR^{17}R^{18}$}, —$NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2).

16. The compound as claimed in claim 1 wherein $R^3$ is C6-C14 substituted aryl (having as a substituent one or more selected from the group consisting of halogen, —CN, —$NO_2$, -G-$R^{15}$ {G is a bond; $R^{15}$ is C6-C14 optionally substituted aryl, optionally substituted heterocyclyl, optionally substituted heterocyclylalkyl, —$OR^{16}$ or —$NR^{17}R^{18}$}, —$NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2).

17. The compound as claimed in claim 1 wherein $R^3$ is C6-C14 substituted aryl (having as a substituent one or more selected from the group consisting of halogen, —CN, —$NO_2$, -G-$R^{15}$ {G is a bond or —C(O)—; $R^{15}$ is C1-C8 optionally substituted alkyl, C3-C8 optionally substituted cycloalkyl, —$OR^{16}$ or —$NR^{17}R^{18}$}, —$NR^{17}C(=O)R^{19}$ and $S(O)_mR^{17}$; wherein $R^{16}$, $R^{17}$, $R^{18}$ or $R^{19}$ are as defined in claim 1; m is 0, 1 or 2).

18. The compound as claimed in claim 1 wherein $R^3$ is C6-C14 substituted aryl (having as a substituent one or more selected from the group consisting of halogen, —CN, —$NO_2$, -G-$R^{15}$ {G is a bond or —C(=O)—; $R^{15}$ is C1-C8 optionally substituted alkyl, C3-C8 optionally substituted cycloalkyl, —$OR^{16}$ or —$NR^{17}R^{18}$}, —$NR^{17}C(=O)R^{19}$ and $S(O)_mR^{17}$; wherein $R^{16}$, $R^{17}$, $R^{18}$ or $R^{19}$, which may be the same or different, are hydrogen, C1-C8 optionally substituted alkyl, C3-C8 optionally substituted cycloalkyl; m is 0, 1 or 2).

19. The compound as claimed in claim 1 wherein $R^3$ is C6-C14 substituted aryl (having as a substituent one or more selected from the group consisting of halogen, —CN, —$NO_2$ and -G-$R^{15}$ {G is —C(=O)—; $R^{15}$ is C1-C8 optionally substituted alkyl, C3-C8 optionally substituted cycloalkyl, C6-C14 optionally substituted aryl, optionally substituted heterocyclyl, —$OR^{16}$ or —$NR^{17}R^{18}$}; wherein $R^{16}$, $R^{17}$ or $R^{18}$ are as defined in claim 1).

20. The compound as claimed in claim 1 wherein $R^3$ is unsubstituted heterocyclyl.

21. The compound as claimed in claim 1 wherein $R^3$ is substituted heterocyclyl.

22. The compound as claimed in claim 1 wherein $R^3$ is substituted heterocyclyl (having as a substituent one or more selected from the group consisting of halogen, —CN, —$NO_2$, -G-$R^{23}$, —$NR^{24}C(=O)R^{25}$ and —$S(O)_mR^{24}$; wherein $R^{23}$, $R^{24}$, $R^{25}$ or G are as defined in claim 1; m is 0, 1 or 2).

23. The compound as claimed in claim 1 wherein $R^3$ is unsubstituted bicyclic heteroaryl.

24. The compound as claimed in claim 1 wherein $R^3$ is substituted bicyclic heteroaryl (having as a substituent one or more selected from the group consisting of halogen, —CN, —$NO_2$, -G-$R^{23}$, —$NR^{24}C(=O)R^{25}$ and —$S(O)_mR^{24}$; wherein $R^{23}$, $R^{24}$, $R^{25}$ or fined in claim 1; m is 0, 1 or 2).

25. The compound as claimed in claim 1 wherein $R^4$ is halogen, C1-C8 optionally substituted alkyl, C3-C8 optionally substituted cycloalkyl, optionally substituted arylalkyl, optionally substituted heterocyclylalkyl, —$OR^{30}$; wherein $R^{30}$ is as defined in claim 1.

26. The compound as claimed in claim 1 wherein $R^4$ is C1-C8 optionally substituted alkyl.

27. The compound as claimed in claim 1 wherein $R^4$ methyl.

28. The compound as claimed in claim 1 wherein $R^4$ is hydrogen.

29. The compound as claimed in claim 1 wherein $R^5$ is C3-C8 substituted cycloalkyl, unsubstituted heterocyclyl or substituted heterocyclyl.

30. The compound as claimed in claim 1 wherein $R^5$ is C3-C8 substituted cycloalkyl (having as a substituent one or more selected from the group consisting of halogen, —CN, C1-C8 optionally substituted alkyl, C2-C8 optionally substituted alkenyl, C3-C8 optionally substituted cycloalkyl and —$NR^{17}R^{18}$; wherein $R^{17}$ or $R^{18}$ is as defined in claim 1).

31. The compound as claimed in claim 1 wherein $R^5$ is substituted cyclohexyl (having as a substituent one or more selected from the group consisting of halogen, —CN, C1-C8 optionally substituted alkyl, C2-C8 optionally substituted alkenyl, C3-C8 optionally substituted cycloalkyl and —$NR^{17}R^{18}$; wherein $R^{17}$ or $R^{18}$ is as defined in claim 1).

32. The compound as claimed in claim 1 wherein $R^5$ is 4-amino-cyclohexyl.

33. The compound as claimed in claim 1 wherein $R^5$ is unsubstituted heterocyclyl or substituted heterocyclyl (having as a substituent one or more selected from the group consisting of halogen, —CN, C1-C8 optionally substituted alkyl, C2-C8 optionally substituted alkenyl, C3-C8 optionally substituted cycloalkyl and —$NR^{17}R^{18}$; wherein $R^{17}$ or $R^{18}$ is as defined in claim 1).

34. The compound as claimed in claim 1 wherein $R^5$ is unsubstituted piperidin-3-yl, unsubstituted piperidin-4-yl or unsubstituted pyrrolidin-3-yl.

35. The compound as claimed in claim 1 wherein $R^5$ is substituted piperidin-3-yl, substituted piperidin-4-yl or substituted pyrrolidin-3-yl.

36. The compound as claimed in claim 1 wherein $R^5$ is substituted piperidin-3-yl, substituted piperidin-4-yl or substituted pyrrolidin-3-yl (having as a substituent one or more selected from the group consisting of halogen, —CN, C1-C8 optionally substituted alkyl, C2-C8 optionally substituted alkenyl and C3-C8 optionally substituted cycloalkyl).

37. The compound as claimed in claim 1 wherein $R^6$ hydrogen.

38. The compound as claimed in claim 1 wherein $R^6$ is C1-C8 optionally substituted alkyl or optionally substituted arylalkyl.

39. A compound of the formula II-26:

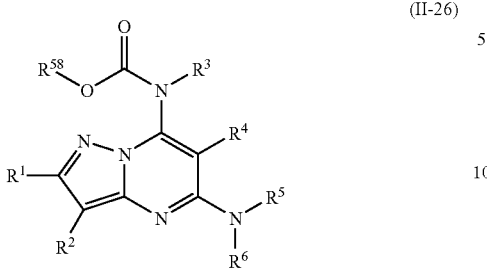

(II-26)

wherein R$^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^2$ is hydrogen, halogen, —CN, —NO$_2$, —CHO, -G-R$^7$ (G is a bond, —C(=O)— or —O—C(=O)—; and R$^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^8$ (R$^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl). —NR$^9$R$^{10}$ (R$^9$ is as defined for R$^8$; R$^{10}$ is hydrogen, C1-C8 optionally substituted alkyl, C3-C8 optionally substituted cycloalkyl, C6-Cl4 optionally substituted aryl, optionally substituted heterocyclyl, optionally substituted arylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl; provided that when R$^7$ is C6-C14 optionally substituted aryl or optionally substituted heteroaryl, then G is not a bond), —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which maybe the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^{13}$, which may be same or different, are as defined for R$^8$), —SR$^9$ (R$^9$ is as defined for R$^8$) or —S(O)$_m$R$^9$ (R$^9$ is as defined for R$^8$; m is 1 or 2);

R$^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl (having as a substituent one or more selected from the group consisting of halogen, —CN, —NO$_2$ —CHO, -G-R$^{15}$ {G is a bond, —C(=O)— or —O—C(=O)—; R$^{15}$ is C1-C8 optionally substituted alkyl, C2-C8 optionally substituted alkenyl, C2-C8 optionally substituted alkynyl, C3 -C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X is O, S, N—CN or NH), —NR$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) and —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)), unsubstituted heterocyclyl, substituted heterocyclyl (having as a substituent one or more selected from the group consisting of halogen, —CN, —NO$_2$, —CHO, -G-R$^{23}$ {G is a bond, —C(=O)— or —O—C(O)—; R$^{23}$ is as defined for R$^{15}$}, —NR$^{24}$C(=O)R$^{25}$ (R$^{24}$ is as defined for R$^8$; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), —NR$^{24}$C(=X) NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$ R$^{24}$ (R$^{24}$ is as defined for R$^8$; m is 0, 1 or 2) and —SO$_2$NR$^{28}$R$^{29}$ (R$^{28}$ and R$^{29}$, which may be the same or different, are as defined for R$^8$; R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)). optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ as defined for R$^8$), —SR$^{30}$ (R$^{30}$is as defined for R$^8$), —NR$^{30}$R$^{31}$ (R$^{30}$ and R$^{31}$, which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$(R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$SO$_2$R$^{31}$ (R$^{30}$ and R$^{31}$, which may be the same or different, are as defined for R$^8$);

R$^5$ is C1-C8 substituted alkyl, C2-C8 optionally substituted alkenyl, C2-C8 optionally substituted alkynyl, C3-C8 substituted cycloalkyl )having as a substituent one or more selected from the group consisting of halogen, —CN, —NO$_2$, —CHO, -G-R$^{34}$ {G is a bond, —C(=O)— or —O—C(=O)—; R$^{34}$ is as defined for R$^{15}$}, —NR$^{35}$C(=O)R$^{36}$ (R$^{35}$ is as defined for R$^8$; R$^{36}$ is as defined for R$^{12}$), —NR$^{35}$C(=X)OR$^{37}$ (R$^{35}$ and R$^{37}$, which may be the same or different, are as defined for R$^8$; X is O, S, N—CN or NH ), —NR$^{35}$C(=X)NR$^{37}$R$^{38}$ (R$^{35}$, R$^{37}$ and R$^{38}$, which may be the same or different, are as defined for R$^8$; X is O, S, N—CN or NH) and NR$^{35}$SO$_2$R$^{37}$ (R$^{35}$ and R$^{37}$, which may be the same or different, are as defined for R$^8$)), unsubstituted heterocyclyl, substituted heterocyclyl (having as a substituent one or more selected from the group consisting of halogen, —CN, —NO$_2$, —CHO, -G-R$^{39}$ {G is a bond, —C(=O)— or —O—C(=O)—; R$^{39}$ is as defined for R$^{15}$}, —NR$^{40}$C(=O)R$^{41}$ (R$^{40}$ is as defined for R$^8$; R$^{41}$ is as defined for R$^{12}$), —NR$^{40}$C(=X)OR$^{42}$ (R$^{40}$ and R$^{42}$, which may be the same or different, are as defined for R$^8$; X is O, S, N—CN or NH), —NR$^{40}$C(=X)NR$^{42}$R$^{43}$ (R$^{40}$, R$^{42}$ and R$^{43}$, which may be the same or different, are as defined for R$^8$; X is O, S, N—CN or NH) and —NR$^{40}$SO$_2$R$^{42}$ (R$^{40}$ and R$^{42}$, which may be the same or different, are as defined for R$^8$)), optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl or —NR$^{44}$R$^{45}$ (R$^{44}$ and R$^{45}$, which may be the same or different, are C1-C8 optionally substituted alkyl; R$^{44}$ and R$^{45}$ to get her may be taken together with the nitrogen to which they are attached to form a mono heterocycle with 5-7 members and optionally containing, in addition to the nitrogen, one or two additional heteroatoms selected from N, O and S, the said mono heterocycle may optionally be substituted with one or more substituents);

R$^6$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl;

R$^{58}$ is C1-C8 optionally substituted alkyl or optionally substituted arylalkyl;

with the provisos:

that R$^1$, R$^2$ and R$^4$ are not all H.

40. A compound of the formula III-01:

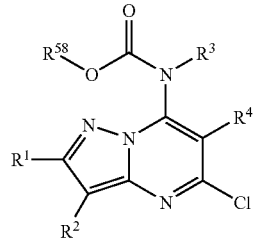

(III-01)

wherein R$^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^2$ is hydrogen, halogen, —CN, —NO$_2$, —CHO, -G-R$^7$ (G is a bond, —C(=O)— or —O—C(=O)—; and R$^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^8$ (R$^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —NR$^9$R$^{10}$ (R$^9$ is as defined for R$^8$; R$^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —OCH$_3$), —R$^{11}$ (R$^{11}$ is an optionally substituted saturated heterocyclyl with 5 to 7 members containing one to four heteroatoms selected from N, O and S), C6-C14 optionally substituted aryl or optionally substituted heteroaryl provided that when R$^7$ is C6-C14 optionally substituted aryl or optionally substituted heteroaryl, then G is not a bond), —NR$^9$C(=O)R$^{12}$ (R$^9$ is as defined for R$^8$; R$^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^{13}$, which may be the same or different, are as defined for R$^8$), —SR$^9$ (R$^9$ is as defined for R$^8$) or —S(O)$_m$R$^9$ R$^9$ is as defined for R$^8$; m is 1 or 2);

$R^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl (having as a substituent one or more selected from the group consisting of halogen, —CN, —NO₂—CHO, -G-R¹⁵ {G is a bond, —C(=O)— or —O—C(=O)—; $R^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR¹⁶ ($R^{16}$ is as defined for $R^8$) or —NR¹⁷R¹⁸ ($R^{17}$ and $R^{18}$, which may be the same or different, are as defined for $R^8$)}, —NR¹⁷C(=O)R¹⁹ ($R^{17}$ is as defined for $R^8$; $R^{19}$ is as defined for $R^{12}$), NR¹⁷C(=X)OR¹⁸ ($R^{17}$ and $R^{18}$, which maybe the same or different, are as defined for $R^8$; X O, S, N—CN or NH), —NR¹⁷C(=X)NR¹⁸R²⁰ ($R^{17}$, $R^{18}$ and $R^{20}$, which may be the same or different, are as defined for $R^8$; X is O, S, N—CN or NH), NR¹⁷SO₂R¹⁸ ($R^{17}$ and $R^{18}$, which ma be the same or different are as defined for $R^8$), —S(O)$_m$R¹⁷ ($R^{17}$ is as defined for $R^8$; m is 0, 1 or 2) and —SO₂NR²¹R²² ($R^{21}$ and $R^{22}$, which may be the same or different, are as defined for $R^8$; $R^{21}$ and $R^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)), unsubstituted heterocyclyl, substituted heterocyclyl (haying as a substituent one or more selected from the group consisting of halogen, —CN, —NO₂, —CHO, -G-R²³ {G is a bond, —C(=O)— or —O—C(=O)—; $R^{23}$ is as defined for $R^{15}$}, —NR²⁴C(=O)R²⁵ ($R^{24}$ is as defined for $R^8$; $R^{25}$ is as defined for $R^{12}$), —NR²⁴C(=X)OR²⁶ ($R^{24}$ and $R^{26}$, which maybe the same or different, are as defined for $R^8$; X is O, S, N—CN or NH), —NR²⁴C(=X)NR²⁶R²⁷ ($R^{24}$, $R^{26}$ and $R^{27}$, which may be the same or different, are as defined for $R^8$; X is O, S, N—CN or NH), —NR²⁴SO₂R²⁶ (wherein $R^{24}$ and $R^{26}$, which may be the same or different, are as defined for $R^8$), —S(O)$_m$R²⁴ ($R^{24}$ is as defined for $R^8$; m is 0, 1 or 2) and —SO₂NR²⁸ R²⁹ ($R^{28}$ and $R^{29}$, which may be the same or different, are as defined for $R^8$; $R^{28}$ and $R^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O, and S, the said monocyclic or bicyclic heterocycle may optionally be substituted with one or more substituents)), optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR³⁰ ($R^{30}$ is as defined for $R^8$), —SR³⁰ ($R^{30}$ is for $R^8$), —NR³⁰R³¹ ($R^{30}$ and $R^{31}$, which may be the same or different, are as defined for $R^8$), —NR³⁰C(=O)R³² ($R^{30}$ is as defined for $R^8$; and $R^{32}$ is as defined for $R^{12}$), —NR³⁰C(=X)OR³¹($R^{30}$ and $R^{31}$, which may be the same or different, are as defined $R^8$; X is O, S, N—CN or NH), —NR³⁰C(=X)NR³¹R³³ ($R^{30}$, $R^{31}$ and $R^{33}$, which may be the same or different, are as defined for $R^8$; X is O, S, N—CN or NH) or —NR³⁰SO₂R³¹ ($R^{30}$ and $R^{31}$, which may be the same or different, are as defined for $R^8$);

$R^{58}$ is C1-C8 optionally substituted alkyl or optionally substituted arylalkyl;

with the provisos:

that $R^1$, $R^2$ and $R^4$ are not all H.

41. A compound of the formula IV:

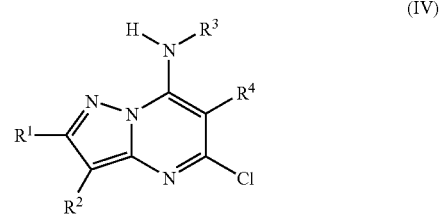

(IV)

wherein $R^1$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

$R^2$ is hydrogen, halogen, —CN, —NO₂, —CHO, -G-R⁷ (G is bond, —C(=O)— or —O—C(=O)—; and $R^7$ is C1-C8 optionally substituted alkyl, C2-C8 optionally substituted alkenyl, C2-C8 optionally substituted alkynyl, C3-C8 optionally substituted cycloalkyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR⁸ ($R^8$ is hydrogen, C1-C8 optionally substituted alkyl, C3-C8 optionally substituted cycloalkyl, C6-C14 optionally substituted aryl, optionally substituted heterocyclyl, optionally substituted arylalkyl or optionally substituted heterocyclylalkyl), —NR⁹R¹⁰ ($R^9$ is as defined for $R^8$; $R^{10}$ is hydrogen, C1-C8 optionally substituted alkyl, C3-C8 optionally substituted cycloalkyl, C6-C14 optionally substituted aryl, optionally substituted heterocyclyl, optionally substituted arylalkyl, optionally substituted heterocyclylalkyl or —OCH₃), —R¹¹ ($R^{11}$ is an optionally substituted saturated heterocyclyl with 5 to 7 members containing one to four heteroatoms selected from N, O and S), C6-C14 optionally substituted aryl or optionally substituted heteroaryl: provided that when $R^7$ is C6-C14 optionally substituted aryl or optionally substituted heteroaryl, then G is not a bond), —NR⁹C(=O)R¹² ($R^9$ is as defined for $R^8$; $R^{12}$ is hydrogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl), —NR$^9$C(=X)OR$^{13}$ (R$^9$ and R$^{13}$, which may be the same or different, are as defined for R$^8$; X is O, S, N—CN or NH), —NR$^9$C(=X)NR$^{13}$R$^{14}$ (R$^9$, R$^{13}$ and R$^{14}$, which may be the same or different, are as defined for R$^8$; X is O, S, N—CN or NH), —NR$^9$SO$_2$R$^{13}$ (R$^9$ and R$^{13}$, which may be the same or different, are as defined for R$^8$), —SR$^9$ (R$^9$ is as defined for R$^8$) or —S(O)$_m$R$^9$ (R$^9$ is as defined for R$^8$; m is 1 or 2);

R$^3$ is C1-C8 optionally substituted alkyl, C2-C8 optionally substituted alkenyl, C2-C8 optionally substituted alkynyl, C3-C8 optionally substituted cycloalkyl, C6-C14 unsubstituted aryl, C6-C14 substituted aryl (having as a substituent one or more selected from the group consisting of halogen, —CN, —NO$_2$—CHO, -G-R$^{15}$ {G is a bond, —C(=O)— or —O—C(=O)—; R$^{15}$ is C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{16}$ (R$^{16}$ is as defined for R$^8$) or —NR$^{17}$R$^{18}$ (R$^{17}$ and R$^{18}$, which may be the same or different, are as defined for R$^8$)}, —NR$^{17}$C(=O)R$^{19}$ (R$^{17}$ is as defined for R$^8$; R$^{19}$ is as defined for R$^{12}$), —NR$^{17}$C(=X)OR$^{18}$ (R$^{17}$ and R$^{18}$, which may be the same or different, are as defined for R$^8$; X O, S, N—CN or NH), —NR$^{17}$C(=X)NR$^{18}$R$^{20}$ (R$^{17}$, R$^{18}$ and R$^{20}$, which may be the same or different, are as defined for R$^8$; X is O, S, N—CN or NH), —NR$^{17}$SO$_2$R$^{18}$ (R$^{17}$ and R$^{18}$, which may be the same or different, are as defined for R$^8$), —S(O)$_m$R$^{17}$ (R$^{17}$ is as defined for R$^8$; m is 0, 1 or 2) and —SO$_2$NR$^{21}$R$^{22}$ (R$^{21}$ and R$^{22}$, which may be the same or different, are as defined for R$^8$; R$^{21}$ and R$^{22}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituentsb, unsubstituted heterocyclyl. substituted heterocyclyl (having as a substituent one or more selected from the group consisting of halogen, —CN, —NO$_2$, —CHO, -G-R$^{23}$ {G is a bond, —C(=O)— or —O—C(=O)—; R$^{23}$ is as defined for R$^{15}$}, —NR$^{24}$C(=O)R$^{25}$ (R$^{24}$ is as defined for R$^8$; R$^{25}$ is as defined for R$^{12}$), —NR$^{24}$C(=X)OR$^{26}$ (R$^{24}$ and R$^{26}$, which may be the same or different, are as defined for R$^8$; X is O, S, N—CN or NH), —NR$^{24}$C(=X)NR$^{26}$R$^{27}$ (R$^{24}$, R$^{26}$ and R$^{27}$, which may be the same or different, are as defined for R$^8$; X is O, S, N—CN or NH), —NR$^{24}$SO$_2$R$^{26}$ (wherein R$^{24}$ and R$^{26}$, which may be the same or different, are as defined for R$^8$), —S(O)$_m$R$^{24}$ (R$^{24}$ as defined for R$^8$; m is 0, 1 or 2) and —SO$_2$NR$^{28}$ R$^{29}$ (R$^{28}$ and R$^{29}$, which maybe the same or different, are as defined for R$^8$; R$^{28}$ and R$^{29}$ together may be taken together with the nitrogen to which they are attached to form a monocyclic or bicyclic heterocycle with 5-7 members in each ring and optionally containing, in addition to the nitrogen, one or two additional heteroatoms selected from N, O and S, the said monocyclic or bicyclic heterocycle may optionally be substituted with one or more substituents)), optionally substituted arylalkyl, optionally substituted heterocyclylalkyl, optionally substituted arylalkenyl, optionally substituted heterocyclylalkenyl, optionally substituted arylalkynyl or optionally substituted heterocyclylalkynyl;

R$^4$ is hydrogen, halogen, C1-C8 optionally substituted alkyl, C2-C8 optionally substituted alkenyl, C2-C8 optionally substituted alkynyl, C3-C8 optionally substituted cycloalkyl, C6-C14 optionally substituted aryl, optionally substituted heterocyclyl, optionally substituted arylalkyl, optionally substituted heterocyclylalkyl, optionally substituted arylalkenyl, optionally substituted heterocyclylalkenyl, optionally substituted arylalkynyl, optionally substituted heterocyclylalkynyl, —OR$^{30}$ (R$^{30}$ is as defined for R$^8$), —SR$^{30}$ (R$^{30}$ is as defined for R$^8$), —NR$^{30}$R$^{31}$ (R$^{30}$ and R$^{31}$ which may be the same or different, are as defined for R$^8$), —NR$^{30}$C(=O)R$^{32}$ (R$^{30}$ is as defined for R$^8$; and R$^{32}$ is as defined for R$^{12}$), —NR$^{30}$C(=X)OR$^{31}$ (R$^{30}$ and R$^{31}$, which may be the same or different, are as defined R$^8$; X is O, S, N—CN or NH), —NR$^{30}$C(=X)NR$^{31}$R$^{33}$ (R$^{30}$, R$^{31}$ and R$^{33}$, which may be the same or different, are as defined for R$^8$; X is O, S, N—CN or NH) or —NR$^{30}$S$_2$R$^{31}$ (R$^{30}$ and R$^{31}$, which may be the same or different, are as defined for R$^8$);

with the provisos:

that R$^1$, R$^2$ and R$^4$ are not all H;

that R$^4$ is not optionally substituted aryl or optionally substituted heteroaryl.

42. The compound as claimed in any one of claims 39, 40 and 41 wherein R$^1$ is hydrogen.

43. The compound as claimed in any one of claims 39, 40 and 41 wherein R$^2$ is hydrogen, halogen, —CN, C1-C8 optionally substituted alkyl, C3-C8 optionally substituted cycloalkyl, —OR$^8$ (R$^8$ is hydrogen or C1-C8 optionally substituted alkyl), —NR$^9$R$^{10}$ (R$^9$ and R$^{10}$, which may be the same or different, hydrogen or C1-C8 optionally substituted alkyl), —C(=O)NR$^9$R$^{10}$ (R$^9$ and R$^{10}$, which may be the same or different, are hydrogen, C1-C8 optionally substituted alkyl, C3-C8 optionally substituted cycloalkyl, C6-C14 optionally substituted aryl or optionally substituted heterocyclyl), —NR$^9$C(=O)R$^{12}$ (R$^9$ is hydrogen or C1-C8 optionally substituted alkyl; R$^{12}$ is C1-C8 optionally substituted alkyl, C3-C8 optionally substituted cycloalkyl, C6-C14 optionally substituted aryl or optionally substituted heterocyclyl), —NR$^9$C(=O)OR$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —NR$^9$C(=O)NR$^{13}$R$^{14}$ (R$^9$ and R$^{13}$, which may be the same or different, are hydrogen or C1-C8 optionally substituted alkyl; R$^{14}$ C1-C8 optionally substituted alkyl, C3-C8 optionally substituted cycloalkyl, C6-C14 optionally substituted aryl or optionally substituted heterocyclyl), —NR$^9$SO$_2$R$^{13}$ (R$^9$ is hydrogen or C1-C8 optionally substituted alkyl; R$^{13}$ is C1-C8 optionally substituted alkyl, C3-C8 optionally substituted cycloalkyl, C6-C14 optionally substituted aryl or optionally substituted heterocyclyl), —SR$^9$ (R$^9$ is hydrogen, C1-C8 optionally substituted alkyl, C3-C8 optionally substituted cycloalkyl, C6-C14 optionally substituted, aryl or optionally substituted heterocyclyl) or —$SO_2R^9$ ($R^9$ is C1-C8 optionally substituted alkyl, C3-C8 optionally substituted cycloalkyl, C6-C14 optionally substituted aryl or optionally substituted heterocyclyl).

44. The compound as claimed in any one of claims 39, 40 and 41 wherein $R^3$ is substituted phenyl (having as a substituent one or more selected from the group consisting of halogen, —CN, —$NO_2$, C1-C8 optionally substituted alkyl, C2-C8 optionally substituted alkynyl, C6-C14 optionally substituted aryl, optionally substituted heterocyclyl, —$OR^{16}$ ($R^{16}$ is hydrogen, C1-C8 optionally substituted alkyl, optionally substituted arylalkyl or optionally substituted heterocyclylalkyl), —$NR^{17}R^{18}$ ($R^{17}$ and $R^{18}$, which may be the same or different, are hydrogen or C1-C8 optionally substituted alkyl) and —C(=O)$NR^{17}R^{18}$ ($R^{17}$ and $R^{18}$, which may be the same or different, are hydrogen, C1-C8 optionally substituted alkyl, C3-C8 optionally substituted cycloalkyl, C6-C14 optionally substituted aryl or optionally substituted heterocyclyl)), unsubstituted bicyclic heteroaryl, substituted bicyclic heteroaryl (having as a sub stituent one or more selected from the group consisting of halogen, —CN, —$NO_2$, C1-C8 optionally substituted alkyl, C6-C14 optionally substituted aryl, optionally substituted heterocyclyl, —$OR^{16}$ ($R^{16}$ is hydrogen, C1-C8 optionally substituted alkyl, optionally substituted arylalkyl or optionally substituted heterocyclylalkyl), —$NR^{17}R^{18}$ ($R^{17}$ and $R^{18}$, which may be the same or different, are hydrogen or C1-C8 optionally substituted alkyl), —NHC(=O)$R^{19}$ ($R^{19}$ is C1-C8 optionally substituted alkyl, C3-C8 optionally substituted cycloalkyl, C6-C14 optionally substituted aryl or optionally substituted heterocyclyl) and —$SR^{17}$ ($R^{17}$ is C1-C8 optionally substituted alkyl.

45. The compound as claimed in any one of claims 39, 40 and 41 wherein $R^4$ is hydrogen, methyl or ethyl.

46. The compound as claimed in claim 39 wherein $R^5$ preferably selected from cyclohexyl (having as a substituent one or more selected from the group consisting of halogen, C1-C8 optionally substituted alkyl, —OH and —$NH_2$), unsubstituted saturated heterocyclyl or substituted saturated heterocyclyl (having as a sub stituentone or more selected from the group consisting of halogen, C1-C8 optionally, substituted alkyl, —OH and —$NH_2$).

47. The compound as claimed in claim 39 wherein $R^6$ is hydrogen.

48. The compound as claimed in any one of claims 39, 40 and 41 wherein $R^{58}$ is tert-butyl or benzyl.

49. The compound as claimed in claim 39 wherein $R^1$ is hydrogen; $R^2$ is hydrogen, —CN, —$SCH_3$, —$NH_2$, —COOH or $COCF_3$; $R^3$ is substituted phenyl (having as a substituent one or more selected from the group consisting of halogen, —CN, —OH, —$OCH_3$, —OEt, —COOH); $R^4$ is hydrogen or —$CH_3$; $R^5$ is 4-amino-cyclohexyl or piperidin-3-yl; $R^6$ is hydrogen; $R^{58}$ is tert -butyl; with the proviso that $R^1$, $R^2$ and $R^4$ are not all H.

50. The compound as claimed in claim 40 wherein $R^1$ is hydrogen; $R^2$ is hydrogen, —CN, —$SCH_3$, —$NH_2$, —COOH or $COCF_3$; $R^3$ is substituted phenyl (having as a substituent one or more selected from the group consisting of halogen, —CN, —OH, —$OCH_3$, —OEt, —COOH); $R^4$ hydrogen or —$CH_3$; $R^{58}$ is tert -butyl; with the proviso that $R^1$, $R^2$ and $R^4$ are not all H.

51. The compound as claimed in claim 41 wherein $R^1$ is hydrogen; $R^2$ is hydrogen, —CN, —$SCH_3$, —$NH_2$, —COOH or $COCF_3$; $R^3$ is substituted phenyl (having as a substituent one or more selected from the group consisting of halogen, —CN, —OH, —$OCH_3$, —OEt, —COOH); $R^4$ is hydrogen or —$CH_3$; with the provisos that $R^1$, $R^2$ and $R^4$ are not all H.

52. A pharmaceutical composition comprising a compound as defined in claim 1 in combination with a pharmaceutically acceptable carrier, diluent or excipient.

53. A process for the manufacture of a pharmaceutical composition as defined in claim 52 comprising combining a compound as defined in any one of claims 1 and 3 to 38 with the pharmaceutically acceptable carrier or diluent.

* * * * *